US011713347B2

(12) United States Patent
Chattopadhyay et al.

(10) Patent No.: US 11,713,347 B2
(45) Date of Patent: Aug. 1, 2023

(54) CD38-BINDING PROTEINS COMPRISING DE-IMMUNIZED SHIGA TOXIN A SUBUNIT EFFECTORS

(71) Applicants: Milennium Pharmaceuticals, Inc., Cambridge, MA (US); MOLECULAR TEMPLATES, INC., Austin, TX (US)

(72) Inventors: Nibedita Chattopadhyay, Wellesley, MA (US); Eric Poma, New York, NY (US); Erin Willert, Round Rock, TX (US)

(73) Assignees: Millennium Pharmaceuticals, Inc., Cambridge, MA (US); Molecular Templates, Inc., Austin, TX (US)

( * ) Notice: Subject to any disclaimer, the term of this patent is extended or adjusted under 35 U.S.C. 154(b) by 311 days.

(21) Appl. No.: 16/751,144

(22) Filed: Jan. 23, 2020

(65) Prior Publication Data
US 2020/0231650 A1    Jul. 23, 2020

Related U.S. Application Data

(60) Provisional application No. 62/945,106, filed on Dec. 6, 2019, provisional application No. 62/945,107, filed on Dec. 6, 2019, provisional application No. 62/795,633, filed on Jan. 23, 2019.

(51) Int. Cl.
| | |
|---|---|
| *C07K 1/14* | (2006.01) |
| *A61P 35/00* | (2006.01) |
| *C12N 15/63* | (2006.01) |
| *A61K 38/00* | (2006.01) |
| *C07K 14/705* | (2006.01) |

(52) U.S. Cl.
CPC ........ *C07K 14/70521* (2013.01); *A61P 35/00* (2018.01); *C12N 15/63* (2013.01); *A61K 38/00* (2013.01); *C07K 2317/565* (2013.01); *C07K 2317/92* (2013.01)

(58) Field of Classification Search
None
See application file for complete search history.

(56) References Cited

U.S. PATENT DOCUMENTS

| | | |
|---|---|---|
| 7,887,801 B2 | 2/2011 | Wels et al. |
| 8,530,637 B2 | 9/2013 | Wels et al. |
| 9,603,927 B2 | 3/2017 | Doshi |
| 10,815,469 B2 | 10/2020 | Poma et al. |
| 11,414,496 B2 | 8/2022 | Elias et al. |
| 2015/0259428 A1 | 9/2015 | Poma et al. |
| 2016/0068577 A1 | 3/2016 | Poma et al. |
| 2016/0177284 A1 | 6/2016 | Poma et al. |
| 2016/0340394 A1 | 11/2016 | Poma et al. |
| 2016/0347798 A1 | 12/2016 | Poma et al. |
| 2016/0376328 A1 | 12/2016 | Poma et al. |
| 2017/0143814 A1 | 5/2017 | Poma et al. |
| 2018/0258143 A1* | 9/2018 | Poma .............. A61P 25/28 |
| 2020/0231696 A1 | 7/2020 | Elias et al. |
| 2022/0275030 A1 | 9/2022 | Poma et al. |

FOREIGN PATENT DOCUMENTS

| | | |
|---|---|---|
| WO | WO 98/11125 A1 | 3/1998 |
| WO | WO 2012/092612 A1 | 7/2012 |
| WO | WO 2014/164680 A1 | 10/2014 |
| WO | WO 2014/164693 A2 | 10/2014 |
| WO | WO 2015/113005 A1 | 7/2015 |
| WO | WO 2015/113007 A1 | 7/2015 |
| WO | WO 2015/138435 A1 | 9/2015 |
| WO | WO 2015/138452 A1 | 9/2015 |
| WO | WO 2015/191764 A1 | 12/2015 |
| WO | WO 2016/126950 A1 | 8/2016 |
| WO | WO 2016/196344 A1 | 12/2016 |
| WO | WO 2017/019623 A2 | 2/2017 |
| WO | WO 2018/106895 A1 | 6/2018 |
| WO | WO 2018/140427 A1 | 8/2018 |
| WO | WO 2018/159615 A1 | 9/2018 |
| WO | WO 2020/154540 A1 | 7/2020 |

OTHER PUBLICATIONS

[No Author Listed], Darzalex, Annex I: Summary of Product Characteristics, European Medicines Agency, 2016, 32 pages.
Al-Jaufy, A. Y. et al., "Cytotoxicity of a Shiga toxin A Subunit-CD4 Fusion Protein to Human Immunodeficiency Virus-Infected Cells," Infection and Immunity, 62(3):956-960 (1994).
Au, T. K. et al., "The plant ribosome inactivating proteins luffin and saporin are potent inhibitors of HIV-1 integrase," FEBS Letters, 471:169-172 (2000).

(Continued)

*Primary Examiner* — Laura B Goddard
*Assistant Examiner* — Sarah A Alsomairy
(74) *Attorney, Agent, or Firm* — Cooley LLP; Ivor Elrifi

(57) ABSTRACT

The instant invention provides binding proteins ("CD38-binding proteins") which each comprise (1) a CD38-binding region for cell-targeting and (2) a Shiga toxin A Subunit effector polypeptide ("Shiga toxin effector polypeptide"). The Shiga toxin effector polypeptide components of the CD38-binding proteins may comprise a combination of mutations relative to a wild-type Shiga toxin sequence providing (1) de-immunization and/or (2) a reduction in protease sensitivity; wherein each Shiga toxin effector polypeptide retains one or more Shiga toxin function, such as, e.g., stimulating cellular internalization, directing intracellular routing, catalytic activity, and/or potent cytotoxicity. The CD38-binding proteins may have one or multiple uses, e.g., the selective killing of a specific CD38-expressing cell-type; and more generally, for the diagnosis and treatment of cancers and disorders involving CD38-expressing cells, e.g., in CD38-positive hematopoietic cancers such as multiple myeloma.

Figure 1A:
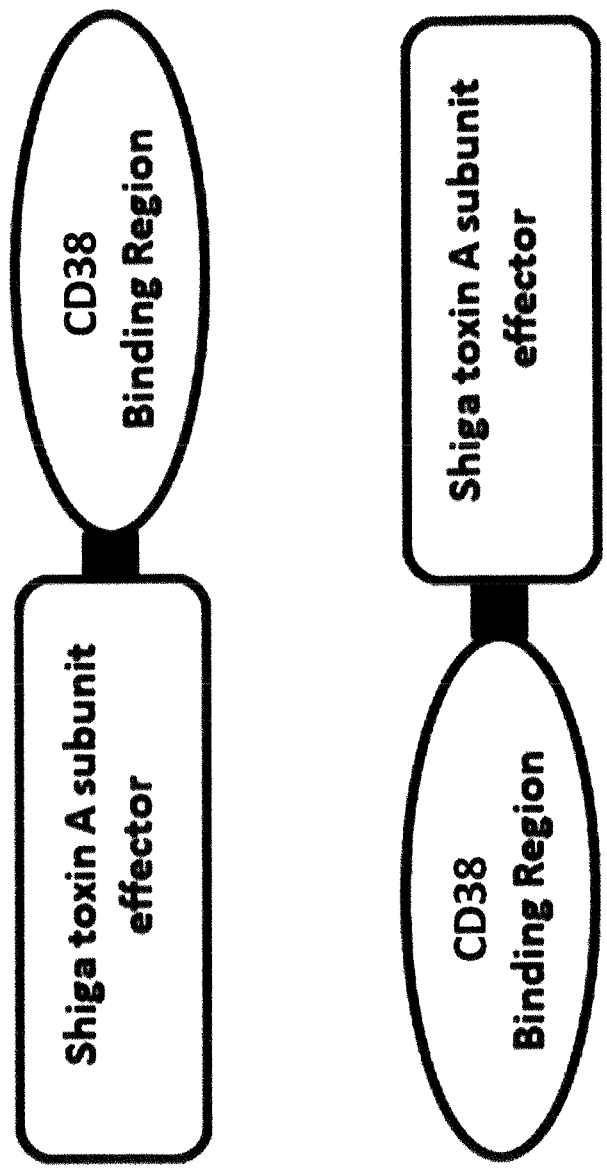

18 Claims, 39 Drawing Sheets
Specification includes a Sequence Listing.

(56) References Cited

OTHER PUBLICATIONS

Bagga, S. et al., "The Cytotoxic Activity of Ribosome-inactivating Protein Saporin-6 Is Attributed to Its rRNA N-Glycosidase and Internucleosomal DNA Fragmentation Activities," The Journal of Biological Chemistry, 278(7):4813-4820 (2003).
Barbieri, L. et al., "Some ribosome-inactivating proteins depurinate ribosomal RNA at multiple sites," Biochem. J., 286:1-4 (1992).
Barbieri, L. et al., "Unexpected activity of saporins," Nature, 372:624 (1994).
Barbieri, L. et al., "Polynucleotide:adenosine glycosidase activity of saporin-L1: effect on DNA, RNA and poly(A)," Biochem. J., 319:507-513 (1996).
Barbieri, L. et al., "Polynucleotide: adenosine glycosidase activity of ribosome-inactivating proteins: effect on DNA, RNA and poly(A)," Nucleic Acids Research, 25(3):518-522 (1997).
Barbieri, L. et al., "Polynucleotide: adenosine glycosidase activity of saporin-L1: effect on various forms of mammalian DNA," Biochimica et Biophysica Acta, 1480:258-266 (2000).
Barbieri, L. et al., "Polynucleotide: Adenosine Glycosidase Is the Sole Activity of Ribosome-Inactivating Proteins on DNA," J. Biochem, 128:883-889 (2000).
Bielaszewska, M. et al., "Shiga Toxin Gene Loss and Transfer In Vitro and In Vivo during Enterohemorrhagic *Escherichia coli* O26 Infection in Humans," Applied and Environmental Microbiology, 73(10):3144-3150 (2007).
Boes, A. et al., "Affinity Purification of a Framework 1 Engineered Mouse/Human Chimeric IgA2 Antibody from Tobacco," Biotechnology Bioengineering, 108(12):2804-2814 (2011).
Bowie, J. U. et al., "Deciphering the Message in Protein Sequences: Tolerance to Amino Acid Substitutions," Science, 247:1306-1310 (1990).
Bresnahan, P. A. et al., "Human fur Gene Encodes a Yeast KEX2-like Endoprotease That Cleaves Pro-ß-NGF In Vivo," The Journal of Cell Biology, 111(No. 6, Pt. 2):2851-2859 (1990).
Brigotti, M. et al., "Shiga toxin 1: damage to DNA in vitro," Toxicon, 39:341-348 (2001).
Brigotti, M. et al., "Damage to nuclear DNA induced by Shiga toxin 1 and ricin in human endothelial cells," The FASEB Journal, 16:365-372 (2002).
Brigotti, M. et al., "The RNA-N-Glycosidase Activity of Shiga-like Toxin 1: Kinetic Parameters of the Native and Activated Toxin," Toxicon, 35(9):1431-1437 (1997).
Burgess, B. J. et al., "Proteolytic cleavage at arginine residues within the hydrophilic disulphide loop of the *Escherichia coli* Shiga-like toxin I A subunit is not essential for cytotoxicity," Molecular Microbiology, 10(1):171-179 (1993).
CD38 recombinant monoclonal antibody, clone HB7 mAb Datasheet, Abnova, http://www.abnova.com/products/products_detail.asp, 1 page.
Cao, C. et al., "Construction of Mutant Genes for a Non-Toxic Verotoxin 2 Variant (VT2vp1 of *Escherichia coli* and Characterization of Purified Mutant Toxins," Microbiol. Immunol., 38(6):441-447 (1994).
Cheung, M. C. et al., "An evolved ribo-in activating protein targets and kills human melanoma cells in vitro and in vivo," Molecular Cancer, 9(28):1-14 (2010).
Deresiewicz, R. L. et al., "Mutations Affecting the Activity of the Shiga-like Toxin I A-Chain," Biochemistry, 31(12):3272-3280 (1992).
Deresiewicz, R. L. et al., "The role of tyrosine-114 in the enzymatic activity of the Shiga-like toxin I A-chain," Mol. Gen. Genet., 241:467-473 (1993).
Déret, S. et al., "SUBIM: a program for analysing the Kabat database and determining the variability subgroup of a new immunoglobulin sequence," CABIOS, 11(4):435-439 (1995).
Di, R. et al., "Identification of amino acids critical for the cytotoxicity of Shiga toxin 1 and 2 in *Saccharomyces cerevisiae*," Toxicon, 57(4):525-539 (2011).
Duda, A. et al., "Prototype Foamy Virus Envelope Glycoprotein Leader Peptide Processing Is Mediated by a Furin-Like Cellular Protease, but Cleavage Is Not Essential for Viral Infectivity," Journal of Virology, 78(24):13865-13870 (2004).
Erice, A. et al., "Anti-Human Immunodeficiency Virus Type 1 Activity of an Anti-CD4 Immunoconjugate Containing Pokeweed Antiviral Protein," Antimicrobial Agents and Chemotherapy, 37(4):835-838 (1993).
Engedal, N. et al., "Shiga toxin and its use in targeted cancer therapy and imaging," Microbial Biotechnology, 4(1):32-46 (2011).
Grotiuz, G. et al., "Shiga Toxin-2 Producing Acinetobacter haemolyticus Associated with a Case of Bloody Diarrhea," Journal of Clinical Microbiology, 44(10):3838-3841 (2006).
Haddad, J. E. et al., "Minimum Domain of the Shiga Toxin A subunit Required for Enzymatic Activity," Journal of Bacteriology, 175(16):4970-4978 (1993).
Hatsuzawa, K. et al., "Structure and Expression of Mouse Furin, a Yeast Kex2-related Protease," The Journal of Biological Chemistry, 265(36):22075-22078 (1990).
Head, S. C. et al., "Preparation of VT1 and VT2 Hybrid Toxins from Their Purified Dissociated Subunits," The Journal of Biological Chemistry, 266(6):3617-3621 (1991).
Henrich, S. et al., "The crystal structure of the proprotein processing proteinase furin explains its stringent specificity," Nature Structural Biology, 10(7):520-526 (2003).
Hovde, C. J. et al., "Evidence that glutamic acid 167 is an active-site residue of Shiga-like toxin-I," Proceedings of the National Academy of Sciences of the United States of America, 85(8):2568-2572 (1988).
Johannes, L. & Römer, W., "Shiga Toxins—from cell biology to biomedical applications," Nature Reviews Microbiology, 8:105-116 (2010).
Lakhrif, Z. et al., "A method to confer protein L binding ability to any antibody fragment," MAbs, 8(2):379-388 (2016).
Lapointe, P. et al., "A Role for the Protease-sensitive Loop Region of Shiga-like Toxin 1 in the Retrotranslocation of its A Domain from the Endoplasmic Reticulum Lumen," Journal of Biological Chemistry, 280(24):23310-23318 (2005).
Lea, N. et al., "Proteolytic cleavage of the A subunit is essential for maximal cytotoxicity of *Escherichia coli* O157:h7 Shiga-like toxin-1," Microbiology, 145(5):999-1004 (1999).
Lim, S. I. et al., "Site-specific albumination of a therapeutic protein with multi-subunit to prolong activity in vivo," Journal of Controlled Release, 207:93-100 (2015).
Ling, J. et al., "Cleavage of supercoiled double-stranded DNA by several ribosome-inactivating proteins in vitro," FEBS Letters, 345:143-146 (1994).
McCluskey et al., "Charged and hydrophobic Surfaces on the A chain of Shiga-like Toxin 1 recognize the C-terminal Domain of Ribosomal Stalk Proteins," PLoS One 7(2):e31191 (2012).
Molloy, S. S. et al., "Human Furin Is a Calcium-dependent Serine Endoprotease That Recognizes the Sequence Arg-X-X-Arg and Efficiently Cleaves Anthrax Toxin Protective Antigen," The Journal of Biological Chemistry, 267(23):16396-16402 (1992).
Muzard, J. et al., "Grafting of protein L-binding activity onto recombinant antibody fragments," Analytical Biochemistry, 388:331-338 (2009).
Nilson, B. H. K. et al., "Protein L from *Peptostreptococcus magnus* Binds to the κ Light Chain Variable Domain," The Journal of Biological Chemistry, 267(4):2234-2239 (1992).
Nilson, B. H. K. et al., "Purification of antibodies using protein L-binding framework structures in the light chain variable domain," Journal of Immunological Methods, 164:33-40 (1993).
O'brien, A. D. et al., "Shiga Toxin: Biochemistry, Genetics, Mode of Action, and Role in Pathogenesis," Current Topics in Microbiology and Immunology, 180:65-94 (1992).
Ohmura, M. et al., "Characterization of non-toxic mutant toxins of Vero toxin I that were constructed by replacing amino acids in the A subunit," Microbial Pathogenesis, 15(3):169-176 (1993).
Parikh, B. A. & Tumer, N. E., "Antiviral Activity Of Ribosome Inactivating Proteins In Medicine," Mini-Reviews in Medicinal Chemistry, 4:523-543 (2004).
Picard, D. et al., "Pokeweed Antiviral Protein Inhibits Brome Mosaic Virus Replication in Plant Cells," The Journal of Biological Chemistry, 280(20):20069-20075 (2005).

(56) References Cited

OTHER PUBLICATIONS

Press Release Molecular Templates' Presentations at the American Association of Cancer Research (AACR) Annual Meeting 2019 Highlight Evolution of ETB Platform, Apr. 2, 2019, 3 pages.
Press Release New Data on Molecular Templates' Engineered Toxin Bodies to be Presented at the American Association of Cancer Research (AACR) Annual Meeting 2019, Feb. 27, 2019, 4 pages.
Press Release Molecular Templates Announces Presentations Featuring Engineered Toxin Bodies at the 2017 American Association for Cancer Research (AACR) Annual Meeting, Mar. 30, 2017, 2 pages.
Press Release Molecular Templates Presents Preclinical Data on De-Immunized Engineered Toxin Bodies (ETB) with Novel Immuno-Oncology Capabilities (AACR) Annual Meeting, Apr. 16, 2015, 2 pages.
Press Release Molecular Templates Announces FDA Acceptance of IND Application for TAK-169, An Engineered Toxin Body Targeting CD38, Austin, Texas, Jun. 17, 2019, 2 pages.
Press Release Molecular Templates Announces $15.2 Million Award from the Cancer Prevention and Research Institute of Texas, Austin, Texas, Nov. 18, 2016, 1 page.
Press Release Molecular Templates Announces Agreement with Takeda for the Joint Development of a Protein-Based Oncology Therapy, Austin, Texas, Sep. 19, 2018, 3 pages.
Press Release Molecular Templates Announces FDA Acceptance of IND Application for MT-5111, An Engineered Toxin Body Targeting HER2, Austin Texas, Apr. 22, 2019, 2 pages.
Rajagopalan, S. et al., "Next-generation engineered toxin bodies: CD38, PD-L1 and HER2 targeted ETBs," American Association for Cancer Research (AACR) Annual Meeting, 2016, Abstract #595 (Apr. 16-20, 2016).
Roncuzzi, L. & Gasperi-Campani, A., "DNA-nuclease activity of the single-chain ribosome-inactivating proteins dianthin 30, saporin 6 and gelonin," FEBS Letters, 392:16-20 (1996).
Schalken, J. A. et al., "fur Gene Expression as a Discriminating Marker for Small Cell and Nonsmall Cell Lung Carcinomas," J. Clin. Invest., 80:1545-1549 (1987).
Schechter, I. & Berger, A., "On the Active Site of Proteases. III. Mapping the Active Site of Papain; Specific Peptide Inhibitors of Papain," Biochemical and Biophysical Research Communications, 32(5):898-902 (1968).
Scheutz, F. et al., "Multicenter Evaluation of a Sequence-Based Protocol for Subtyping Shiga Toxins and Standardizing Stx Nomenclature," Journal of Clinical Microbiology, 50(9):2951-2963 (2012).
Sharma, N. et al., "Isolation and Characterization of an RIP (Ribosome-Inactivating Protein)-Like Protein from Tobacco with Dual Enzymatic Activity," Plant Physiology, 134:171-181 (2004).
Stirpe, F. et al., "Activities associated with the presence of ribosome-inactivating proteins increase in senescent and stressed levels," FEBS Letters, 382:309-312 (1996).
Strauch, E. et al., "Characterization of a Shiga Toxin-Encoding Temperate Bacteriophage of Shigella sonnei," Infection and Immunity, 69(12):7588-7595 (2001).
Suhan, M. L. et al., "Disruption of an Internal Membrane-Spanning Region in Shiga Toxin I Reduces Cytotoxicity," Infection and Immunity, 66(11):5252-5259 (1998).
Tesh, V. L. et al., "Comparison of the Relative Toxicities of Shiga-Like Toxins Type 1 and Type II for Mice," Infection and Immunity, 61(8):3392-3402 (1993).
Tian, S., "A 20 Residues Motif Delineates the Furin Cleavage Site and its Physical Properties May Influence Viral Fusion," Biochemistry Insights, 2:9-20 (2009).
Tian, S. et al., "Computational prediction of furin cleavage sites by a hybrid method and understanding mechanism underlying diseases," Scientific Reports, 2:261 (2012), 7 pages; doi:10.1038/srep00261/.
Tian, S. et al., "FurinDB: A Database of 20-Residue Furin Cleavage Site Motifs, Substrates and Their Associated Drugs," Int. J. Mol. Sci., 12:1060-1065 (2011).
Wels, W. et al., "Selective Inhibition of Tumor Cell Growth by a Recombinant Single-Chain Antibody-Toxin Specific for the erbB-2 Receptor," Cancer Research, 52:6310-6317 (1992).
Von Minckwitz, G. et al., "Phase I clinical study of the recombinant antibody toxin scFv(FRP5)-ETA specific for the ErbB2/HER2 receptor in patients with advanced solid malignomas," Breast Cancer Research, 7(5):R617-R626 (2005).
Wang, P. & Tumer, N. E., "Pokeweed antiviral protein cleaves double-stranded supercoiled DNA using the same active site required to depurinate rRNA," Nucleic Acids Research, 27(8):1900-1905 (1999).
Wise, R. J. et al., "Expression of a human proprotein processing enzyme: Correct cleavage of the von Willebrand factor precursor at a paired basic amino acid site," Proc. Natl. Acad. Sci., 87:9378-9382 (1990).
Zhang, C. et al., "Site-Specific PEGylation of Therapeutic Proteins via Optimization of Both Accessible Reactive Amino Acid Residues and PEG Derivatives," Biodrugs, 26(4):209-215 (2012).
Zhao, Y. J. et al., "Cytosolic CD38 Protein Forms Intact Disulfides and Is Active in Elevating Intracellular Cyclic ADP-ribose," The Journal of Biological Chemistry, 286(25):22170-22177 (2011).
Zhaxybayeva, O. & Doolittle, W. F. "Lateral gene transfer," Current Biology, 21(7):R242-R246 (2011).
U.S. Appl. No. 17/810,377, filed Jul. 1, 2022, Elias et al.

* cited by examiner

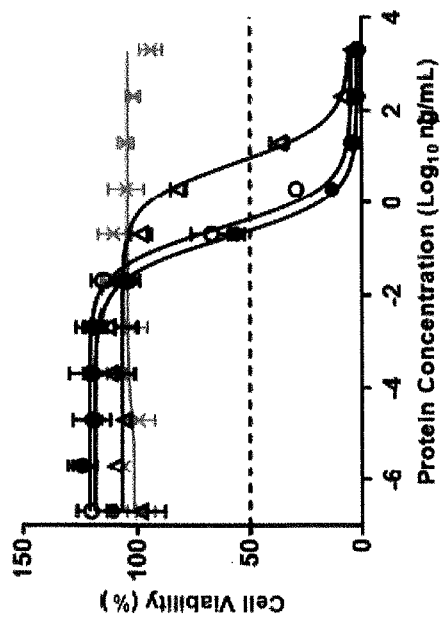
FIG 3A
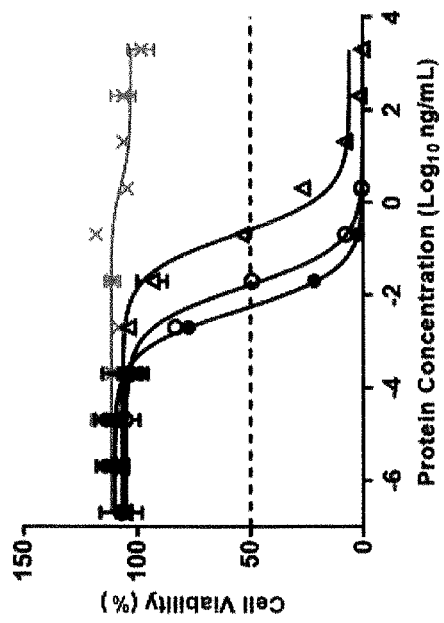
FIG 3B
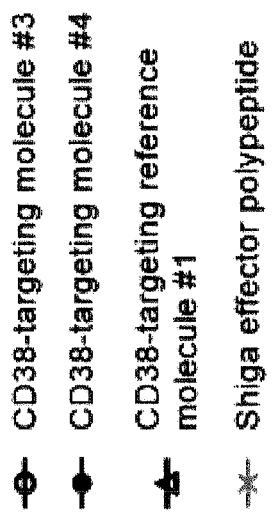
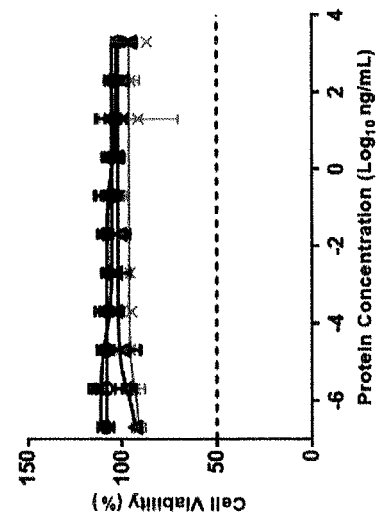
FIG 3C

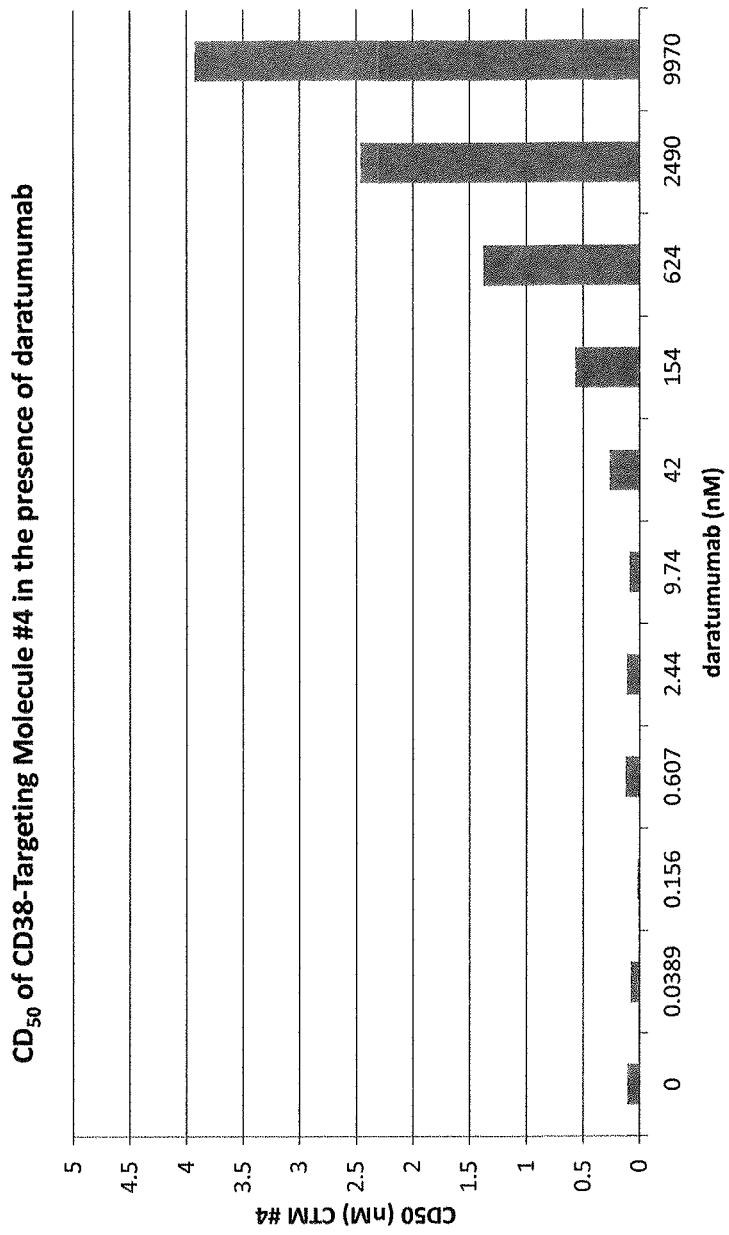

Figure 11A:
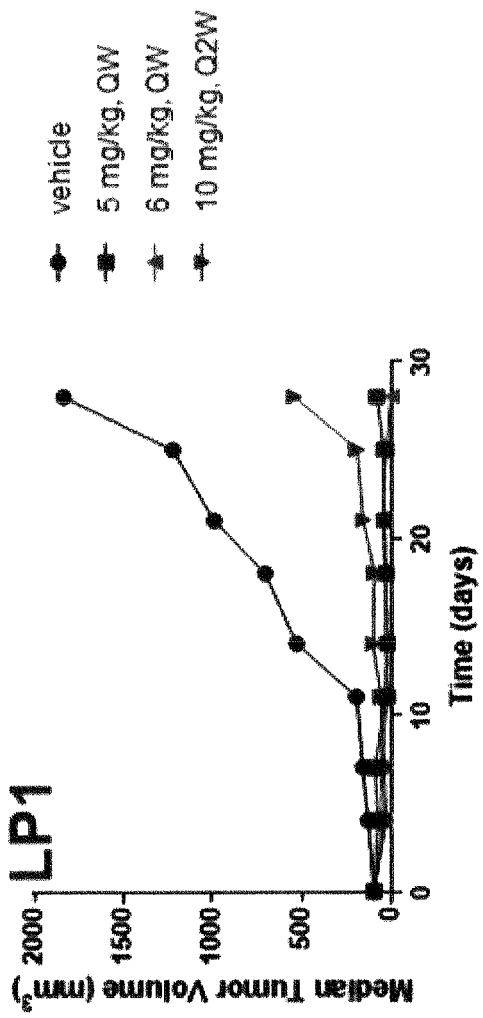
Figure 11B:
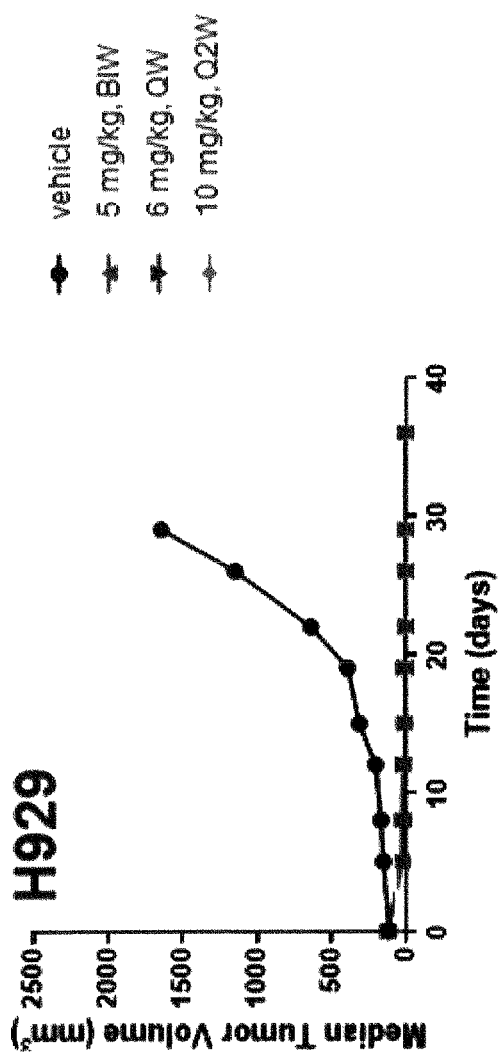

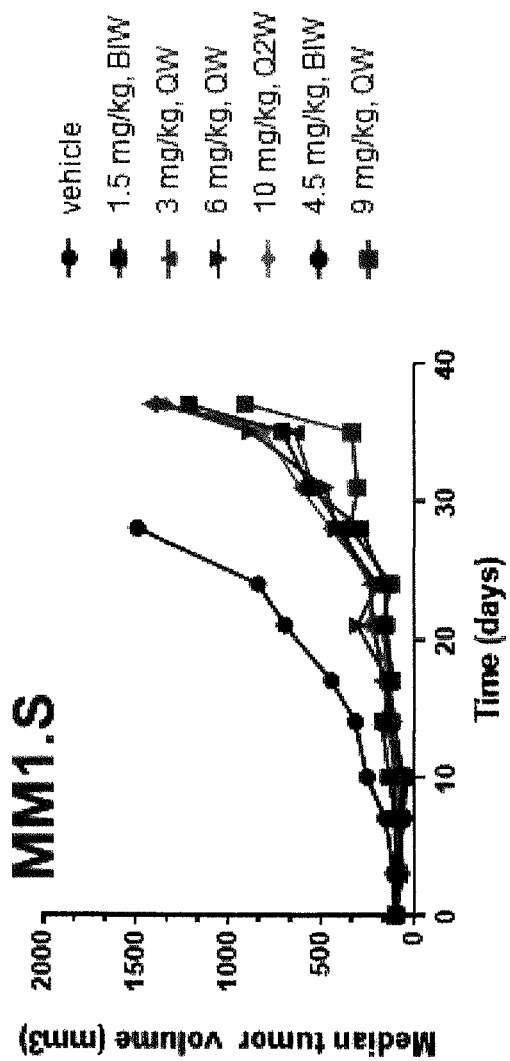
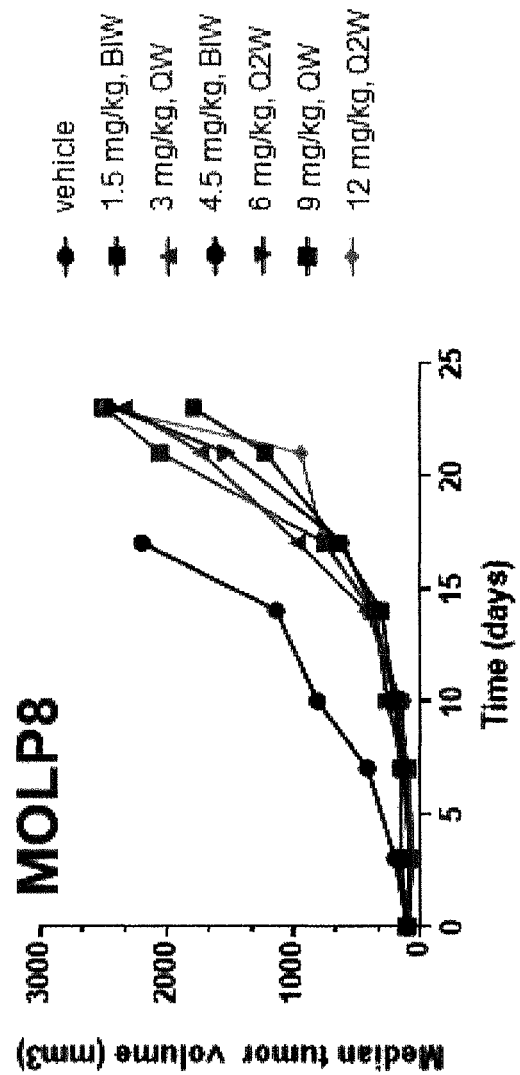
FIG 11C
FIG 11D

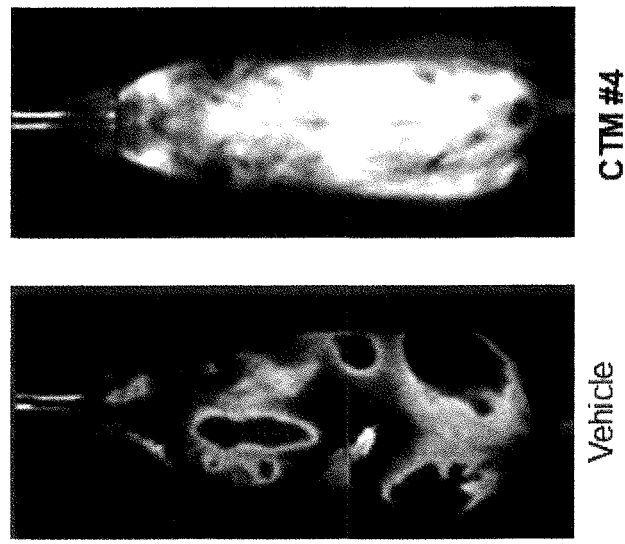
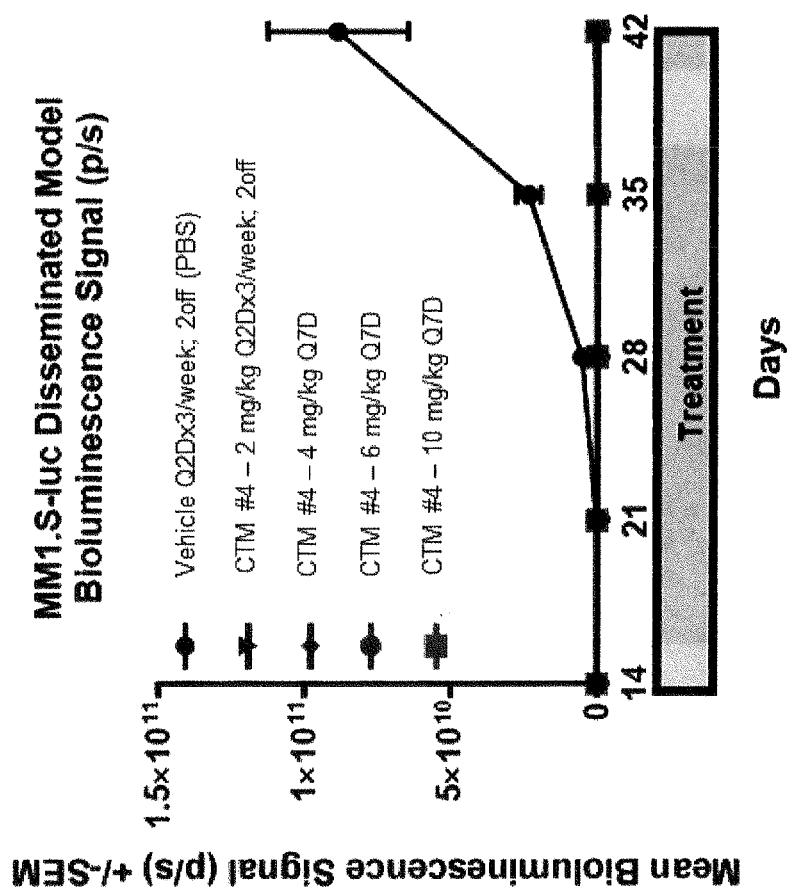
FIG 12A
FIG 12B

Phase I First-In-Human Study of CTM#4 Monotherapy

PRIMARY OBJECTIVES

Part 1
- To evaluate the safety and tolerability of CTM#4 monotherapy in patients with RRMM, and establish the maximum tolerated dose/recommended phase 2 dose

Part 2
- To provide a preliminary evaluation of the clinical activity of CTM#4 monotherapy in patients with RRMM

SECONDARY OBJECTIVES

Part 1
- To characterize pharmacokinetics of CTM#4 in patients
- To conduct a preliminary evaluation of the anti-MM-tumor activity of CTM #4 monotherapy in patients with RRMM
- To assess the immunogenicity of CTM#4 by evaluating the immunogenicity status (anti-drug antibody incidence) in patient serum

Part 2
- To further evaluate safety at the maximum tolerated dose/recommended phase 2 dose
- To further evaluate the clinical efficacy (e.g., duration of response and time to event), pharmacokinetics, and immunogenicity of CTM#4

FIG 22A

Phase I First-In-Human Study of CTM#4 Monotherapy

EXPLORATORY OBJECTIVES

Part 1 & Part 2
- To characterize pharmacodynamic profile of CTM#4 in blood and bone marrow
- To determine the impact of CTM#4 on depth of response by assessing frequency of minimal residual disease negativity in blood and marrow at complete response, and monitoring changes in circulating cell free DNA during treatment and at relapse
- To evaluate overall response rate and progression free survival in patients with high-risk cytogenetics (del17, t(4;14), t(14;16), and/or amp1q)
- To evaluate the impact of patient baseline immune system and microbiome makeup on CTM#4 efficacy and safety
- To explore the impact of CTM#4 on the immune system (including cytokines and chemokines) during treatment and at relapse and correlation with efficacy and safety
- To evaluate the relationship of baseline molecular characteristics of MM tumor (such as protein and mRNA expression) with the efficacy and safety of CTM#4

FIG 22B

| Binding | CD38-targeting reference molecule #1 | CD38TM2 fusion protein | CD38TM1 fusion protein | CD38TM3 fusion protein |
|---|---|---|---|---|
| Dara | 4% | 50% | 53% | 5% |
| HB-7 | 0% | 103% | 93% | 3% |
| AT13-5 | 2% | 103% | 87% | 6% |
| OKT-10 | 65% | 109% | 112% | 120% |
| CD38 TM2 (scFv) | 41% | 3% | 3% | 14% |
| CD38 TM1 (scFv) | 40% | 2% | 3% | 28% |
| CD38 TM3 (scFv) | 6% | 9% | 9% | 16% |

| 10% |
| 50% |
| 100% |

| What | sequence | SEQ ID NO: |
|---|---|---|
| VH domain | EVQLLESGGGLVQPGGSLRLSCAASGFTFSDYYMSWVRQAPGKGLEWVSAISGSGGSTYYADSVKGRFTISRDNSKNTLYLQMNSLRAEDTAVYYCAREHSNYFYGMDVWGQGTLVTVSS | 109 |
| vhCDR1 | GFTFSDYY | 110 |
| vhCDR2 | ISGSGGST | 111 |
| vhCDR3 | AREHSNYFYGMDV | 112 |
| VL domain | QSVLTQPPSASGTPGQRVTISCSGSSSNIGSNYVYWYQQLPGTAPKLLIYGNSNRPSGVPDRFSGSKSGTSASLAISGLRSEDEADYYCQSYDSSLSGSGVFGGGTKLTVL | 113 |
| vlCDR1 | SSNIGSNY | 114 |
| vlCDR2 | GNS | 115 |
| vlCDR3 | QSYDSSLSGSG | 116 |

FIG 25A

| What | sequence | SEQ ID NO: |
|---|---|---|
| VH domain | EVQLLESGGGLVQPGGSLRLSCAASGFTFSSYWMHWVRQAPGKGLEWVSAISGSGGGTFYADSVKGRFTISRDNSKNTLYLQMNSLRAEDTAVYYCAREGETSFGLDVWGQGTLVTVSS | 117 |
| vhCDR1 | GFTFSSYW | 118 |
| vhCDR2 | ISGSGGGT | 119 |
| vhCDR3 | AREGETSFGLDV | 120 |
| VL domain | QSVLTQPPSASGTPGQRVTISCSGSSSNIGGNYVYWYQQLPGTAPKLLIYRNNQRPSGVPDRFSGSKSGTSASLAISGLRSEDEADYYCQSYDSSLSVSVFGGGTKLTVLG | 121 |
| vlCDR1 | SSNIGGNY | 122 |
| vlCDR2 | RNN | 123 |
| vlCDR3 | QSYDSSLSVS | 124 |

FIG 25B

| What | sequence | SEQ ID NO: |
|---|---|---|
| VH domain | QVQLVQSGAEVKKPGESLKISCKGSGYSFTSYWIGWVRQMPGKGLEWMGII YPGDSDTRYSPSFQGQVTISADKSISTAYLQWSSLKASDTAMYYCARGPSTGF WSGNYFDYWGQGTLVTVSS | 101 |
| vhCDR1 | GYSFTSYW | 102 |
| vhCDR2 | IYPGDSDT | 103 |
| vhCDR3 | ARGPSTGFWSGNYFDY | 104 |
| VL domain | QTVVTQEPSLTVSPGETVTLTCASSTGAVTSGFYPNWFQQKPGQAPRALIYAT NNKYSWTPARFSGSLLGDKAALTLSRVQPEDEADYYCLVYYDGAWVFGGGTK LTVLG | 105 |
| vlCDR1 | TGAVTSGFY | 106 |
| vlCDR2 | ATN | 107 |
| vlCDR3 | LVYYDGAW | 108 |

FIG 25C

| What | sequence | SEQ ID NO: |
|---|---|---|
| VH domain | QVQLVQSGAEVKKPGESLKISCKGSGYSFTSYWIGWVRQMPGKGLEWM GIIYPGDSDTRYSPSFQGQVTISADKSISTAYLQWSSLKASDTAMYYCARGP STGFWSGNYFDYWGQGTLVTVSS | 101 |
| vhCDR1 | GYSFTSYW | 102 |
| vhCDR2 | IYPGDSDT | 103 |
| vhCDR3 | ARGPSTGFWSGNYFDY | 104 |
| VL domain | DIQMTQSPSSLSASVGDRVTITCASSTGAVTSGFYPNWFQQKPGQAPRAL IYATNNKYSWTPARFSGSLLGDKAALTLSRVQPEDEADYYCLVYYDGAWVF GGGTKLTVLG | 125 |
| vlCDR1 | TGAVTSGFY | 106 |
| vlCDR2 | ATN | 107 |
| vlCDR3 | LVYYDGAW | 108 |

FIG 25D

SEQUENCE LISTING

<160> NUMBER OF SEQ ID NOS: 233

<210> SEQ ID NO 1
<211> LENGTH: 293
<212> TYPE: PRT
<213> ORGANISM: Artificial Sequence
<220> FEATURE:
<223> OTHER INFORMATION: Shiga-like toxin 1 Subunit A (SLT-1A)

<400> SEQUENCE: 1

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg Met Ala Ser Asp Glu
                245                 250                 255

Phe Pro Ser Met Cys Pro Ala Asp Gly Arg Val Arg Gly Ile Thr His
            260                 265                 270

Asn Lys Ile Leu Trp Asp Ser Thr Leu Gly Ala Ile Leu Met Arg
        275                 280                 285

Arg Thr Ile Ser Ser
    290

<210> SEQ ID NO 2
<211> LENGTH: 293
<212> TYPE: PRT
<213> ORGANISM: Artificial Sequence
<220> FEATURE:
<223> OTHER INFORMATION: Shiga toxin Subunit A (StxA)

<400> SEQUENCE: 2

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Thr Gly Asp Asn
        35                  40                  45

```
Leu Phe Ala Val Asp Val Arg Gly Ile Asp Pro Glu Glu Gly Arg Phe
 50                  55                  60

Asn Asn Leu Arg Leu Ile Val Glu Arg Asn Asn Leu Tyr Val Thr Gly
 65                  70                  75                  80

Phe Val Asn Arg Thr Asn Asn Val Phe Tyr Arg Phe Ala Asp Phe Ser
                 85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg Met Ala Ser Asp Glu
                245                 250                 255

Phe Pro Ser Met Cys Pro Ala Asp Gly Arg Val Arg Gly Ile Thr His
            260                 265                 270

Asn Lys Ile Leu Trp Asp Ser Thr Leu Gly Ala Ile Leu Met Arg
        275                 280                 285

Arg Thr Ile Ser Ser
    290

<210> SEQ ID NO 3
<211> LENGTH: 297
<212> TYPE: PRT
<213> ORGANISM: Artificial Sequence
<220> FEATURE:
<223> OTHER INFORMATION: Shiga-like toxin 2 Subunit A (SLT-2A)

<400> SEQUENCE: 3

Asp Glu Phe Thr Val Asp Phe Ser Ser Gln Lys Ser Tyr Val Asp Ser
 1               5                  10                  15

Leu Asn Ser Ile Arg Ser Ala Ile Ser Thr Pro Leu Gly Asn Ile Ser
                 20                  25                  30

Gln Gly Gly Val Ser Val Ser Val Ile Asn His Val Leu Gly Gly Asn
             35                  40                  45

Tyr Ile Ser Leu Asn Val Arg Gly Leu Asp Pro Tyr Ser Glu Arg Phe
 50                  55                  60

Asn His Leu Arg Leu Ile Met Glu Arg Asn Asn Leu Tyr Val Ala Gly
 65                  70                  75                  80

Phe Ile Asn Thr Glu Thr Asn Ile Phe Tyr Arg Phe Ser Asp Phe Ser
                 85                  90                  95

His Ile Ser Val Pro Asp Val Ile Thr Val Ser Met Thr Thr Asp Ser
            100                 105                 110
```

-continued

Ser Tyr Ser Ser Leu Gln Arg Ile Ala Asp Leu Glu Arg Thr Gly Met
        115                 120                 125

Gln Ile Gly Arg His Ser Leu Val Gly Ser Tyr Leu Asp Leu Met Glu
    130                 135                 140

Phe Arg Gly Arg Ser Met Thr Arg Ala Ser Ser Arg Ala Met Leu Arg
145                 150                 155                 160

Phe Val Thr Val Ile Ala Glu Ala Leu Arg Phe Arg Gln Ile Gln Arg
                165                 170                 175

Gly Phe Arg Pro Ala Leu Ser Glu Ala Ser Pro Leu Tyr Thr Met Thr
            180                 185                 190

Ala Gln Asp Val Asp Leu Thr Leu Asn Trp Gly Arg Ile Ser Asn Val
        195                 200                 205

Leu Pro Glu Tyr Arg Gly Glu Glu Gly Val Arg Ile Gly Arg Ile Ser
    210                 215                 220

Phe Asn Ser Leu Ser Ala Ile Leu Gly Ser Val Ala Val Ile Leu Asn
225                 230                 235                 240

Cys His Ser Thr Gly Ser Tyr Ser Val Arg Ser Val Ser Gln Lys Gln
                245                 250                 255

Lys Thr Glu Cys Gln Ile Val Gly Asp Arg Ala Ala Ile Lys Val Asn
            260                 265                 270

Asn Val Leu Trp Glu Ala Asn Thr Ile Ala Ala Leu Leu Asn Arg Lys
        275                 280                 285

Pro Gln Asp Leu Thr Glu Pro Asn Gln
    290                 295

<210> SEQ ID NO 4
<211> LENGTH: 251
<212> TYPE: PRT
<213> ORGANISM: Artificial Sequence
<220> FEATURE:
<223> OTHER INFORMATION: Shiga toxin subtype c Subunit A (Stx1cA)

<400> SEQUENCE: 4

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Thr Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

```
Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Val Asn Ala Ile Leu Gly Ser Val Ala Leu Ile Leu
225                 230                 235                 240

Asn Cys His His His Ala Ser Arg Val Ala Arg
                245                 250

<210> SEQ ID NO 5
<211> LENGTH: 251
<212> TYPE: PRT
<213> ORGANISM: Artificial Sequence
<220> FEATURE:
<223> OTHER INFORMATION: Shiga toxin subtype d Subunit A (Stx1dA)

<400> SEQUENCE: 5

Lys Glu Phe Thr Leu Asp Phe Ser Thr Ala Lys Lys Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Thr Gly Asp Asn
        35                  40                  45

Leu Phe Ala Val Asp Ile Met Gly Leu Glu Pro Glu Glu Glu Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Arg Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

Tyr Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Ile Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250

<210> SEQ ID NO 6
<211> LENGTH: 251
<212> TYPE: PRT
<213> ORGANISM: Artificial Sequence
<220> FEATURE:
```

<223> OTHER INFORMATION: Shiga toxin subtype e Subunit A (Stx1eA)

<400> SEQUENCE: 6

Gln Asp Phe Thr Val Asp Phe Ser Thr Ala Lys Lys Tyr Val Asp Ser
1               5                   10                  15

Leu Asn Ala Ile Arg Ser Ala Ile Gly Thr Pro Leu His Ser Ile Ser
            20                  25                  30

Ser Gly Gly Thr Ser Leu Leu Met Ile Asp Asn Gly Thr Gly Asp Asn
        35                  40                  45

Leu Phe Ala Val Asp Ile Arg Gly Leu Asp Pro Glu Glu Glu Arg Phe
    50                  55                  60

Asp Asn Leu Arg Leu Ile Ile Glu Arg Asn Asn Leu Tyr Val Thr Gly
65                  70                  75                  80

Phe Val Asn Arg Thr Ser Asn Ile Phe Tyr Arg Phe Ala Asp Phe Ser
                85                  90                  95

His Val Thr Phe Pro Gly Thr Arg Ala Val Thr Leu Ser Gly Asp Ser
            100                 105                 110

Ser Tyr Thr Thr Leu Gln Arg Val Ala Gly Ile Gly Arg Thr Gly Met
        115                 120                 125

Gln Ile Asn Arg His Ser Leu Thr Thr Ser Tyr Leu Asp Leu Met Ser
130                 135                 140

Tyr Ser Gly Ser Ser Leu Thr Gln Pro Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Val Ser Gly His Ser Tyr Thr Met
            180                 185                 190

Thr Val Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Gly Val Asn Ala Ile Leu Gly Ser Val Ala Leu Ile Leu
225                 230                 235                 240

Asn Cys His His His Thr Ser Arg Val Ser Arg
                245                 250

<210> SEQ ID NO 7
<211> LENGTH: 250
<212> TYPE: PRT
<213> ORGANISM: Artificial Sequence
<220> FEATURE:
<223> OTHER INFORMATION: Shiga toxin subtype 2c Subunit A (Stx2cA)
      variant 1

<400> SEQUENCE: 7

Arg Glu Phe Thr Ile Asp Phe Ser Thr Gln Gln Ser Tyr Val Ser Ser
1               5                   10                  15

Leu Asn Ser Ile Arg Thr Glu Ile Ser Thr Pro Leu Glu His Ile Ser
            20                  25                  30

Gln Gly Thr Thr Ser Val Ser Val Ile Asn His Thr Pro Pro Gly Ser
        35                  40                  45

Tyr Phe Ala Val Asp Ile Arg Gly Leu Asp Val Tyr Gln Ala Arg Phe
    50                  55                  60

Asp His Leu Arg Leu Ile Ile Glu Gln Asn Asn Leu Tyr Val Ala Gly
65                  70                  75                  80

Phe Val Asn Thr Ala Thr Asn Thr Phe Tyr Arg Phe Ser Asp Phe Thr

```
                    85                  90                  95
His Ile Ser Val Pro Gly Val Thr Thr Val Ser Met Thr Thr Asp Ser
                100                 105                 110

Ser Tyr Thr Thr Leu Gln Arg Val Ala Ala Leu Glu Arg Ser Gly Met
            115                 120                 125

Gln Ile Ser Arg His Ser Leu Val Ser Ser Tyr Leu Ala Leu Met Glu
    130                 135                 140

Phe Ser Gly Asn Thr Met Thr Arg Asp Ala Ser Arg Ala Val Leu Arg
145                 150                 155                 160

Phe Val Thr Val Thr Ala Glu Ala Leu Arg Phe Arg Gln Ile Gln Arg
                165                 170                 175

Glu Phe Arg Gln Ala Leu Ser Glu Thr Ala Pro Val Tyr Thr Met Thr
            180                 185                 190

Pro Gly Asp Val Asp Leu Thr Leu Asn Trp Gly Arg Ile Ser Asn Val
    195                 200                 205

Leu Pro Glu Tyr Arg Gly Glu Asp Gly Val Arg Val Gly Arg Ile Ser
210                 215                 220

Phe Asn Asn Ile Ser Ala Ile Leu Gly Thr Val Ala Val Ile Leu Asn
225                 230                 235                 240

Cys His His Gln Gly Ala Arg Ser Val Arg
                245                 250

<210> SEQ ID NO 8
<211> LENGTH: 250
<212> TYPE: PRT
<213> ORGANISM: Artificial Sequence
<220> FEATURE:
<223> OTHER INFORMATION: Shiga toxin subtype 2c Subunit A (Stx2cA)
      variant 2

<400> SEQUENCE: 8

Arg Glu Phe Thr Ile Asp Phe Ser Thr Gln Gln Ser Tyr Val Ser Ser
1               5                   10                  15

Leu Asn Ser Ile Arg Thr Glu Ile Ser Thr Pro Leu Glu His Ile Ser
            20                  25                  30

Gln Gly Thr Thr Ser Val Ser Val Ile Asn His Thr Pro Pro Gly Ser
        35                  40                  45

Tyr Phe Ala Val Asp Ile Arg Gly Leu Asp Val Tyr Gln Ala Arg Phe
    50                  55                  60

Asp His Leu Arg Leu Ile Ile Glu Gln Asn Asn Leu Tyr Val Ala Gly
65                  70                  75                  80

Phe Val Asn Thr Ala Thr Asn Thr Phe Tyr Arg Phe Ser Asp Phe Ala
                85                  90                  95

His Ile Ser Val Pro Gly Val Thr Thr Val Ser Met Thr Thr Asp Ser
            100                 105                 110

Ser Tyr Thr Thr Leu Gln Arg Val Ala Ala Leu Glu Arg Ser Gly Met
        115                 120                 125

Gln Ile Ser Arg His Ser Leu Val Ser Ser Tyr Leu Ala Leu Met Glu
    130                 135                 140

Phe Ser Gly Asn Thr Met Thr Arg Asp Ala Ser Arg Ala Val Leu Arg
145                 150                 155                 160

Phe Val Thr Val Thr Ala Glu Ala Leu Arg Phe Arg Gln Ile Gln Arg
                165                 170                 175

Glu Phe Arg Gln Ala Leu Ser Glu Thr Ala Pro Val Tyr Thr Met Thr
            180                 185                 190
```

```
Pro Gly Asp Val Asp Leu Thr Leu Asn Trp Gly Arg Ile Ser Asn Val
        195                 200                 205

Leu Pro Glu Tyr Arg Gly Glu Asp Gly Val Arg Val Gly Arg Ile Ser
    210                 215                 220

Phe Asn Asn Ile Ser Ala Ile Leu Gly Thr Val Ala Val Ile Leu Asn
225                 230                 235                 240

Cys His His Gln Gly Ala Arg Ser Val Arg
                245                 250

<210> SEQ ID NO 9
<211> LENGTH: 250
<212> TYPE: PRT
<213> ORGANISM: Artificial Sequence
<220> FEATURE:
<223> OTHER INFORMATION: Shiga toxin subtype 2c Subunit A (Stx2cA)
      variant 3

<400> SEQUENCE: 9

Arg Glu Phe Thr Ile Asp Phe Ser Thr Gln Gln Ser Tyr Val Ser Ser
1               5                   10                  15

Leu Asn Ser Ile Arg Thr Glu Ile Ser Thr Pro Leu Glu His Ile Ser
            20                  25                  30

Gln Gly Thr Thr Ser Val Ser Val Ile Asn His Thr Pro Pro Gly Ser
        35                  40                  45

Tyr Phe Ala Val Asp Ile Arg Gly Leu Asp Ile Tyr Gln Ala Arg Phe
    50                  55                  60

Asp His Leu Arg Leu Ile Ile Glu Gln Asn Asn Leu Tyr Val Ala Gly
65                  70                  75                  80

Phe Val Asn Thr Ala Thr Asn Thr Phe Tyr Arg Phe Ser Asp Phe Thr
                85                  90                  95

His Ile Ser Val Pro Gly Val Thr Thr Val Ser Met Thr Thr Asp Ser
            100                 105                 110

Ser Tyr Thr Thr Leu Gln Arg Val Ala Ala Leu Glu Arg Ser Gly Met
        115                 120                 125

Gln Ile Ser Arg His Ser Leu Val Ser Ser Tyr Leu Ala Leu Met Glu
    130                 135                 140

Phe Ser Gly Asn Thr Met Thr Arg Asp Ala Ser Arg Ala Val Leu Arg
145                 150                 155                 160

Phe Val Thr Val Thr Ala Glu Ala Leu Arg Phe Arg Gln Ile Gln Arg
                165                 170                 175

Glu Phe Arg Gln Ala Leu Ser Glu Thr Ala Pro Val Tyr Thr Met Thr
            180                 185                 190

Pro Gly Asp Val Asp Leu Thr Leu Asn Trp Gly Arg Ile Ser Asn Val
        195                 200                 205

Leu Pro Glu Tyr Arg Gly Glu Asp Gly Val Arg Val Gly Arg Ile Ser
    210                 215                 220

Phe Asn Asn Ile Ser Ala Ile Leu Gly Thr Val Ala Val Ile Leu Asn
225                 230                 235                 240

Cys His His Gln Gly Ala Arg Ser Val Arg
                245                 250

<210> SEQ ID NO 10
<211> LENGTH: 250
<212> TYPE: PRT
<213> ORGANISM: Artificial Sequence
<220> FEATURE:
<223> OTHER INFORMATION: Shiga toxin subtype 2c Subunit A (Stx2cA)
      variant 4
```

<400> SEQUENCE: 10

```
Arg Glu Phe Thr Ile Asp Phe Ser Thr Gln Gln Ser Tyr Val Ser Ser
1               5                   10                  15

Leu Asn Ser Ile Arg Thr Glu Ile Ser Thr Pro Leu Glu His Ile Ser
            20                  25                  30

Gln Gly Thr Thr Ser Val Ser Val Ile Asn His Thr Pro Pro Gly Ser
        35                  40                  45

Tyr Phe Ala Val Asp Ile Arg Gly Leu Asp Val Tyr Gln Ala Arg Phe
    50                  55                  60

Asp His Leu Arg Leu Ile Ile Glu Gln Asn Asn Leu Tyr Val Ala Gly
65                  70                  75                  80

Phe Val Asn Thr Ala Thr Asn Thr Phe Tyr Arg Phe Ser Asp Phe Thr
                85                  90                  95

His Ile Ser Val Pro Ser Val Thr Val Ser Met Thr Thr Asp Ser
            100                 105                 110

Ser Tyr Thr Thr Leu Gln Arg Val Ala Ala Leu Glu Arg Ser Gly Met
            115                 120                 125

Gln Ile Ser Arg His Ser Leu Val Ser Ser Tyr Leu Ala Leu Met Glu
130                 135                 140

Phe Ser Gly Asn Thr Met Thr Arg Asp Ala Ser Arg Ala Val Leu Arg
145                 150                 155                 160

Phe Val Thr Val Thr Ala Glu Ala Leu Arg Phe Arg Gln Ile Gln Arg
                165                 170                 175

Glu Phe Arg Gln Ala Leu Ser Glu Thr Ala Pro Val Tyr Thr Met Thr
            180                 185                 190

Pro Gly Asp Val Asp Leu Thr Leu Asn Trp Gly Arg Ile Ser Asn Val
            195                 200                 205

Leu Pro Glu Tyr Arg Gly Glu Asp Gly Val Arg Val Gly Arg Ile Ser
        210                 215                 220

Phe Asn Asn Ile Ser Ala Ile Leu Gly Thr Val Ala Val Ile Leu Asn
225                 230                 235                 240

Cys His His Gln Gly Ala Arg Ser Val Arg
                245                 250
```

<210> SEQ ID NO 11
<211> LENGTH: 250
<212> TYPE: PRT
<213> ORGANISM: Artificial Sequence
<220> FEATURE:
<223> OTHER INFORMATION: Shiga toxin subtype 2c Subunit A (Stx2cA) variant 5

<400> SEQUENCE: 11

```
Arg Glu Phe Thr Ile Asp Phe Ser Thr Gln Gln Ser Tyr Val Ser Ser
1               5                   10                  15

Leu Asn Ser Ile Arg Thr Glu Ile Ser Thr Pro Leu Glu His Ile Ser
            20                  25                  30

Gln Gly Thr Thr Ser Val Ser Val Ile Asn His Thr Pro Pro Gly Ser
        35                  40                  45

Tyr Phe Ala Val Asp Ile Arg Gly Leu Asp Val Tyr Gln Ala Arg Phe
    50                  55                  60

Asp His Leu Arg Leu Ile Ile Glu Gln Asn Asn Leu Tyr Met Ala Gly
65                  70                  75                  80

Phe Val Asn Thr Ala Thr Asn Thr Phe Tyr Arg Phe Ser Asp Phe Thr
                85                  90                  95
```

```
His Ile Ser Val Pro Ser Val Thr Thr Val Ser Met Thr Thr Asp Ser
                100                 105                 110

Ser Tyr Thr Thr Leu Gln Arg Val Ala Ala Leu Glu Arg Ser Gly Met
            115                 120                 125

Gln Ile Ser Arg His Ser Leu Val Ser Ser Tyr Leu Ala Leu Met Glu
        130                 135                 140

Phe Ser Gly Asn Thr Met Thr Arg Asp Ala Ser Arg Ala Val Leu Arg
145                 150                 155                 160

Phe Val Thr Val Thr Ala Glu Ala Leu Arg Phe Arg Gln Ile Gln Arg
                165                 170                 175

Glu Phe Arg Gln Ala Leu Ser Glu Thr Ala Pro Val Tyr Thr Met Thr
            180                 185                 190

Pro Gly Asp Val Asp Leu Thr Leu Asn Trp Gly Arg Ile Ser Asn Val
        195                 200                 205

Leu Pro Glu Tyr Arg Gly Glu Asp Gly Val Arg Val Gly Arg Ile Ser
210                 215                 220

Phe Asn Asn Ile Ser Ala Ile Leu Gly Thr Val Ala Val Ile Leu Asn
225                 230                 235                 240

Cys His His Gln Gly Ala Arg Ser Val Arg
                245                 250

<210> SEQ ID NO 12
<211> LENGTH: 250
<212> TYPE: PRT
<213> ORGANISM: Artificial Sequence
<220> FEATURE:
<223> OTHER INFORMATION: Shiga toxin subtype 2c Subunit A (Stx2cA)
      variant 6

<400> SEQUENCE: 12

Arg Glu Phe Thr Ile Asp Phe Ser Thr Gln Gln Ser Tyr Val Ser Ser
1               5                   10                  15

Leu Asn Ser Ile Arg Thr Glu Ile Ser Thr Pro Leu Glu His Ile Ser
            20                  25                  30

Gln Gly Thr Thr Ser Val Ser Val Ile Asn His Thr Pro Pro Gly Ser
        35                  40                  45

Tyr Phe Ala Val Asp Ile Arg Gly Leu Asp Val Tyr Gln Ala Arg Phe
    50                  55                  60

Asp His Leu Arg Leu Ile Ile Glu Gln Asn Asn Leu Tyr Val Ala Gly
65                  70                  75                  80

Phe Val Asn Thr Ala Thr Asn Thr Phe Tyr Arg Phe Ser Asp Phe Thr
                85                  90                  95

His Ile Ser Val Pro Gly Val Thr Thr Val Ser Met Thr Thr Asp Ser
                100                 105                 110

Ser Tyr Thr Thr Leu Gln Arg Val Ala Ala Leu Glu Arg Ser Gly Met
            115                 120                 125

Gln Ile Ser Arg His Ser Leu Val Ser Ser Tyr Leu Ala Leu Met Glu
        130                 135                 140

Phe Ser Gly Asn Thr Met Thr Arg Asp Ala Ser Arg Ala Val Leu Arg
145                 150                 155                 160

Phe Val Thr Val Thr Ala Glu Ala Leu Arg Phe Arg Gln Ile Gln Arg
                165                 170                 175

Glu Phe Arg Gln Val Leu Ser Glu Thr Ala Pro Val Tyr Thr Met Thr
            180                 185                 190

Pro Gly Asp Val Asp Leu Thr Leu Asn Trp Gly Arg Ile Ser Asn Val
```

```
                195                 200                 205
Leu Pro Glu Tyr Arg Gly Glu Asp Gly Val Arg Val Gly Arg Ile Ser
210                 215                 220

Phe Asn Asn Ile Ser Ala Ile Leu Ser Thr Val Ala Val Ile Leu Asn
225                 230                 235                 240

Cys His His Gln Gly Ala Arg Ser Val Arg
                245                 250

<210> SEQ ID NO 13
<211> LENGTH: 250
<212> TYPE: PRT
<213> ORGANISM: Artificial Sequence
<220> FEATURE:
<223> OTHER INFORMATION: Shiga toxin subtype 2d Subunit A (Stx2dA)
      variant 1

<400> SEQUENCE: 13

Arg Glu Phe Thr Ile Asp Phe Ser Thr Gln Gln Ser Tyr Val Ser Ser
1               5                   10                  15

Leu Asn Ser Ile Arg Thr Glu Ile Ser Thr Pro Leu Glu His Ile Ser
                20                  25                  30

Gln Gly Thr Thr Ser Val Ser Val Ile Asn His Thr Pro Pro Gly Ser
            35                  40                  45

Tyr Phe Ala Val Asp Ile Arg Gly Leu Asp Val Tyr Gln Ala Arg Phe
    50                  55                  60

Asp His Leu Arg Leu Ile Ile Glu Gln Asn Asn Leu Tyr Val Ala Gly
65                  70                  75                  80

Phe Val Asn Thr Ala Thr Asn Thr Phe Tyr Arg Phe Ser Asp Phe Ala
                85                  90                  95

His Ile Ser Val Pro Gly Val Thr Thr Val Ser Met Thr Thr Asp Ser
            100                 105                 110

Ser Tyr Thr Thr Leu Gln Arg Val Ala Ala Leu Glu Arg Ser Gly Met
    115                 120                 125

Gln Ile Ser Arg His Ser Leu Val Ser Ser Tyr Leu Ala Leu Met Glu
130                 135                 140

Phe Ser Gly Asn Thr Met Thr Arg Asp Ala Ser Arg Ala Val Leu Arg
145                 150                 155                 160

Phe Val Thr Val Thr Ala Glu Ala Leu Arg Phe Arg Gln Ile Gln Arg
                165                 170                 175

Glu Phe Arg Gln Ala Leu Ser Glu Thr Ala Pro Val Tyr Thr Met Thr
            180                 185                 190

Pro Gly Asp Val Asp Leu Thr Leu Asn Trp Gly Arg Ile Ser Asn Val
    195                 200                 205

Ile Pro Glu Tyr Arg Gly Glu Asp Gly Val Arg Val Gly Arg Ile Ser
210                 215                 220

Phe Asn Asn Ile Ser Ala Ile Leu Gly Thr Val Ala Val Ile Leu Asn
225                 230                 235                 240

Cys His His Gln Gly Ala Arg Ser Val Arg
                245                 250

<210> SEQ ID NO 14
<211> LENGTH: 250
<212> TYPE: PRT
<213> ORGANISM: Artificial Sequence
<220> FEATURE:
<223> OTHER INFORMATION: Shiga toxin subtype 2d Subunit A (Stx2dA)
      variant 2
```

```
<400> SEQUENCE: 14

Arg Glu Phe Met Ile Asp Phe Ser Thr Gln Gln Ser Tyr Val Ser Ser
1               5                   10                  15

Leu Asn Ser Ile Arg Thr Glu Ile Ser Thr Pro Leu Glu His Ile Ser
            20                  25                  30

Gln Gly Thr Thr Ser Val Ser Val Ile Asn His Thr Pro Pro Gly Ser
        35                  40                  45

Tyr Phe Ala Val Asp Ile Arg Gly Leu Asp Val Tyr Gln Ala Arg Phe
    50                  55                  60

Asp His Leu Arg Leu Ile Ile Glu Gln Asn Asn Leu Tyr Val Ala Gly
65                  70                  75                  80

Phe Val Asn Thr Ala Thr Asn Thr Phe Tyr Arg Phe Ser Asp Phe Thr
                85                  90                  95

His Ile Ser Val Pro Gly Val Thr Val Ser Met Thr Thr Asp Ser
            100                 105                 110

Ser Tyr Thr Thr Leu Gln Arg Val Ala Ala Leu Glu Arg Ser Gly Met
            115                 120                 125

Gln Ile Ser Arg His Ser Leu Val Ser Ser Tyr Leu Ala Leu Met Glu
    130                 135                 140

Phe Ser Gly Asn Thr Met Thr Arg Asp Ala Ser Arg Ala Val Leu Arg
145                 150                 155                 160

Phe Val Thr Val Thr Ala Glu Ala Leu Arg Phe Arg Gln Ile Gln Arg
                165                 170                 175

Glu Phe Arg Gln Ala Leu Ser Glu Thr Ala Pro Val Tyr Thr Met Thr
            180                 185                 190

Pro Glu Glu Val Asp Leu Thr Leu Asn Trp Gly Arg Ile Ser Asn Val
        195                 200                 205

Leu Pro Glu Phe Arg Gly Glu Gly Val Arg Val Gly Arg Ile Ser
    210                 215                 220

Phe Asn Asn Ile Ser Ala Ile Leu Gly Thr Val Ala Val Ile Leu Asn
225                 230                 235                 240

Cys His His Gln Gly Ala Arg Ser Val Arg
                245                 250

<210> SEQ ID NO 15
<211> LENGTH: 250
<212> TYPE: PRT
<213> ORGANISM: Artificial Sequence
<220> FEATURE:
<223> OTHER INFORMATION: Shiga toxin subtype 2d Subunit A (Stx2dA)
      variant 3

<400> SEQUENCE: 15

Arg Glu Phe Thr Ile Asp Phe Ser Thr Gln Gln Ser Tyr Val Ser Ser
1               5                   10                  15

Leu Asn Ser Ile Arg Thr Glu Ile Ser Thr Pro Leu Glu His Ile Ser
            20                  25                  30

Gln Gly Thr Thr Ser Val Ser Val Ile Asn His Thr Pro Pro Gly Ser
        35                  40                  45

Tyr Phe Ala Val Asp Ile Arg Gly Leu Asp Val Tyr Gln Ala Arg Phe
    50                  55                  60

Asp His Leu Arg Leu Ile Ile Glu Gln Asn Asn Leu Tyr Val Ala Gly
65                  70                  75                  80

Phe Val Asn Thr Ala Thr Asn Thr Phe Tyr Arg Phe Ser Asp Phe Thr
                85                  90                  95
```

```
His Ile Ser Val Pro Gly Val Thr Thr Val Ser Met Thr Thr Asp Ser
            100                 105                 110

Ser Tyr Thr Thr Leu Gln Arg Val Ala Ala Leu Glu Arg Ser Gly Met
        115                 120                 125

Gln Ile Ser Arg His Ser Leu Val Ser Ser Tyr Leu Ala Leu Met Glu
    130                 135                 140

Phe Ser Gly Asn Thr Met Thr Arg Asp Ala Ser Arg Ala Val Leu Arg
145                 150                 155                 160

Phe Val Thr Val Thr Ala Glu Ala Leu Arg Phe Arg Gln Ile Gln Arg
                165                 170                 175

Glu Phe Arg Gln Ala Leu Ser Glu Thr Ala Pro Val Tyr Thr Met Thr
            180                 185                 190

Pro Gly Asp Val Asp Leu Thr Leu Asn Trp Gly Arg Ile Ser Asn Val
        195                 200                 205

Ile Pro Glu Tyr Arg Gly Glu Asp Gly Val Arg Val Gly Arg Ile Ser
    210                 215                 220

Phe Asn Asn Ile Ser Ala Ile Leu Ser Thr Val Ala Val Ile Leu Asn
225                 230                 235                 240

Cys His His Gln Gly Ala Arg Ser Val Arg
                245                 250

<210> SEQ ID NO 16
<211> LENGTH: 250
<212> TYPE: PRT
<213> ORGANISM: Artificial Sequence
<220> FEATURE:
<223> OTHER INFORMATION: Shiga toxin subtype 2e Subunit A (Stx2eA)
      variant 1

<400> SEQUENCE: 16

Gln Glu Phe Thr Ile Asp Phe Ser Thr Gln Gln Ser Tyr Val Ser Ser
1               5                   10                  15

Leu Asn Ser Ile Arg Thr Ala Ile Ser Thr Pro Leu Glu His Ile Ser
            20                  25                  30

Gln Gly Ala Thr Ser Val Ser Val Ile Asn His Thr Pro Pro Gly Ser
        35                  40                  45

Tyr Ile Ser Val Gly Ile Arg Gly Leu Asp Val Tyr Gln Glu Arg Phe
    50                  55                  60

Asp His Leu Arg Leu Ile Ile Glu Arg Asn Asn Leu Tyr Val Ala Gly
65                  70                  75                  80

Phe Val Asn Thr Thr Thr Asn Thr Phe Tyr Arg Phe Ser Asp Phe Ala
                85                  90                  95

His Ile Ser Leu Pro Gly Val Thr Thr Ile Ser Met Thr Thr Asp Ser
            100                 105                 110

Ser Tyr Thr Thr Leu Gln Arg Val Ala Ala Leu Glu Arg Ser Gly Met
        115                 120                 125

Gln Ile Ser Arg His Ser Leu Val Ser Ser Tyr Leu Ala Leu Met Glu
    130                 135                 140

Phe Ser Gly Asn Thr Met Thr Arg Asp Ala Ser Arg Ala Val Leu Arg
145                 150                 155                 160

Phe Val Thr Val Thr Ala Glu Ala Leu Arg Phe Arg Gln Ile Gln Arg
                165                 170                 175

Glu Phe Arg Leu Ala Leu Ser Glu Thr Ala Pro Val Tyr Thr Met Thr
            180                 185                 190

Pro Glu Asp Val Asp Leu Thr Leu Asn Trp Gly Arg Ile Ser Asn Val
        195                 200                 205
```

Leu Pro Glu Tyr Arg Gly Glu Ala Gly Val Arg Val Gly Arg Ile Ser
            210                 215                 220

Phe Asn Asn Ile Ser Ala Ile Leu Gly Thr Val Ala Val Ile Leu Asn
225                 230                 235                 240

Cys His His Gln Gly Ala Arg Ser Val Arg
                245                 250

<210> SEQ ID NO 17
<211> LENGTH: 250
<212> TYPE: PRT
<213> ORGANISM: Artificial Sequence
<220> FEATURE:
<223> OTHER INFORMATION: Shiga toxin subtype 2e Subunit A (Stx2eA)
      variant 2

<400> SEQUENCE: 17

Gln Glu Phe Thr Ile Asp Phe Ser Thr Gln Gln Ser Tyr Val Ser Ser
1               5                   10                  15

Leu Asn Ser Ile Arg Thr Ala Ile Ser Thr Pro Leu Glu His Ile Ser
            20                  25                  30

Gln Gly Ala Thr Ser Val Ser Val Ile Asn His Thr Pro Pro Gly Ser
        35                  40                  45

Tyr Ile Ser Val Gly Ile Arg Gly Leu Asp Val Tyr Gln Ala His Phe
    50                  55                  60

Asp His Leu Arg Leu Ile Ile Glu Gln Asn Asn Leu Tyr Val Ala Gly
65                  70                  75                  80

Phe Val Asn Thr Ala Thr Asn Thr Phe Tyr Arg Phe Ser Asp Phe Ala
                85                  90                  95

His Ile Ser Leu Pro Gly Val Thr Thr Ile Ser Met Thr Thr Asp Ser
            100                 105                 110

Ser Tyr Thr Thr Leu Gln Arg Val Ala Ala Leu Glu Arg Ser Gly Met
        115                 120                 125

Gln Ile Ser Arg His Ser Leu Val Ser Ser Tyr Leu Ala Leu Met Glu
    130                 135                 140

Phe Ser Gly Asn Thr Met Thr Arg Glu Ala Ser Arg Ala Val Leu Arg
145                 150                 155                 160

Phe Val Thr Val Thr Ala Glu Ala Leu Arg Phe Arg Gln Ile Gln Arg
                165                 170                 175

Glu Phe Arg Gln Ala Leu Ser Glu Thr Ala Pro Val Tyr Thr Met Thr
            180                 185                 190

Pro Glu Asp Val Asp Leu Thr Leu Asn Trp Gly Arg Ile Ser Asn Val
        195                 200                 205

Leu Pro Glu Tyr Arg Gly Glu Asp Gly Val Arg Val Gly Arg Ile Ser
    210                 215                 220

Phe Asn Asn Ile Ser Ala Ile Leu Gly Thr Val Ala Val Ile Leu Asn
225                 230                 235                 240

Cys His His Gln Gly Ala Arg Ser Val Arg
                245                 250

<210> SEQ ID NO 18
<211> LENGTH: 250
<212> TYPE: PRT
<213> ORGANISM: Artificial Sequence
<220> FEATURE:
<223> OTHER INFORMATION: Shiga toxin subtype 2f Subunit A (Stx2fA)

<400> SEQUENCE: 18

```
Asp Glu Phe Thr Val Asp Phe Ser Ser Gln Lys Ser Tyr Val Asp Ser
1               5                   10                  15

Leu Asn Ser Ile Arg Ser Ala Ile Ser Thr Pro Leu Gly Asn Ile Ser
            20                  25                  30

Gln Gly Gly Val Ser Val Ser Val Ile Asn His Val Pro Gly Gly Asn
        35                  40                  45

Tyr Ile Ser Leu Asn Val Arg Gly Leu Asp Pro Tyr Ser Glu Arg Phe
    50                  55                  60

Asn His Leu Arg Leu Ile Met Glu Arg Asn Asn Leu Tyr Val Ala Gly
65                  70                  75                  80

Phe Ile Asn Thr Glu Thr Asn Thr Phe Tyr Arg Phe Ser Asp Phe Ser
                85                  90                  95

His Ile Ser Val Pro Asp Val Ile Thr Val Ser Met Thr Thr Asp Ser
                100                 105                 110

Ser Tyr Ser Ser Leu Gln Arg Ile Ala Asp Leu Glu Arg Thr Gly Met
                115                 120                 125

Gln Ile Gly Arg His Ser Leu Val Gly Ser Tyr Leu Asp Leu Met Glu
        130                 135                 140

Phe Arg Gly Arg Ser Met Thr Arg Ala Ser Ser Arg Ala Met Leu Arg
145                 150                 155                 160

Phe Val Thr Val Ile Ala Glu Ala Leu Arg Phe Arg Gln Ile Gln Arg
                165                 170                 175

Gly Phe Arg Pro Ala Leu Ser Glu Ala Ser Pro Leu Tyr Thr Met Thr
                180                 185                 190

Ala Gln Asp Val Asp Leu Thr Leu Asn Trp Gly Arg Ile Ser Asn Val
            195                 200                 205

Leu Pro Glu Tyr Arg Gly Glu Glu Val Arg Ile Gly Arg Ile Ser
    210                 215                 220

Phe Asn Ser Leu Ser Ala Ile Leu Gly Ser Val Ala Val Ile Leu Asn
225                 230                 235                 240

Cys His Ser Thr Gly Ser Tyr Ser Val Arg
                245                 250

<210> SEQ ID NO 19
<211> LENGTH: 8
<212> TYPE: PRT
<213> ORGANISM: Mus musculus

<400> SEQUENCE: 19

Ser Ser Asn Ile Gly Ser Asn Tyr
1               5

<210> SEQ ID NO 20
<211> LENGTH: 3
<212> TYPE: PRT
<213> ORGANISM: Mus musculus

<400> SEQUENCE: 20

Gly Asn Ser
1

<210> SEQ ID NO 21
<211> LENGTH: 11
<212> TYPE: PRT
<213> ORGANISM: Mus musculus

<400> SEQUENCE: 21

Gln Ser Tyr Asp Ser Ser Leu Ser Gly Ser Gly
```

<210> SEQ ID NO 22
<211> LENGTH: 8
<212> TYPE: PRT
<213> ORGANISM: Mus musculus

<400> SEQUENCE: 22

Gly Phe Thr Phe Ser Asp Tyr Tyr
1               5

<210> SEQ ID NO 23
<211> LENGTH: 8
<212> TYPE: PRT
<213> ORGANISM: Mus musculus

<400> SEQUENCE: 23

Ile Ser Gly Ser Gly Gly Ser Thr
1               5

<210> SEQ ID NO 24
<211> LENGTH: 13
<212> TYPE: PRT
<213> ORGANISM: Mus musculus

<400> SEQUENCE: 24

Ala Arg Glu His Ser Asn Tyr Phe Tyr Gly Met Asp Val
1               5                   10

<210> SEQ ID NO 25
<211> LENGTH: 8
<212> TYPE: PRT
<213> ORGANISM: Mus musculus

<400> SEQUENCE: 25

Ser Ser Asn Ile Gly Gly Asn Tyr
1               5

<210> SEQ ID NO 26
<211> LENGTH: 3
<212> TYPE: PRT
<213> ORGANISM: Mus musculus

<400> SEQUENCE: 26

Arg Asn Asn
1

<210> SEQ ID NO 27
<211> LENGTH: 10
<212> TYPE: PRT
<213> ORGANISM: Mus musculus

<400> SEQUENCE: 27

Gln Ser Tyr Asp Ser Ser Leu Ser Val Ser
1               5                   10

<210> SEQ ID NO 28
<211> LENGTH: 8
<212> TYPE: PRT
<213> ORGANISM: Mus musculus

<400> SEQUENCE: 28

Gly Phe Thr Phe Ser Ser Tyr Trp
1               5

```
<210> SEQ ID NO 29
<211> LENGTH: 8
<212> TYPE: PRT
<213> ORGANISM: Mus musculus

<400> SEQUENCE: 29

Ile Ser Gly Ser Gly Gly Gly Thr
1               5

<210> SEQ ID NO 30
<211> LENGTH: 12
<212> TYPE: PRT
<213> ORGANISM: Mus musculus

<400> SEQUENCE: 30

Ala Arg Glu Gly Glu Thr Ser Phe Gly Leu Asp Val
1               5                   10

<210> SEQ ID NO 31
<211> LENGTH: 9
<212> TYPE: PRT
<213> ORGANISM: Mus musculus

<400> SEQUENCE: 31

Thr Gly Ala Val Thr Ser Gly Phe Tyr
1               5

<210> SEQ ID NO 32
<211> LENGTH: 3
<212> TYPE: PRT
<213> ORGANISM: Mus musculus

<400> SEQUENCE: 32

Ala Thr Asn
1

<210> SEQ ID NO 33
<211> LENGTH: 8
<212> TYPE: PRT
<213> ORGANISM: Mus musculus

<400> SEQUENCE: 33

Leu Val Tyr Tyr Asp Gly Ala Trp
1               5

<210> SEQ ID NO 34
<211> LENGTH: 8
<212> TYPE: PRT
<213> ORGANISM: Mus musculus

<400> SEQUENCE: 34

Gly Tyr Ser Phe Thr Ser Tyr Trp
1               5

<210> SEQ ID NO 35
<211> LENGTH: 8
<212> TYPE: PRT
<213> ORGANISM: Mus musculus

<400> SEQUENCE: 35

Ile Tyr Pro Gly Asp Ser Asp Thr
1               5

<210> SEQ ID NO 36
```

```
<211> LENGTH: 16
<212> TYPE: PRT
<213> ORGANISM: Mus musculus

<400> SEQUENCE: 36

Ala Arg Gly Pro Ser Thr Gly Phe Trp Ser Gly Asn Tyr Phe Asp Tyr
1               5                   10                  15

<210> SEQ ID NO 37
<211> LENGTH: 112
<212> TYPE: PRT
<213> ORGANISM: Artificial Sequence
<220> FEATURE:
<223> OTHER INFORMATION: light chain

<400> SEQUENCE: 37

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Gly Asn Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Tyr Asp Ser Ser Leu
                85                  90                  95

Ser Gly Ser Gly Val Phe Gly Gly Gly Thr Lys Leu Thr Val Leu Gly
            100                 105                 110

<210> SEQ ID NO 38
<211> LENGTH: 120
<212> TYPE: PRT
<213> ORGANISM: Artificial Sequence
<220> FEATURE:
<223> OTHER INFORMATION: heavy chain

<400> SEQUENCE: 38

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu His Ser Asn Tyr Phe Tyr Gly Met Asp Val Trp Gly Gln
            100                 105                 110

Gly Thr Leu Val Thr Val Ser Ser
        115                 120

<210> SEQ ID NO 39
<211> LENGTH: 111
<212> TYPE: PRT
<213> ORGANISM: Artificial Sequence
```

<220> FEATURE:
<223> OTHER INFORMATION: light chain

<400> SEQUENCE: 39

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Gly Asn
            20                  25                  30

Tyr Val Tyr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Tyr Asp Ser Ser Leu
                85                  90                  95

Ser Val Ser Val Phe Gly Gly Gly Thr Lys Leu Thr Val Leu Gly
            100                 105                 110

<210> SEQ ID NO 40
<211> LENGTH: 119
<212> TYPE: PRT
<213> ORGANISM: Artificial Sequence
<220> FEATURE:
<223> OTHER INFORMATION: heavy chain

<400> SEQUENCE: 40

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
        35                  40                  45

Ser Ala Ile Ser Gly Ser Gly Gly Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Glu Thr Ser Phe Gly Leu Asp Val Trp Gly Gln Gly
            100                 105                 110

Thr Leu Val Thr Val Ser Ser
        115

<210> SEQ ID NO 41
<211> LENGTH: 110
<212> TYPE: PRT
<213> ORGANISM: Artificial Sequence
<220> FEATURE:
<223> OTHER INFORMATION: light chain

<400> SEQUENCE: 41

Gln Thr Val Val Thr Gln Glu Pro Ser Leu Thr Val Ser Pro Gly Glu
1               5                   10                  15

Thr Val Thr Leu Thr Cys Ala Ser Ser Thr Gly Ala Val Thr Ser Gly
            20                  25                  30

Phe Tyr Pro Asn Trp Phe Gln Gln Lys Pro Gly Gln Ala Pro Arg Ala
        35                  40                  45

```
Leu Ile Tyr Ala Thr Asn Asn Lys Tyr Ser Trp Thr Pro Ala Arg Phe
 50                  55                  60

Ser Gly Ser Leu Leu Gly Asp Lys Ala Ala Leu Thr Leu Ser Arg Val
 65                  70                  75                  80

Gln Pro Glu Asp Glu Ala Asp Tyr Tyr Cys Leu Val Tyr Tyr Asp Gly
                 85                  90                  95

Ala Trp Val Phe Gly Gly Gly Thr Lys Leu Thr Val Leu Gly
                100                 105                 110

<210> SEQ ID NO 42
<211> LENGTH: 123
<212> TYPE: PRT
<213> ORGANISM: Artificial Sequence
<220> FEATURE:
<223> OTHER INFORMATION: heavy chain

<400> SEQUENCE: 42

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
             35                  40                  45

Gly Ile Ile Tyr Pro Gly Asp Ser Asp Thr Arg Tyr Ser Pro Ser Phe
         50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Gly Pro Ser Thr Gly Phe Trp Ser Gly Asn Tyr Phe Asp Tyr
                100                 105                 110

Trp Gly Gln Gly Thr Leu Val Thr Val Ser Ser
            115                 120

<210> SEQ ID NO 43
<211> LENGTH: 111
<212> TYPE: PRT
<213> ORGANISM: Artificial Sequence
<220> FEATURE:
<223> OTHER INFORMATION: light chain

<400> SEQUENCE: 43

Asp Ile Gln Met Thr Gln Ser Pro Ser Ser Leu Ser Ala Ser Val Gly
 1               5                  10                  15

Asp Arg Val Thr Ile Thr Cys Ala Ser Ser Thr Gly Ala Val Thr Ser
                20                  25                  30

Gly Phe Tyr Pro Asn Trp Phe Gln Lys Pro Gly Gln Ala Pro Arg
             35                  40                  45

Ala Leu Ile Tyr Ala Thr Asn Asn Lys Tyr Ser Trp Thr Pro Ala Arg
         50                  55                  60

Phe Ser Gly Ser Leu Leu Gly Asp Lys Ala Ala Leu Thr Leu Ser Arg
 65                  70                  75                  80

Val Gln Pro Glu Asp Glu Ala Asp Tyr Tyr Cys Leu Val Tyr Tyr Asp
                 85                  90                  95

Gly Ala Trp Val Phe Gly Gly Gly Thr Lys Leu Thr Val Leu Gly
                100                 105                 110

<210> SEQ ID NO 44
```

```
<211> LENGTH: 123
<212> TYPE: PRT
<213> ORGANISM: Artificial Sequence
<220> FEATURE:
<223> OTHER INFORMATION: heavy chain

<400> SEQUENCE: 44

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Pro Ser Thr Gly Phe Trp Ser Gly Asn Tyr Phe Asp Tyr
                100                 105                 110

Trp Gly Gln Gly Thr Leu Val Thr Val Ser Ser
            115                 120

<210> SEQ ID NO 45
<211> LENGTH: 251
<212> TYPE: PRT
<213> ORGANISM: Artificial Sequence
<220> FEATURE:
<223> OTHER INFORMATION: Shiga toxin effector polypeptide SLT-1A-DI

<400> SEQUENCE: 45

Ala Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
                20                  25                  30

Ser Gly Gly Thr Ser Leu Leu Met Ile Asp Ser Gly Ile Gly Asp Asn
            35                  40                  45

Leu Phe Ala Val Asp Ile Leu Gly Phe Asp Thr Leu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Ala Asp Ser
                100                 105                 110

Ser Tyr Thr Thr Leu Gln Arg Val Ala Gly Ile Ser Arg Thr Gly Met
            115                 120                 125

Gln Ile Asn Arg His Ser Leu Thr Thr Ser Tyr Leu Asp Leu Met Ser
    130                 135                 140

His Ser Ala Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
                180                 185                 190

Thr Ala Glu Asp Val Asp Leu Thr Leu Asn Trp Gly Arg Leu Ser Ser
```

```
                195                 200                 205
Val Leu Pro Asp Tyr His Gly Gln Asp Ser Val Arg Val Gly Arg Ile
            210                 215                 220

Ser Phe Gly Ser Ile Asn Ala Ile Leu Gly Ser Val Ala Leu Ile Leu
225                 230                 235                 240

Asn Ser His His His Ala Ser Ala Val Ala Ala
                245                 250

<210> SEQ ID NO 46
<211> LENGTH: 251
<212> TYPE: PRT
<213> ORGANISM: Artificial Sequence
<220> FEATURE:
<223> OTHER INFORMATION: Shiga toxin effector polypeptide SLT-1A-DI-1

<400> SEQUENCE: 46

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ile Gly Asp Asn
        35                  40                  45

Leu Phe Ala Val Asp Ile Leu Gly Phe Asp Phe Thr Leu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Ala Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Ala Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Ser His His His Ala Ser Ala Val Ala Ala
                245                 250

<210> SEQ ID NO 47
<211> LENGTH: 251
<212> TYPE: PRT
<213> ORGANISM: Artificial Sequence
<220> FEATURE:
<223> OTHER INFORMATION: Shiga toxin effector polypeptide SLT-1A-DI-2

<400> SEQUENCE: 47
```

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ile Gly Asp Asn
        35                  40                  45

Leu Phe Ala Val Asp Ile Leu Gly Phe Asp Phe Thr Leu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Ala Asp Ser
                100                 105                 110

Ser Tyr Thr Thr Leu Gln Arg Val Ala Gly Ile Ser Arg Thr Gly Met
            115                 120                 125

Gln Ile Asn Arg His Ser Leu Thr Thr Ser Tyr Leu Ala Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Ala Ser Tyr Val Met
                180                 185                 190

Thr Ala Glu Asp Val Asp Leu Thr Leu Asn Trp Gly Arg Leu Ser Ser
            195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Ser His His His Ala Ser Ala Val Ala Ala
                245                 250

<210> SEQ ID NO 48
<211> LENGTH: 251
<212> TYPE: PRT
<213> ORGANISM: Artificial Sequence
<220> FEATURE:
<223> OTHER INFORMATION: Shiga toxin effector polypeptide SLT-1A-DI-3

<400> SEQUENCE: 48

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ile Gly Asp Asn
        35                  40                  45

Leu Phe Ala Val Asp Ile Leu Gly Phe Asp Phe Thr Leu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Ala Phe Tyr Arg Phe Ala Asp Phe Ser
                85                  90                  95

His Val Thr Phe Pro Gly Thr Thr Ala Val Thr Leu Ser Ala Asp Ser
                100                 105                 110

Ser Tyr Thr Thr Leu Gln Arg Val Ala Gly Ile Ser Arg Thr Gly Met
          115                 120                 125

Gln Ile Asn Arg His Ser Leu Thr Thr Ser Tyr Leu Ala Leu Met Ser
    130                 135                 140

His Ser Gly Thr Ser Leu Thr Gln Ser Ala Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Ala Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Ser His His His Ala Ser Ala Val Ala Ala
                245                 250

<210> SEQ ID NO 49
<211> LENGTH: 251
<212> TYPE: PRT
<213> ORGANISM: Artificial Sequence
<220> FEATURE:
<223> OTHER INFORMATION: Shiga toxin effector polypeptide SLT-1A-DI-4

<400> SEQUENCE: 49

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

```
Ser Phe Gly Ser Ile Asn Ala Ile Leu Gly Ser Val Ala Leu Ile Leu
225                 230                 235                 240

Asn Cys His His His Ala Ser Ala Val Ala Ala
            245                 250

<210> SEQ ID NO 50
<211> LENGTH: 251
<212> TYPE: PRT
<213> ORGANISM: Artificial Sequence
<220> FEATURE:
<223> OTHER INFORMATION: Shiga toxin effector polypeptide SLT-1A-DI
      inactive

<400> SEQUENCE: 50

Ala Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ile Gly Asp Asn
        35                  40                  45

Leu Phe Ala Val Asp Ile Leu Gly Phe Asp Thr Leu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Ala Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Ala Thr Ser Leu Thr Gln Ser Val Ala Arg Ala Met Leu Arg
145                 150                 155                 160

Phe Val Thr Val Thr Ala Asp Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Ser His His His Ala Ser Ala Val Ala Ala
                245                 250

<210> SEQ ID NO 51
<211> LENGTH: 251
<212> TYPE: PRT
<213> ORGANISM: Artificial Sequence
<220> FEATURE:
<223> OTHER INFORMATION: Shiga toxin effector polypeptide SLT-1A-DI-1
      inactive

<400> SEQUENCE: 51

Lys Glu Phe Thr Leu Asp Phe Ser Thr Ala Lys Thr Tyr Val Asp Ser
1               5                   10                  15
```

```
Leu Asn Val Ile Arg Ser Ala Ile Gly Thr Pro Leu Gln Thr Ile Ser
             20                  25                  30

Ser Gly Gly Thr Ser Leu Leu Met Ile Asp Ser Gly Ile Gly Asp Asn
         35                  40                  45

Leu Phe Ala Val Asp Ile Leu Gly Phe Asp Phe Thr Leu Gly Arg Phe
     50                  55                  60

Asn Asn Leu Arg Leu Ile Val Glu Arg Asn Asn Leu Tyr Val Thr Gly
 65                  70                  75                  80

Phe Val Asn Arg Thr Asn Asn Val Phe Tyr Arg Phe Ala Asp Phe Ser
                 85                  90                  95

His Val Thr Phe Pro Gly Thr Thr Ala Val Thr Leu Ser Ala Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser

Gln Ile Asn Arg His Ser Leu Thr Thr Ser Tyr Leu Ala Leu Met Ser
            130                 135                 140

His Ser Gly Thr Ser Leu Thr Gln Ser Val Ala Arg Ala Met Leu Arg
145                 150                 155                 160

Phe Val Thr Val Thr Ala Asp Ala Leu Arg Phe Arg Gln Ile Gln Arg
                165                 170                 175

Gly Phe Arg Thr Thr Leu Asp Asp Leu Ser Gly Ala Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Ser His His His Ala Ser Ala Val Ala Ala
                245                 250

<210> SEQ ID NO 53
<211> LENGTH: 251
<212> TYPE: PRT
<213> ORGANISM: Artificial Sequence
<220> FEATURE:
<223> OTHER INFORMATION: Shiga toxin effector polypeptide SLT-1A-DI-3
      inactive

<400> SEQUENCE: 53

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ile Gly Asp Asn
        35                  40                  45

Leu Phe Ala Val Asp Ile Leu Gly Phe Asp Phe Thr Leu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Ala Phe Tyr Arg Phe Ala Asp Phe Ser
                85                  90                  95

His Val Thr Phe Pro Gly Thr Thr Ala Val Thr Leu Ser Ala Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Ala Leu Met Ser
            130                 135                 140

His Ser Gly Thr Ser Leu Thr Gln Ser Ala Ala Arg Ala Met Leu Arg
145                 150                 155                 160

Phe Val Thr Val Thr Ala Asp Ala Leu Arg Phe Arg Gln Ile Gln Arg
                165                 170                 175

Gly Phe Arg Thr Thr Leu Asp Asp Leu Ser Gly Ala Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu

```
225                 230                 235                 240
Asn Ser His His His Ala Ser Ala Val Ala Ala
                245                 250

<210> SEQ ID NO 54
<211> LENGTH: 251
<212> TYPE: PRT
<213> ORGANISM: Artificial Sequence
<220> FEATURE:
<223> OTHER INFORMATION: Shiga toxin effector polypeptide SLT-1A-DI-4

<400> SEQUENCE: 54

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Asp Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Ala Val Ala Ala
                245                 250

<210> SEQ ID NO 55
<211> LENGTH: 251
<212> TYPE: PRT
<213> ORGANISM: Artificial Sequence
<220> FEATURE:
<223> OTHER INFORMATION: SLT-1A-combo variant 1

<400> SEQUENCE: 55

Lys Glu Phe Ile Leu Arg Phe Ser Val Ala His Lys Tyr Val Asp Ser
1               5                   10                  15

Leu Asn Val Ile Arg Ser Ala Ile Gly Thr Pro Leu Gln Thr Ile Ser
            20                  25                  30
```

```
Ser Gly Gly Thr Ser Leu Leu Met Ile Asp Ser Gly Ser Gly Asp Asn
            35                  40                  45

Leu Phe Ala Val Asp Val Arg Gly Ile Asp Pro Glu Glu Gly Arg Phe
 50                  55                  60

Asn Asn Leu Arg Leu Ile Val Glu Arg Asn Asn Leu Tyr Val Thr Gly
 65                  70                  75                  80

Phe Val Asn Arg Thr Asn Asn Val Phe Tyr Arg Phe Ala Asp Phe Ser
                 85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
            115                 120                 125

Gln Ile Asn Arg His Ser Leu Thr Thr Ser Tyr Leu Asp Leu Met Ser
130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
            195                 200                 205

Val Leu Pro Asp Tyr His Gly Gln Asp Ser Val Arg Val Gly Arg Ile
            210                 215                 220

Ser Phe Gly Ser Ile Asn Ala Ile Leu Gly Ser Val Ala Leu Ile Leu
225                 230                 235                 240

Asn Cys His His His Ala Ser Ala Val Ala Ala
                245                 250

<210> SEQ ID NO 56
<211> LENGTH: 251
<212> TYPE: PRT
<213> ORGANISM: Artificial Sequence
<220> FEATURE:
<223> OTHER INFORMATION: SLT-1A-combo variant 2

<400> SEQUENCE: 56

Lys Glu Phe Thr Leu Asp Phe Ser Thr Ala Lys Thr T

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
                180                 185                 190

Thr Ala Glu Asp Val Asp Leu Thr Leu Asn Trp Gly Arg Leu Ser Ser
            195                 200                 205

Val Leu Pro Asp Tyr His Gly Gln Asp Ser Val Arg Val Gly Arg Ile
210                 215                 220

Ser Phe Gly Ser Ile Asn Ala Ile Leu Gly Ser Val Ala Leu Ile Leu
225                 230                 235                 240

Asn Cys His His His Ala Ser Ala Val Ala Ala
                245                 250

<210> SEQ ID NO 57
<211> LENGTH: 251
<212> TYPE: PRT
<213> ORGANISM: Artificial Sequence
<220> FEATURE:
<223> OTHER INFORMATION: SLT-1A-combo variant 3

<400> SEQUENCE: 57

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
                20                  25                  30

Ser Gly Gly Thr Ser Leu Leu Met Ile Asp Ser Asn Leu Val Pro Met
            35                  40                  45

Val Ala Thr Val Asp Val Arg Gly Ile Asp Pro Glu Glu Gly Arg Phe
        50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
                100                 105                 110

Ser Tyr Thr Thr Leu Gln Arg Val Ala Gly Ile Ser Arg Thr Gly Met
            115                 120                 125

Gln Ile Asn Arg His Ser Leu Thr Thr Ser Tyr Leu Asp Leu Met Ser
130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
                180                 185                 190

Thr Ala Glu Asp Val Asp Leu Thr Leu Asn Trp Gly Arg Leu Ser Ser
            195                 200                 205

Val Leu Pro Asp Tyr His Gly Gln Asp Ser Val Arg Val Gly Arg Ile
210                 215                 220

Ser Phe Gly Ser Ile Asn Ala Ile Leu Gly Ser Val Ala Leu Ile Leu
225                 230                 235                 240

Asn Cys His His His Ala Ser Ala Val Ala Ala
                245                 250

```
<210> SEQ ID NO 58
<211> LENGTH: 251
<212> TYPE: PRT
<213> ORGANISM: Artificial Sequence
<220> FEATURE:
<223> OTHER INFORMATION: SLT-1A-combo variant 4

<400> SEQUENCE: 58

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser

```
Asn Asn Leu Arg Leu Ile Val Glu Arg Asn Asn Leu Tyr Val Thr Gly
 65                  70                  75                  80

Phe Val Asn Arg Thr Asn Asn Val Phe Tyr Arg Phe Ala Asp Phe Ser
                 85                  90                  95

His Val Thr Phe Pro Gly Thr Thr Ala Val Thr Leu Ser Gly Asp Ser
                100                 105                 110

Ser Tyr Thr Thr Leu Gln Arg Val Ala Gly Ile Ser Arg Thr Gly Met
            115                 120                 125

Gln Ile Asn Arg His Ser Leu Thr Thr Ser Tyr Leu Asp Leu Met Ser
130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
                180                 185                 190

Thr Ala Glu Asp Val Asp Leu Thr Leu Asn Trp Gly Arg Leu Ser Ser
            195                 200                 205

Val Leu Pro Asp Tyr His Gly Gln Asp Ser Val Arg Val Gly Arg Ile
210                 215                 220

Ser Phe Gly Ser Ile Asn Ala Ile Leu Gly Ser Val Ala Leu Ile Leu
225                 230                 235                 240

Asn Cys His His His Ala Ser Ala Val Ala Ala
                245                 250

<210> SEQ ID NO 60
<211> LENGTH: 251
<212> TYPE: PRT
<213> ORGANISM: Artificial Sequence
<220> FEATURE:
<223> OTHER INFORMATION: SLT-1A-combo variant 6

<400> SEQUENCE: 60

Lys Glu Phe Thr Leu Asp Phe Ser Thr Ala Lys Thr Tyr Val Asp Ser
1               5                  10                  15

Leu Asn Val Ile Arg

Gly Phe Arg Thr Thr Leu Asp Asp Leu Ser Gly Arg Ser Tyr Val Met
                180                 185                 190

Thr Ala Glu Asp Val Asp Leu Thr Leu Asn Trp Gly Arg Leu Ser Ser
            195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Ala Val Ala Ala
                245                 250

<210> SEQ ID NO 61
<211> LENGTH: 251
<212> TYPE: PRT
<213> ORGANISM: Artificial Sequence
<220> FEATURE:
<223> OTHER INFORMATION: SLT-1A-combo variant 7

<400> SEQUENCE: 61

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20

<220> FEATURE:
<223> OTHER INFORMATION: SLT-1A-combo variant 8

<400> SEQUENCE: 62

Lys Glu Phe Thr Leu Asp Phe Ser Thr Ala Lys Thr Tyr Val Asp Ser
1 5 10 15

Leu Asn Val Ile Arg Ser Ala Ile Gly Thr Pro Leu Gln Thr Ile Ser
20 25 30

Ser Gly Gly Thr Ser Leu Leu Met Ile Asp Ser Gly Ser Gly Asp Asn
35 40 45

Leu Phe Ala Val Gly Ile Leu Gly Phe Val Phe Thr Leu Gly Arg Phe
50 55 60

Asn Asn Leu Arg Leu Ile Val Glu Arg Asn Asn Leu Tyr Val Thr Gly
65 70 75 80

Phe Val Asn Arg Thr Asn Asn Val Phe Tyr Arg Phe Ala Asp Phe Ser
85 90 95

His Val Thr Phe Pro Gly Thr Thr Ala Val Thr Leu Ser Gly Asp Ser
100 105 110

Ser Tyr Thr Thr Leu Gln Arg Val Ala Gly Ile Ser Arg Thr Gly Met
115 120 125

Gln Ile Asn Arg His Ser Leu Thr Thr Ser Tyr Leu Asp Leu Met Ser
130 135 140

His Ser Gly Thr Ser Leu Thr Gln Ser Val Ala Arg Ala Met Leu Arg
145 150 155 160

Phe Val Thr Val Thr Ala Glu Ala Leu Arg Phe Arg Gln Ile Gln Arg
165 170 175

Gly Phe Arg Thr Thr Leu Asp Asp Leu Ser Gly Arg Ser Tyr Val Met
180 185 190

Thr Ala Glu Asp Val Asp Leu Thr Leu Asn Trp Gly Arg Leu Ser Ser
195 200 205

Val Leu Pro Asp Tyr His Gly Gln Asp Ser Val Arg Val Gly Arg Ile
210 215 220

Ser Phe Gly Ser Ile Asn Ala Ile Leu Gly Ser Val Ala Leu Ile Leu
225 230 235 240

Asn Cys His His His Ala Ser Ala Val Ala Ala
245 250

<210> SEQ ID NO 63
<211> LENGTH: 251
<212> TYPE: PRT
<213> ORGANISM: Artificial Sequence
<220> FEATURE:
<223> OTHER INFORMATION: SLT-1A-combo variant 9

<400> SEQUENCE: 63

Lys Glu Phe Ile Leu Asp Phe Ser Thr Ala Lys Thr Tyr Val Asp Ser
1 5 10 15

Leu Asn Val Ile Arg Ser Ala Ile Gly Thr Pro Leu Gln Thr Ile Ser
20 25 30

Ser Gly Gly Thr Ser Leu Leu Met Ile Asp Ser Gly Ile Gly Asp Asn
35 40 45

Leu Phe Ala Val Asp Val Arg Gly Ile Ala Pro Ile Glu Ala Arg Phe
50 55 60

Asn Asn Leu Arg Leu Ile Val Glu Arg Asn Asn Leu Tyr Val Thr Gly
65 70 75 80

Phe Val Asn Arg Thr Asn Asn Val Phe Tyr Arg Phe Ala Asp Phe Ser

```
                85                  90                  95
His Val Thr Phe Pro Gly Thr Thr Ala Val Thr Leu Ser Ala Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Ala Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Ala Ala Leu Ser Gly Ala Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Ser His His His Ala Ser Ala Val Ala Ala
                245                 250

<210> SEQ ID NO 64
<211> LENGTH: 252
<212> TYPE: PRT
<213> ORGANISM: Artificial Sequence
<220> FEATURE:
<223> OTHER INFORMATION: SLT-1A-combo variant 10

<400> SEQUENCE: 64

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
                20                  25                  30

Ser Gly Gly Thr Ser Leu Leu Met Ile Asp Ser Gly Ser Gly Asp Asn
        35                  40                  45

Leu Phe Ala Val Gly Ile Leu Gly Phe Val Phe Thr Leu Glu Gly Arg
    50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Gly Asp
            100                 105                 110

Ser Ser Tyr Thr Thr Leu Gln Arg Val Ala Gly Ile Ser Arg Thr Gly
        115                 120                 125

Met Gln Ile Asn Arg His Ser Leu Thr Thr Ser Tyr Leu Asp Leu Met
    130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Arg Ser Tyr Val
            180                 185                 190

Met Thr Ala Glu Asp Val Asp Leu Thr Leu Asn Trp Gly Arg Leu Ser
```

```
              195                 200                 205
Ser Val Leu Pro Asp Tyr His Gly Gln Asp Ser Val Arg Val Gly Arg
    210                 215                 220

Ile Ser Phe Gly Ser Ile Asn Ala Ile Leu Gly Ser Val Ala Leu Ile
225                 230                 235                 240

Leu Asn Cys His His His Ala Ser Ala Val Ala Ala
                245                 250
```

<210> SEQ ID NO 65
<211> LENGTH: 251
<212> TYPE: PRT
<213> ORGANISM: Artificial Sequence
<220> FEATURE:
<223> OTHER INFORMATION: SLT-1A-combo variant 11

<400> SEQUENCE: 65

```
Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Asn Leu Val Pro Met Val Ala Thr Val
                100                 105                 110

Ser Tyr Thr Thr Leu Gln Arg Val Ala Gly Ile Ser Arg Thr Gly Met
                115                 120                 125

Gln Ile Asn Arg His Ser Leu Thr Thr Ser Tyr Leu Asp Leu Met Ser
        130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
                180                 185                 190

Thr Ala Glu Asp Val Asp Leu Thr Leu Asn Trp Gly Arg Leu Ser Ser
                195                 200                 205

Val Leu Pro Asp Tyr His Gly Gln Asp Ser Val Arg Val Gly Arg Ile
        210                 215                 220

Ser Phe Gly Ser Ile Asn Ala Ile Leu Gly Ser Val Ala Leu Ile Leu
225                 230                 235                 240

Asn Cys His His His Ala Ser Ala Val Ala Ala
                245                 250

<210> SEQ ID NO 67
<211> LENGTH: 251
<212> TYPE: PRT
<213> ORGANISM: Artificial Sequence
<220> FEATURE:
<223> OTHER INFORMATION: SLT-1A-combo vari Ser Tyr Thr Thr Leu Gln Arg Val Ala Gly Ile Ser Arg Thr Gly Met
115                 120                 125

Gln Ile Asn Arg His Ser Leu Thr Thr Ser Tyr Leu Asp Leu Met Ser
130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Gly Ile Leu Gly Asp Val Phe Thr Leu Ser Tyr Val Met
                180                 185                 190

Thr Ala Glu Asp Val Asp Leu Thr Leu Asn Trp Gly Arg Leu Ser Ser
                195                 200                 205

Val Leu Pro Asp Tyr His Gly Gln Asp Ser Val Arg Val Gly Arg Ile
            210                 215                 220

Ser Phe Gly Ser Ile Asn Ala Ile Leu Gly Ser Val Ala Leu Ile Leu
225                 230                 235                 240

Asn Ser His His His Ala Ser Ala Val Ala Ala
                245                 250

<210> SEQ ID NO 68
<211> LENGTH: 260
<212> TYPE: PRT
<213> ORGANISM: Artificial Sequence
<220> FEATURE:
<223> OTHER INFORMATION: SLT-1A-combo variant 14

<400> SEQUENCE: 68

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
                20

```
Ser Phe Gly Ser Ile Asn Ala Ile Leu Gly Ser Val Ala Leu Ile Leu
225                 230                 235                 240

Asn Cys His His His Ile Leu Arg Phe Ser Val Ala His Lys Ala Ser
                245                 250                 255

Ala Val Ala Ala
            260

<210> SEQ ID NO 69
<211> LENGTH: 262
<212> TYPE: PRT
<213> ORGANISM: Artificial Sequence
<220> FEATURE:
<223> OTHER INFORMATION: SLT-1A-combo variant 15

<400> SEQUENCE: 69

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn

Glu Phe Pro Lys Pro Ser Thr Pro Pro Gly Ser Ser Gly Gly Ala Pro
1               5                   10                  15

<210> SEQ ID NO 71
<211> LENGTH: 25
<212> TYPE: PRT
<213> ORGANISM: Artificial Sequence
<220> FEATURE:
<223> OTHER INFORMATION: linker 2

<400> SEQUENCE: 71

Glu Phe Pro Lys Pro Ser Thr Pro Pro Gly Ser Ser Gly Gly Ala Pro
1               5                   10                  15

Gly Ile Leu Gly Phe Val Phe Thr Leu
            20                  25

<210> SEQ ID NO 72
<211> LENGTH: 7
<212> TYPE: PRT
<213> ORGANISM: Artificial Sequence
<220> FEATURE:
<223> OTHER INFORMATION: linker 3

<400> SEQUENCE: 72

Gly Gly Gly Gly Ser Gly Gly
1               5

<210> SEQ ID NO 73
<211> LENGTH: 25
<212> TYPE: PRT
<213> ORGANISM: Artificial Sequence
<220> FEATURE:
<223> OTHER INFORMATION: linker 4

<400> SEQUENCE: 73

Gly Gly Gly Gly Ser Gly Gly Gly Ser Gly Gly Gly Ser Gly
1               5                   10                  15

Gly Gly Gly Ser Gly Gly Gly Gly Ser
            20                  25

<210> SEQ ID NO 74
<211> LENGTH: 15
<212> TYPE: PRT
<213> ORGANISM: Artificial Sequence
<220> FEATURE:
<223> OTHER INFORMATION: linker 5

<400> SEQUENCE: 74

Gly Ser Thr Ser Gly Ser Gly Lys Pro Gly Ser Gly Glu Gly Ser
1               5                   10                  15

<210> SEQ ID NO 75
<211> LENGTH: 5
<212> TYPE: PRT
<213> ORGANISM: Artificial Sequence
<220> FEATURE:
<223> OTHER INFORMATION: linker 6

<400> SEQUENCE: 75

Gly Gly Gly Gly Ser
1               5

<210> SEQ ID NO 76
<211> LENGTH: 505
<212> TYPE: PRT

```
<213> ORGANISM: Artificial Sequence
<220> FEATURE:
<223> OTHER INFORMATION: CD38-binding protein 1

<400> SEQUENCE: 76

Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
            20                  25                  30

Ser Ser Gly Gly Thr Ser Leu Leu Met Ile Asp Ser Ile Gly Ile Asp
        35                  40                  45

Asn Leu Phe Ala Val Asp Ile Leu Gly Phe Asp Phe Thr Leu Gly Arg
    50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Ala Asp
            100                 105                 110

Ser Ser Tyr Thr Thr Leu Gln Arg Val Ala Gly Ile Ser Arg Thr Gly
        115                 120                 125

Met Gln Ile Asn Arg His Ser Leu Thr Thr Ser Tyr Leu Asp Leu Met
    130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Ala Ser Tyr Val
            180                 185                 190

Met Thr Ala Glu Asp Val Asp Leu Thr Leu Asn Trp Gly Arg Leu Ser
        195                 200                 205

Ser Val Leu Pro Asp Tyr His Gly Gln Asp Ser Val Arg Val Gly Arg
    210                 215                 220

Ile Ser Phe Gly Ser Ile Asn Ala Ile Leu Gly Ser Val Ala Leu Ile
225                 230                 235                 240

Leu Asn Ser His His His Ala Ser Ala Val Ala Ala Glu Phe Pro Lys
                245                 250                 255

Pro Ser Thr Pro Pro Gly Ser Ser Gly Ala Pro Gln Ser Val Leu
            260                 265                 270

Thr Gln Pro Pro Ser Ala Ser Gly Thr Pro Gly Gln Arg Val Thr Ile
        275                 280                 285

Ser Cys Ser Gly Ser Ser Asn Ile Gly Ser Asn Tyr Val Tyr Trp
    290                 295                 300

Tyr Gln Gln Leu Pro Gly Thr Ala Pro Lys Leu Leu Ile Tyr Gly Asn
305                 310                 315                 320

Ser Asn Arg Pro Ser Gly Val Pro Asp Arg Phe Ser Gly Ser Lys Ser
                325                 330                 335

Gly Thr Ser Ala Ser Leu Ala Ile Ser Gly Leu Arg Ser Glu Asp Glu
            340                 345                 350

Ala Asp Tyr Tyr Cys Gln Ser Tyr Asp Ser Ser Leu Ser Gly Ser Gly
        355                 360                 365

Val Phe Gly Gly Gly Thr Lys Leu Thr Val Leu Gly Gly Gly Gly
    370                 375                 380

Ser Glu Val Gln Leu Leu Glu Ser Gly Gly Gly Leu Val Gln Pro Gly
```

385                 390                 395                 400
Gly Ser Leu Arg Leu Ser Cys Ala Ala Ser Gly Phe Thr Phe Ser Asp
                405                 410                 415

Tyr Tyr Met Ser Trp Val Arg Gln Ala Pro Gly Lys Gly Leu Glu Trp
            420                 425                 430

Val Ser Ala Ile Ser Gly Ser Gly Gly Ser Thr Tyr Tyr Ala Asp Ser
                435                 440                 445

Val Lys Gly Arg Phe Thr Ile Ser Arg Asp Asn Ser Lys Asn Thr Leu
        450                 455                 460

Tyr Leu Gln Met Asn Ser Leu Arg Ala Glu Asp Thr Ala Val Tyr Tyr
465                 470                 475                 480

Cys Ala Arg Glu His Ser Asn Tyr Phe Tyr Gly Met Asp Val Trp Gly
                485                 490                 495

Gln Gly Thr Leu Val Thr Val Ser Ser
            500                 505

<210> SEQ ID NO 77
<211> LENGTH: 503
<212> TYPE: PRT
<213> ORGANISM: Artificial Sequence
<220> FEATURE:
<223> OTHER INFORMATION: CD38-binding protein 2

<400> SEQUENCE: 77

Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
            20                  25                  30

Ser Ser Gly Gly Thr Ser Leu Leu Met Ile Asp Ser Gly Ile Gly Asp
        35                  40                  45

Asn Leu Phe Ala Val Asp Ile Leu Gly Phe Asp Phe Thr Leu Gly Arg
    50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Ala Asp
                100                 105                 110

Ser Ser Tyr Thr Thr Leu Gln Arg Val Ala Gly Ile Ser Arg Thr Gly
            115                 120                 125

Met Gln Ile Asn Arg His Ser Leu Thr Thr Ser Tyr Leu Asp Leu Met
        130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Ala Ser Tyr Val
            180                 185                 190

Met Thr Ala Glu Asp Val Asp Leu Thr Leu Asn Trp Gly Arg Leu Ser
        195                 200                 205

Ser Val Leu Pro Asp Tyr His Gly Gln Asp Ser Val Arg Val Gly Arg
    210                 215                 220

Ile Ser Phe Gly Ser Ile Asn Ala Ile Leu Gly Ser Val Ala Leu Ile
225                 230                 235                 240

Leu Asn Ser His His His Ala Ser Ala Val Ala Ala Glu Phe Pro Lys

```
            245                 250                 255
Pro Ser Thr Pro Pro Gly Ser Ser Gly Gly Ala Pro Gln Ser Val Leu
                260                 265                 270

Thr Gln Pro Pro Ser Ala Ser Gly Thr Pro Gly Gln Arg Val Thr Ile
            275                 280                 285

Ser Cys Ser Gly Ser Ser Ser Asn Ile Gly Gly Asn Tyr Val Tyr Trp
        290                 295                 300

Tyr Gln Gln Leu Pro Gly Thr Ala Pro Lys Leu Leu Ile Tyr Arg Asn
305                 310                 315                 320

Asn Gln Arg Pro Ser Gly Val Pro Asp Arg Phe Ser Gly Ser Lys Ser
                325                 330                 335

Gly Thr Ser Ala Ser Leu Ala Ile Ser Gly Leu Arg Ser Glu Asp Glu
            340                 345                 350

Ala Asp Tyr Tyr Cys Gln Ser Tyr Asp Ser Ser Leu Ser Val Ser Val
        355                 360                 365

Phe Gly Gly Gly Thr Lys Leu Thr Val Leu Gly Gly Gly Gly Ser
    370                 375                 380

Glu Val Gln Leu Leu Glu Ser Gly Gly Gly Leu Val Gln Pro Gly Gly
385                 390                 395                 400

Ser Leu Arg Leu Ser Cys Ala Ala Ser Gly Phe Thr Phe Ser Ser Tyr
                405                 410                 415

Trp Met His Trp Val Arg Gln Ala Pro Gly Lys Gly Leu Glu Trp Val
            420                 425                 430

Ser Ala Ile Ser Gly Ser Gly Gly Thr Phe Tyr Ala Asp Ser Val
        435                 440                 445

Lys Gly Arg Phe Thr Ile Ser Arg Asp Asn Ser Lys Asn Thr Leu Tyr
450                 455                 460

Leu Gln Met Asn Ser Leu Arg Ala Glu Asp Thr Ala Val Tyr Tyr Cys
465                 470                 475                 480

Ala Arg Glu Gly Glu Thr Ser Phe Gly Leu Asp Val Trp Gly Gln Gly
                485                 490                 495

Thr Leu Val Thr Val Ser Ser
            500

<210> SEQ ID NO 78
<211> LENGTH: 509
<212> TYPE: PRT
<213> ORGANISM: Artificial Sequence
<220> FEATURE:
<223> OTHER INFORMATION: CD38-binding protein 3

<400> SEQUENCE: 78

Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
                20                  25                  30

Ser Ser Gly Gly Thr Ser Leu Leu Met Ile Asp Ser Gly Ile Gly Asp
            35                  40                  45

Asn Leu Phe Ala Val Asp Ile Leu Gly Phe Asp Phe Thr Leu Gly Arg
        50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Ala Asp
```

```
              100                 105                 110
Ser Ser Tyr Thr Thr Leu Gln Arg Val Ala Gly Ile Ser Arg Thr Gly
            115                 120                 125
Met Gln Ile Asn Arg His Ser Leu Thr Thr Ser Tyr Leu Asp Leu Met
            130                 135                 140
Ser His Ser Gly Thr Ser Leu Thr Gln Ser Val Ala Arg Ala Met Leu
145                 150                 155                 160
Arg Phe Val Thr Val Thr Ala Glu Ala Leu Arg Phe Arg Gln Ile Gln
                165                 170                 175
Arg Gly Phe Arg Thr Thr Leu Asp Asp Leu Ser Gly Ala Ser Tyr Val
            180                 185                 190
Met Thr Ala Glu Asp Val Asp Leu Thr Leu Asn Trp Gly Arg Leu Ser
            195                 200                 205
Ser Val Leu Pro Asp Tyr His Gly Gln Asp Ser Val Arg Val Gly Arg
210                 215                 220
Ile Ser Phe Gly Ser Ile Asn Ala Ile Leu Gly Ser Val Ala Leu Ile
225                 230                 235                 240
Leu Asn Ser His His His His His His Ala Ser Ala Val Ala Ala Glu
                245                 250                 255
Phe Pro Lys Pro Ser Thr Pro Pro Gly Ser Ser Gly Gly Ala Pro Gln
            260                 265                 270
Val Gln Leu Val Gln Ser Gly Ala Glu Val Lys Lys Pro Gly Glu Ser
            275                 280                 285
Leu Lys Ile Ser Cys Lys Gly Ser Gly Tyr Ser Phe Thr Ser Tyr Trp
            290                 295                 300
Ile Gly Trp Val Arg Gln Met Pro Gly Lys Gly Leu Glu Trp Met Gly
305                 310                 315                 320
Ile Ile Tyr Pro Gly Asp Ser Asp Thr Arg Tyr Ser Pro Ser Phe Gln
                325                 330                 335
Gly Gln Val Thr Ile Ser Ala Asp Lys Ser Ile Ser Thr Ala Tyr Leu
            340                 345                 350
Gln Trp Ser Ser Leu Lys Ala Ser Asp Thr Ala Met Tyr Tyr Cys Ala
            355                 360                 365
Arg Gly Pro Ser Thr Gly Phe Trp Ser Gly Asn Tyr Phe Asp Tyr Trp
            370                 375                 380
Gly Gln Gly Thr Leu Val Thr Val Ser Ser Gly Gly Gly Gly Ser Gln
385                 390                 395                 400
Thr Val Val Thr Gln Glu Pro Ser Leu Thr Val Ser Pro Gly Glu Thr
                405                 410                 415
Val Thr Leu Thr Cys Ala Ser Ser Thr Gly Ala Val Thr Ser Gly Phe
            420                 425                 430
Tyr Pro Asn Trp Phe Gln Gln Lys Pro Gly Gln Ala Pro Arg Ala Leu
            435                 440                 445
Ile Tyr Ala Thr Asn Asn Lys Tyr Ser Trp Thr Pro Ala Arg Phe Ser
            450                 455                 460
Gly Ser Leu Leu Gly Asp Lys Ala Ala Leu Thr Leu Ser Arg Val Gln
465                 470                 475                 480
Pro Glu Asp Glu Ala Asp Tyr Tyr Cys Leu Val Tyr Tyr Asp Gly Ala
                485                 490                 495
Trp Val Phe Gly Gly Gly Thr Lys Leu Thr Val Leu Gly
            500                 505

<210> SEQ ID NO 79
```

```
<211> LENGTH: 507
<212> TYPE: PRT
<213> ORGANISM: Artificial Sequence
<220> FEATURE:
<223> OTHER INFORMATION: CD38-binding protein 4

<400> SEQUENCE: 79
```

| Met<br>1 | Lys | Glu | Phe | Thr<br>5 | Leu | Asp | Phe | Ser | Thr<br>10 | Ala | Lys | Thr | Tyr | Val<br>15 | Asp |
|---|---|---|---|---|---|---|---|---|---|---|---|---|---|---|---|
| Ser | Leu | Asn | Val<br>20 | Ile | Arg | Ser | Ala | Ile<br>25 | Gly | Thr | Pro | Leu | Gln<br>30 | Thr | Ile |
| Ser | Ser | Gly<br>35 | Gly | Thr | Ser | Leu | Leu<br>40 | Met | Ile | Asp | Ser | Gly<br>45 | Ile | Gly | Asp |
| Asn | Leu<br>50 | Phe | Ala | Val | Asp | Ile<br>55 | Leu | Gly | Phe | Asp | Phe<br>60 | Thr | Leu | Gly | Arg |
| Phe<br>65 | Asn | Asn | Leu | Arg | Leu<br>70 | Ile | Val | Glu | Arg | Asn<br>75 | Asn | Leu | Tyr | Val | Thr<br>80 |
| Gly | Phe | Val | Asn | Arg<br>85 | Thr | Asn | Asn | Val | Phe<br>90 | Tyr | Arg | Phe | Ala | Asp<br>95 | Phe |
| Ser | His | Val | Thr<br>100 | Phe | Pro | Gly | Thr | Thr<br>105 | Ala | Val | Thr | Leu | Ser<br>110 | Ala | Asp |
| Ser | Ser | Tyr<br>115 | Thr | Thr | Leu | Gln | Arg<br>120 | Val | Ala | Gly | Ile | Ser<br>125 | Arg | Thr | Gly |
| Met | Gln<br>130 | Ile | Asn | Arg | His | Ser<br>135 | Leu | Thr | Thr | Ser | Tyr<br>140 | Leu | Asp | Leu | Met |
| Ser<br>145 | His | Ser | Gly | Thr | Ser<br>150 | Leu | Thr | Gln | Ser | Val<br>155 | Ala | Arg | Ala | Met | Leu<br>160 |
| Arg | Phe | Val | Thr | Val<br>165 | Thr | Ala | Glu | Ala | Leu<br>170 | Arg | Phe | Arg | Gln | Ile<br>175 | Gln |
| Arg | Gly | Phe | Arg<br>180 | Thr | Thr | Leu | Asp | Asp<br>185 | Leu | Ser | Gly | Ala | Ser<br>190 | Tyr | Val |
| Met | Thr | Ala<br>195 | Glu | Asp | Val | Asp | Leu<br>200 | Thr | Leu | Asn | Trp | Gly<br>205 | Arg | Leu | Ser |
| Ser | Val<br>210 | Leu | Pro | Asp | Tyr | His<br>215 | Gly | Gln | Asp | Ser | Val<br>220 | Arg | Val | Gly | Arg |
| Ile<br>225 | Ser | Phe | Gly | Ser | Ile<br>230 | Asn | Ala | Ile | Leu | Gly<br>235 | Ser | Val | Ala | Leu | Ile<br>240 |
| Leu | Asn | Ser | His | His<br>245 | His | Ala | Ser | Ala | Val<br>250 | Ala | Ala | Glu | Phe | Pro<br>255 | Lys |
| Pro | Ser | Thr | Pro<br>260 | Pro | Gly | Ser | Ser | Gly<br>265 | Gly | Ala | Pro | Gln | Val<br>270 | Gln | Leu |
| Val | Gln<br>275 | Ser | Gly | Ala | Glu | Val<br>280 | Lys | Lys | Pro | Gly | Glu<br>285 | Ser | Leu | Lys | Ile |
| Ser<br>290 | Cys | Lys | Gly | Ser | Gly<br>295 | Tyr | Ser | Phe | Thr | Ser<br>300 | Tyr | Trp | Ile | Gly | Trp |
| Val<br>305 | Arg | Gln | Met | Pro | Gly<br>310 | Lys | Gly | Leu | Glu | Trp<br>315 | Met | Gly | Ile | Ile | Tyr<br>320 |
| Pro | Gly | Asp | Ser | Asp<br>325 | Thr | Arg | Tyr | Ser | Pro<br>330 | Ser | Phe | Gln | Gly | Gln<br>335 | Val |
| Thr | Ile | Ser | Ala<br>340 | Asp | Lys | Ser | Ile | Ser<br>345 | Thr | Ala | Tyr | Leu | Gln<br>350 | Trp | Ser |
| Ser | Leu | Lys<br>355 | Ala | Ser | Asp | Thr | Ala<br>360 | Met | Tyr | Tyr | Cys | Ala<br>365 | Arg | Gly | Pro |
| Ser | Thr<br>370 | Gly | Phe | Trp | Ser | Gly<br>375 | Asn | Tyr | Phe | Asp | Tyr<br>380 | Trp | Gly | Gln | Gly |

```
Thr Leu Val Thr Val Ser Ser Gly Gly Gly Ser Asp Ile Gln Met
385                 390                 395                 400

Thr Gln Ser Pro Ser Ser Leu Ser Ala Ser Val Gly Asp Arg Val Thr
            405                 410                 415

Ile Thr Cys Ala Ser Ser Thr Gly Ala Val Thr Ser Gly Phe Tyr Pro
        420                 425                 430

Asn Trp Phe Gln Gln Lys Pro Gly Gln Ala Pro Arg Ala Leu Ile Tyr
            435                 440                 445

Ala Thr Asn Asn Lys Tyr Ser Trp Thr Pro Ala Arg Phe Ser Gly Ser
    450                 455                 460

Leu Leu Gly Asp Lys Ala Ala Leu Thr Leu Ser Arg Val Gln Pro Glu
465                 470                 475                 480

Asp Glu Ala Asp Tyr Tyr Cys Leu Val Tyr Tyr Asp Gly Ala Trp Val
                485                 490                 495

Phe Gly Gly Gly Thr Lys Leu Thr Val Leu Gly
            500                 505
```

```
<210> SEQ ID NO 80
<211> LENGTH: 527
<212> TYPE: PRT
<213> ORGANISM: Artificial Sequence
<220> FEATURE:
<223> OTHER INFORMATION: CD38-binding protein 5

<400> SEQUENCE: 80

Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
            20                  25                  30

Ser Ser Gly Gly Thr Ser Leu Leu Met Ile Asp Ser Gly Ile Gly Asp
        35                  40                  45

Asn Leu Phe Ala Val Asp Ile Leu Gly Phe Asp Phe Thr Leu Gly Arg
    50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Ala Asp
            100                 105                 110

Ser Ser Tyr Thr Thr Leu Gln Arg Val Ala Gly Ile Ser Arg Thr Gly
        115                 120                 125

Met Gln Ile Asn Arg His Ser Leu Thr Thr Ser Tyr Leu Asp Leu Met
130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Ala Ser Tyr Val
            180                 185                 190

Met Thr Ala Glu Asp Val Asp Leu Thr Leu Asn Trp Gly Arg Leu Ser
        195                 200                 205

Ser Val Leu Pro Asp Tyr His Gly Gln Asp Ser Val Arg Val Gly Arg
    210                 215                 220

Ile Ser Phe Gly Ser Ile Asn Ala Ile Leu Gly Ser Val Ala Leu Ile
225                 230                 235                 240
```

```
Leu Asn Ser His His His Ala Ser Ala Val Ala Ala Glu Phe Pro Lys
            245                 250                 255

Pro Ser Thr Pro Pro Gly Ser Ser Gly Ala Pro Gln Ser Val Leu
        260                 265                 270

Thr Gln Pro Pro Ser Ala Ser Gly Thr Pro Gly Gln Arg Val Thr Ile
        275                 280                 285

Ser Cys Ser Gly Ser Asn Ser Asn Ile Gly Ser Asn Thr Val Asn Trp
290                 295                 300

Tyr Gln Gln Leu Pro Gly Thr Ala Pro Lys Leu Leu Ile Tyr Ser Asp
305                 310                 315                 320

Ser Asn Arg Pro Ser Gly Val Pro Asp Arg Phe Ser Gly Ser Lys Ser
            325                 330                 335

Gly Thr Ser Ala Ser Leu Ala Ile Ser Gly Leu Arg Ser Glu Asp Glu
            340                 345                 350

Ala Asp Tyr Tyr Cys Gln Ser Tyr Asp Ser Ser Leu Ser Gly Ser Arg
            355                 360                 365

Val Phe Gly Gly Gly Thr Lys Leu Thr Val Leu Gly Gly Gly Gly
            370                 375                 380

Ser Gly Gly Gly Gly Ser Gly Gly Gly Ser Gly Gly Gly Gly Ser
385                 390                 395                 400

Gly Gly Gly Gly Ser Glu Val Gln Leu Leu Glu Ser Gly Gly Gly Leu
            405                 410                 415

Val Gln Pro Gly Gly Ser Leu Arg Leu Ser Cys Ala Ala Ser Gly Phe
            420                 425                 430

Thr Phe Asn Asn Tyr Asp Met Thr Trp Val Arg Gln Ala Pro Gly Lys
            435                 440                 445

Gly Leu Glu Trp Val Ala Val Ile Ser Tyr Asp Gly Ser Asp Lys Asp
450                 455                 460

Tyr Ala Asp Ser Val Lys Gly Arg Phe Thr Ile Ser Arg Asp Asn Ser
465                 470                 475                 480

Lys Asn Thr Leu Tyr Leu Gln Met Asn Ser Leu Arg Ala Glu Asp Thr
            485                 490                 495

Ala Val Tyr Tyr Cys Ala Arg Val Tyr Tyr Gly Phe Ser Gly Pro
            500                 505                 510

Ser Met Asp Val Trp Gly Gln Gly Thr Leu Val Thr Val Ser Ser
            515                 520                 525

<210> SEQ ID NO 81
<211> LENGTH: 507
<212> TYPE: PRT
<213> ORGANISM: Artificial Sequence
<220> FEATURE:
<223> OTHER INFORMATION: CD38-binding protein 6

<400> SEQUENCE: 81

Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
            20                  25                  30

Ser Ser Gly Gly Thr Ser Leu Leu Met Ile Asp Ser Gly Ile Gly Asp
        35                  40                  45

Asn Leu Phe Ala Val Asp Ile Leu Gly Phe Asp Phe Thr Leu Gly Arg
    50                  55                  60

Phe Asn Asn Leu Arg Leu Ile Val Glu Arg Asn Asn Leu Tyr Val Thr
65                  70                  75                  80
```

```
Gly Phe Val Asn Arg Thr Asn Val Phe Tyr Arg Phe Ala Asp Phe
                85              90              95

Ser His Val Thr Phe Pro Gly Thr Thr Ala Val Thr Leu Ser Ala Asp
                100             105             110

Ser Ser Tyr Thr Thr Leu Gln Arg Val Ala Gly Ile Ser Arg Thr Gly
            115             120             125

Met Gln Ile Asn Arg His Ser Leu Thr Thr Ser Tyr Leu Asp Leu Met
130             135             140

Ser His Ser Gly Thr Ser Leu Thr Gln Ser Val Ala Arg Ala Met Leu
145             150             155             160

Arg Phe Val Thr Val Thr Ala Glu Ala Leu Arg Phe Arg Gln Ile Gln
                165             170             175

Arg Gly Phe Arg Thr Thr Leu Asp Asp Leu Ser Gly Ala Ser Tyr Val
            180             185             190

Met Thr Ala Glu Asp Val Asp Leu Thr Leu Asn Trp Gly Arg Leu Ser
            195             200             205

Ser Val Leu Pro Asp Tyr His Gly Gln Asp Ser Val Arg Val Gly Arg
210             215             220

Ile Ser Phe Gly Ser Ile Asn Ala Ile Leu Gly Ser Val Ala Leu Ile
225             230             235             240

Leu Asn Ser His His His His His Ala Ser Ala Val Ala Ala Glu
                245             250             255

Phe Pro Lys Pro Ser Thr Pro Pro Gly Ser Ser Gly Gly Ala Pro Gln
                260             265             270

Ser Val Leu Thr Gln Pro Pro Ser Ala Ser Gly Thr Pro Gly Gln Arg
            275             280             285

Val Thr Ile Ser Cys Ser Gly Ser Ser Ser Asn Ile Gly Ser Asn Tyr
            290             295             300

Val Tyr Trp Tyr Gln Gln Leu Pro Gly Thr Ala Pro Lys Leu Leu Ile
305             310             315             320

Tyr Gly Asn Ser Asn Arg Pro Ser Gly Val Pro Asp Arg Phe Ser Gly
                325             330             335

Ser Lys Ser Gly Thr Ser Ala Ser Leu Ala Ile Ser Gly Leu Arg Ser
            340             345             350

Glu Asp Glu Ala Asp Tyr Tyr Cys Gln Ser Tyr Asp Asn Thr Leu Ser
            355             360             365

Gly Val Ile Phe Gly Gly Gly Thr Lys Leu Thr Val Leu Gly Gly Gly
370             375             380

Gly Gly Ser Glu Val Gln Leu Leu Glu Ser Gly Gly Gly Leu Val Gln
385             390             395             400

Pro Gly Gly Ser Leu Arg Leu Ser Cys Ala Ala Ser Gly Phe Thr Phe
                405             410             415

Ser Asp Tyr Tyr Met Asn Trp Ile Arg Gln Ala Pro Gly Lys Gly Leu
            420             425             430

Glu Trp Val Ser Ser Ile Ser Ser Ser Ser Tyr Ile Tyr Tyr Ala
                435             440             445

Asp Ser Val Lys Gly Arg Phe Thr Ile Ser Arg Asp Asn Ser Lys Asn
450             455             460

Thr Leu Tyr Leu Gln Met Asn Ser Leu Arg Ala Glu Asp Thr Ala Val
465             470             475             480

Tyr Tyr Cys Ala Thr Glu Gly Pro Tyr Tyr Leu Tyr Gly Phe Asp Ile
                485             490             495
```

Trp Gly Gln Gly Thr Leu Val Thr Val Ser Ser
          500                 505

<210> SEQ ID NO 82
<211> LENGTH: 507
<212> TYPE: PRT
<213> ORGANISM: Artificial Sequence
<220> FEATURE:
<223> OTHER INFORMATION: CD38-binding protein 7

<400> SEQUENCE: 82

Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
            20                  25                  30

Ser Ser Gly Gly Thr Ser Leu Leu Met Ile Asp Ser Gly Ile Gly Asp
        35                  40                  45

Asn Leu Phe Ala Val Asp Ile Leu Gly Phe Asp Phe Thr Leu Gly Arg
    50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Ala Asp
            100                 105                 110

Ser Ser Tyr Thr Thr Leu Gln Arg Val Ala Gly Ile Ser Arg Thr Gly
        115                 120                 125

Met Gln Ile Asn Arg His Ser Leu Thr Thr Ser Tyr Leu Asp Leu Met
130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Ala Ser Tyr Val
            180                 185                 190

Met Thr Ala Glu Asp Val Asp Leu Thr Leu Asn Trp Gly Arg Leu Ser
        195                 200                 205

Ser Val Leu Pro Asp Tyr His Gly Gln Asp Ser Val Arg Val Gly Arg
    210                 215                 220

Ile Ser Phe Gly Ser Ile Asn Ala Ile Leu Gly Ser Val Ala Leu Ile
225                 230                 235                 240

Leu Asn Ser His His His Ala Ser Ala Val Ala Ala Glu Phe Pro Lys
                245                 250                 255

Pro Ser Thr Pro Pro Gly Ser Ser Gly Gly Ala Pro Gln Ser Val Leu
            260                 265                 270

Thr Gln Pro Pro Ser Ala Ser Gly Thr Pro Gly Gln Arg Val Thr Ile
        275                 280                 285

Ser Cys Ser Gly Ser Ser Ser Asn Ile Gly Asn Ser Tyr Val Ser Trp
    290                 295                 300

Tyr Gln Gln Leu Pro Gly Thr Ala Pro Lys Leu Leu Ile Tyr Arg Asn
305                 310                 315                 320

Asn Gln Arg Pro Ser Gly Val Pro Asp Arg Phe Ser Gly Ser Lys Ser
                325                 330                 335

Gly Thr Ser Ala Ser Leu Ala Ile Ser Gly Leu Arg Ser Glu Asp Glu
            340                 345                 350

Ala Asp Tyr Tyr Cys Ser Ala Trp Asp Asp Asn Leu Ser Val Leu Phe
            355                 360                 365

Gly Gly Gly Thr Lys Leu Thr Val Leu Gly Gly Gly Gly Ser Glu
        370                 375                 380

Val Gln Leu Leu Glu Ser Gly Gly Leu Val Gln Pro Gly Gly Ser
385                 390                 395                 400

Leu Arg Leu Ser Cys Ala Ala Ser Gly Phe Thr Phe Asp Asp Tyr Gly
                405                 410                 415

Met Thr Trp Val Arg Gln Ala Pro Gly Lys Gly Leu Glu Trp Val Ser
            420                 425                 430

Gly Ile Asn Trp Asn Gly Gly Ser Thr Gly Tyr Ala Asp Ser Val Lys
        435                 440                 445

Gly Arg Phe Thr Ile Ser Arg Asp Asn Ser Lys Asn Thr Leu Tyr Leu
    450                 455                 460

Gln Met Asn Ser Leu Arg Ala Glu Asp Thr Ala Val Tyr Tyr Cys Ala
465                 470                 475                 480

Arg Gly Gly Leu Phe His Asp Ser Ser Gly Tyr Tyr Phe Gly His Trp
                485                 490                 495

Gly Gln Gly Thr Leu Val Thr Val Ser Ser Ala
            500                 505

<210> SEQ ID NO 83
<211> LENGTH: 499
<212> TYPE: PRT
<213> ORGANISM: Artificial Sequence
<220> FEATURE:
<223> OTHER INFORMATION: CD38-targeting reference molecule 1

<400> SEQUENCE: 83

Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
            20                  25                  30

Ser Ser Gly Gly Thr Ser Leu Leu Met Ile Asp Ser Gly Ile Gly Asp
        35                  40                  45

Asn Leu Phe Ala Val Asp Ile Leu Gly Phe Asp Phe Thr Leu Gly Arg
    50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Ala Asp
            100                 105                 110

Ser Ser Tyr Thr Thr Leu Gln Arg Val Ala Gly Ile Ser Arg Thr Gly
        115                 120                 125

Met Gln Ile Asn Arg His Ser Leu Thr Thr Ser Tyr Leu Asp Leu Met
130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Ala Ser Tyr Val
            180                 185                 190

Met Thr Ala Glu Asp Val Asp Leu Thr Leu Asn Trp Gly Arg Leu Ser
        195                 200                 205

Ser Val Leu Pro Asp Tyr His Gly Gln Asp Ser Val Arg Val Gly Arg
        210                 215                 220

Ile Ser Phe Gly Ser Ile Asn Ala Ile Leu Gly Ser Val Ala Leu Ile
225                 230                 235                 240

Leu Asn Ser His His His Ala Ser Ala Val Ala Ala Glu Phe Pro Lys
                    245                 250                 255

Pro Ser Thr Pro Pro Gly Ser Ser Gly Ala Pro Asp Ile Gln Met
        260                 265                 270

Thr Gln Ser Pro Ser Ser Leu Ser Ala Ser Val Gly Asp Arg Val Thr
                275                 280                 285

Ile Thr Cys Lys Ala Ser Glu Asp Ile Tyr Asn Arg Leu Thr Trp Tyr
        290                 295                 300

Gln Gln Lys Pro Gly Lys Ala Pro Lys Leu Leu Ile Ser Gly Ala Thr
305                 310                 315                 320

Ser Leu Glu Thr Gly Val Pro Ser Arg Phe Ser Gly Ser Gly Ser Gly
                    325                 330                 335

Thr Asp Phe Thr Phe Thr Ile Ser Ser Leu Gln Pro Glu Asp Ile Ala
                340                 345                 350

Thr Tyr Tyr Cys Gln Gln Tyr Trp Ser Asn Pro Tyr Thr Phe Gly Gln
                355                 360                 365

Gly Thr Lys Val Glu Ile Lys Gly Gly Gly Ser Gln Val Gln Leu
        370                 375                 380

Gln Glu Ser Gly Pro Gly Leu Val Arg Pro Ser Gln Thr Leu Ser Leu
385                 390                 395                 400

Thr Cys Thr Val Ser Gly Phe Ser Leu Thr Ser Tyr Gly Val His Trp
                    405                 410                 415

Val Arg Gln Pro Pro Gly Arg Gly Leu Glu Trp Ile Gly Val Met Trp
                420                 425                 430

Arg Gly Gly Ser Thr Asp Tyr Asn Ala Ala Phe Met Ser Arg Leu Asn
                435                 440                 445

Ile Thr Lys Asp Asn Ser Lys Asn Gln Val Ser Leu Arg Leu Ser Ser
        450                 455                 460

Val Thr Ala Ala Asp Thr Ala Val Tyr Tyr Cys Ala Lys Ser Met Ile
465                 470                 475                 480

Thr Thr Gly Phe Val Met Asp Ser Trp Gly Gln Gly Ser Leu Val Thr
                    485                 490                 495

Val Ser Ser

<210> SEQ ID NO 84
<211> LENGTH: 499
<212> TYPE: PRT
<213> ORGANISM: Artificial Sequence
<220> FEATURE:
<223> OTHER INFORMATION: CD38-targeting control molecule 1

<400> SEQUENCE: 84

Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
                20                  25                  30

Ser Ser Gly Gly Thr Ser Leu Leu Met Ile Asp Ser Gly Ser Gly Asp
                35                  40                  45

Asn Leu Phe Ala Val Asp Val Arg Gly Ile Asp Pro Glu Glu Gly Arg
        50                  55                  60

Phe Asn Asn Leu Arg Leu Ile Val Glu Arg Asn Asn Leu Tyr Val Thr

```
            65                  70                  75                  80

Gly Phe Val Asn Arg Thr Asn Asn Val Phe Tyr Arg Phe Ala Asp Phe
                    85                  90                  95

Ser His Val Thr Phe Pro Gly Thr Thr Ala Val Thr Leu Ser Gly Asp
                    100                 105                 110

Ser Ser Tyr Thr Thr Leu Gln Arg Val Ala Gly Ile Ser Arg Thr Gly
                    115                 120                 125

Met Gln Ile Asn Arg His Ser Leu Thr Thr Ser Tyr Leu Asp Leu Met
            130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                        165                 170                 175

Arg Gly Phe Arg Thr Thr Leu Asp Asp Leu Ser Gly Arg Ser Tyr Val
                    180                 185                 190

Met Thr Ala Glu Asp Val Asp Leu Thr Leu Asn Trp Gly Arg Leu Ser
                195                 200                 205

Ser Val Leu Pro Asp Tyr His Gly Gln Asp Ser Val Arg Val Gly Arg
    210                 215                 220

Ile Ser Phe Gly Ser Ile Asn Ala Ile Leu Gly Ser Val Ala Leu Ile
225                 230                 235                 240

Leu Asn Cys His His His Ala Ser Ala Val Ala Ala Glu Phe Pro Lys
                    245                 250                 255

Pro Ser Thr Pro Pro Gly Ser Ser Gly Gly Ala Pro Asp Ile Gln Met
                    260                 265                 270

Thr Gln Ser Pro Ser Ser Leu Ser Ala Ser Val Gly Asp Arg Val Thr
                275                 280                 285

Ile Thr Cys Lys Ala Ser Glu Asp Ile Tyr Asn Arg Leu Thr Trp Tyr
            290                 295                 300

Gln Gln Lys Pro Gly Lys Ala Pro Lys Leu Leu Ile Ser Gly Ala Thr
305                 310                 315                 320

Ser Leu Glu Thr Gly Val Pro Ser Arg Phe Ser Gly Ser Gly Ser Gly
                    325                 330                 335

Thr Asp Phe Thr Phe Thr Ile Ser Ser Leu Gln Pro Glu Asp Ile Ala
                    340                 345                 350

Thr Tyr Tyr Cys Gln Gln Tyr Trp Ser Asn Pro Tyr Thr Phe Gly Gln
                355                 360                 365

Gly Thr Lys Val Glu Ile Lys Gly Gly Gly Ser Gln Val Gln Leu
            370                 375                 380

Gln Glu Ser Gly Pro Gly Leu Val Arg Pro Ser Gln Thr Leu Ser Leu
385                 390                 395                 400

Thr Cys Thr Val Ser Gly Phe Ser Leu Thr Ser Tyr Gly Val His Trp
                    405                 410                 415

Val Arg Gln Pro Pro Gly Arg Gly Leu Glu Trp Ile Gly Val Met Trp
                420                 425                 430

Arg Gly Gly Ser Thr Asp Tyr Asn Ala Ala Phe Met Ser Arg Leu Asn
            435                 440                 445

Ile Thr Lys Asp Asn Ser Lys Asn Gln Val Ser Leu Arg Leu Ser Ser
            450                 455                 460

Val Thr Ala Ala Asp Thr Ala Val Tyr Tyr Cys Ala Lys Ser Met Ile
465                 470                 475                 480

Thr Thr Gly Phe Val Met Asp Ser Trp Gly Gln Gly Ser Leu Val Thr
                    485                 490                 495
```

Val Ser Ser

<210> SEQ ID NO 85
<211> LENGTH: 300
<212> TYPE: PRT
<213> ORGANISM: Homo sapiens

<400> SEQUENCE: 85

```
Met Ala Asn Cys Glu Phe Ser Pro Val Ser Gly Asp Lys Pro Cys Cys
1               5                   10                  15

Arg Leu Ser Arg Arg Ala Gln Leu Cys Leu Gly Val Ser Ile Leu Val
            20                  25                  30

Leu Ile Leu Val Val Val Leu Ala Val Val Pro Arg Trp Arg Gln
        35                  40                  45

Gln Trp Ser Gly Pro Gly Thr Thr Lys Arg Phe Pro Glu Thr Val Leu
    50                  55                  60

Ala Arg Cys Val Lys Tyr Thr Glu Ile His Pro Glu Met Arg His Val
65                  70                  75                  80

Asp Cys Gln Ser Val Trp Asp Ala Phe Lys Gly Ala Phe Ile Ser Lys
                85                  90                  95

His Pro Cys Asn Ile Thr Glu Glu Asp Tyr Gln Pro Leu Met Lys Leu
            100                 105                 110

Gly Thr Gln Thr Val Pro Cys Asn Lys Ile Leu Leu Trp Ser Arg Ile
        115                 120                 125

Lys Asp Leu Ala His Gln Phe Thr Gln Val Gln Arg Asp Met Phe Thr
    130                 135                 140

Leu Glu Asp Thr Leu Leu Gly Tyr Leu Ala Asp Asp Leu Thr Trp Cys
145                 150                 155                 160

Gly Glu Phe Asn Thr Ser Lys Ile Asn Tyr Gln Ser Cys Pro Asp Trp
                165                 170                 175

Arg Lys Asp Cys Ser Asn Asn Pro Val Ser Val Phe Trp Lys Thr Val
            180                 185                 190

Ser Arg Arg Phe Ala Glu Ala Ala Cys Asp Val Val His Val Met Leu
        195                 200                 205

Asn Gly Ser Arg Ser Lys Ile Phe Asp Lys Asn Ser Thr Phe Gly Ser
    210                 215                 220

Val Glu Val His Asn Leu Gln Pro Glu Lys Val Gln Thr Leu Glu Ala
225                 230                 235                 240

Trp Val Ile His Gly Gly Arg Glu Asp Ser Arg Asp Leu Cys Gln Asp
                245                 250                 255

Pro Thr Ile Lys Glu Leu Glu Ser Ile Ile Ser Lys Arg Asn Ile Gln
            260                 265                 270

Phe Ser Cys Lys Asn Ile Tyr Arg Pro Asp Lys Phe Leu Gln Cys Val
        275                 280                 285

Lys Asn Pro Glu Asp Ser Ser Cys Thr Ser Glu Ile
    290                 295                 300
```

<210> SEQ ID NO 86
<211> LENGTH: 258
<212> TYPE: PRT
<213> ORGANISM: Homo sapiens

<400> SEQUENCE: 86

```
Val Pro Arg Trp Arg Gln Gln Trp Ser Gly Pro Gly Thr Thr Lys Arg
1               5                   10                  15
```

```
Phe Pro Glu Thr Val Leu Ala Arg Cys Val Lys Tyr Thr Glu Ile His
             20                  25                  30

Pro Glu Met Arg His Val Asp Cys Gln Ser Val Trp Asp Ala Phe Lys
         35                  40                  45

Gly Ala Phe Ile Ser Lys His Pro Cys Asn Ile Thr Glu Glu Asp Tyr
     50                  55                  60

Gln Pro Leu Met Lys Leu Gly Thr Gln Thr Val Pro Cys Asn Lys Ile
65                  70                  75                  80

Leu Leu Trp Ser Arg Ile Lys Asp Leu Ala His Gln Phe Thr Gln Val
                 85                  90                  95

Gln Arg Asp Met Phe Thr Leu Glu Asp Thr Leu Leu Gly Tyr Leu Ala
            100                 105                 110

Asp Asp Leu Thr Trp Cys Gly Glu Phe Asn Thr Ser Lys Ile Asn Tyr
        115                 120                 125

Gln Ser Cys Pro Asp Trp Arg Lys Asp Cys Ser Asn Asn Pro Val Ser
    130                 135                 140

Val Phe Trp Lys Thr Val Ser Arg Arg Phe Ala Glu Ala Ala Cys Asp
145                 150                 155                 160

Val Val His Val Met Leu Asn Gly Ser Arg Ser Lys Ile Phe Asp Lys
                165                 170                 175

Asn Ser Thr Phe Gly Ser Val Glu Val His Asn Leu Gln Pro Glu Lys
            180                 185                 190

Val Gln Thr Leu Glu Ala Trp Val Ile His Gly Gly Arg Glu Asp Ser
        195                 200                 205

Arg Asp Leu Cys Gln Asp Pro Thr Ile Lys Glu Leu Glu Ser Ile Ile
    210                 215                 220

Ser Lys Arg Asn Ile Gln Phe Ser Cys Lys Asn Ile Tyr Arg Pro Asp
225                 230                 235                 240

Lys Phe Leu Gln Cys Val Lys Asn Pro Glu Asp Ser Ser Cys Thr Ser
                245                 250                 255

Glu Ile

<210> SEQ ID NO 87
<211> LENGTH: 301
<212> TYPE: PRT
<213> ORGANISM: Macaca fasicularis

<400> SEQUENCE: 87

Met Ala Asn Cys Glu Phe Ser Pro Val Ser Gly Asp Lys Pro Cys Cys
1               5                   10                  15

Arg Leu Ser Arg Arg Ala Gln Val Cys Leu Gly Val Cys Leu Leu Val
             20                  25                  30

Leu Leu Ile Leu Val Val Val Ala Val Leu Pro Arg Trp Arg
         35                  40                  45

Gln Gln Trp Ser Gly Ser Gly Thr Thr Ser Arg Phe Pro Glu Thr Val
     50                  55                  60

Leu Ala Arg Cys Val Lys Tyr Thr Glu Val His Pro Glu Met Arg His
65                  70                  75                  80

Val Asp Cys Gln Ser Val Trp Asp Ala Phe Lys Gly Ala Phe Ile Ser
                 85                  90                  95

Lys Tyr Pro Cys Asn Ile Thr Glu Glu Asp Tyr Gln Pro Leu Val Lys
            100                 105                 110

Leu Gly Thr Gln Thr Val Pro Cys Asn Lys Thr Leu Leu Trp Ser Arg
        115                 120                 125
```

```
Ile Lys Asp Leu Ala His Gln Phe Thr Gln Val Gln Arg Asp Met Phe
    130                 135                 140
Thr Leu Glu Asp Met Leu Leu Gly Tyr Leu Ala Asp Asp Leu Thr Trp
145                 150                 155                 160
Cys Gly Glu Phe Asn Thr Phe Glu Ile Asn Tyr Gln Ser Cys Pro Asp
                    165                 170                 175
Trp Arg Lys Asp Cys Ser Asn Asn Pro Val Ser Val Phe Trp Lys Thr
                180                 185                 190
Val Ser Arg Arg Phe Ala Glu Thr Ala Cys Gly Val Val His Val Met
            195                 200                 205
Leu Asn Gly Ser Arg Ser Lys Ile Phe Asp Lys Asn Ser Thr Phe Gly
210                 215                 220
Ser Val Glu Val His Asn Leu Gln Pro Glu Lys Val Gln Ala Leu Glu
225                 230                 235                 240
Ala Trp Val Ile His Gly Gly Arg Glu Asp Ser Arg Asp Leu Cys Gln
                    245                 250                 255
Asp Pro Thr Ile Lys Glu Leu Glu Ser Ile Ser Lys Arg Asn Ile
                260                 265                 270
Arg Phe Phe Cys Lys Asn Ile Tyr Arg Pro Asp Lys Phe Leu Gln Cys
            275                 280                 285
Val Lys Asn Pro Glu Asp Ser Ser Cys Leu Ser Gly Ile
290                 295                 300

<210> SEQ ID NO 88
<211> LENGTH: 258
<212> TYPE: PRT
<213> ORGANISM: Macaca fasicularis

<400> SEQUENCE: 88

Leu Pro Arg Trp Arg Gln Gln Trp Ser Gly Ser Gly Thr Thr Ser Arg
1               5                   10                  15
Phe Pro Glu Thr Val Leu Ala Arg Cys Val Lys Tyr Thr Glu Val His
                20                  25                  30
Pro Glu Met Arg His Val Asp Cys Gln Ser Val Trp Asp Ala Phe Lys
            35                  40                  45
Gly Ala Phe Ile Ser Lys Tyr Pro Cys Asn Ile Thr Glu Glu Asp Tyr
        50                  55                  60
Gln Pro Leu Val Lys Leu Gly Thr Gln Thr Val Pro Cys Asn Lys Thr
65                  70                  75                  80
Leu Leu Trp Ser Arg Ile Lys Asp Leu Ala His Gln Phe Thr Gln Val
                85                  90                  95
Gln Arg Asp Met Phe Thr Leu Glu Asp Met Leu Leu Gly Tyr Leu Ala
                100                 105                 110
Asp Asp Leu Thr Trp Cys Gly Glu Phe Asn Thr Phe Glu Ile Asn Tyr
            115                 120                 125
Gln Ser Cys Pro Asp Trp Arg Lys Asp Cys Ser Asn Asn Pro Val Ser
        130                 135                 140
Val Phe Trp Lys Thr Val Ser Arg Arg Phe Ala Glu Thr Ala Cys Gly
145                 150                 155                 160
Val Val His Val Met Leu Asn Gly Ser Arg Ser Lys Ile Phe Asp Lys
                165                 170                 175
Asn Ser Thr Phe Gly Ser Val Glu Val His Asn Leu Gln Pro Glu Lys
                180                 185                 190
Val Gln Ala Leu Glu Ala Trp Val Ile His Gly Gly Arg Glu Asp Ser
            195                 200                 205
```

```
Arg Asp Leu Cys Gln Asp Pro Thr Ile Lys Glu Leu Glu Ser Ile Ile
    210                 215                 220
Ser Lys Arg Asn Ile Arg Phe Phe Cys Lys Asn Ile Tyr Arg Pro Asp
225                 230                 235                 240
Lys Phe Leu Gln Cys Val Lys Asn Pro Glu Asp Ser Ser Cys Leu Ser
                245                 250                 255
Gly Ile
```

<210> SEQ ID NO 89

<400> SEQUENCE: 89

000

<210> SEQ ID NO 90

<400> SEQUENCE: 90

000

<210> SEQ ID NO 91

<400> SEQUENCE: 91

000

<210> SEQ ID NO 92

<400> SEQUENCE: 92

000

<210> SEQ ID NO 93

<400> SEQUENCE: 93

000

<210> SEQ ID NO 94

<400> SEQUENCE: 94

000

<210> SEQ ID NO 95

<400> SEQUENCE: 95

000

<210> SEQ ID NO 96

<400> SEQUENCE: 96

000

<210> SEQ ID NO 97

<400> SEQUENCE: 97

000

<210> SEQ ID NO 98

<400> SEQUENCE: 98

000

<210> SEQ ID NO 99

<400> SEQUENCE: 99

000

<210> SEQ ID NO 100

<400> SEQUENCE: 100

000

<210> SEQ ID NO 101
<211> LENGTH: 123
<212> TYPE: PRT
<213> ORGANISM: Artificial Sequence
<220> FEATURE:
<223> OTHER INFORMATION: VH domain

<400> SEQUENCE: 101

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Pro Ser Thr Gly Phe Trp Ser Gly Asn Tyr Phe Asp Tyr
            100                 105                 110

Trp Gly Gln Gly Thr Leu Val Thr Val Ser Ser
        115                 120

<210> SEQ ID NO 102
<211> LENGTH: 8
<212> TYPE: PRT
<213> ORGANISM: Mus musculus

<400> SEQUENCE: 102

Gly Tyr Ser Phe Thr Ser Tyr Trp
1               5

<210> SEQ ID NO 103
<211> LENGTH: 8
<212> TYPE: PRT
<213> ORGANISM: Mus musculus

<400> SEQUENCE: 103

Ile Tyr Pro Gly Asp Ser Asp Thr
1               5

<210> SEQ ID NO 104
<211> LENGTH: 16
<212> TYPE: PRT
<213> ORGANISM: Mus musculus

<400> SEQUENCE: 104

Ala Arg Gly Pro Ser Thr Gly Phe Trp Ser Gly Asn Tyr Phe Asp Tyr
1               5                   10                  15

<210> SEQ ID NO 105
<211> LENGTH: 110
<212> TYPE: PRT
<213> ORGANISM: Artificial Sequence
<220> FEATURE:
<223> OTHER INFORMATION: VL domain

<400> SEQUENCE: 105

Gln Thr Val Val Thr Gln Glu Pro Ser Leu Thr Val Ser Pro Gly Glu
1               5                   10                  15

Thr Val Thr Leu Thr Cys Ala Ser Ser Thr Gly Ala Val Thr Ser Gly
            20                  25                  30

Phe Tyr Pro Asn Trp Phe Gln Gln Lys Pro Gly Gln Ala Pro Arg Ala
        35                  40                  45

Leu Ile Tyr Ala Thr Asn Asn Lys Tyr Ser Trp Thr Pro Ala Arg Phe
    50                  55                  60

Ser Gly Ser Leu Leu Gly Asp Lys Ala Ala Leu Thr Leu Ser Arg Val
65                  70                  75                  80

Gln Pro Glu Asp Glu Ala Asp Tyr Tyr Cys Leu Val Tyr Tyr Asp Gly
                85                  90                  95

Ala Trp Val Phe Gly Gly Gly Thr Lys Leu Thr Val Leu Gly
            100                 105                 110

<210> SEQ ID NO 106
<211> LENGTH: 9
<212> TYPE: PRT
<213> ORGANISM: Mus musculus

<400> SEQUENCE: 106

Thr Gly Ala Val Thr Ser Gly Phe Tyr
1               5

<210> SEQ ID NO 107
<211> LENGTH: 3
<212> TYPE: PRT
<213> ORGANISM: Mus musculus

<400> SEQUENCE: 107

Ala Thr Asn
1

<210> SEQ ID NO 108
<211> LENGTH: 8
<212> TYPE: PRT
<213> ORGANISM: Mus musculus

<400> SEQUENCE: 108

Leu Val Tyr Tyr Asp Gly Ala Trp
1               5

<210> SEQ ID NO 109
<211> LENGTH: 120
<212> TYPE: PRT
<213> ORGANISM: Artificial Sequence
<220> FEATURE:
<223> OTHER INFORMATION: VH domain

<400> SEQUENCE: 109

-continued

```
Glu Val Gln Leu Leu Glu Ser Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu His Ser Asn Tyr Phe Tyr Gly Met Asp Val Trp Gly Gln
            100                 105                 110

Gly Thr Leu Val Thr Val Ser Ser
            115                 120
```

<210> SEQ ID NO 110
<211> LENGTH: 8
<212> TYPE: PRT
<213> ORGANISM: Mus musculus

<400> SEQUENCE: 110

```
Gly Phe Thr Phe Ser Asp Tyr Tyr
1               5
```

<210> SEQ ID NO 111
<211> LENGTH: 8
<212> TYPE: PRT
<213> ORGANISM: Mus musculus

<400> SEQUENCE: 111

```
Ile Ser Gly Ser Gly Gly Ser Thr
1               5
```

<210> SEQ ID NO 112
<211> LENGTH: 13
<212> TYPE: PRT
<213> ORGANISM: Mus musculus

<400> SEQUENCE: 112

```
Ala Arg Glu His Ser Asn Tyr Phe Tyr Gly Met Asp Val
1               5                   10
```

<210> SEQ ID NO 113
<211> LENGTH: 112
<212> TYPE: PRT
<213> ORGANISM: Artificial Sequence
<220> FEATURE:
<223> OTHER INFORMATION: VL domain

<400> SEQUENCE: 113

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Gly Asn Ser Asn Arg Pro Ser Gly Val Pro Asp Arg Phe Ser
50                  55                  60
```

```
Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Tyr Asp Ser Ser Leu
                85                  90                  95

Ser Gly Ser Gly Val Phe Gly Gly Gly Thr Lys Leu Thr Val Leu Gly
            100                 105                 110

<210> SEQ ID NO 114
<211> LENGTH: 8
<212> TYPE: PRT
<213> ORGANISM: Mus musculus

<400> SEQUENCE: 114

Ser Ser Asn Ile Gly Ser Asn Tyr
1               5

<210> SEQ ID NO 115
<211> LENGTH: 3
<212> TYPE: PRT
<213> ORGANISM: Mus musculus

<400> SEQUENCE: 115

Gly Asn Ser
1

<210> SEQ ID NO 116
<211> LENGTH: 11
<212> TYPE: PRT
<213> ORGANISM: Mus musculus

<400> SEQUENCE: 116

Gln Ser Tyr Asp Ser Ser Leu Ser Gly Ser Gly
1               5                   10

<210> SEQ ID NO 117
<211> LENGTH: 119
<212> TYPE: PRT
<213> ORGANISM: Artificial Sequence
<220> FEATURE:
<223> OTHER INFORMATION: VH domain

<400> SEQUENCE: 117

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
        35                  40                  45

Ser Ala Ile Ser Gly Ser Gly Gly Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Glu Thr Ser Phe Gly Leu Asp Val Trp Gly Gln Gly
            100                 105                 110

Thr Leu Val Thr Val Ser Ser
        115

<210> SEQ ID NO 118
<211> LENGTH: 8
```

```
<212> TYPE: PRT
<213> ORGANISM: Mus musculus

<400> SEQUENCE: 118

Gly Phe Thr Phe Ser Ser Tyr Trp
1               5

<210> SEQ ID NO 119
<211> LENGTH: 8
<212> TYPE: PRT
<213> ORGANISM: Mus musculus

<400> SEQUENCE: 119

Ile Ser Gly Ser Gly Gly Gly Thr
1               5

<210> SEQ ID NO 120
<211> LENGTH: 12
<212> TYPE: PRT
<213> ORGANISM: Mus musculus

<400> SEQUENCE: 120

Ala Arg Glu Gly Glu Thr Ser Phe Gly Leu Asp Val
1               5                   10

<210> SEQ ID NO 121
<211> LENGTH: 111
<212> TYPE: PRT
<213> ORGANISM: Artificial Sequence
<220> FEATURE:
<223> OTHER INFORMATION: VL domain

<400> SEQUENCE: 121

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Gly Asn
            20                  25                  30

Tyr Val Tyr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Tyr Asp Ser Ser Leu
                85                  90                  95

Ser Val Ser Val Phe Gly Gly Gly Thr Lys Leu Thr Val Leu Gly
            100                 105                 110

<210> SEQ ID NO 122
<211> LENGTH: 8
<212> TYPE: PRT
<213> ORGANISM: Mus musculus

<400> SEQUENCE: 122

Ser Ser Asn Ile Gly Gly Asn Tyr
1               5

<210> SEQ ID NO 123
<211> LENGTH: 3
<212> TYPE: PRT
<213> ORGANISM: Mus musculus

<400> SEQUENCE: 123
```

Arg Asn Asn
1

<210> SEQ ID NO 124
<211> LENGTH: 10
<212> TYPE: PRT
<213> ORGANISM: Mus musculus

<400> SEQUENCE: 124

Gln Ser Tyr Asp Ser Ser Leu Ser Val Ser
1               5                   10

<210> SEQ ID NO 125
<211> LENGTH: 110
<212> TYPE: PRT
<213> ORGANISM: Artificial Sequence
<220> FEATURE:
<223> OTHER INFORMATION: VL domain

<400> SEQUENCE: 125

Gln Thr Val Val Thr Gln Glu Pro Ser Leu Thr Val Ser Pro Gly Glu
1               5                   10                  15

Thr Val Thr Leu Thr Cys Ala Ser Ser Thr Gly Ala Val Thr Ser Gly
            20                  25                  30

Phe Tyr Pro Asn Trp Phe Gln Gln Lys Pro Gly Gln Ala Pro Arg Ala
        35                  40                  45

Leu Ile Tyr Ala Thr Asn Asn Lys Tyr Ser Trp Thr Pro Ala Arg Phe
    50                  55                  60

Ser Gly Ser Leu Leu Gly Asp Lys Ala Ala Leu Thr Leu Ser Arg Val
65                  70                  75                  80

Gln Pro Glu Asp Glu Ala Asp Tyr Tyr Cys Leu Val Tyr Tyr Asp Gly
                85                  90                  95

Ala Trp Val Phe Gly Gly Gly Thr Lys Leu Thr Val Leu Gly
            100                 105                 110

<210> SEQ ID NO 126
<211> LENGTH: 119
<212> TYPE: PRT
<213> ORGANISM: Artificial Sequence
<220> FEATURE:
<223> OTHER INFORMATION: VH domain

<400> SEQUENCE: 126

Gln Val Gln Leu Gln Glu Ser Gly Pro Gly Leu Val Arg Pro Ser Gln
1               5                   10                  15

Thr Leu Ser Leu Thr Cys Thr Val Ser Gly Phe Ser Leu Thr Ser Tyr
            20                  25                  30

Gly Val His Trp Val Arg Gln Pro Pro Gly Arg Gly Leu Glu Trp Ile
        35                  40                  45

Gly Val Met Trp Arg Gly Gly Ser Thr Asp Tyr Asn Ala Ala Phe Met
    50                  55                  60

Ser Arg Leu Asn Ile Thr Lys Asp Asn Ser Lys Asn Gln Val Ser Leu
65                  70                  75                  80

Arg Leu Ser Ser Val Thr Ala Ala Asp Thr Ala Val Tyr Tyr Cys Ala
                85                  90                  95

Lys Ser Met Ile Thr Thr Gly Phe Val Met Asp Ser Trp Gly Gln Gly
            100                 105                 110

Ser Leu Val Thr Val Ser Ser
            115

```
<210> SEQ ID NO 127
<211> LENGTH: 107
<212> TYPE: PRT
<213> ORGANISM: Artificial Sequence
<220> FEATURE:
<223> OTHER INFORMATION: VL domain

<400> SEQUENCE: 127

Asp Ile Gln Met Thr Gln Ser Pro Ser Ser Leu Ser Ala Ser Val Gly
1               5                   10                  15

Asp Arg Val Thr Ile Thr Cys Lys Ala Ser Glu Asp Ile Tyr Asn Arg
            20                  25                  30

Leu Thr Trp Tyr Gln Gln Lys Pro Gly Lys Ala Pro Lys Leu Leu Ile
        35                  40                  45

Ser Gly Ala Thr Ser Leu Glu Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Trp Ser Asn Pro Tyr
                85                  90                  95

Thr Phe Gly Gln Gly Thr Lys Val Glu Ile Lys
            100                 105

<210> SEQ ID NO 128
<211> LENGTH: 300
<212> TYPE: PRT
<213> ORGANISM: Homo sapiens

<400> SEQUENCE: 128

Met Ala Asn Cys Glu Phe Ser Pro Val Ser Gly Asp Lys Pro Cys Cys
1               5                   10                  15

Arg Leu Ser Arg Arg Ala Gln Leu Cys Leu Gly Val Ser Ile Leu Val
            20                  25                  30

Leu Ile Leu Val Val Val Leu Ala Val Val Val Pro Arg Trp Arg Gln
        35                  40                  45

Gln Trp Ser Gly Pro Gly Thr Thr Lys Arg Phe Pro Glu Thr Val Leu
50                  55                  60

Ala Arg Cys Val Lys Tyr Thr Glu Ile His Pro Glu Met Arg His Val
65                  70                  75                  80

Asp Cys Gln Ser Val Trp Asp Ala Phe Lys Gly Ala Phe Ile Ser Lys
                85                  90                  95

His Pro Cys Asn Ile Thr Glu Glu Asp Tyr Gln Pro Leu Met Lys Leu
            100                 105                 110

Gly Thr Gln Thr Val Pro Cys Asn Lys Ile Leu Leu Trp Ser Arg Ile
        115                 120                 125

Lys Asp Leu Ala His Gln Phe Thr Gln Val Gln Arg Asp Met Phe Thr
130                 135                 140

Leu Glu Asp Thr Leu Leu Gly Tyr Leu Ala Asp Asp Leu Thr Trp Cys
145                 150                 155                 160

Gly Glu Phe Asn Thr Ser Lys Ile Asn Tyr Gln Ser Cys Pro Asp Trp
                165                 170                 175

Arg Lys Asp Cys Ser Asn Asn Pro Val Ser Val Phe Trp Lys Thr Val
            180                 185                 190

Ser Arg Arg Phe Ala Glu Ala Ala Cys Asp Val Val His Val Met Leu
        195                 200                 205
```

```
Asn Gly Ser Arg Ser Lys Ile Phe Asp Lys Asn Ser Thr Phe Gly Ser
    210                 215                 220

Val Glu Val His Asn Leu Gln Pro Glu Lys Val Gln Thr Leu Glu Ala
225                 230                 235                 240

Trp Val Ile His Gly Gly Arg Glu Asp Ser Arg Asp Leu Cys Gln Asp
                245                 250                 255

Pro Thr Ile Lys Glu Leu Glu Ser Ile Ile Ser Lys Arg Asn Ile Gln
            260                 265                 270

Phe Ser Cys Lys Asn Ile Tyr Arg Pro Asp Lys Phe Leu Gln Cys Val
        275                 280                 285

Lys Asn Pro Glu Asp Ser Ser Cys Thr Ser Glu Ile
    290                 295                 300
```

<210> SEQ ID NO 129
<211> LENGTH: 258
<212> TYPE: PRT
<213> ORGANISM: Homo sapiens

<400> SEQUENCE: 129

```
Val Pro Arg Trp Arg Gln Gln Trp Ser Gly Pro Gly Thr Thr Lys Arg
1               5                   10                  15

Phe Pro Glu Thr Val Leu Ala Arg Cys Val Lys Tyr Thr Glu Ile His
                20                  25                  30

Pro Glu Met Arg His Val Asp Cys Gln Ser Val Trp Asp Ala Phe Lys
            35                  40                  45

Gly Ala Phe Ile Ser Lys His Pro Cys Asn Ile Thr Glu Glu Asp Tyr
        50                  55                  60

Gln Pro Leu Met Lys Leu Gly Thr Gln Thr Val Pro Cys Asn Lys Ile
65                  70                  75                  80

Leu Leu Trp Ser Arg Ile Lys Asp Leu Ala His Gln Phe Thr Gln Val
                85                  90                  95

Gln Arg Asp Met Phe Thr Leu Glu Asp Thr Leu Leu Gly Tyr Leu Ala
            100                 105                 110

Asp Asp Leu Thr Trp Cys Gly Glu Phe Asn Thr Ser Lys Ile Asn Tyr
        115                 120                 125

Gln Ser Cys Pro Asp Trp Arg Lys Asp Cys Ser Asn Asn Pro Val Ser
    130                 135                 140

Val Phe Trp Lys Thr Val Ser Arg Arg Phe Ala Glu Ala Ala Cys Asp
145                 150                 155                 160

Val Val His Val Met Leu Asn Gly Ser Arg Ser Lys Ile Phe Asp Lys
                165                 170                 175

Asn Ser Thr Phe Gly Ser Val Glu Val His Asn Leu Gln Pro Glu Lys
            180                 185                 190

Val Gln Thr Leu Glu Ala Trp Val Ile His Gly Gly Arg Glu Asp Ser
        195                 200                 205

Arg Asp Leu Cys Gln Asp Pro Thr Ile Lys Glu Leu Glu Ser Ile Ile
    210                 215                 220

Ser Lys Arg Asn Ile Gln Phe Ser Cys Lys Asn Ile Tyr Arg Pro Asp
225                 230                 235                 240

Lys Phe Leu Gln Cys Val Lys Asn Pro Glu Asp Ser Ser Cys Thr Ser
                245                 250                 255

Glu Ile
```

<210> SEQ ID NO 130
<211> LENGTH: 301

<212> TYPE: PRT
<213> ORGANISM: Macaca fasicularis

<400> SEQUENCE: 130

```
Met Ala Asn Cys Glu Phe Ser Pro Val Ser Gly Asp Lys Pro Cys Cys
1               5                   10                  15

Arg Leu Ser Arg Arg Ala Gln Val Cys Leu Gly Val Cys Leu Leu Val
            20                  25                  30

Leu Leu Ile Leu Val Val Val Ala Val Val Leu Pro Arg Trp Arg
        35                  40                  45

Gln Gln Trp Ser Gly Ser Gly Thr Thr Ser Arg Phe Pro Glu Thr Val
    50                  55                  60

Leu Ala Arg Cys Val Lys Tyr Thr Glu Val His Pro Glu Met Arg His
65              70                  75                  80

Val Asp Cys Gln Ser Val Trp Asp Ala Phe Lys Gly Ala Phe Ile Ser
                85                  90                  95

Lys Tyr Pro Cys Asn Ile Thr Glu Glu Asp Tyr Gln Pro Leu Val Lys
            100                 105                 110

Leu Gly Thr Gln Thr Val Pro Cys Asn Lys Thr Leu Leu Trp Ser Arg
        115                 120                 125

Ile Lys Asp Leu Ala His Gln Phe Thr Gln Val Gln Arg Asp Met Phe
130                 135                 140

Thr Leu Glu Asp Met Leu Leu Gly Tyr Leu Ala Asp Asp Leu Thr Trp
145                 150                 155                 160

Cys Gly Glu Phe Asn Thr Phe Glu Ile Asn Tyr Gln Ser Cys Pro Asp
                165                 170                 175

Trp Arg Lys Asp Cys Ser Asn Asn Pro Val Ser Val Phe Trp Lys Thr
            180                 185                 190

Val Ser Arg Arg Phe Ala Glu Thr Ala Cys Gly Val Val His Val Met
        195                 200                 205

Leu Asn Gly Ser Arg Ser Lys Ile Phe Asp Lys Asn Ser Thr Phe Gly
210                 215                 220

Ser Val Glu Val His Asn Leu Gln Pro Glu Lys Val Gln Ala Leu Glu
225                 230                 235                 240

Ala Trp Val Ile His Gly Gly Arg Glu Asp Ser Arg Asp Leu Cys Gln
                245                 250                 255

Asp Pro Thr Ile Lys Glu Leu Glu Ser Ile Ser Lys Arg Asn Ile
            260                 265                 270

Arg Phe Phe Cys Lys Asn Ile Tyr Arg Pro Asp Lys Phe Leu Gln Cys
        275                 280                 285

Val Lys Asn Pro Glu Asp Ser Ser Cys Leu Ser Gly Ile
290                 295                 300
```

<210> SEQ ID NO 131
<211> LENGTH: 258
<212> TYPE: PRT
<213> ORGANISM: Macaca fasicularis

<400> SEQUENCE: 131

```
Leu Pro Arg Trp Arg Gln Gln Trp Ser Gly Ser Gly Thr Thr Ser Arg
1               5                   10                  15

Phe Pro Glu Thr Val Leu Ala Arg Cys Val Lys Tyr Thr Glu Val His
            20                  25                  30

Pro Glu Met Arg His Val Asp Cys Gln Ser Val Trp Asp Ala Phe Lys
        35                  40                  45
```

```
Gly Ala Phe Ile Ser Lys Tyr Pro Cys Asn Ile Thr Glu Glu Asp Tyr
 50                  55                  60

Gln Pro Leu Val Lys Leu Gly Thr Gln Thr Val Pro Cys Asn Lys Thr
 65                  70                  75                  80

Leu Leu Trp Ser Arg Ile Lys Asp Leu Ala His Gln Phe Thr Gln Val
                 85                  90                  95

Gln Arg Asp Met Phe Thr Leu Glu Asp Met Leu Leu Gly Tyr Leu Ala
            100                 105                 110

Asp Asp Leu Thr Trp Cys Gly Glu Phe Asn Thr Phe Glu Ile Asn Tyr
            115                 120                 125

Gln Ser Cys Pro Asp Trp Arg Lys Asp Cys Ser Asn Asn Pro Val Ser
130                 135                 140

Val Phe Trp Lys Thr Val Ser Arg Arg Phe Ala Glu Thr Ala Cys Gly
145                 150                 155                 160

Val Val His Val Met Leu Asn Gly Ser Arg Ser Lys Ile Phe Asp Lys
                165                 170                 175

Asn Ser Thr Phe Gly Ser Val Glu Val His Asn Leu Gln Pro Glu Lys
            180                 185                 190

Val Gln Ala Leu Glu Ala Trp Val Ile His Gly Gly Arg Glu Asp Ser
            195                 200                 205

Arg Asp Leu Cys Gln Asp Pro Thr Ile Lys Glu Leu Glu Ser Ile Ile
210                 215                 220

Ser Lys Arg Asn Ile Arg Phe Phe Cys Lys Asn Ile Tyr Arg Pro Asp
225                 230                 235                 240

Lys Phe Leu Gln Cys Val Lys Asn Pro Glu Asp Ser Ser Cys Leu Ser
                245                 250                 255

Gly Ile

<210> SEQ ID NO 132
<211> LENGTH: 4
<212> TYPE: PRT
<213> ORGANISM: Unknown
<220> FEATURE:
<223> OTHER INFORMATION: endoplasmic reticulum retention/retrieval
      signal motif

<400> SEQUENCE: 132

Lys Asp Glu Leu
1

<210> SEQ ID NO 133
<211> LENGTH: 4
<212> TYPE: PRT
<213> ORGANISM: Unknown
<220> FEATURE:
<223> OTHER INFORMATION: endoplasmic reticulum retention/retrieval
      signal motif

<400> SEQUENCE: 133

His Asp Glu Phe
1

<210> SEQ ID NO 134
<211> LENGTH: 4
<212> TYPE: PRT
<213> ORGANISM: Unknown
<220> FEATURE:
<223> OTHER INFORMATION: endoplasmic reticulum retention/retrieval
      signal motif

<400> SEQUENCE: 134
```

His Asp Glu Leu
1

<210> SEQ ID NO 135
<211> LENGTH: 4
<212> TYPE: PRT
<213> ORGANISM: Unknown
<220> FEATURE:
<223> OTHER INFORMATION: endoplasmic reticulum retention/retrieval
      signal motif

<400> SEQUENCE: 135

Arg Asp Glu Phe
1

<210> SEQ ID NO 136
<211> LENGTH: 4
<212> TYPE: PRT
<213> ORGANISM: Unknown
<220> FEATURE:
<223> OTHER INFORMATION: endoplasmic reticulum retention/retrieval
      signal motif

<400> SEQUENCE: 136

Arg Asp Glu Leu
1

<210> SEQ ID NO 137
<211> LENGTH: 4
<212> TYPE: PRT
<213> ORGANISM: Unknown
<220> FEATURE:
<223> OTHER INFORMATION: endoplasmic reticulum retention/retrieval
      signal motif

<400> SEQUENCE: 137

Trp Asp Glu Leu
1

<210> SEQ ID NO 138
<211> LENGTH: 4
<212> TYPE: PRT
<213> ORGANISM: Unknown
<220> FEATURE:
<223> OTHER INFORMATION: endoplasmic reticulum retention/retrieval
      signal motif

<400> SEQUENCE: 138

Tyr Asp Glu Leu
1

<210> SEQ ID NO 139
<211> LENGTH: 4
<212> TYPE: PRT
<213> ORGANISM: Unknown
<220> FEATURE:
<223> OTHER INFORMATION: endoplasmic reticulum retention/retrieval
      signal motif

<400> SEQUENCE: 139

His Glu Glu Phe
1

<210> SEQ ID NO 140
<211> LENGTH: 4
<212> TYPE: PRT
<213> ORGANISM: Unknown

```
<220> FEATURE:
<223> OTHER INFORMATION: endoplasmic reticulum retention/retrieval
      signal motif

<400> SEQUENCE: 140

His Glu Glu Leu
1

<210> SEQ ID NO 141
<211> LENGTH: 4
<212> TYPE: PRT
<213> ORGANISM: Unknown
<220> FEATURE:
<223> OTHER INFORMATION: endoplasmic reticulum retention/retrieval
      signal motif

<400> SEQUENCE: 141

Lys Glu Glu Leu
1

<210> SEQ ID NO 142
<211> LENGTH: 4
<212> TYPE: PRT
<213> ORGANISM: Unknown
<220> FEATURE:
<223> OTHER INFORMATION: endoplasmic reticulum retention/retrieval
      signal motif

<400> SEQUENCE: 142

Arg Glu Glu Leu
1

<210> SEQ ID NO 143
<211> LENGTH: 4
<212> TYPE: PRT
<213> ORGANISM: Unknown
<220> FEATURE:
<223> OTHER INFORMATION: endoplasmic reticulum retention/retrieval
      signal motif

<400> SEQUENCE: 143

Lys Ala Glu Leu
1

<210> SEQ ID NO 144
<211> LENGTH: 4
<212> TYPE: PRT
<213> ORGANISM: Unknown
<220> FEATURE:
<223> OTHER INFORMATION: endoplasmic reticulum retention/retrieval
      signal motif

<400> SEQUENCE: 144

Lys Cys Glu Leu
1

<210> SEQ ID NO 145
<211> LENGTH: 4
<212> TYPE: PRT
<213> ORGANISM: Unknown
<220> FEATURE:
<223> OTHER INFORMATION: endoplasmic reticulum retention/retrieval
      signal motif

<400> SEQUENCE: 145

Lys Phe Glu Leu
1
```

<210> SEQ ID NO 146
<211> LENGTH: 4
<212> TYPE: PRT
<213> ORGANISM: Unknown
<220> FEATURE:
<223> OTHER INFORMATION: endoplasmic reticulum retention/retrieval
      signal motif

<400> SEQUENCE: 146

Lys Gly Glu Leu
1

<210> SEQ ID NO 147
<211> LENGTH: 4
<212> TYPE: PRT
<213> ORGANISM: Unknown
<220> FEATURE:
<223> OTHER INFORMATION: endoplasmic reticulum retention/retrieval
      signal motif

<400> SEQUENCE: 147

Lys His Glu Leu
1

<210> SEQ ID NO 148
<211> LENGTH: 4
<212> TYPE: PRT
<213> ORGANISM: Unknown
<220> FEATURE:
<223> OTHER INFORMATION: endoplasmic reticulum retention/retrieval
      signal motif

<400> SEQUENCE: 148

Lys Leu Glu Leu
1

<210> SEQ ID NO 149
<211> LENGTH: 4
<212> TYPE: PRT
<213> ORGANISM: Unknown
<220> FEATURE:
<223> OTHER INFORMATION: endoplasmic reticulum retention/retrieval
      signal motif

<400> SEQUENCE: 149

Lys Asn Glu Leu
1

<210> SEQ ID NO 150
<211> LENGTH: 4
<212> TYPE: PRT
<213> ORGANISM: Unknown
<220> FEATURE:
<223> OTHER INFORMATION: endoplasmic reticulum retention/retrieval
      signal motif

<400> SEQUENCE: 150

Lys Gln Glu Leu
1

<210> SEQ ID NO 151
<211> LENGTH: 4
<212> TYPE: PRT
<213> ORGANISM: Unknown
<220> FEATURE:
<223> OTHER INFORMATION: endoplasmic reticulum retention/retrieval
      signal motif

```
<400> SEQUENCE: 151

Lys Arg Glu Leu
1

<210> SEQ ID NO 152
<211> LENGTH: 4
<212> TYPE: PRT
<213> ORGANISM: Unknown
<220> FEATURE:
<223> OTHER INFORMATION: endoplasmic reticulum retention/retrieval
      signal motif

<400> SEQUENCE: 152

Lys Ser Glu Leu
1

<210> SEQ ID NO 153
<211> LENGTH: 4
<212> TYPE: PRT
<213> ORGANISM: Unknown
<220> FEATURE:
<223> OTHER INFORMATION: endoplasmic reticulum retention/retrieval
      signal motif

<400> SEQUENCE: 153

Lys Val Glu Leu
1

<210> SEQ ID NO 154
<211> LENGTH: 4
<212> TYPE: PRT
<213> ORGANISM: Unknown
<220> FEATURE:
<223> OTHER INFORMATION: endoplasmic reticulum retention/retrieval
      signal motif

<400> SEQUENCE: 154

Lys Trp Glu Leu
1

<210> SEQ ID NO 155
<211> LENGTH: 4
<212> TYPE: PRT
<213> ORGANISM: Unknown
<220> FEATURE:
<223> OTHER INFORMATION: endoplasmic reticulum retention/retrieval
      signal motif

<400> SEQUENCE: 155

Lys Tyr Glu Leu
1

<210> SEQ ID NO 156
<211> LENGTH: 4
<212> TYPE: PRT
<213> ORGANISM: Unknown
<220> FEATURE:
<223> OTHER INFORMATION: endoplasmic reticulum retention/retrieval
      signal motif

<400> SEQUENCE: 156

Lys Glu Asp Leu
1

<210> SEQ ID NO 157
<211> LENGTH: 4
<212> TYPE: PRT
```

-continued

```
<213> ORGANISM: Unknown
<220> FEATURE:
<223> OTHER INFORMATION: endoplasmic reticulum retention/retrieval
      signal motif

<400> SEQUENCE: 157

Lys Ile Glu Leu
1

<210> SEQ ID NO 158
<211> LENGTH: 4
<212> TYPE: PRT
<213> ORGANISM: Unknown
<220> FEATURE:
<223> OTHER INFORMATION: endoplasmic reticulum retention/retrieval
      signal motif

<400> SEQUENCE: 158

Asp Lys Glu Leu
1

<210> SEQ ID NO 159
<211> LENGTH: 4
<212> TYPE: PRT
<213> ORGANISM: Unknown
<220> FEATURE:
<223> OTHER INFORMATION: endoplasmic reticulum retention/retrieval
      signal motif

<400> SEQUENCE: 159

Phe Asp Glu Leu
1

<210> SEQ ID NO 160
<211> LENGTH: 4
<212> TYPE: PRT
<213> ORGANISM: Unknown
<220> FEATURE:
<223> OTHER INFORMATION: endoplasmic reticulum retention/retrieval
      signal motif

<400> SEQUENCE: 160

Lys Asp Glu Phe
1

<210> SEQ ID NO 161
<211> LENGTH: 4
<212> TYPE: PRT
<213> ORGANISM: Unknown
<220> FEATURE:
<223> OTHER INFORMATION: endoplasmic reticulum retention/retrieval
      signal motif

<400> SEQUENCE: 161

Lys Lys Glu Leu
1

<210> SEQ ID NO 162
<211> LENGTH: 4
<212> TYPE: PRT
<213> ORGANISM: Unknown
<220> FEATURE:
<223> OTHER INFORMATION: endoplasmic reticulum retention/retrieval
      signal motif

<400> SEQUENCE: 162

His Ala Asp Leu
1
```

<210> SEQ ID NO 163
<211> LENGTH: 4
<212> TYPE: PRT
<213> ORGANISM: Unknown
<220> FEATURE:
<223> OTHER INFORMATION: endoplasmic reticulum retention/retrieval
       signal motif

<400> SEQUENCE: 163

His Ala Glu Leu
1

<210> SEQ ID NO 164
<211> LENGTH: 4
<212> TYPE: PRT
<213> ORGANISM: Unknown
<220> FEATURE:
<223> OTHER INFORMATION: endoplasmic reticulum retention/retrieval
       signal motif

<400> SEQUENCE: 164

His Ile Glu Leu
1

<210> SEQ ID NO 165
<211> LENGTH: 4
<212> TYPE: PRT
<213> ORGANISM: Unknown
<220> FEATURE:
<223> OTHER INFORMATION: endoplasmic reticulum retention/retrieval
       signal motif

<400> SEQUENCE: 165

His Asn Glu Leu
1

<210> SEQ ID NO 166
<211> LENGTH: 4
<212> TYPE: PRT
<213> ORGANISM: Unknown
<220> FEATURE:
<223> OTHER INFORMATION: endoplasmic reticulum retention/retrieval
       signal motif

<400> SEQUENCE: 166

His Thr Glu Leu
1

<210> SEQ ID NO 167
<211> LENGTH: 4
<212> TYPE: PRT
<213> ORGANISM: Unknown
<220> FEATURE:
<223> OTHER INFORMATION: endoplasmic reticulum retention/retrieval
       signal motif

<400> SEQUENCE: 167

Lys Thr Glu Leu
1

<210> SEQ ID NO 168
<211> LENGTH: 4
<212> TYPE: PRT
<213> ORGANISM: Unknown
<220> FEATURE:
<223> OTHER INFORMATION: endoplasmic reticulum retention/retrieval
       signal motif -continued

```
<400> SEQUENCE: 168

His Val Glu Leu
1

<210> SEQ ID NO 169
<211> LENGTH: 4
<212> TYPE: PRT
<213> ORGANISM: Unknown
<220> FEATURE:
<223> OTHER INFORMATION: endoplasmic reticulum retention/retrieval
      signal motif

<400> SEQUENCE: 169

Asn Asp Glu Leu
1

<210> SEQ ID NO 170
<211> LENGTH: 4
<212> TYPE: PRT
<213> ORGANISM: Unknown
<220> FEATURE:
<223> OTHER INFORMATION: endoplasmic reticulum retention/retrieval
      signal motif

<400> SEQUENCE: 170

Gln Asp Glu Leu
1

<210> SEQ ID NO 171
<211> LENGTH: 4
<212> TYPE: PRT
<213> ORGANISM: Unknown
<220> FEATURE:
<223> OTHER INFORMATION: endoplasmic reticulum retention/retrieval
      signal motif

<400> SEQUENCE: 171

Arg Glu Asp Leu
1

<210> SEQ ID NO 172
<211> LENGTH: 4
<212> TYPE: PRT
<213> ORGANISM: Unknown
<220> FEATURE:
<223> OTHER INFORMATION: endoplasmic reticulum retention/retrieval
      signal motif

<400> SEQUENCE: 172

Arg Asn Glu Leu
1

<210> SEQ ID NO 173
<211> LENGTH: 4
<212> TYPE: PRT
<213> ORGANISM: Unknown
<220> FEATURE:
<223> OTHER INFORMATION: endoplasmic reticulum retention/retrieval
      signal motif

<400> SEQUENCE: 173

Arg Thr Asp Leu
1

<210> SEQ ID NO 174
<211> LENGTH: 4
```

```
<212> TYPE: PRT
<213> ORGANISM: Unknown
<220> FEATURE:
<223> OTHER INFORMATION: endoplasmic reticulum retention/retrieval
      signal motif

<400> SEQUENCE: 174

Arg Thr Glu Leu
1

<210> SEQ ID NO 175
<211> LENGTH: 4
<212> TYPE: PRT
<213> ORGANISM: Unknown
<220> FEATURE:
<223> OTHER INFORMATION: endoplasmic reticulum retention/retrieval
      signal motif

<400> SEQUENCE: 175

Ser Asp Glu Leu
1

<210> SEQ ID NO 176
<211> LENGTH: 4
<212> TYPE: PRT
<213> ORGANISM: Unknown
<220> FEATURE:
<223> OTHER INFORMATION: endoplasmic reticulum retention/retrieval
      signal motif

<400> SEQUENCE: 176

Thr Asp Glu Leu
1

<210> SEQ ID NO 177
<211> LENGTH: 4
<212> TYPE: PRT
<213> ORGANISM: Unknown
<220> FEATURE:
<223> OTHER INFORMATION: endoplasmic reticulum retention/retrieval
      signal motif

<400> SEQUENCE: 177

Ser Lys Glu Leu
1

<210> SEQ ID NO 178
<211> LENGTH: 4
<212> TYPE: PRT
<213> ORGANISM: Unknown
<220> FEATURE:
<223> OTHER INFORMATION: endoplasmic reticulum retention/retrieval
      signal motif

<400> SEQUENCE: 178

Ser Thr Glu Leu
1

<210> SEQ ID NO 179
<211> LENGTH: 4
<212> TYPE: PRT
<213> ORGANISM: Unknown
<220> FEATURE:
<223> OTHER INFORMATION: endoplasmic reticulum retention/retrieval
      signal motif

<400> SEQUENCE: 179

Glu Asp Glu Leu
```

```
<210> SEQ ID NO 180
<211> LENGTH: 4
<212> TYPE: PRT
<213> ORGANISM: Artificial Sequence
<220> FEATURE:
<223> OTHER INFORMATION: Furin cleavage motif
<220> FEATURE:
<221> NAME/KEY: MISC_FEATURE
<222> LOCATION: (1)..(1)
<223> OTHER INFORMATION: Xaa is Arg or Tyr
<220> FEATURE:
<221> NAME/KEY: MISC_FEATURE
<222> LOCATION: (2)..(3)
<223> OTHER INFORMATION: Xaa can be any naturally occurring amino acid

<400> SEQUENCE: 180

Xaa Xaa Xaa Arg
1

<210> SEQ ID NO 181
<211> LENGTH: 4
<212> TYPE: PRT
<213> ORGANISM: Artificial Sequence
<220> FEATURE:
<223> OTHER INFORMATION: Furin cleavage motif
<220> FEATURE:
<221> NAME/KEY: MISC_FEATURE
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa is Arg, Lys or any naturally occurring
      amino acid

<400> SEQUENCE: 181

Arg Xaa Xaa Arg
1

<210> SEQ ID NO 182
<211> LENGTH: 5
<212> TYPE: PRT
<213> ORGANISM: Artificial Sequence
<220> FEATURE:
<223> OTHER INFORMATION: Furin cleavage motif
<220> FEATURE:
<221> NAME/KEY: MISC_FEATURE
<222> LOCATION: (2)..(2)
<223> OTHER INFORMATION: Xaa is Arg or Tyr
<220> FEATURE:
<221> NAME/KEY: MISC_FEATURE
<222> LOCATION: (3)..(4)
<223> OTHER INFORMATION: Xaa can be any naturally occurring amino acid

<400> SEQUENCE: 182

Ser Xaa Xaa Xaa Arg
1               5

<210> SEQ ID NO 183
<211> LENGTH: 4
<212> TYPE: PRT
<213> ORGANISM: Artificial Sequence
<220> FEATURE:
<223> OTHER INFORMATION: Furin cleavage motif
<220> FEATURE:
<221> NAME/KEY: MISC_FEATURE
<222> LOCATION: (2)..(3)
<223> OTHER INFORMATION: Xaa can be any naturally occurring amino acid

<400> SEQUENCE: 183
```

Arg Xaa Xaa Arg
1

<210> SEQ ID NO 184
<211> LENGTH: 16
<212> TYPE: PRT
<213> ORGANISM: Artificial Sequence
<220> FEATURE:
<223> OTHER INFORMATION: scFv linker

<400> SEQUENCE: 184

Gly Gly Gly Ser Gly Gly Gly Ser Gly Gly Gly Ser Gly Gly Gly Ser
1               5                   10                  15

<210> SEQ ID NO 185
<211> LENGTH: 4
<212> TYPE: PRT
<213> ORGANISM: Artificial Sequence
<220> FEATURE:
<223> OTHER INFORMATION: scFv linker

<400> SEQUENCE: 185

Gly Gly Gly Ser
1

<210> SEQ ID NO 186
<211> LENGTH: 5
<212> TYPE: PRT
<213> ORGANISM: Artificial Sequence
<220> FEATURE:
<223> OTHER INFORMATION: scFv linker

<400> SEQUENCE: 186

Gly Gly Gly Gly Ser
1               5

<210> SEQ ID NO 187
<211> LENGTH: 8
<212> TYPE: PRT
<213> ORGANISM: Artificial Sequence
<220> FEATURE:
<223> OTHER INFORMATION: scFv linker

<400> SEQUENCE: 187

Gly Gly Gly Gly Ser Gly Gly Gly
1               5

<210> SEQ ID NO 188
<211> LENGTH: 7
<212> TYPE: PRT
<213> ORGANISM: Artificial Sequence
<220> FEATURE:
<223> OTHER INFORMATION: scFv linker

<400> SEQUENCE: 188

Gly Gly Ser Gly Gly Gly Gly
1               5

<210> SEQ ID NO 189
<211> LENGTH: 18
<212> TYPE: PRT
<213> ORGANISM: Artificial Sequence
<220> FEATURE:
<223> OTHER INFORMATION: scFv linker

<400> SEQUENCE: 189

```
Gly Ser Thr Ser Gly Gly Gly Ser Gly Gly Gly Ser Gly Gly Gly Gly
1               5                   10                  15
Ser Ser

<210> SEQ ID NO 190
<211> LENGTH: 4
<212> TYPE: PRT
<213> ORGANISM: Artificial Sequence
<220> FEATURE:
<223> OTHER INFORMATION: Synthetic inhibitor of furin

<400> SEQUENCE: 190

Arg Val Lys Arg
1

<210> SEQ ID NO 191
<211> LENGTH: 4
<212> TYPE: PRT
<213> ORGANISM: Artificial Sequence
<220> FEATURE:
<223> OTHER INFORMATION: Furin cleavage motif
<220> FEATURE:
<221> NAME/KEY: MISC_FEATURE
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa is Lys or Arg

<400> SEQUENCE: 191

Arg Xaa Xaa Arg
1

<210> SEQ ID NO 192
<211> LENGTH: 4
<212> TYPE: PRT
<213> ORGANISM: Artificial Sequence
<220> FEATURE:
<223> OTHER INFORMATION: Furin cleavage motif
<220> FEATURE:
<221> NAME/KEY: MISC_FEATURE
<222> LOCATION: (1)..(4)
<223> OTHER INFORMATION: Xaa can be any naturally occurring amino acid

<400> SEQUENCE: 192

Xaa Xaa Xaa Xaa
1

<210> SEQ ID NO 193
<211> LENGTH: 2
<212> TYPE: PRT
<213> ORGANISM: Artificial Sequence
<220> FEATURE:
<223> OTHER INFORMATION: scFv linker

<400> SEQUENCE: 193

Gly Ser
1

<210> SEQ ID NO 194
<211> LENGTH: 10
<212> TYPE: PRT
<213> ORGANISM: Artificial Sequence
<220> FEATURE:
<223> OTHER INFORMATION: scFv linker

<400> SEQUENCE: 194
```

```
Gly Ser Gly Gly Ser Gly Ser Gly Gly Ser
1               5                   10
```

<210> SEQ ID NO 195
<211> LENGTH: 15
<212> TYPE: PRT
<213> ORGANISM: Artificial Sequence
<220> FEATURE:
<223> OTHER INFORMATION: scFv linker

<400> SEQUENCE: 195

```
Gly Gly Gly Gly Ser Gly Gly Gly Ser Gly Gly Gly Gly Ser
1               5                   10                  15
```

<210> SEQ ID NO 196
<211> LENGTH: 16
<212> TYPE: PRT
<213> ORGANISM: Artificial Sequence
<220> FEATURE:
<223> OTHER INFORMATION: scFv linker

<400> SEQUENCE: 196

```
Gly Gly Gly Ser Gly Gly Gly Ser Gly Gly Gly Ser Gly Gly Gly Ser
1               5                   10                  15
```

<210> SEQ ID NO 197
<211> LENGTH: 6
<212> TYPE: PRT
<213> ORGANISM: Artificial Sequence
<220> FEATURE:
<223> OTHER INFORMATION: proteinaceous linker

<400> SEQUENCE: 197

```
Ala Ser Gly Gly Pro Glu
1               5
```

<210> SEQ ID NO 198
<211> LENGTH: 54
<212> TYPE: PRT
<213> ORGANISM: Artificial Sequence
<220> FEATURE:
<223> OTHER INFORMATION: proteinaceous linker
<220> FEATURE:
<221> NAME/KEY: MISC_FEATURE
<222> LOCATION: (5)..(6)
<223> OTHER INFORMATION: Up to 2 residues may be absent
<220> FEATURE:
<221> NAME/KEY: MISC_FEATURE
<222> LOCATION: (7)..(12)
<223> OTHER INFORMATION: May be absent
<220> FEATURE:
<221> NAME/KEY: MISC_FEATURE
<222> LOCATION: (10)..(11)
<223> OTHER INFORMATION: Up to 2 residues may be absent
<220> FEATURE:
<221> NAME/KEY: MISC_FEATURE
<222> LOCATION: (13)..(17)
<223> OTHER INFORMATION: May be absent
<220> FEATURE:
<221> NAME/KEY: MISC_FEATURE
<222> LOCATION: (15)..(16)
<223> OTHER INFORMATION: Up to 2 residues may be absent
<220> FEATURE:
<221> NAME/KEY: MISC_FEATURE
<222> LOCATION: (18)..(22)
<223> OTHER INFORMATION: May be absent
<220> FEATURE:
<221> NAME/KEY: MISC_FEATURE
<222> LOCATION: (20)..(21)
<223> OTHER INFORMATION: Up to 2 residues may be absent
<220> FEATURE:
<221> NAME/KEY: MISC_FEATURE

```
<222> LOCATION: (23)..(27)
<223> OTHER INFORMATION: May be absent
<220> FEATURE:
<221> NAME/KEY: MISC_FEATURE
<222> LOCATION: (25)..(26)
<223> OTHER INFORMATION: Up to 2 residues may be absent
<220> FEATURE:
<221> NAME/KEY: MISC_FEATURE
<222> LOCATION: (28)..(32)
<223> OTHER INFORMATION: May be absent
<220> FEATURE:
<221> NAME/KEY: MISC_FEATURE
<222> LOCATION: (30)..(31)
<223> OTHER INFORMATION: Up to 2 residues may be absent
<220> FEATURE:
<221> NAME/KEY: MISC_FEATURE
<222> LOCATION: (33)..(37)
<223> OTHER INFORMATION: May be absent
<220> FEATURE:
<221> NAME/KEY: MISC_FEATURE
<222> LOCATION: (35)..(36)
<223> OTHER INFORMATION: Up to 2 residues may be absent
<220> FEATURE:
<221> NAME/KEY: MISC_FEATURE
<222> LOCATION: (38)..(42)
<223> OTHER INFORMATION: May be absent
<220> FEATURE:
<221> NAME/KEY: MISC_FEATURE
<222> LOCATION: (40)..(41)
<223> OTHER INFORMATION: Up to 2 residues may be absent
<220> FEATURE:
<221> NAME/KEY: MISC_FEATURE
<222> LOCATION: (43)..(47)
<223> OTHER INFORMATION: May be absent
<220> FEATURE:
<221> NAME/KEY: MISC_FEATURE
<222> LOCATION: (45)..(46)
<223> OTHER INFORMATION: Up to 2 residues may be absent
<220> FEATURE:
<221> NAME/KEY: MISC_FEATURE
<222> LOCATION: (48)..(52)
<223> OTHER INFORMATION: May be absent
<220> FEATURE:
<221> NAME/KEY: MISC_FEATURE
<222> LOCATION: (50)..(51)
<223> OTHER INFORMATION: Up to 2 residues may be absent

<400> SEQUENCE: 198

Ala Met Gly Gly Gly Gly Ser Gly Gly Gly Gly Ser Gly Gly Gly Gly
1               5                   10                  15

Ser Gly Gly Gly Gly Ser Gly Gly Gly Gly Ser Gly Gly Gly Gly Ser
            20                  25                  30

Gly Gly Gly Gly Ser Gly Gly Gly Gly Ser Gly Gly Gly Gly Ser Gly
        35                  40                  45

Gly Gly Gly Ser Ala Met
    50

<210> SEQ ID NO 199
<211> LENGTH: 210
<212> TYPE: PRT
<213> ORGANISM: Artificial Sequence
<220> FEATURE:
<223> OTHER INFORMATION: proteinaceous linker
<220> FEATURE:
<221> NAME/KEY: MISC_FEATURE
<222> LOCATION: (2)..(6)
<223> OTHER INFORMATION: Up to 5 residues may be absent
<220> FEATURE:
<221> NAME/KEY: MISC_FEATURE
<222> LOCATION: (8)..(14)
<223> OTHER INFORMATION: May be absent
<220> FEATURE:
<221> NAME/KEY: MISC_FEATURE
<222> LOCATION: (9)..(13)
```

```
<223> OTHER INFORMATION: Up to 5 residues may be absent
<220> FEATURE:
<221> NAME/KEY: MISC_FEATURE
<222> LOCATION: (15)..(21)
<223> OTHER INFORMATION: May be absent
<220> FEATURE:
<221> NAME/KEY: MISC_FEATURE
<222> LOCATION: (16)..(20)
<223> OTHER INFORMATION: Up to 5 residues may be absent
<220> FEATURE:
<221> NAME/KEY: MISC_FEATURE
<222> LOCATION: (22)..(28)
<223> OTHER INFORMATION: May be absent
<220> FEATURE:
<221> NAME/KEY: MISC_FEATURE
<222> LOCATION: (23)..(27)
<223> OTHER INFORMATION: Up to 5 residues may be absent
<220> FEATURE:
<221> NAME/KEY: MISC_FEATURE
<222> LOCATION: (29)..(35)
<223> OTHER INFORMATION: May be absent
<220> FEATURE:
<221> NAME/KEY: MISC_FEATURE
<222> LOCATION: (30)..(34)
<223> OTHER INFORMATION: Up to 5 residues may be absent
<220> FEATURE:
<221> NAME/KEY: MISC_FEATURE
<222> LOCATION: (36)..(42)
<223> OTHER INFORMATION: May be absent
<220> FEATURE:
<221> NAME/KEY: MISC_FEATURE
<222> LOCATION: (37)..(41)
<223> OTHER INFORMATION: Up to 5 residues may be absent
<220> FEATURE:
<221> NAME/KEY: MISC_FEATURE
<222> LOCATION: (43)..(49)
<223> OTHER INFORMATION: May be absent
<220> FEATURE:
<221> NAME/KEY: MISC_FEATURE
<222> LOCATION: (42)..(48)
<223> OTHER INFORMATION: Up to 5 residues may be absent
<220> FEATURE:
<221> NAME/KEY: MISC_FEATURE
<222> LOCATION: (50)..(56)
<223> OTHER INFORMATION: May be absent
<220> FEATURE:
<221> NAME/KEY: MISC_FEATURE
<222> LOCATION: (51)..(55)
<223> OTHER INFORMATION: Up to 5 residues may be absent
<220> FEATURE:
<221> NAME/KEY: MISC_FEATURE
<222> LOCATION: (57)..(63)
<223> OTHER INFORMATION: May be absent
<220> FEATURE:
<221> NAME/KEY: MISC_FEATURE
<222> LOCATION: (58)..(61)
<223> OTHER INFORMATION: Up to 5 residues may be absent
<220> FEATURE:
<221> NAME/KEY: MISC_FEATURE
<222> LOCATION: (64)..(70)
<223> OTHER INFORMATION: May be absent
<220> FEATURE:
<221> NAME/KEY: MISC_FEATURE
<222> LOCATION: (65)..(69)
<223> OTHER INFORMATION: Up to 5 residues may be absent
<220> FEATURE:
<221> NAME/KEY: MISC_FEATURE
<222> LOCATION: (71)..(77)
<223> OTHER INFORMATION: May be absent
<220> FEATURE:
<221> NAME/KEY: MISC_FEATURE
<222> LOCATION: (72)..(76)
<223> OTHER INFORMATION: Up to 5 residues may be absent
<220> FEATURE:
<221> NAME/KEY: MISC_FEATURE
<222> LOCATION: (78)..(84)
<223> OTHER INFORMATION: May be absent
<220> FEATURE:
<221> NAME/KEY: MISC_FEATURE
```

```
<222> LOCATION: (79)..(83)
<223> OTHER INFORMATION: Up to 5 residues may be absent
<220> FEATURE:
<221> NAME/KEY: MISC_FEATURE
<222> LOCATION: (85)..(91)
<223> OTHER INFORMATION: May be absent
<220> FEATURE:
<221> NAME/KEY: MISC_FEATURE
<222> LOCATION: (86)..(90)
<223> OTHER INFORMATION: Up to 5 residues may be absent
<220> FEATURE:
<221> NAME/KEY: MISC_FEATURE
<222> LOCATION: (92)..(98)
<223> OTHER INFORMATION: May be absent
<220> FEATURE:
<221> NAME/KEY: MISC_FEATURE
<222> LOCATION: (93)..(97)
<223> OTHER INFORMATION: Up to 5 residues may be absent
<220> FEATURE:
<221> NAME/KEY: MISC_FEATURE
<222> LOCATION: (99)..(105)
<223> OTHER INFORMATION: May be absent
<220> FEATURE:
<221> NAME/KEY: MISC_FEATURE
<222> LOCATION: (100)..(104)
<223> OTHER INFORMATION: Up to 5 residues may be absent
<220> FEATURE:
<221> NAME/KEY: MISC_FEATURE
<222> LOCATION: (106)..(112)
<223> OTHER INFORMATION: May be absent
<220> FEATURE:
<221> NAME/KEY: MISC_FEATURE
<222> LOCATION: (107)..(111)
<223> OTHER INFORMATION: Up to 5 residues may be absent
<220> FEATURE:
<221> NAME/KEY: MISC_FEATURE
<222> LOCATION: (113)..(119)
<223> OTHER INFORMATION: May be absent
<220> FEATURE:
<221> NAME/KEY: MISC_FEATURE
<222> LOCATION: (114)..(118)
<223> OTHER INFORMATION: Up to 5 residues may be absent
<220> FEATURE:
<221> NAME/KEY: MISC_FEATURE
<222> LOCATION: (120)..(126)
<223> OTHER INFORMATION: May be absent
<220> FEATURE:
<221> NAME/KEY: MISC_FEATURE
<222> LOCATION: (121)..(125)
<223> OTHER INFORMATION: Up to 5 residues may be absent
<220> FEATURE:
<221> NAME/KEY: MISC_FEATURE
<222> LOCATION: (127)..(133)
<223> OTHER INFORMATION: May be absent
<220> FEATURE:
<221> NAME/KEY: MISC_FEATURE
<222> LOCATION: (128)..(132)
<223> OTHER INFORMATION: Up to 5 residues may be absent
<220> FEATURE:
<221> NAME/KEY: MISC_FEATURE
<222> LOCATION: (134)..(140)
<223> OTHER INFORMATION: May be absent
<220> FEATURE:
<221> NAME/KEY: MISC_FEATURE
<222> LOCATION: (135)..(139)
<223> OTHER INFORMATION: Up to 5 residues may be absent
<220> FEATURE:
<221> NAME/KEY: MISC_FEATURE
<222> LOCATION: (141)..(147)
<223> OTHER INFORMATION: May be absent
<220> FEATURE:
<221> NAME/KEY: MISC_FEATURE
<222> LOCATION: (142)..(146)
<223> OTHER INFORMATION: Up to 5 residues may be absent
<220> FEATURE:
<221> NAME/KEY: MISC_FEATURE
<222> LOCATION: (148)..(154)
<223> OTHER INFORMATION: May be absent
<220> FEATURE:
```

```
<221> NAME/KEY: MISC_FEATURE
<222> LOCATION: (149)..(153)
<223> OTHER INFORMATION: Up to 5 residues may be absent
<220> FEATURE:
<221> NAME/KEY: MISC_FEATURE
<222> LOCATION: (155)..(161)
<223> OTHER INFORMATION: May be absent
<220> FEATURE:
<221> NAME/KEY: MISC_FEATURE
<222> LOCATION: (156)..(160)
<223> OTHER INFORMATION: Up to 5 residues may be absent
<220> FEATURE:
<221> NAME/KEY: MISC_FEATURE
<222> LOCATION: (162)..(168)
<223> OTHER INFORMATION: May be absent
<220> FEATURE:
<221> NAME/KEY: MISC_FEATURE
<222> LOCATION: (163)..(167)
<223> OTHER INFORMATION: Up to 5 residues may be absent
<220> FEATURE:
<221> NAME/KEY: MISC_FEATURE
<222> LOCATION: (169)..(175)
<223> OTHER INFORMATION: May be absent
<220> FEATURE:
<221> NAME/KEY: MISC_FEATURE
<222> LOCATION: (170)..(174)
<223> OTHER INFORMATION: Up to 5 residues may be absent
<220> FEATURE:
<221> NAME/KEY: MISC_FEATURE
<222> LOCATION: (176)..(182)
<223> OTHER INFORMATION: May be absent
<220> FEATURE:
<221> NAME/KEY: MISC_FEATURE
<222> LOCATION: (177)..(181)
<223> OTHER INFORMATION: Up to 5 residues may be absent
<220> FEATURE:
<221> NAME/KEY: MISC_FEATURE
<222> LOCATION: (183)..(189)
<223> OTHER INFORMATION: May be absent
<220> FEATURE:
<221> NAME/KEY: MISC_FEATURE
<222> LOCATION: (184)..(188)
<223> OTHER INFORMATION: Up to 5 residues may be absent
<220> FEATURE:
<221> NAME/KEY: MISC_FEATURE
<222> LOCATION: (190)..(196)
<223> OTHER INFORMATION: May be absent
<220> FEATURE:
<221> NAME/KEY: MISC_FEATURE
<222> LOCATION: (191)..(195)
<223> OTHER INFORMATION: Up to 5 residues may be absent
<220> FEATURE:
<221> NAME/KEY: MISC_FEATURE
<222> LOCATION: (197)..(203)
<223> OTHER INFORMATION: May be absent
<220> FEATURE:
<221> NAME/KEY: MISC_FEATURE
<222> LOCATION: (198)..(202)
<223> OTHER INFORMATION: Up to 5 residues may be absent
<220> FEATURE:
<221> NAME/KEY: MISC_FEATURE
<222> LOCATION: (204)..(210)
<223> OTHER INFORMATION: May be absent
<220> FEATURE:
<221> NAME/KEY: MISC_FEATURE
<222> LOCATION: (205)..(209)
<223> OTHER INFORMATION: Up to 5 residues may be absent

<400> SEQUENCE: 199

Gly Gly Gly Gly Gly Gly Ser Gly Gly Gly Gly Gly Ser Gly Gly
1               5                   10                  15

Gly Gly Gly Gly Ser Gly Gly Gly Gly Gly Ser Gly Gly Gly Gly
                20                  25                  30

Gly Gly Ser Gly Gly Gly Gly Gly Gly Ser Gly Gly Gly Gly Gly
            35                  40                  45
```

```
Ser Gly Gly Gly Gly Gly Ser Gly Gly Gly Gly Gly Ser Gly
 50                  55                  60
Gly Gly Gly Gly Gly Ser Gly Gly Gly Gly Gly Ser Gly Gly
 65                  70                  75                  80
Gly Gly Gly Ser Gly Gly Gly Gly Gly Ser Gly Gly Gly Gly
                 85                  90                  95
Gly Ser Gly Gly Gly Gly Gly Ser Gly Gly Gly Gly Gly Ser
        100                 105                 110
Gly Gly Gly Gly Gly Ser Gly Gly Gly Gly Gly Ser Gly Gly
            115                 120                 125
Gly Gly Gly Ser Gly Gly Gly Gly Gly Ser Gly Gly Gly Gly
        130                 135                 140
Gly Gly Ser Gly Gly Gly Gly Gly Ser Gly Gly Gly Gly Gly
145                 150                 155                 160
Ser Gly Gly Gly Gly Gly Ser Gly Gly Gly Gly Gly Ser Gly
            165                 170                 175
Gly Gly Gly Gly Gly Ser Gly Gly Gly Gly Gly Ser Gly Gly
        180                 185                 190
Gly Gly Gly Ser Gly Gly Gly Gly Gly Ser Gly Gly Gly Gly
    195                 200                 205
Gly Ser
    210

<210> SEQ ID NO 200
<211> LENGTH: 210
<212> TYPE: PRT
<213> ORGANISM: Artificial Sequence
<220> FEATURE:
<223> OTHER INFORMATION: proteinaceous linker
<220> FEATURE:
<221> NAME/KEY: MISC_FEATURE
<222> LOCATION: (2)..(6)
<223> OTHER INFORMATION: Up to 5 residues may be absent
<220> FEATURE:
<221> NAME/KEY: MISC_FEATURE
<222> LOCATION: (8)..(14)
<223> OTHER INFORMATION: May be absent
<220> FEATURE:
<221> NAME/KEY: MISC_FEATURE
<222> LOCATION: (9)..(13)
<223> OTHER INFORMATION: Up to 5 residues may be absent
<220> FEATURE:
<221> NAME/KEY: MISC_FEATURE
<222> LOCATION: (15)..(21)
<223> OTHER INFORMATION: May be absent
<220> FEATURE:
<221> NAME/KEY: MISC_FEATURE
<222> LOCATION: (16)..(20)
<223> OTHER INFORMATION: Up to 5 residues may be absent
<220> FEATURE:
<221> NAME/KEY: MISC_FEATURE
<222> LOCATION: (22)..(28)
<223> OTHER INFORMATION: May be absent
<220> FEATURE:
<221> NAME/KEY: MISC_FEATURE
<222> LOCATION: (23)..(27)
<223> OTHER INFORMATION: Up to 5 residues may be absent
<220> FEATURE:
<221> NAME/KEY: MISC_FEATURE
<222> LOCATION: (29)..(35)
<223> OTHER INFORMATION: May be absent
<220> FEATURE:
<221> NAME/KEY: MISC_FEATURE
<222> LOCATION: (30)..(34)
<223> OTHER INFORMATION: Up to 5 residues may be absent
<220> FEATURE:
<221> NAME/KEY: MISC_FEATURE
<222> LOCATION: (36)..(42)
```

```
<223> OTHER INFORMATION: May be absent
<220> FEATURE:
<221> NAME/KEY: MISC_FEATURE
<222> LOCATION: (37)..(41)
<223> OTHER INFORMATION: Up to 5 residues may be absent
<220> FEATURE:
<221> NAME/KEY: MISC_FEATURE
<222> LOCATION: (43)..(49)
<223> OTHER INFORMATION: May be absent
<220> FEATURE:
<221> NAME/KEY: MISC_FEATURE
<222> LOCATION: (42)..(48)
<223> OTHER INFORMATION: Up to 5 residues may be absent
<220> FEATURE:
<221> NAME/KEY: MISC_FEATURE
<222> LOCATION: (50)..(56)
<223> OTHER INFORMATION: May be absent
<220> FEATURE:
<221> NAME/KEY: MISC_FEATURE
<222> LOCATION: (51)..(55)
<223> OTHER INFORMATION: Up to 5 residues may be absent
<220> FEATURE:
<221> NAME/KEY: MISC_FEATURE
<222> LOCATION: (57)..(63)
<223> OTHER INFORMATION: May be absent
<220> FEATURE:
<221> NAME/KEY: MISC_FEATURE
<222> LOCATION: (58)..(61)
<223> OTHER INFORMATION: Up to 5 residues may be absent
<220> FEATURE:
<221> NAME/KEY: MISC_FEATURE
<222> LOCATION: (64)..(70)
<223> OTHER INFORMATION: May be absent
<220> FEATURE:
<221> NAME/KEY: MISC_FEATURE
<222> LOCATION: (65)..(69)
<223> OTHER INFORMATION: Up to 5 residues may be absent
<220> FEATURE:
<221> NAME/KEY: MISC_FEATURE
<222> LOCATION: (71)..(77)
<223> OTHER INFORMATION: May be absent
<220> FEATURE:
<221> NAME/KEY: MISC_FEATURE
<222> LOCATION: (72)..(76)
<223> OTHER INFORMATION: Up to 5 residues may be absent
<220> FEATURE:
<221> NAME/KEY: MISC_FEATURE
<222> LOCATION: (78)..(84)
<223> OTHER INFORMATION: May be absent
<220> FEATURE:
<221> NAME/KEY: MISC_FEATURE
<222> LOCATION: (79)..(83)
<223> OTHER INFORMATION: Up to 5 residues may be absent
<220> FEATURE:
<221> NAME/KEY: MISC_FEATURE
<222> LOCATION: (85)..(91)
<223> OTHER INFORMATION: May be absent
<220> FEATURE:
<221> NAME/KEY: MISC_FEATURE
<222> LOCATION: (86)..(90)
<223> OTHER INFORMATION: Up to 5 residues may be absent
<220> FEATURE:
<221> NAME/KEY: MISC_FEATURE
<222> LOCATION: (92)..(98)
<223> OTHER INFORMATION: May be absent
<220> FEATURE:
<221> NAME/KEY: MISC_FEATURE
<222> LOCATION: (93)..(97)
<223> OTHER INFORMATION: Up to 5 residues may be absent
<220> FEATURE:
<221> NAME/KEY: MISC_FEATURE
<222> LOCATION: (99)..(105)
<223> OTHER INFORMATION: May be absent
<220> FEATURE:
<221> NAME/KEY: MISC_FEATURE
<222> LOCATION: (100)..(104)
<223> OTHER INFORMATION: Up to 5 residues may be absent
<220> FEATURE:
<221> NAME/KEY: MISC_FEATURE
```

```
<222> LOCATION: (106)..(112)
<223> OTHER INFORMATION: May be absent
<220> FEATURE:
<221> NAME/KEY: MISC_FEATURE
<222> LOCATION: (107)..(111)
<223> OTHER INFORMATION: Up to 5 residues may be absent
<220> FEATURE:
<221> NAME/KEY: MISC_FEATURE
<222> LOCATION: (113)..(119)
<223> OTHER INFORMATION: May be absent
<220> FEATURE:
<221> NAME/KEY: MISC_FEATURE
<222> LOCATION: (114)..(118)
<223> OTHER INFORMATION: Up to 5 residues may be absent
<220> FEATURE:
<221> NAME/KEY: MISC_FEATURE
<222> LOCATION: (120)..(126)
<223> OTHER INFORMATION: May be absent
<220> FEATURE:
<221> NAME/KEY: MISC_FEATURE
<222> LOCATION: (121)..(125)
<223> OTHER INFORMATION: Up to 5 residues may be absent
<220> FEATURE:
<221> NAME/KEY: MISC_FEATURE
<222> LOCATION: (127)..(133)
<223> OTHER INFORMATION: May be absent
<220> FEATURE:
<221> NAME/KEY: MISC_FEATURE
<222> LOCATION: (128)..(132)
<223> OTHER INFORMATION: Up to 5 residues may be absent
<220> FEATURE:
<221> NAME/KEY: MISC_FEATURE
<222> LOCATION: (134)..(140)
<223> OTHER INFORMATION: May be absent
<220> FEATURE:
<221> NAME/KEY: MISC_FEATURE
<222> LOCATION: (135)..(139)
<223> OTHER INFORMATION: Up to 5 residues may be absent
<220> FEATURE:
<221> NAME/KEY: MISC_FEATURE
<222> LOCATION: (141)..(147)
<223> OTHER INFORMATION: May be absent
<220> FEATURE:
<221> NAME/KEY: MISC_FEATURE
<222> LOCATION: (142)..(146)
<223> OTHER INFORMATION: Up to 5 residues may be absent
<220> FEATURE:
<221> NAME/KEY: MISC_FEATURE
<222> LOCATION: (148)..(154)
<223> OTHER INFORMATION: May be absent
<220> FEATURE:
<221> NAME/KEY: MISC_FEATURE
<222> LOCATION: (149)..(153)
<223> OTHER INFORMATION: Up to 5 residues may be absent
<220> FEATURE:
<221> NAME/KEY: MISC_FEATURE
<222> LOCATION: (155)..(161)
<223> OTHER INFORMATION: May be absent
<220> FEATURE:
<221> NAME/KEY: MISC_FEATURE
<222> LOCATION: (156)..(160)
<223> OTHER INFORMATION: Up to 5 residues may be absent
<220> FEATURE:
<221> NAME/KEY: MISC_FEATURE
<222> LOCATION: (162)..(168)
<223> OTHER INFORMATION: May be absent
<220> FEATURE:
<221> NAME/KEY: MISC_FEATURE
<222> LOCATION: (163)..(167)
<223> OTHER INFORMATION: Up to 5 residues may be absent
<220> FEATURE:
<221> NAME/KEY: MISC_FEATURE
<222> LOCATION: (169)..(175)
<223> OTHER INFORMATION: May be absent
<220> FEATURE:
<221> NAME/KEY: MISC_FEATURE
<222> LOCATION: (170)..(174)
<223> OTHER INFORMATION: Up to 5 residues may be absent
<220> FEATURE:
```

```
<221> NAME/KEY: MISC_FEATURE
<222> LOCATION: (176)..(182)
<223> OTHER INFORMATION: May be absent
<220> FEATURE:
<221> NAME/KEY: MISC_FEATURE
<222> LOCATION: (177)..(181)
<223> OTHER INFORMATION: Up to 5 residues may be absent
<220> FEATURE:
<221> NAME/KEY: MISC_FEATURE
<222> LOCATION: (183)..(189)
<223> OTHER INFORMATION: May be absent
<220> FEATURE:
<221> NAME/KEY: MISC_FEATURE
<222> LOCATION: (184)..(188)
<223> OTHER INFORMATION: Up to 5 residues may be absent
<220> FEATURE:
<221> NAME/KEY: MISC_FEATURE
<222> LOCATION: (190)..(196)
<223> OTHER INFORMATION: May be absent
<220> FEATURE:
<221> NAME/KEY: MISC_FEATURE
<222> LOCATION: (191)..(195)
<223> OTHER INFORMATION: Up to 5 residues may be absent
<220> FEATURE:
<221> NAME/KEY: MISC_FEATURE
<222> LOCATION: (197)..(203)
<223> OTHER INFORMATION: May be absent
<220> FEATURE:
<221> NAME/KEY: MISC_FEATURE
<222> LOCATION: (198)..(202)
<223> OTHER INFORMATION: Up to 5 residues may be absent
<220> FEATURE:
<221> NAME/KEY: MISC_FEATURE
<222> LOCATION: (204)..(210)
<223> OTHER INFORMATION: May be absent
<220> FEATURE:
<221> NAME/KEY: MISC_FEATURE
<222> LOCATION: (205)..(209)
<223> OTHER INFORMATION: Up to 5 residues may be absent

<400> SEQUENCE: 200

Ser Ser Ser Ser Ser Gly Ser Ser Ser Ser Ser Gly Ser Ser
1               5                   10                  15

Ser Ser Ser Ser Gly Ser Ser Ser Ser Ser Gly Ser Ser Ser
            20                  25                  30

Ser Ser Gly Ser Ser Ser Ser Ser Gly Ser Ser Ser Ser Ser
        35                  40                  45

Gly Ser Ser Ser Ser Ser Gly Ser Ser Ser Ser Ser Gly Ser
    50                  55                  60

Ser Ser Ser Ser Ser Gly Ser Ser Ser Ser Ser Gly Ser Ser
65                  70                  75                  80

Ser Ser Ser Gly Ser Ser Ser Ser Ser Gly Ser Ser Ser Ser
            85                  90                  95

Ser Gly Ser Ser Ser Ser Ser Gly Ser Ser Ser Ser Ser Gly
        100                 105                 110

Ser Ser Ser Ser Ser Gly Ser Ser Ser Ser Ser Gly Ser Ser
    115                 120                 125

Ser Ser Ser Ser Gly Ser Ser Ser Ser Ser Gly Ser Ser Ser
        130                 135                 140

Ser Ser Gly Ser Ser Ser Ser Ser Gly Ser Ser Ser Ser Ser
145                 150                 155                 160

Gly Ser Ser Ser Ser Ser Gly Ser Ser Ser Ser Ser Gly Ser
            165                 170                 175

Ser Ser Ser Ser Gly Ser Ser Ser Ser Ser Gly Ser Ser Ser
        180                 185                 190

Ser Ser Gly Ser Ser Ser Ser Ser Gly Ser Ser Ser Ser Ser
```

```
                    195                 200                 205
Ser Gly
    210

<210> SEQ ID NO 201
<211> LENGTH: 30
<212> TYPE: PRT
<213> ORGANISM: Artificial Sequence
<220> FEATURE:
<223> OTHER INFORMATION: proteinaceous linker
<220> FEATURE:
<221> NAME/KEY: MISC_FEATURE
<222> LOCATION: (2)..(30)
<223> OTHER INFORMATION: Up to 29 residues may be absent

<400> SEQUENCE: 201

Gly Gly Gly Gly Gly Gly Gly Gly Gly Gly Gly Gly Gly Gly Gly
1               5                   10                  15

Gly Gly Gly Gly Gly Gly Gly Gly Gly Gly Gly Gly Gly Gly
            20                  25                  30

<210> SEQ ID NO 202
<211> LENGTH: 12
<212> TYPE: PRT
<213> ORGANISM: Artificial Sequence
<220> FEATURE:
<223> OTHER INFORMATION: proteinaceous linker

<400> SEQUENCE: 202

Gly Lys Ser Ser Gly Ser Gly Ser Glu Ser Lys Ser
1               5                   10

<210> SEQ ID NO 203
<211> LENGTH: 14
<212> TYPE: PRT
<213> ORGANISM: Artificial Sequence
<220> FEATURE:
<223> OTHER INFORMATION: proteinaceous linker

<400> SEQUENCE: 203

Glu Gly Lys Ser Ser Gly Ser Gly Ser Glu Ser Lys Glu Phe
1               5                   10

<210> SEQ ID NO 204
<211> LENGTH: 14
<212> TYPE: PRT
<213> ORGANISM: Artificial Sequence
<220> FEATURE:
<223> OTHER INFORMATION: proteinaceous linker

<400> SEQUENCE: 204

Gly Ser Thr Ser Gly Ser Gly Lys Ser Ser Glu Gly Lys Gly
1               5                   10

<210> SEQ ID NO 205
<211> LENGTH: 18
<212> TYPE: PRT
<213> ORGANISM: Artificial Sequence
<220> FEATURE:
<223> OTHER INFORMATION: proteinaceous linker

<400> SEQUENCE: 205

Gly Ser Thr Ser Gly Ser Gly Lys Ser Ser Glu Gly Ser Gly Ser Thr
1               5                   10                  15

Lys Gly
```

```
<210> SEQ ID NO 206
<211> LENGTH: 18
<212> TYPE: PRT
<213> ORGANISM: Artificial Sequence
<220> FEATURE:
<223> OTHER INFORMATION: proteinaceous linker

<400> SEQUENCE: 206

Gly Ser Thr Ser Gly Ser Gly Lys Pro Gly Ser Gly Glu Gly Ser Thr
1               5                   10                  15

Lys Gly

<210> SEQ ID NO 207
<211> LENGTH: 5
<212> TYPE: PRT
<213> ORGANISM: Artificial Sequence
<220> FEATURE:
<223> OTHER INFORMATION: proteinaceous linker

<400> SEQUENCE: 207

Ser Arg Ser Ser Gly
1               5

<210> SEQ ID NO 208
<211> LENGTH: 5
<212> TYPE: PRT
<213> ORGANISM: Artificial Sequence
<220> FEATURE:
<223> OTHER INFORMATION: proteinaceous linker

<400> SEQUENCE: 208

Ser Gly Ser Ser Cys
1               5

<210> SEQ ID NO 209
<211> LENGTH: 18
<212> TYPE: PRT
<213> ORGANISM: Artificial Sequence
<220> FEATURE:
<223> OTHER INFORMATION: proteinaceous linker

<400> SEQUENCE: 209

Gly Ser Thr Ser Gly Ser Gly Lys Pro Gly Ser Ser Glu Gly Ser Thr
1               5                   10                  15

Lys Gly

<210> SEQ ID NO 210
<211> LENGTH: 8
<212> TYPE: PRT
<213> ORGANISM: Mus musculus

<400> SEQUENCE: 210

Gly Phe Thr Phe Asn Asn Tyr Asp
1               5

<210> SEQ ID NO 211
<211> LENGTH: 8
<212> TYPE: PRT
<213> ORGANISM: Mus musculus

<400> SEQUENCE: 211

Ile Ser Tyr Asp Gly Ser Asp Lys
1               5
```

```
<210> SEQ ID NO 212
<211> LENGTH: 15
<212> TYPE: PRT
<213> ORGANISM: Mus musculus

<400> SEQUENCE: 212

Ala Arg Val Tyr Tyr Tyr Gly Phe Ser Gly Pro Ser Met Asp Val
1               5                   10                  15

<210> SEQ ID NO 213
<211> LENGTH: 8
<212> TYPE: PRT
<213> ORGANISM: Mus musculus

<400> SEQUENCE: 213

Asn Ser Asn Ile Gly Ser Asn Thr
1               5

<210> SEQ ID NO 214
<211> LENGTH: 3
<212> TYPE: PRT
<213> ORGANISM: Mus musculus

<400> SEQUENCE: 214

Ser Asp Ser
1

<210> SEQ ID NO 215
<211> LENGTH: 11
<212> TYPE: PRT
<213> ORGANISM: Mus musculus

<400> SEQUENCE: 215

Gln Ser Tyr Asp Ser Ser Leu Ser Gly Ser Arg
1               5                   10

<210> SEQ ID NO 216
<211> LENGTH: 8
<212> TYPE: PRT
<213> ORGANISM: Mus musculus

<400> SEQUENCE: 216

Gly Phe Thr Phe Ser Asp Tyr Tyr
1               5

<210> SEQ ID NO 217
<211> LENGTH: 8
<212> TYPE: PRT
<213> ORGANISM: Mus musculus

<400> SEQUENCE: 217

Ile Ser Ser Ser Ser Ser Tyr Ile
1               5

<210> SEQ ID NO 218
<211> LENGTH: 13
<212> TYPE: PRT
<213> ORGANISM: Mus musculus

<400> SEQUENCE: 218

Ala Thr Glu Gly Pro Tyr Tyr Leu Tyr Gly Phe Asp Ile
1               5                   10

<210> SEQ ID NO 219
<211> LENGTH: 8
```

```
<212> TYPE: PRT
<213> ORGANISM: Mus musculus

<400> SEQUENCE: 219

Ser Ser Asn Ile Gly Ser Asn Tyr
1               5

<210> SEQ ID NO 220
<211> LENGTH: 3
<212> TYPE: PRT
<213> ORGANISM: Mus musculus

<400> SEQUENCE: 220

Gly Asn Ser
1

<210> SEQ ID NO 221
<211> LENGTH: 10
<212> TYPE: PRT
<213> ORGANISM: Mus musculus

<400> SEQUENCE: 221

Gln Ser Tyr Asp Asn Thr Leu Ser Gly Val
1               5                   10

<210> SEQ ID NO 222
<211> LENGTH: 8
<212> TYPE: PRT
<213> ORGANISM: Mus musculus

<400> SEQUENCE: 222

Gly Phe Thr Phe Asp Asp Tyr Gly
1               5

<210> SEQ ID NO 223
<211> LENGTH: 8
<212> TYPE: PRT
<213> ORGANISM: Mus musculus

<400> SEQUENCE: 223

Ile Asn Trp Asn Gly Gly Ser Thr
1               5

<210> SEQ ID NO 224
<211> LENGTH: 16
<212> TYPE: PRT
<213> ORGANISM: Mus musculus

<400> SEQUENCE: 224

Ala Arg Gly Gly Leu Phe His Asp Ser Ser Gly Tyr Tyr Phe Gly His
1               5                   10                  15

<210> SEQ ID NO 225
<211> LENGTH: 8
<212> TYPE: PRT
<213> ORGANISM: Mus musculus

<400> SEQUENCE: 225

Ser Ser Asn Ile Gly Asn Ser Tyr
1               5

<210> SEQ ID NO 226
<211> LENGTH: 3
<212> TYPE: PRT
<213> ORGANISM: Mus musculus
```

<400> SEQUENCE: 226

Arg Asn Asn
1

<210> SEQ ID NO 227
<211> LENGTH: 9
<212> TYPE: PRT
<213> ORGANISM: Mus musculus

<400> SEQUENCE: 227

Ser Ala Trp Asp Asp Asn Leu Ser Val
1               5

<210> SEQ ID NO 228
<211> LENGTH: 526
<212> TYPE: PRT
<213> ORGANISM: Artificial Sequence
<220> FEATURE:
<223> OTHER INFORMATION: CD38TM1

<400> SEQUENCE: 228

Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
                20                  25                  30

Ser Ser Gly Gly Thr Ser Leu Leu Met Ile Asp Ser Gly Ile Gly Asp
            35                  40                  45

Asn Leu Phe Ala Val Asp Ile Leu Gly Phe Asp Phe Thr Leu Gly Arg
50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Ala Asp
                100                 105                 110

Ser Ser Tyr Thr Thr Leu Gln Arg Val Ala Gly Ile Ser Arg Thr Gly
            115                 120                 125

Met Gln Ile Asn Arg His Ser Leu Thr Thr Ser Tyr Leu Asp Leu Met
130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Ala Ser Tyr Val
            180                 185                 190

Met Thr Ala Glu Asp Val Asp Leu Thr Leu Asn Trp Gly Arg Leu Ser
        195                 200                 205

Ser Val Leu Pro Asp Tyr His Gly Gln Asp Ser Val Arg Val Gly Arg
210                 215                 220

Ile Ser Phe Gly Ser Ile Asn Ala Ile Leu Gly Ser Val Ala Leu Ile
225                 230                 235                 240

Leu Asn Ser His His His Ala Ser Ala Val Ala Glu Phe Pro Lys
                245                 250                 255

Pro Ser Thr Pro Pro Gly Ser Ser Gly Gly Ala Pro Gln Ser Val Leu
            260                 265                 270

Thr Gln Pro Pro Ser Ala Ser Gly Thr Pro Gly Gln Arg Val Thr Ile

```
                275                 280                 285
Ser Cys Ser Gly Ser Ser Asn Ile Gly Ser Asn Tyr Val Tyr Trp
            290                 295                 300
Tyr Gln Gln Leu Pro Gly Thr Ala Pro Lys Leu Leu Ile Tyr Gly Asn
305                 310                 315                 320
Ser Asn Arg Pro Ser Gly Val Pro Asp Arg Phe Ser Gly Ser Lys Ser
                325                 330                 335
Gly Thr Ser Ala Ser Leu Ala Ile Ser Gly Leu Arg Ser Glu Asp Glu
            340                 345                 350
Ala Asp Tyr Tyr Cys Gln Ser Tyr Asp Ser Ser Leu Ser Gly Ser Gly
                355                 360                 365
Val Phe Gly Gly Gly Thr Lys Leu Thr Val Leu Gly Gly Gly Gly
            370                 375                 380
Ser Gly Gly Gly Gly Ser Gly Gly Gly Ser Gly Gly Gly Gly Ser
385                 390                 395                 400
Gly Gly Gly Gly Ser Ser Glu Val Gln Leu Leu Glu Ser Gly Gly
                405                 410                 415
Leu Val Gln Pro Gly Gly Ser Leu Arg Leu Ser Cys Ala Ala Ser Gly
            420                 425                 430
Phe Thr Phe Ser Asp Tyr Tyr Met Ser Trp Val Arg Gln Ala Pro Gly
            435                 440                 445
Lys Gly Leu Glu Trp Val Ser Ala Ile Ser Gly Ser Gly Gly Ser Thr
    450                 455                 460
Tyr Tyr Ala Asp Ser Val Lys Gly Arg Phe Thr Ile Ser Arg Asp Asn
465                 470                 475                 480
Ser Lys Asn Thr Leu Tyr Leu Gln Met Asn Ser Leu Arg Ala Glu Asp
                485                 490                 495
Thr Ala Val Tyr Tyr Cys Ala Arg Glu His Ser Asn Tyr Phe Tyr Gly
            500                 505                 510
Met Asp Val Trp Gly Gln Gly Thr Leu Val Thr Val Ser Ser
            515                 520                 525
```

<210> SEQ ID NO 229
<211> LENGTH: 503
<212> TYPE: PRT
<213> ORGANISM: Artificial Sequence
<220> FEATURE:
<223> OTHER INFORMATION: CD38TM2

<400> SEQUENCE: 229

```
Met Lys Glu Phe Thr Leu Asp Phe Ser Thr Ala Lys Thr Tyr Val Asp
1               5                   10                  15
Ser Leu Asn Val Ile Arg Ser Ala Ile Gly Thr Pro Leu Gln Thr Ile
            20                  25                  30
Ser Ser Gly Gly Thr Ser Leu Leu Met Ile Asp Ser Gly Ile Gly Asp
        35                  40                  45
Asn Leu Phe Ala Val Asp Ile Leu Gly Phe Asp Phe Thr Leu Gly Arg
    50                  55                  60
Phe Asn Asn Leu Arg Leu Ile Val Glu Arg Asn Asn Leu Tyr Val Thr
65                  70                  75                  80
Gly Phe Val Asn Arg Thr Asn Asn Val Phe Tyr Arg Phe Ala Asp Phe
                85                  90                  95
Ser His Val Thr Phe Pro Gly Thr Thr Ala Val Thr Leu Ser Ala Asp
            100                 105                 110
Ser Ser Tyr Thr Thr Leu Gln Arg Val Ala Gly Ile Ser Arg Thr Gly
```

```
            115                 120                 125
Met Gln Ile Asn Arg His Ser Leu Thr Thr Ser Tyr Leu Asp Leu Met
    130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Ala Ser Tyr Val
            180                 185                 190

Met Thr Ala Glu Asp Val Asp Leu Thr Leu Asn Trp Gly Arg Leu Ser
                195                 200                 205

Ser Val Leu Pro Asp Tyr His Gly Gln Asp Ser Val Arg Val Gly Arg
    210                 215                 220

Ile Ser Phe Gly Ser Ile Asn Ala Ile Leu Gly Ser Val Ala Leu Ile
225                 230                 235                 240

Leu Asn Ser His His His Ala Ser Ala Val Ala Ala Glu Phe Pro Lys
                245                 250                 255

Pro Ser Thr Pro Pro Gly Ser Ser Gly Gly Ala Pro Gln Ser Val Leu
            260                 265                 270

Thr Gln Pro Pro Ser Ala Ser Gly Thr Pro Gly Gln Arg Val Thr Ile
                275                 280                 285

Ser Cys Ser Gly Ser Ser Asn Ile Gly Gly Asn Tyr Val Tyr Trp
    290                 295                 300

Tyr Gln Gln Leu Pro Gly Thr Ala Pro Lys Leu Leu Ile Tyr Arg Asn
305                 310                 315                 320

Asn Gln Arg Pro Ser Gly Val Pro Asp Arg Phe Ser Gly Ser Lys Ser
                325                 330                 335

Gly Thr Ser Ala Ser Leu Ala Ile Ser Gly Leu Arg Ser Glu Asp Glu
            340                 345                 350

Ala Asp Tyr Tyr Cys Gln Ser Tyr Asp Ser Ser Leu Ser Val Ser Val
                355                 360                 365

Phe Gly Gly Gly Thr Lys Leu Thr Val Leu Gly Gly Gly Gly Ser
    370                 375                 380

Glu Val Gln Leu Leu Glu Ser Gly Gly Gly Leu Val Gln Pro Gly Gly
385                 390                 395                 400

Ser Leu Arg Leu Ser Cys Ala Ala Ser Gly Phe Thr Phe Ser Ser Tyr
                405                 410                 415

Trp Met His Trp Val Arg Gln Ala Pro Gly Lys Gly Leu Glu Trp Val
            420                 425                 430

Ser Ala Ile Ser Gly Ser Gly Gly Thr Phe Tyr Ala Asp Ser Val
    435                 440                 445

Lys Gly Arg Phe Thr Ile Ser Arg Asp Asn Ser Lys Asn Thr Leu Tyr
            450                 455                 460

Leu Gln Met Asn Ser Leu Arg Ala Glu Asp Thr Ala Val Tyr Tyr Cys
465                 470                 475                 480

Ala Arg Glu Gly Glu Thr Ser Phe Gly Leu Asp Val Trp Gly Gln Gly
                485                 490                 495

Thr Leu Val Thr Val Ser Ser
            500

<210> SEQ ID NO 230
<211> LENGTH: 506
<212> TYPE: PRT
<213> ORGANISM: Artificial Sequence
```

```
<220> FEATURE:
<223> OTHER INFORMATION: CD38TM3

<400> SEQUENCE: 230

Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
                20                  25                  30

Ser Ser Gly Gly Thr Ser Leu Leu Met Ile Asp Ser Gly Ile Gly Asp
            35                  40                  45

Asn Leu Phe Ala Val Asp Ile Leu Gly Phe Asp Phe Thr Leu Gly Arg
        50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Ala Asp
                100                 105                 110

Ser Ser Tyr Thr Thr Leu Gln Arg Val Ala Gly Ile Ser Arg Thr Gly
            115                 120                 125

Met Gln Ile Asn Arg His Ser Leu Thr Thr Ser Tyr Leu Asp Leu Met
    130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Ala Ser Tyr Val
            180                 185                 190

Met Thr Ala Glu Asp Val Asp Leu Thr Leu Asn Trp Gly Arg Leu Ser
    195                 200                 205

Ser Val Leu Pro Asp Tyr His Gly Gln Asp Ser Val Arg Val Gly Arg
210                 215                 220

Ile Ser Phe Gly Ser Ile Asn Ala Ile Leu Gly Ser Val Ala Leu Ile
225                 230                 235                 240

Leu Asn Ser His His His Ala Ser Ala Val Ala Ala Glu Phe Pro Lys
                245                 250                 255

Pro Ser Thr Pro Pro Gly Ser Ser Gly Gly Ala Pro Gln Val Gln Leu
            260                 265                 270

Val Gln Ser Gly Ala Glu Val Lys Lys Pro Gly Glu Ser Leu Lys Ile
        275                 280                 285

Ser Cys Lys Gly Ser Gly Tyr Ser Phe Thr Ser Tyr Trp Ile Gly Trp
290                 295                 300

Val Arg Gln Met Pro Gly Lys Gly Leu Glu Trp Met Gly Ile Ile Tyr
305                 310                 315                 320

Pro Gly Asp Ser Asp Thr Arg Tyr Ser Pro Ser Phe Gln Gly Gln Val
                325                 330                 335

Thr Ile Ser Ala Asp Lys Ser Ile Ser Thr Ala Tyr Leu Gln Trp Ser
            340                 345                 350

Ser Leu Lys Ala Ser Asp Thr Ala Met Tyr Tyr Cys Ala Arg Gly Pro
        355                 360                 365

Ser Thr Gly Phe Trp Ser Gly Asn Tyr Phe Asp Tyr Trp Gly Gln Gly
    370                 375                 380

Thr Leu Val Thr Val Ser Ser Gly Gly Gly Gly Ser Gln Thr Val Val
385                 390                 395                 400
```

```
Thr Gln Glu Pro Ser Leu Thr Val Ser Pro Gly Glu Thr Val Thr Leu
                405                 410                 415

Thr Cys Ala Ser Ser Thr Gly Ala Val Thr Ser Gly Phe Tyr Pro Asn
            420                 425                 430

Trp Phe Gln Gln Lys Pro Gly Gln Ala Pro Arg Ala Leu Ile Tyr Ala
        435                 440                 445

Thr Asn Asn Lys Tyr Ser Trp Thr Pro Ala Arg Phe Ser Gly Ser Leu
    450                 455                 460

Leu Gly Asp Lys Ala Ala Leu Thr Leu Ser Arg Val Gln Pro Glu Asp
465                 470                 475                 480

Glu Ala Asp Tyr Tyr Cys Leu Val Tyr Tyr Asp Gly Ala Trp Val Phe
                485                 490                 495

Gly Gly Gly Thr Lys Leu Thr Val Leu Gly
                500                 505

<210> SEQ ID NO 231
<211> LENGTH: 507
<212> TYPE: PRT
<213> ORGANISM: Artificial Sequence
<220> FEATURE:
<223> OTHER INFORMATION: CD38TM4

<400> SEQUENCE: 231

Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
            20                  25                  30

Ser Ser Gly Gly Thr Ser Leu Leu Met Ile Asp Ser Gly Ile Gly Asp
        35                  40                  45

Asn Leu Phe Ala Val Asp Ile Leu Gly Phe Asp Phe Thr Leu Gly Arg
    50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Ala Asp
                100                 105                 110

Ser Ser Tyr Thr Thr Leu Gln Arg Val Ala Gly Ile Ser Arg Thr Gly
            115                 120                 125

Met Gln Ile Asn Arg His Ser Leu Thr Thr Ser Tyr Leu Asp Leu Met
        130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Ala Ser Tyr Val
                180                 185                 190

Met Thr Ala Glu Asp Val Asp Leu Thr Leu Asn Trp Gly Arg Leu Ser
            195                 200                 205

Ser Val Leu Pro Asp Tyr His Gly Gln Asp Ser Val Arg Val Gly Arg
        210                 215                 220

Ile Ser Phe Gly Ser Ile Asn Ala Ile Leu Gly Ser Val Ala Leu Ile
225                 230                 235                 240

Leu Asn Ser His His His Ala Ser Ala Val Ala Ala Glu Phe Pro Lys
                245                 250                 255
```

```
Pro Ser Thr Pro Pro Gly Ser Ser Gly Gly Ala Pro Gln Val Gln Leu
            260                 265                 270

Val Gln Ser Gly Ala Glu Val Lys Lys Pro Gly Glu Ser Leu Lys Ile
        275                 280                 285

Ser Cys Lys Gly Ser Gly Tyr Ser Phe Thr Ser Tyr Trp Ile Gly Trp
    290                 295                 300

Val Arg Gln Met Pro Gly Lys Gly Leu Glu Trp Met Gly Ile Ile Tyr
305                 310                 315                 320

Pro Gly Asp Ser Asp Thr Arg Tyr Ser Pro Ser Phe Gln Gly Gln Val
            325                 330                 335

Thr Ile Ser Ala Asp Lys Ser Ile Ser Thr Ala Tyr Leu Gln Trp Ser
            340                 345                 350

Ser Leu Lys Ala Ser Asp Thr Ala Met Tyr Tyr Cys Ala Arg Gly Pro
        355                 360                 365

Ser Thr Gly Phe Trp Ser Gly Asn Tyr Phe Asp Tyr Trp Gly Gln Gly
    370                 375                 380

Thr Leu Val Thr Val Ser Ser Gly Gly Gly Ser Asp Ile Gln Met
385                 390                 395                 400

Thr Gln Ser Pro Ser Ser Leu Ser Ala Ser Val Gly Asp Arg Val Thr
            405                 410                 415

Ile Thr Cys Ala Ser Ser Thr Gly Ala Val Thr Ser Gly Phe Tyr Pro
            420                 425                 430

Asn Trp Phe Gln Gln Lys Pro Gly Gln Ala Pro Arg Ala Leu Ile Tyr
        435                 440                 445

Ala Thr Asn Asn Lys Tyr Ser Trp Thr Pro Ala Arg Phe Ser Gly Ser
    450                 455                 460

Leu Leu Gly Asp Lys Ala Ala Leu Thr Leu Ser Arg Val Gln Pro Glu
465                 470                 475                 480

Asp Glu Ala Asp Tyr Tyr Cys Leu Val Tyr Tyr Asp Gly Ala Trp Val
            485                 490                 495

Phe Gly Gly Gly Thr Lys Leu Thr Val Leu Gly
            500                 505

<210> SEQ ID NO 232
<211> LENGTH: 499
<212> TYPE: PRT
<213> ORGANISM: Artificial Sequence
<220> FEATURE:
<223> OTHER INFORMATION: CD38TR1

<400> SEQUENCE: 232

Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
            20                  25                  30

Ser Ser Gly Gly Thr Ser Leu Leu Met Ile Asp Ser Gly Ser Gly Asp
        35                  40                  45

Asn Leu Phe Ala Val Asp Val Arg Gly Ile Asp Pro Glu Glu Gly Arg
    50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
            85                  90                  95

Ser His Val Thr Phe Pro Gly Thr Ala Val Thr Leu Ser Gly Asp
            100                 105                 110
```

Ser Ser Tyr Thr Thr Leu Gln Arg Val Ala Gly Ile Ser Arg Thr Gly
        115                 120                 125

Met Gln Ile Asn Arg His Ser Leu Thr Thr Ser Tyr Leu Asp Leu Met
130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Arg Ser Tyr Val
            180                 185                 190

Met Thr Ala Glu Asp Val Asp Leu Thr Leu Asn Trp Gly Arg Leu Ser
        195                 200                 205

Ser Val Leu Pro Asp Tyr His Gly Gln Asp Ser Val Arg Val Gly Arg
    210                 215                 220

Ile Ser Phe Gly Ser Ile Asn Ala Ile Leu Gly Ser Val Ala Leu Ile
225                 230                 235                 240

Leu Asn Cys His His His Ala Ser Ala Val Ala Ala Glu Phe Pro Lys
                245                 250                 255

Pro Ser Thr Pro Pro Gly Ser Ser Gly Gly Ala Pro Asp Ile Gln Met
            260                 265                 270

Thr Gln Ser Pro Ser Ser Leu Ser Ala Ser Val Gly Asp Arg Val Thr
        275                 280                 285

Ile Thr Cys Lys Ala Ser Glu Asp Ile Tyr Asn Arg Leu Thr Trp Tyr
    290                 295                 300

Gln Gln Lys Pro Gly Lys Ala Pro Lys Leu Leu Ile Ser Gly Ala Thr
305                 310                 315                 320

Ser Leu Glu Thr Gly Val Pro Ser Arg Phe Ser Gly Ser Gly Ser Gly
                325                 330                 335

Thr Asp Phe Thr Phe Thr Ile Ser Ser Leu Gln Pro Glu Asp Ile Ala
            340                 345                 350

Thr Tyr Tyr Cys Gln Gln Tyr Trp Ser Asn Pro Tyr Thr Phe Gly Gln
        355                 360                 365

Gly Thr Lys Val Glu Ile Lys Gly Gly Gly Ser Gln Val Gln Leu
    370                 375                 380

Gln Glu Ser Gly Pro Gly Leu Val Arg Pro Ser Gln Thr Leu Ser Leu
385                 390                 395                 400

Thr Cys Thr Val Ser Gly Phe Ser Leu Thr Ser Tyr Gly Val His Trp
                405                 410                 415

Val Arg Gln Pro Pro Gly Arg Gly Leu Glu Trp Ile Gly Val Met Trp
            420                 425                 430

Arg Gly Gly Ser Thr Asp Tyr Asn Ala Ala Phe Met Ser Arg Leu Asn
        435                 440                 445

Ile Thr Lys Asp Asn Ser Lys Asn Gln Val Ser Leu Arg Leu Ser Ser
    450                 455                 460

Val Thr Ala Ala Asp Thr Ala Val Tyr Tyr Cys Ala Lys Ser Met Ile
465                 470                 475                 480

Thr Thr Gly Phe Val Met Asp Ser Trp Gly Gln Gly Ser Leu Val Thr
                485                 490                 495

Val Ser Ser

<210> SEQ ID NO 233
<211> LENGTH: 527
<212> TYPE: PRT

<213> ORGANISM: Artificial Sequence
<220> FEATURE:
<223> OTHER INFORMATION: CD38 binding protein monomer

<400> SEQUENCE: 233

```
Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
            20                  25                  30

Ser Ser Gly Gly Thr Ser Leu Leu Met Ile Asp Ser Gly Ile Gly Asp
        35                  40                  45

Asn Leu Phe Ala Val Asp Ile Leu Gly Phe Asp Phe Thr Leu Gly Arg
    50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Ala Asp
            100                 105                 110

Ser Ser Tyr Thr Thr Leu Gln Arg Val Ala Gly Ile Ser Arg Thr Gly
        115                 120                 125

Met Gln Ile Asn Arg His Ser Leu Thr Thr Ser Tyr Leu Asp Leu Met
    130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Ala Ser Tyr Val
            180                 185                 190

Met Thr Ala Glu Asp Val Asp Leu Thr Leu Asn Trp Gly Arg Leu Ser
        195                 200                 205

Ser Val Leu Pro Asp Tyr His Gly Gln Asp Ser Val Arg Val Gly Arg
    210                 215                 220

Ile Ser Phe Gly Ser Ile Asn Ala Ile Leu Gly Ser Val Ala Leu Ile
225                 230                 235                 240

Leu Asn Ser His His His Ala Ser Ala Val Ala Ala Glu Phe Pro Lys
                245                 250                 255

Pro Ser Thr Pro Pro Gly Ser Ser Gly Ala Pro Gln Val Gln Leu
            260                 265                 270

Val Gln Ser Gly Ala Glu Val Lys Lys Pro Gly Glu Ser Leu Lys Ile
        275                 280                 285

Ser Cys Lys Gly Ser Gly Tyr Ser Phe Thr Ser Tyr Trp Ile Gly Trp
    290                 295                 300

Val Arg Gln Met Pro Gly Lys Gly Leu Glu Trp Met Gly Ile Ile Tyr
305                 310                 315                 320

Pro Gly Asp Ser Asp Thr Arg Tyr Ser Pro Ser Phe Gln Gly Gln Val
                325                 330                 335

Thr Ile Ser Ala Asp Lys Ser Ile Ser Thr Ala Tyr Leu Gln Trp Ser
            340                 345                 350

Ser Leu Lys Ala Ser Asp Thr Ala Met Tyr Tyr Cys Ala Arg Gly Pro
        355                 360                 365

Ser Thr Gly Phe Trp Ser Gly Asn Tyr Phe Asp Tyr Trp Gly Gln Gly
    370                 375                 380

Thr Leu Val Thr Val Ser Ser Gly Gly Gly Gly Ser Gly Gly Gly Gly
```

-continued

```
385                 390                 395                 400
Ser Gly Gly Gly Ser Gly Gly Gly Ser Gly Gly Gly Ser
            405                 410                 415

Asp Ile Gln Met Thr Gln Ser Pro Ser Ser Leu Ser Ala Ser Val Gly
            420                 425                 430

Asp Arg Val Thr Ile Thr Cys Ala Ser Ser Thr Gly Ala Val Thr Ser
        435                 440                 445

Gly Phe Tyr Pro Asn Trp Phe Gln Gln Lys Pro Gly Gln Ala Pro Arg
    450                 455                 460

Ala Leu Ile Tyr Ala Thr Asn Asn Lys Tyr Ser Trp Thr Pro Ala Arg
465                 470                 475                 480

Phe Ser Gly Ser Leu Leu Gly Asp Lys Ala Ala Leu Thr Leu Ser Arg
                485                 490                 495

Val Gln Pro Glu Asp Glu Ala Asp Tyr Tyr Cys Leu Val Tyr Tyr Asp
            500                 505                 510

Gly Ala Trp Val Phe Gly Gly Gly Thr Lys Leu Thr Val Leu Gly
        515                 520                 525
```

US 11,713,347 B2

CD38-BINDING PROTEINS COMPRISING DE-IMMUNIZED SHIGA TOXIN A SUBUNIT EFFECTORS

I. CROSS REFERENCE TO RELATED APPLICATIONS

This application claims the benefit of U.S. Provisional Application No. 62/945,107, filed Dec. 6, 2019, U.S. Provisional Application No. 62/945,106, filed Dec. 6, 2019, and U.S. Provisional Application No. 62/795,633, filed Jan. 23, 2019, each of which is incorporated by reference herein in its entirety.

II. DESCRIPTION OF THE TEXT FILE SUBMITTED ELECTRONICALLY

The contents of the text file submitted electronically herewith are incorporated by reference in their entirety: a computer readable format copy of the Sequence Listing (filename: sequencelisting.txt, date recorded Jan. 23, 2020, file size 238 kilobytes).

III. TECHNICAL FIELD

The present invention relates to binding proteins (each binding protein being a "CD38-binding protein") which each comprise (1) a CD38-binding region or domain and (2) a Shiga toxin A Subunit effector polypeptide ("Shiga toxin effector polypeptide").

IV. BACKGROUND OF THE INVENTION

The following includes information that may be useful in understanding the instant invention. It is not an admission that any of the information provided herein is prior art or relevant to the present invention, or that any publication or document that is specifically or implicitly referenced herein is prior art.

CD38 is highly expressed on malignant plasma cells in subjects with multiple myeloma. Multiple myeloma is a hematologic malignancy of plasma cells involving the overproliferation of plasma cells leading to end-organ damage. In multiple myeloma, malignant plasma cells can contribute to the disease by producing an abnormal immunoglobulin called an M protein (also known as a myeloma protein or monoclonal protein), resulting in a monoclonal gammopathy or abnormally high levels of M protein in the plasma. In addition, malignant plasma cells can accumulate in the bone marrow, thereby crowding-out healthy cells.

It would be desirable to have CD38-binding proteins for use as therapeutic molecules to treat a variety of diseases, such as, e.g., hematopoietic cancers, that can be treated by selective killing of, or selective delivery of a beneficial agent into, a CD38-expressing cell. It would be desirable to have cytotoxic, CD38-binding, cell-targeting proteins exhibiting low antigenicity and/or immunogenicity, low off-target toxicity, and potent on-target cytotoxicity. For example, it would be desirable to have CD38-binding proteins comprising cytotoxic Shiga toxin A Subunit derived components that have 1) reduced potential for unwanted antigenicities and/or immunogenicities (e.g. via mutation) and/or 2) reduced potential for non-specific toxicities (e.g. via improved stability) while maintaining potent cytotoxicity to a CD38-expressing cell. Furthermore, it would be desirable to have CD38-binding therapeutic and/or diagnostic proteins exhibiting low antigenicity and/or immunogenicity, low off-target toxicity, high stability, and/or the ability to deliver cargos to a CD38-expressing target cell.

V. BRIEF SUMMARY OF THE INVENTION

As described herein, the present invention provides CD38-binding fusion proteins comprising at least one Shiga toxin A subunit effector polypeptide and at least one CD38-binding domain, with optional linkers.

Accordingly, in some aspects, the invention provides CD38-binding fusion proteins comprising: a) a Shiga toxin A subunit effector polypeptide; b) a heavy chain variable domain (VH) comprising: 1) a vHCDR1 comprising the sequence of SEQ ID NO: 34; 2) a vHCDR2 comprising the sequence of SEQ ID NO: 35; and 3) a vHCDR3 comprising the sequence of SEQ ID NO: 36; and c) a light chain variable domain (VL) comprising: 1) a vLCDR1 comprising the sequence of SEQ ID NO: 31; 2) a vLCDR2 comprising the sequence of SEQ ID NO: 32; and 3) a vLCDR3 comprising the sequence of SEQ ID NO: 33.

In further embodiments, the CD38-binding fusion protein comprises the sequence of SEQ ID NO: 79.

In additional aspects, the CD38-binding fusion proteins has a VL comprising the sequence of SEQ ID NO: 43, and a VH comprising the sequence of SEQ ID NO: 44.

In further aspects, the CD38-binding fusion protein has a a) VL that comprises the sequence of SEQ ID NO: 43, or a sequence having at least 95%, at least 96%, at least 97%, at least 98%, or at least 99% amino acid identity thereto, and a b) VH that comprises the sequence of SEQ ID NO: 44, or a sequence having at least 95%, at least 96%, at least 97%, at least 98%, or at least 99% amino acid sequence identity thereto.

IN additional aspects, the CD38-binding fusion proteins have a VL comprising the sequence of SEQ ID NO: 41, and a VH comprising the sequence of SEQ ID NO: 44.

In further aspects, the CD38-binding fusion proteins has a VL that comprises the sequence of SEQ ID NO: 41, or a sequence having at least 95%, at least 96%, at least 97%, at least 98%, or at least 99% amino acid sequence identity thereto, and has a VH that comprises the sequence of SEQ ID NO: 44, or a sequence having at least 95%, at least 96%, at least 97%, at least 98%, or at least 99% amino acid sequence identity thereto.

In additional aspects, the CD38-binding fusion proteins comprise: a) a Shiga toxin A subunit effector polypeptide; b) a heavy chain variable domain (VH) comprising: 1) a vHCDR1 comprising the sequence of SEQ ID NO: 22; 2) a vHCDR2 comprising the sequence of SEQ ID NO: 23; and 3) a vHCDR3 comprising the sequence of SEQ ID NO: 24; and c) a light chain variable domain (VL) comprising: 1) a vLCDR1 comprising the sequence of SEQ ID NO: 19; 2) a vLCDR2 comprising the sequence of SEQ ID NO: 20; and 3) a vLCDR3 comprising the sequence of SEQ ID NO: 21.

In further aspects, the CD38-binding fusion proteins have a VL that comprises the sequence of SEQ ID NO: 37, and a VH that comprises the sequence of SEQ ID NO: 38.

In additional aspects, the CD38-binding fusion proteins have a VL that comprises the sequence of SEQ ID NO: 37, or a sequence having at least 95%, at least 96%, at least 97%, at least 98%, or at least 99% amino acid sequence identity thereto, and a VH that comprises the sequence of SEQ ID NO: 37, or a sequence having at least 95%, at least 96%, at least 97%, at least 98%, or at least 99% amino acid sequence identity thereto.

In further aspects, the CD38-binding fusion proteins comprise: a) a Shiga toxin A subunit effector polypeptide; b)

a heavy chain variable domain (VH) comprising: 1) a vHCDR1 comprising the sequence of SEQ ID NO: 28; 2) a vHCDR2 comprising the sequence of SEQ ID NO: 29; and 3) a vHCDR3 comprising the sequence of SEQ ID NO: 30; and c) a light chain variable domain (VL) comprising: 1) a vLCDR1 comprising the sequence of SEQ ID NO: 25; 2) a vLCDR2 comprising the sequence of SEQ ID NO: 26; and 3) a vLCDR3 comprising the sequence of SEQ ID NO: 27.

In an additional aspect, the CD38-binding fusion proteins have a VL that comprises the sequence of SEQ ID NO: 39, and a VH that comprises the sequence of SEQ ID NO: 40.

In further aspects, the CD38-binding fusion proteins have a VL that comprises the sequence of SEQ ID NO: 39, or a sequence having at least 95%, at least 96%, at least 97%, at least 98%, or at least 99% amino acid sequence identity thereto, and has a VH that comprises the sequence of SEQ ID NO: 40, or a sequence having at least 95%, at least 96%, at least 97%, at least 98%, or at least 99% amino acid sequence identity thereto.

In further aspects, the CD38-binding fusion proteins comprise a first linker between the Shiga toxin A subunit effector polypeptide and the CD38-binding domain. In some embodiments, the first linker is a proteinaceous linker, and can be from about 1 to about 40 amino acids. In some embodiments, the first linker comprises the sequence of SEQ ID NO: 70.

In additional aspects, the CD38-binding fusion proteins have a first linker that comprises the sequence of any one of SEQ ID NOS: 70-75, or a sequence having at least 95%, at least 96%, at least 97%, at least 98%, or at least 99% amino acid sequence identity thereto.

In further aspects, the CD38-binding fusion proteins comprise a second linker between the VH and the VL. In some embodiments, this second linker comprises the sequence (Gly4Ser)n (SEQ ID NO: 195), wherein n is equal to 1, 2, 3, 4, or 5, with n=1 in some embodiments.

In additional aspects, the CD38-binding fusion proteins comprise, from its N- to C-terminus, the Shiga toxin A subunit effector polypeptide-first linker-VH-second linker-VL.

IN further aspects, the CD38-binding fusion proteins comprise, from its N- to C-terminus, the Shiga toxin A subunit effector polypeptide-first linker-VL-second linker-VH.

In additional aspects, the CD38-binding fusion proteins have a Shiga toxin A subunit effector polypeptide comprising the sequence of SEQ ID NO: 46.

In further aspects, the CD38-binding fusion proteins have a Shiga toxin A subunit effector polypeptide comprising the sequence of any one of SEQ ID NOS: 45-69, or a sequence having at least 95%, at least 96%, at least 97%, at least 95%, at least 99% amino acid sequence identity thereto.

In additional aspects, the CD38-binding fusion proteins of claim 1, wherein the Shiga toxin A subunit effector polypeptide comprises the sequence of SEQ ID NO: 46, the VL comprises the sequence of SEQ ID NO: 43, and the VH comprises the sequence of SEQ ID NO: 44.

In further aspects, the CD38-binding fusion proteins have at least 95% amino acid sequence identity to the sequence of SEQ ID NO: 79.

In additional aspects, the CD38-binding fusion proteins of the invention are homodimers. In some embodiments, the homodimer comprises two identical polypeptides, each polypeptide comprising the sequence of SEQ ID NO: 79. IN some embodiments, the homodimer comprises two identical polypeptides, each polypeptide comprising a sequence at least 95%, at least 96%, at least 97%, at least 98%, at least 99% amino acid sequence identity to SEQ ID NO: 79. IN some embodiments, at least about 90%, 95% or 98% of the CD38-binding fusion protein is in the form of a homodimer.

In some aspects, the invention provides compositions of the CD38-binding fusion proteins of the invention and a pharmaceutically acceptable carrier or excipient.

In further aspects, the invention provides nucleic acids encoding the CD38-binding fusion proteins, as well as expression vectors comprising the nucleic acids, and host cells comprising the nucleic acids and/or expression vectors herein. Similarly, the invention provides comprising culturing a host cell with the nucleic acids and/or expression vectors under conditions wherein the CD38-binding fusion protein is expressed, and recovering the protein. In some embodiments, the protein is purified by contacting the CD38-binding fusion protein with a bacterial protein L. In some cases, the protein L is isolated or derived from *P. magnus*. which can be conjugated to a resin.

In additional aspects, the invention provides methods of treating multiple myeloma, comprising administering to a subject in need thereof the CD38-binding fusion proteins of the invention.

VI. BRIEF DESCRIPTION OF THE DRAWINGS

FIG. 1A-1B: Provided in FIG. 1A and FIG. 1B are schematic drawings of illustrative CD38-targeting molecules, each comprising at least one CD38 binding region and at least one Shiga toxin A subunit effector. In FIG. 1A, the CD38 binding region is generally a scFv comprising an anti-CD38 VH and VL domain separated by a linker, with the scFv being either N- or C-terminal to the Shiga toxin component. In one illustrative CD38-targeting molecule, the CD38 binding region is a scFv, and the scFv is shown participating in intermolecular variable domain exchange with a neighboring scFv (FIG. 1B, bottom left). The depictions of illustrative molecules in FIG. 1A-1B are for illustrative purposes of certain, general arrangements of the structural features of a limited set of embodiments of the present invention. It is to be understood that these illustrative molecules do not intend, nor should any be construed, to be wholly definitive as to the arrangement of any structural features and/or components of a molecule of the present invention. The relative size, location, or number of features shown in the schematics of FIG. 1A-1B have been simplified. The schematics in FIG. 1A-1B are not intended to accurately portray any information regarding the relative sizes of molecular structures in any embodiment of the present invention.

FIG. 2: FIG. 2 shows representative $CD_{50}$ values toward CD38 positive H929 human myeloma cells for various molecules in the pool of fifty-one CD38-targeting molecules. The CD38-target molecules can be in either orientation, VH-VL or VL-VH, as shown. The grey squares represent additional members of the pool. A screening cutoff of 1×103 pM is represented by a vertical dashed line-with $CD_{50}$ values to the left being more potent than the cutoff and $CD_{50}$ values to the right being less potent than the cutoff. Any one of the fifty-two molecules tested that did not exhibit a $CD_{50}$ of 20,000 pM or less in this assay was not included in FIG. 2. Some of the most potent molecules tested were in CD38-targeting molecule Families #6 and #7.

FIG. 3A-3C: FIG. 3A-3C show representative cytotoxicity assays using various concentrations of CD38-targeting molecules #3 and #4. CD38-targeting reference molecule #1 and a Shiga effector polypeptide with no targeting domain were used as a positive and negative control, respectively.

CTM#3 and CTM#4 showed concentration-dependent cytotoxicity to CD38 positive H929 cells (FIG. 3A) and MOLP-8 cells (FIG. 3B). The specificity of cytotoxicity to CD38-expressing cells was investigated by comparing the cytotoxic activities to CD38 positive H929 and MOLP-8 cells (FIG. 3A-3B) to the cytotoxic activities toward CD38 negative U266 cells (FIG. 3C). Neither CTM#3 nor CTM#4 exhibited significant cytotoxic activity to U266 cells under the conditions tested (FIG. 3C).

Figure 4A:
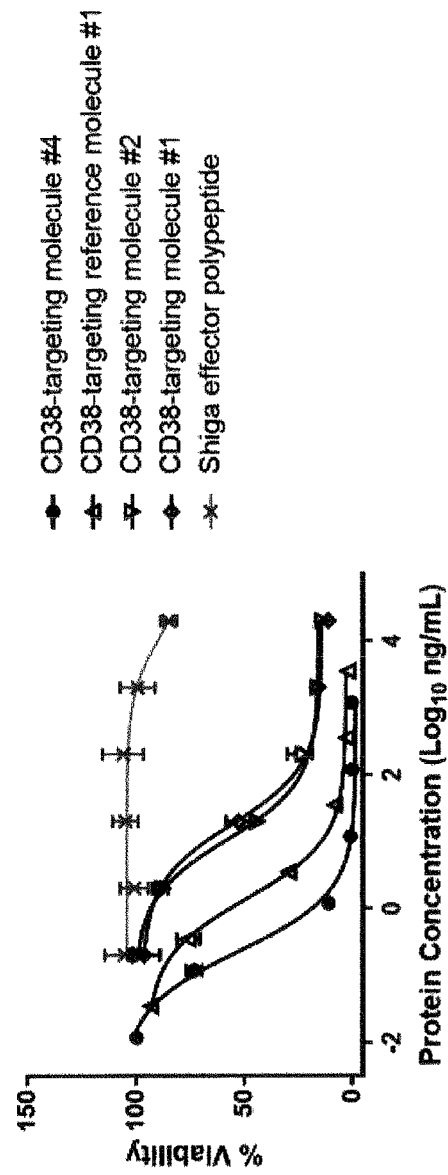
Figure 4B:
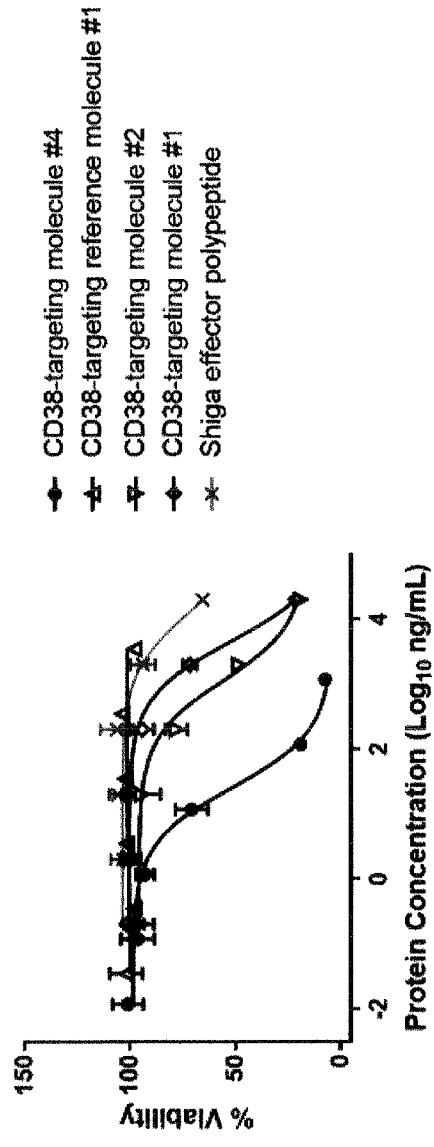

FIG. 4A-4B: FIG. 4A-4B show representative cytotoxicity assays for CD38-targeting molecules #1, #2, and #4 tested using either human cells (FIG. 4A) or non-human primate (FIG. 4B) cells. BLCL-C162 is a rhesus cell line that expresses rhesus CD38. CD38-targeting reference molecule #1 and a Shiga effector polypeptide with no targeting domain were used as a positive and negative control, respectively. CTM#1, CTM#2, and CTM#4 showed concentration-dependent cytotoxicity to CD38 positive MOLP-8 cells (FIG. 4A) and CD38 positive BLCL-C162 cells (FIG. 4B). Note that that the sequences of CD38 in rhesus and cyno are identical.

Figure 5:
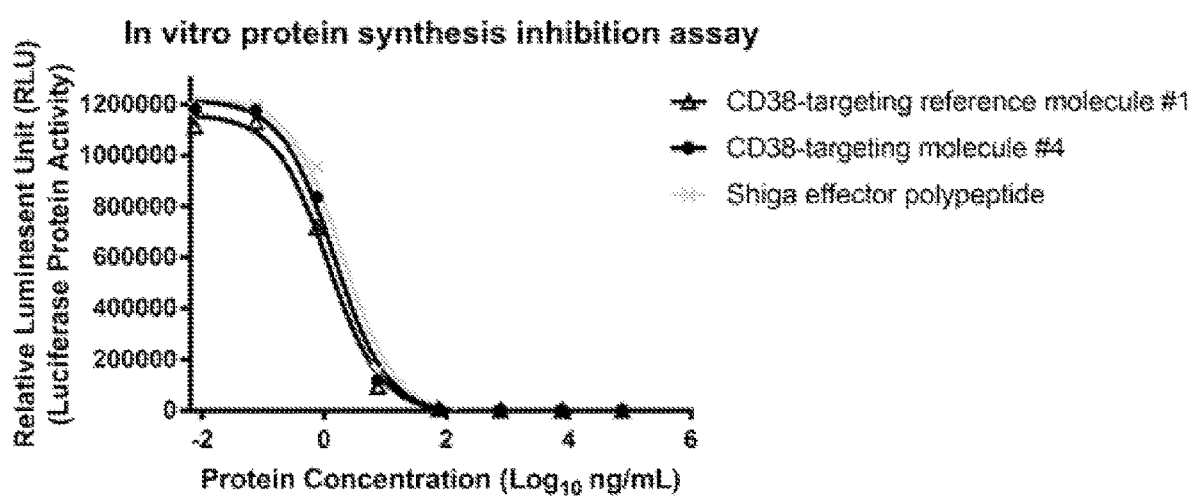

FIG. 5: FIG. 5 shows the concentration-dependent protein synthesis inhibition activities of CD38-targeting molecule #4 in a cell-free in vitro protein translation assay; protein synthesis inhibition is one activity of Shiga toxin as described herein. CD38-targeting reference molecule #1 and a Shiga effector polypeptide with no targeting domain were used as positive controls. Luciferase protein synthesis as measured by relative luminescence units (RLUs) was decreased in a concentration-dependent manner by CTM#4 comparable to the positive control reference molecules.

Figure 6A:
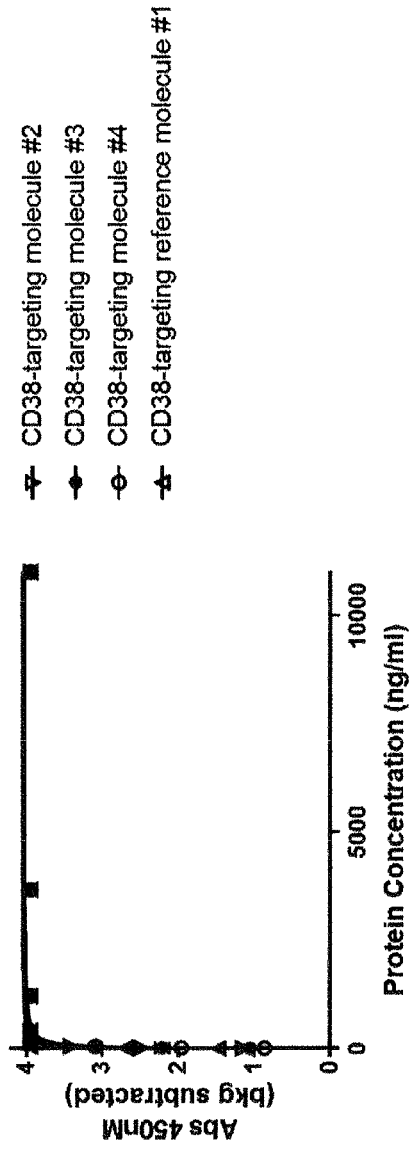
Figure 6B:
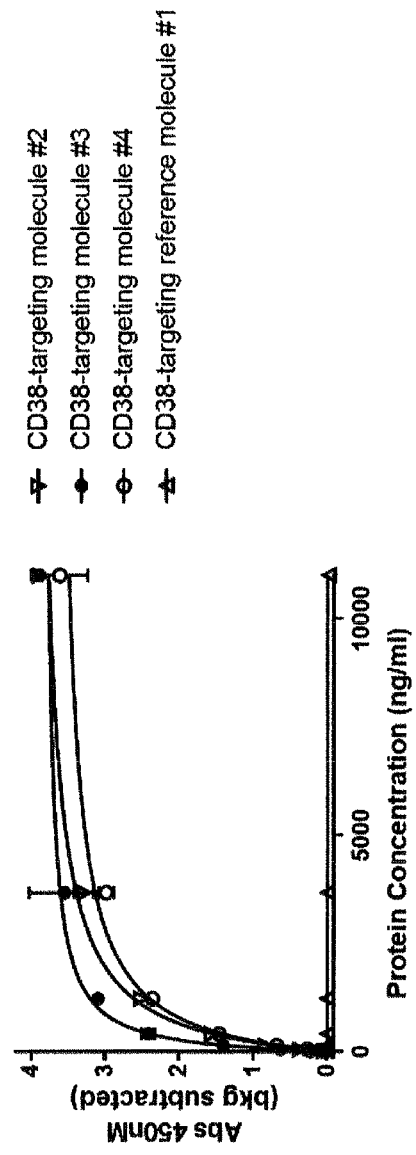

FIG. 6A-6B: In FIG. 6A-6B, binding characteristics of CD38-targeting molecules (CTM#2, CTM#3, and CTM#4) to recombinant human CD38 protein (FIG. 6A) or recombinant cynomolgus CD38 protein (FIG. 6B) were determined with an enzyme-linked immunosorbent assay (ELISA) binding assay. The molecules CD38-targeting molecule #2 (SEQ ID NO:77), CD38-targeting molecule #3 (SEQ ID NO:78), and CD38-targeting molecule #4 (SEQ ID NO:79) each bound to both human and cynomolgus CD38, whereas CD38-targeting reference molecule #1 (SEQ ID NO:83) bound to human CD38 (FIG. 6A) but not cynomolgus CD38 (FIG. 6B).

Figure 7:
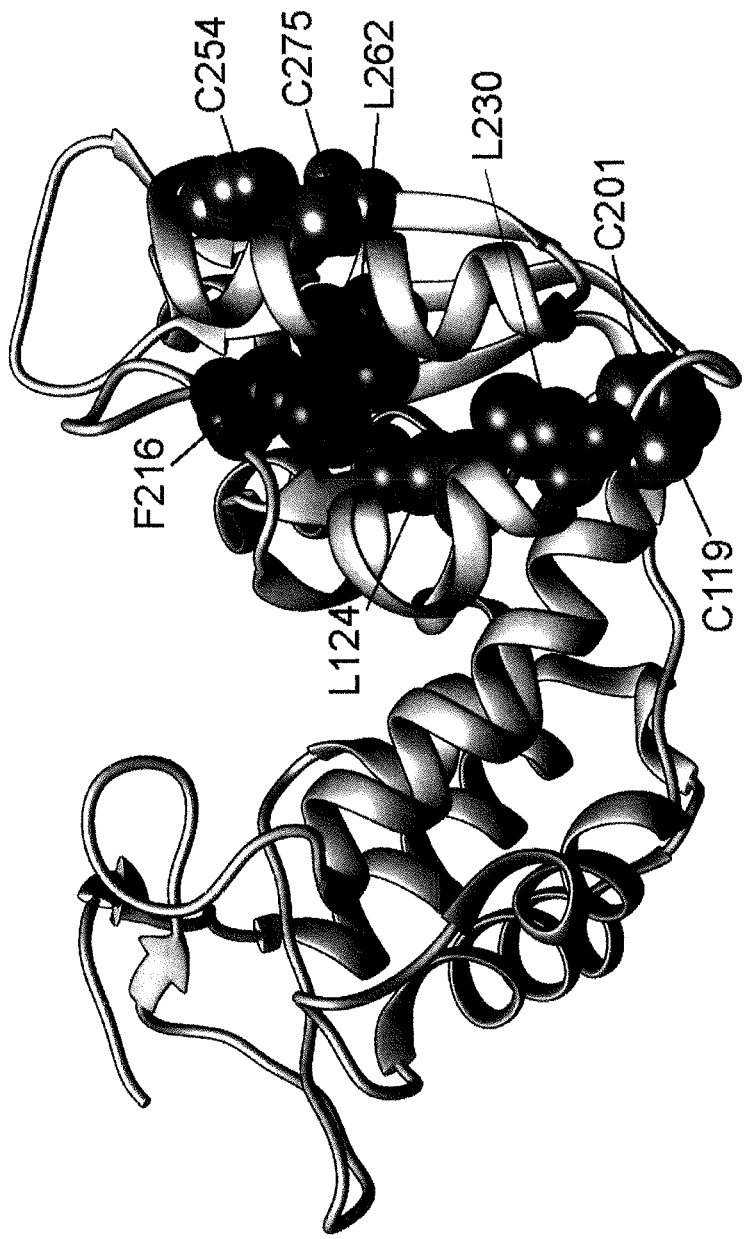

FIG. 7: FIG. 7 shows a 3-dimensional protein structure diagram for CD38, and the location of critical residues in CD38 for binding by CD38-targeting molecule #4 determined by epitope mapping mutagenesis using a human CD38 extracellular domain. In FIG. 7, the critical surface accessible contact residues F216 and L262 are shown in red, critical structural residues L124 and L230 are shown in purple, and critical structural residues participating in disulfide pairs C119/C201 and C254/C275 are shown in grey.

Figure 8A:
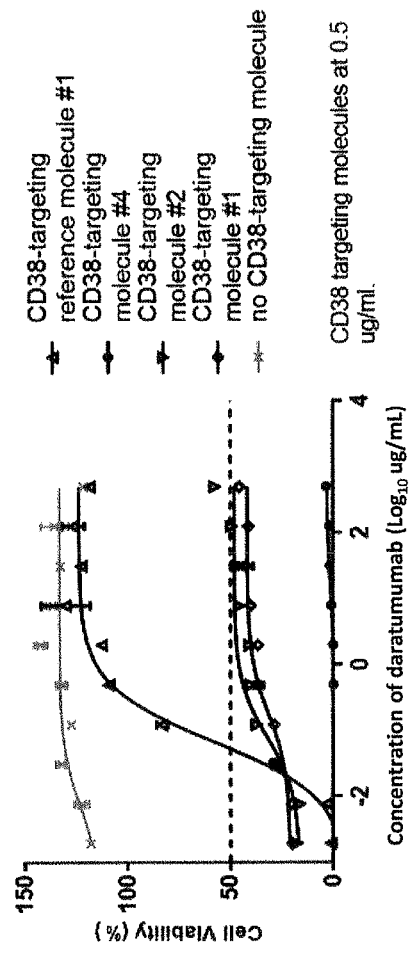
Figure 8B:
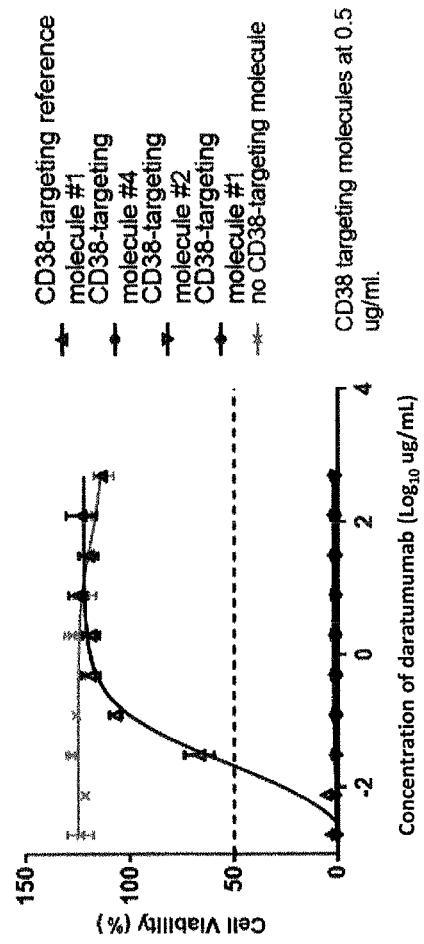
Figure 8C:
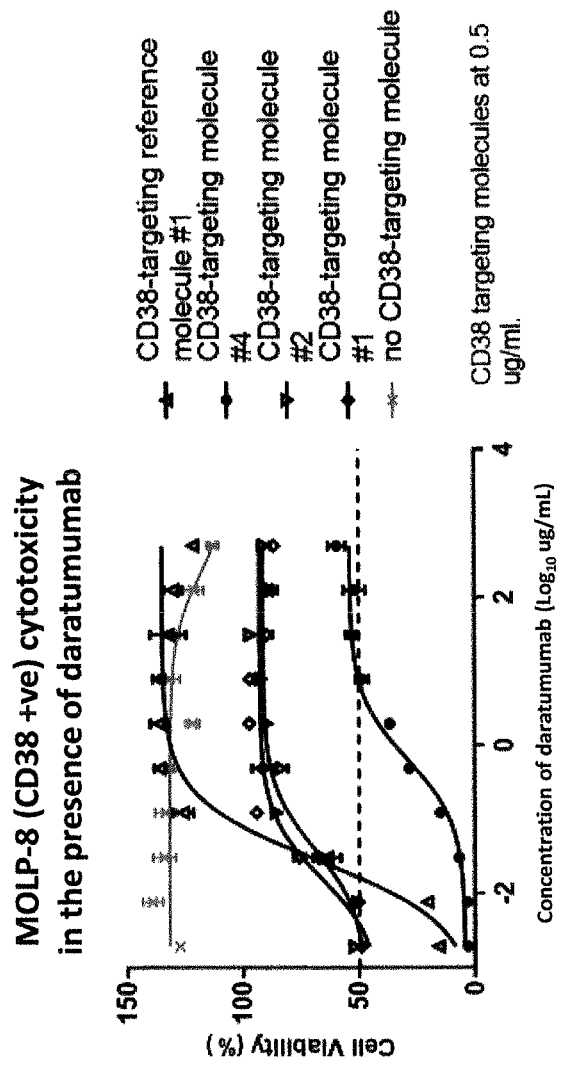
Figure 8D:
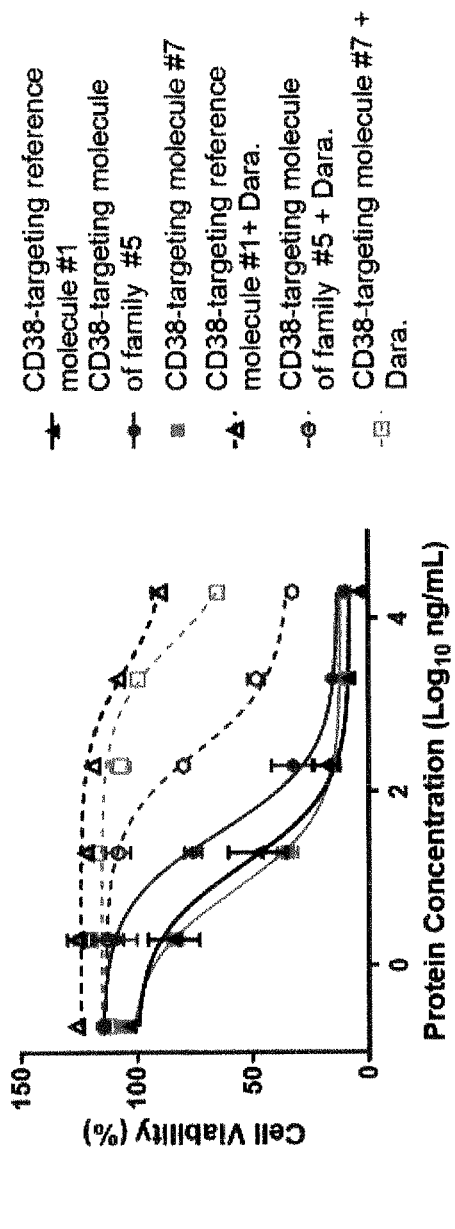
Figure 8E:
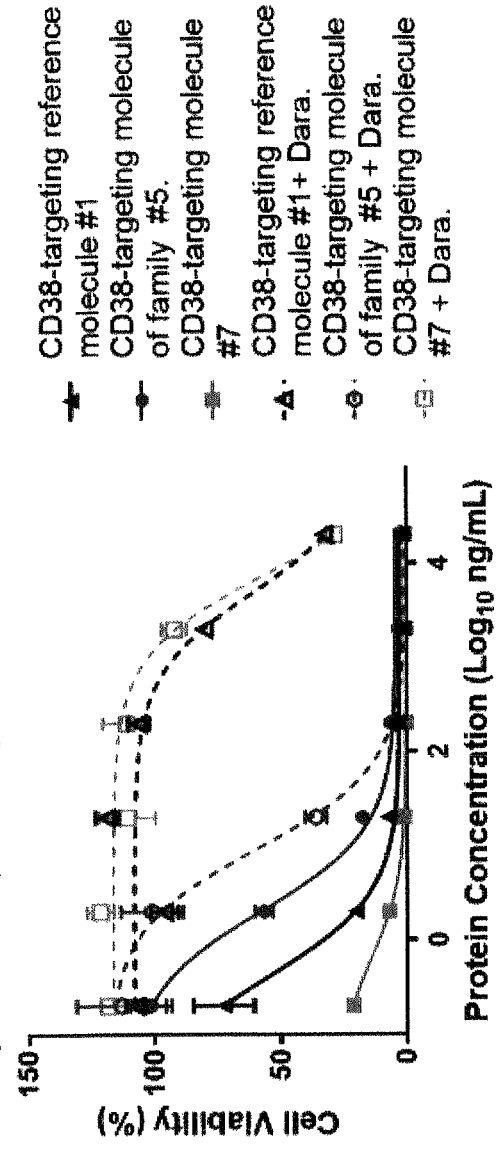
Figure 8F:
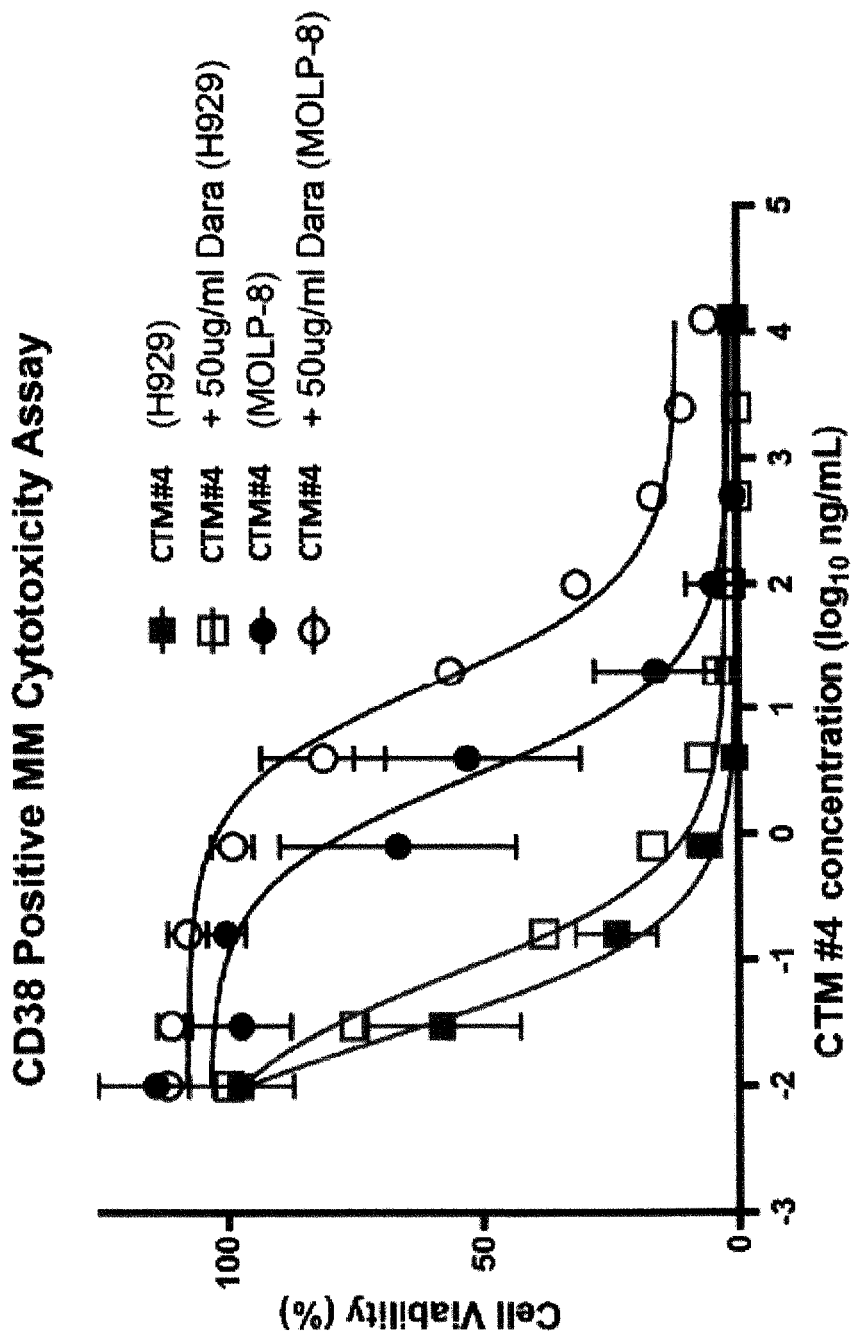
Figure 8H:
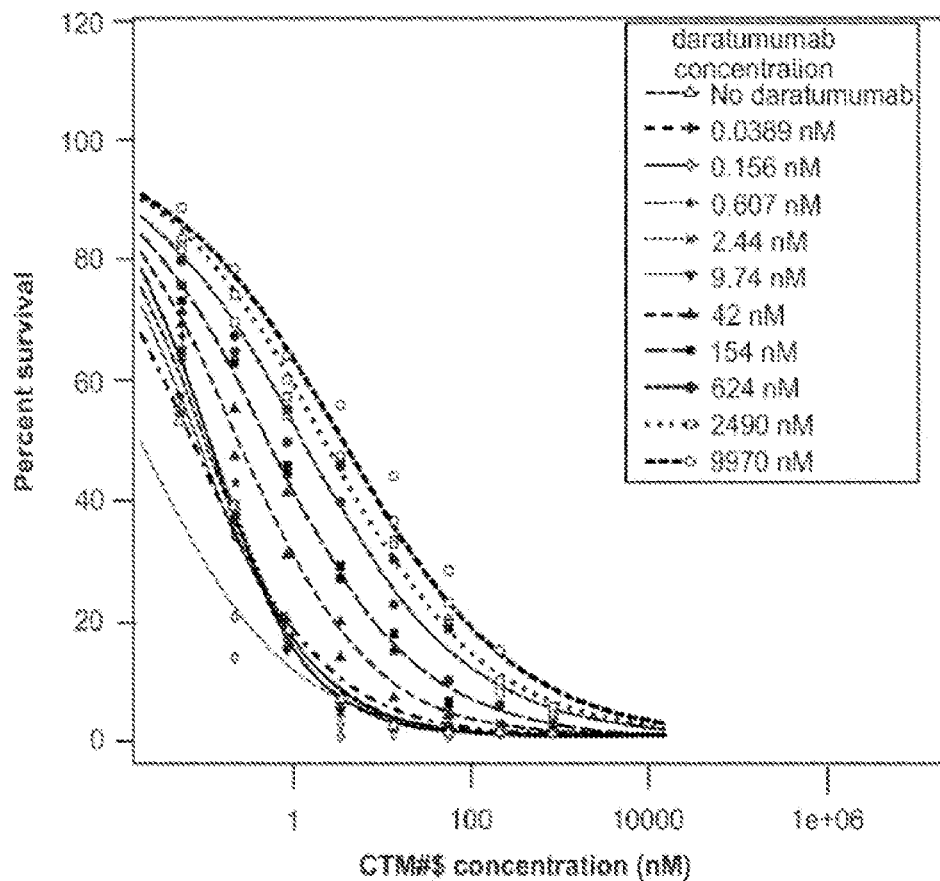

FIG. 8A-8H: FIG. 8A-8H shows the cytotoxic activities of various illustrative CD38-targeting molecules (CTM#1, CTM#2, CTM#4, CTM#7, and a CTM of family #5) to CD38-expressing cells in the presence of daratumumab. Cytotoxic activities of 0.5 μg/mL of CTM#1, CTM#7, or a CD38-targeting molecule of family #5 to CD38 positive cells pre-treated with a dilution series of daratumumab were measured using human myeloma H929 cells (FIG. 8A), human lymphoma ST486 cells (FIG. 8B), and human multiple myeloma MOLP-8 cells (FIG. 8C). Cytotoxic activities of a dilution series of CTM#1, CTM#7, or a CTM of family #5 administered to cells pre-treated with 10 ?g/mL of daratumumab were measured using CD38 positive human lymphoma ST486 cells (FIG. 8D), human multiple myeloma MOLP-8 cells (FIG. 8E). Cytotoxic activities of a dilution series of CTM#4 administered to human CD38-expressing cells exposed to 50 μg/mL daratumumab were measured using either human myeloma H929 cells or human multiple myeloma MOLP-8 cells (FIG. 8F). FIG. 8G shows representative $CD_{50}$ values (nM) of CTM#4 to human myeloma MOLP-8 cells exposed to a concentration series of daratumumab and measured 48 hours after administration of CTM#4. FIG. 8H shows cytotoxic activities and $CD_{50}$ values (nM) of a dilution series of CTM#4 administered to human multiple myeloma MOLP-8 cells treated with a concentration series of daratumumab at 48 hours after exposure with CTM#4. In FIG. 8H, $CD_{50}$ values (nM) for CTM#4 are shown at specific daratumumab concentrations (nM) in the bottom table. Cytotoxic activity of CTM#4 was retained in the presence of daratumumab, with modest shifts in the $CD_{50}$ values at daratumumab concentrations around 10,000 nM.

Figure 9:
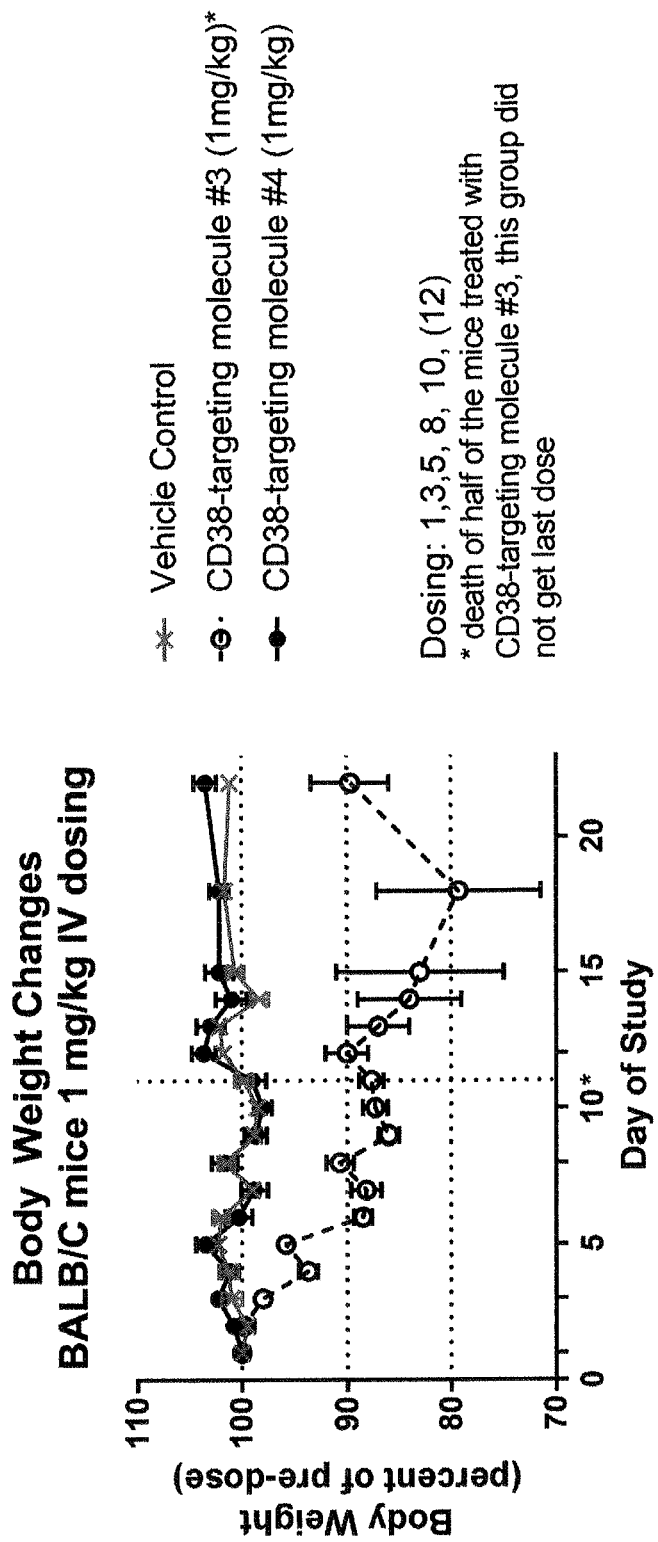

FIG. 9: FIG. 9 shows body weight changes over time of BALB/c mice being administered 1 milligram per kilogram body weight (mg/kg) of CD38-targeting molecule #3 or CD38-targeting molecule #4 for six doses over twelve days. Because half of the mice that received CTM#3 died before the last scheduled dose on Day 12, dosing was discontinued for the CTM#3 group before Day 12.

Figure 10:
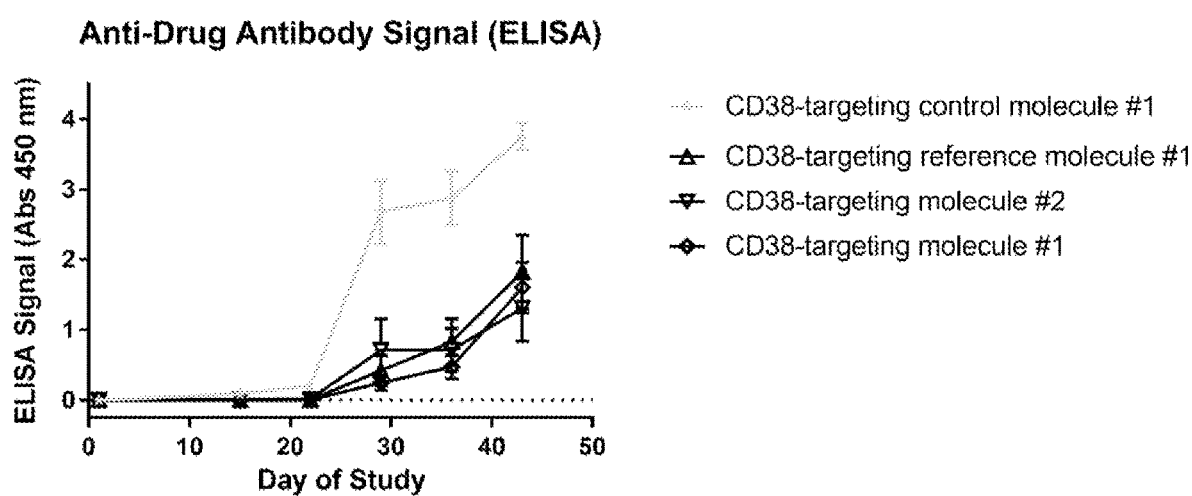

FIG. 10: FIG. 10 shows the quantity of serum anti-drug immunoglobulin G as measured using an in-solution ELISA assay applied to serum samples taken from mice administered CTM#1, CTM#2, or CD38-targeting reference molecule #1 as compared to the less de-immunized CD38-targeting control molecule (SEQ ID NO:84). The mice were each administered 0.25 mg/kg of the respective CD38-targeting molecule three times a week for two weeks and then three more times a week for week 4 and 5 for a total of 12 doses over a 5-week period. Mouse sera was collected at different time-points during the dosing phase of the study and after dosing had concluded.

FIG. 11A-11D: FIG. 11A-11D shows human tumor growth over time in in vivo xenograft mouse models of human cancer. Mice were injected with human myeloma tumor cells expressing low and high amounts of CD38 (LP1 cells, FIG. 11A; H929 cells, FIG. 11B; MM1.S cells, FIG. 11C; MOLP-8 cells, FIG. 11D) and were administered either CD38-targeting molecule #4 or a vehicle-only negative control. Blue indicates measurements for vehicle only control; all other data is for CTM #4 at various doses (e.g. 1.5, 3, 4.5, 5, 6, 9, 10, or 12 mg/kg) and administration schedules (e.g. biweekly, BIW; once per week, QW; or every other week, Q2W).

Figure 12C:
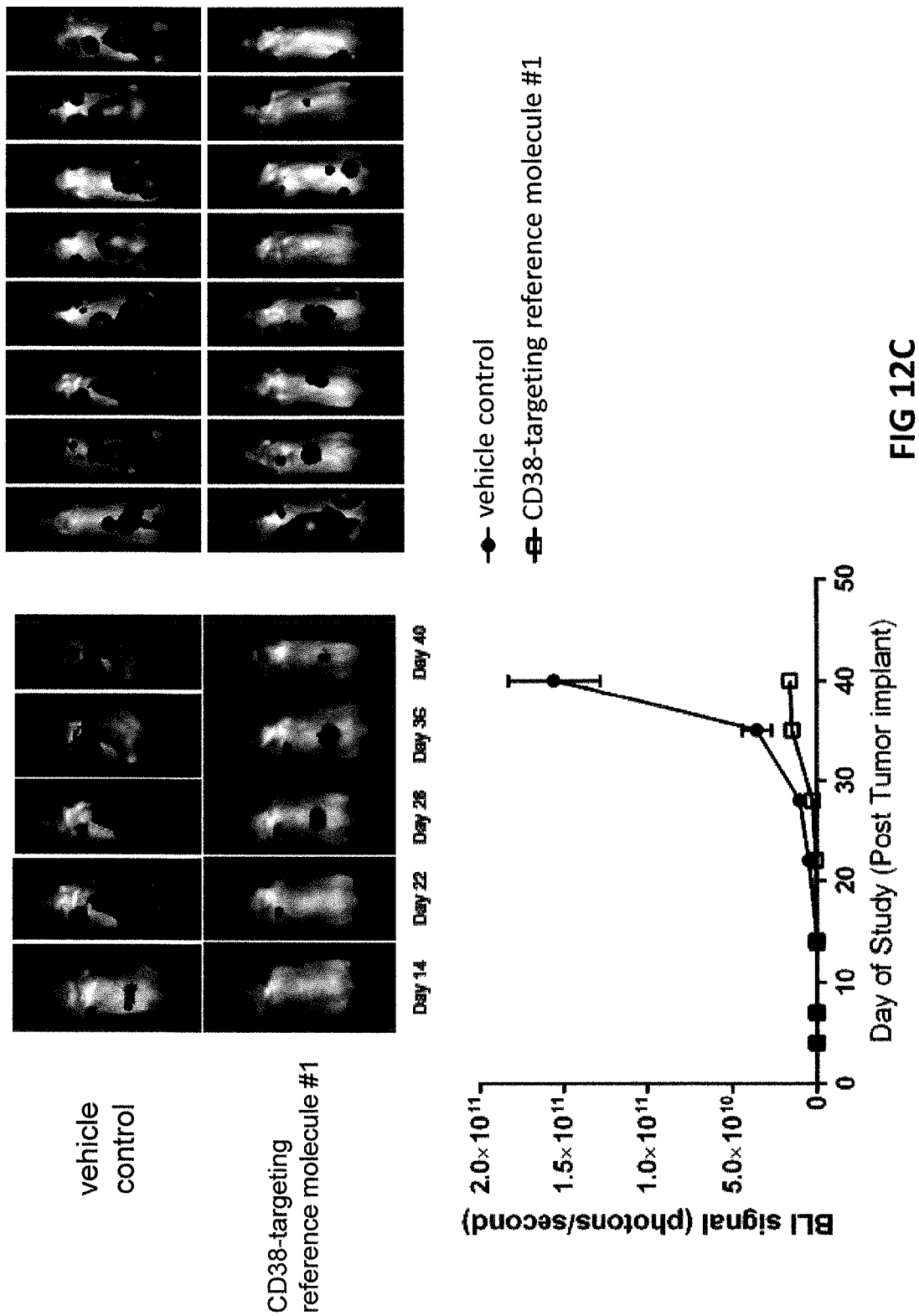

FIG. 12: FIG. 12A shows mean bioluminescence signal in a disseminated xenograft mouse models of cancer receiving treatment with illustrative CD38-targeting molecules. FIG. 12A shows mean bioluminescence signal in a MM1.S-luc disseminated multiple myeloma mouse model. FIG. 12B shows images of mice collected using bioluminescence imaging of luciferase activity in the xenograft tumor cells: the mouse administered vehicle only exhibited an intense signal extensively throughout its body, whereas the mouse administered CD38-targeting molecule #4 (CTM #4) appeared to have no detectable MM1.S-luc tumor cells by this method. Complete tumor elimination was observed in 10 of 10 mice. FIG. 12C shows mean bioluminescence signal in a Daudi-luc disseminated xenograft mouse model. FIG. 12C shows images of mice collected using bioluminescence imaging of luciferase activity in the xenograft tumor cells: mice administered vehicle only exhibited an intense signal extensively throughout their bodies, whereas mice administered CD38-targeting reference molecule #1 displayed reduced signals on the relevant study days.

Figure 13:
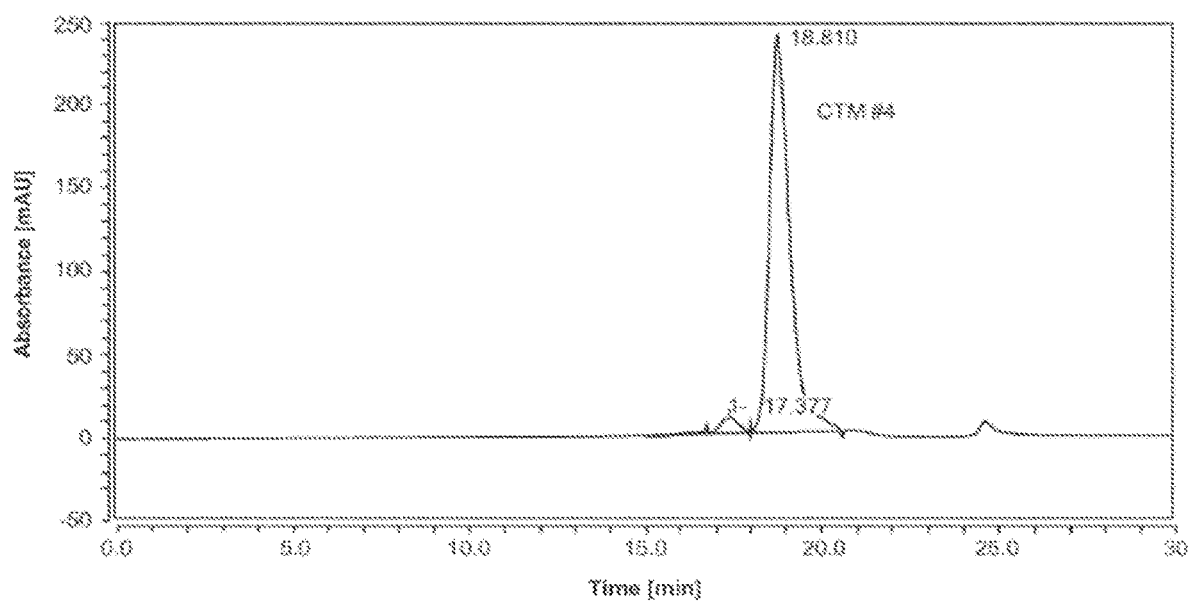

FIG. 13: FIG. 13 graphically shows the sizes and proportions of protein species present in a sample preparation of CTM#4 analyzed by size exclusion chromatography (SEC) under non-denaturing conditions. For the SEC analysis, the absorbance of ultraviolet (uv) light at a wavelength of 280 nanometers (nm) of the material eluted after flowing through a SEC column was plotted in milli-absorbance units (mAU) over the elution time in minutes (min). Software was used to identify individual peaks in the 280 nm trace and the elution time of each peak's maximum absorbance of ultraviolet light at 280 nm. The peak centered at 18.81 minutes (#2) represents a noncovalent homodimeric form of CTM#4 comprising 1014 amino acid residues and having a theoretical molecular weight of about 110 kDa, and the peak (#1) centered at 17.38 minutes represents one or more higher molecular weight species, e.g. a multimer(s) and/or aggregate(s) of CTM#4. The purity of an individual peak may be calculated by dividing the area of that peak by the total peak area of the sample. The peak at around 25 minutes represents an expected signal in the uv light absorbance caused by buffer elution.

Figures 14A, 14B:
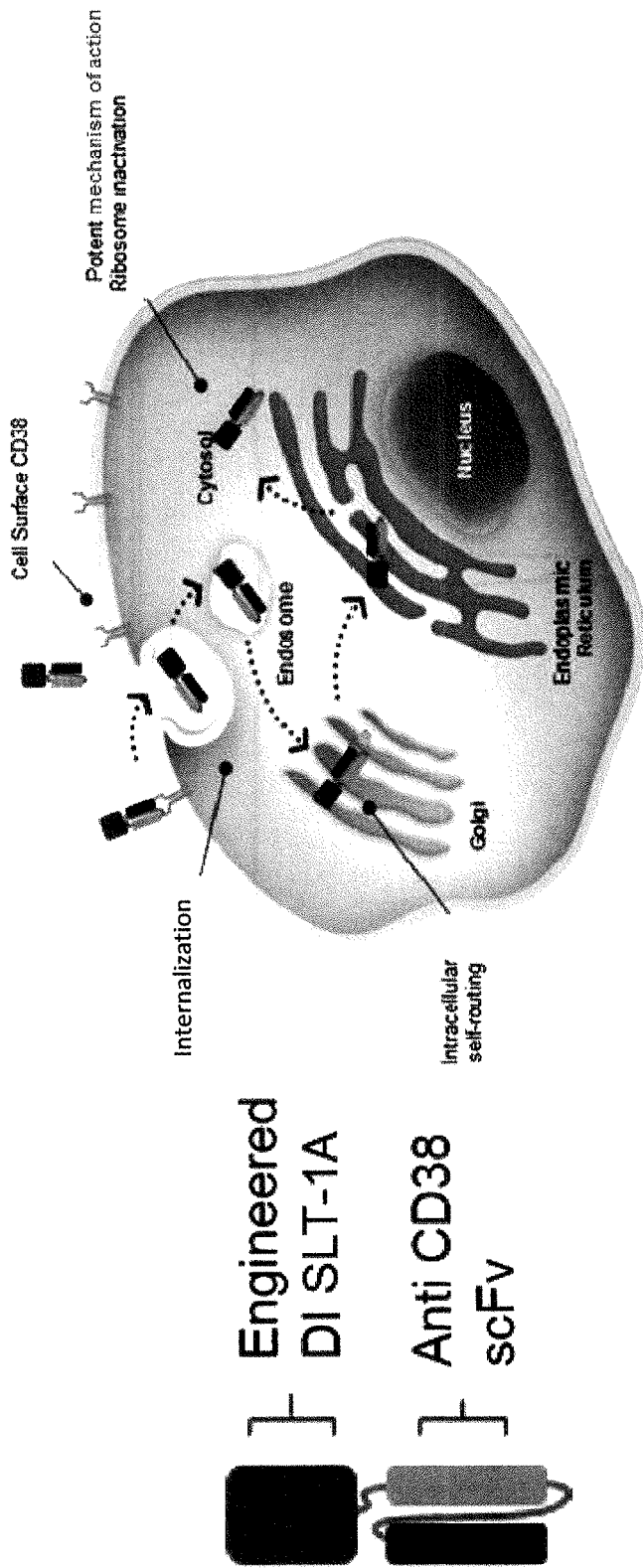

FIG. 14A-14B: FIG. 14A is a schematic drawing of an illustrative CD38-targeting molecule, such as, e.g., CTM #4. CTM#4 comprises a continuous polypeptide comprising an engineered deimmunized (DI) Shiga toxin subunit A effector polypeptide (SLT-1A) and an anti-CD38 single chain variable fragment (scFv) fused via a proteinaceous linker. FIG. 14B is a schematic drawing showing a potential mechanism of action of an illustrative CD38-targeting molecule, such as, e.g., CTM #4, which involves specific binding to CD38-expressing cells via cell-surface CD38, internalization into these target cells; intracellular self-routing in a retrograde pathway from the endosome to the Golgi, then to the endoplasmic reticulum, and then to the cytosol; and once in the cytosol irreversible and enzymatic inactivation of ribosomes to resulting in target cell death. This putative mechanism of action for CTM#4 is independent of patient's immune function status.

Figure 15:
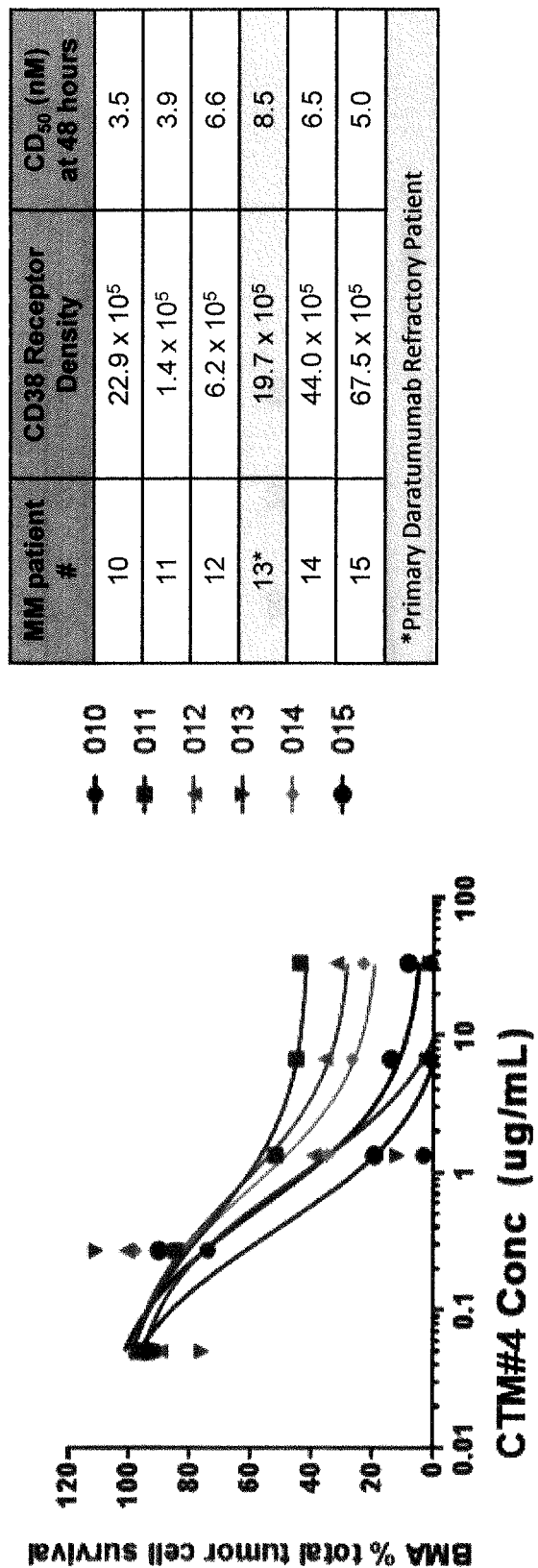

FIG. 15: FIG. 15 shows CTM #4 kills patient-derived multiple myeloma cells in primary cell culture. FIG. 15 shows percent total multiple myeloma cell survival after administration of a concentration (Conc) series of CTM #4 and $CD_{50}$ values (nM) of CTM #4 to multiple myeloma cell samples obtained by bone marrow aspirate (BMA) from six different patients (010, 011, 012, 013, 014, and 015), including one sample from a daratumumab-resistant patient (#13). In FIG. 15, the middle column of the table reports CD38 receptor density for the MM cells in the patient samples. At 48 hours after CTM #4 administration, potent CTM #4 cytotoxicity to primary multiple myeloma cells (e.g. $CD_{50}$ values of 3.5 to 8.5 nM) was observed across a broad range of CD38 expression levels (e.g. CD38 cell-surface densities of 1.4 to $67.5 \times 10^5$ CD38 molecules per cell).

Figure 16:
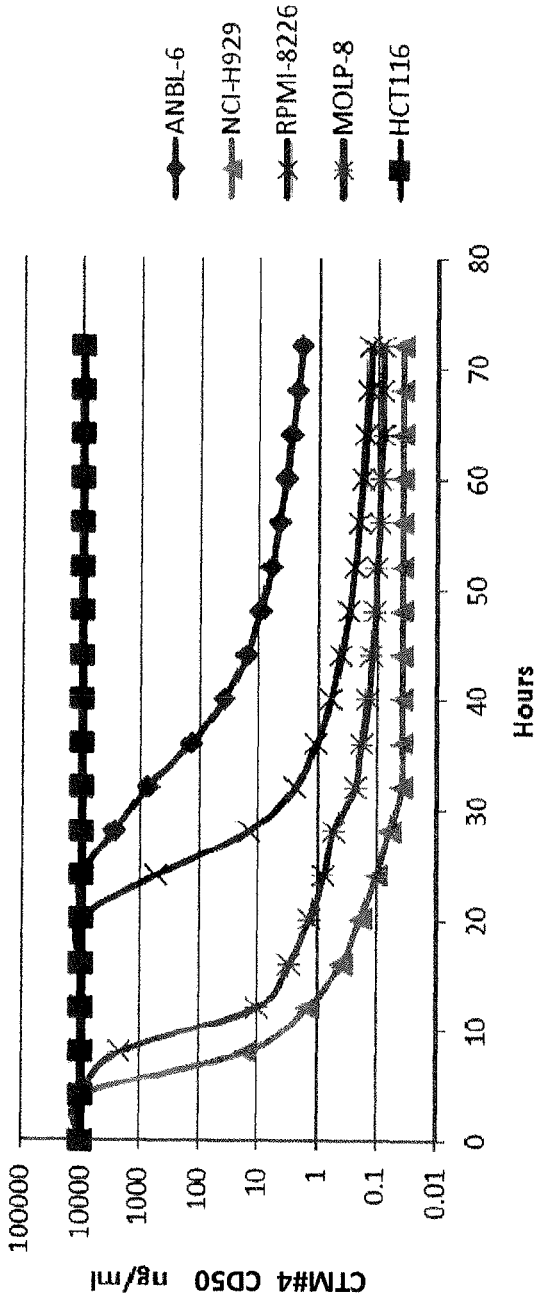

FIG. 16: FIG. 16 shows results from a time-course study of cell viability measured using a Real Time Glo assay after administration of CTM#4 to human multiple myeloma cells in vitro. FIG. 16 shows CTM#4 CD50 values (ng/mL) over time and across different cell types from a multiple myeloma cell panel (ANBL-6, NCI-H929, RMPI-8226, and MOLP-8) and in a non-multiple myeloma control cell line (HCT116). In FIG. 16, the table reports $CD_{50}$ values (pM) in the bottom two lines (CTM#4 or CD38TM4). In FIG. 16, the table reports the expression level of cell surface CD38 and characterizes the values as either high or medium in the CD38 expression line.

Figure 17:
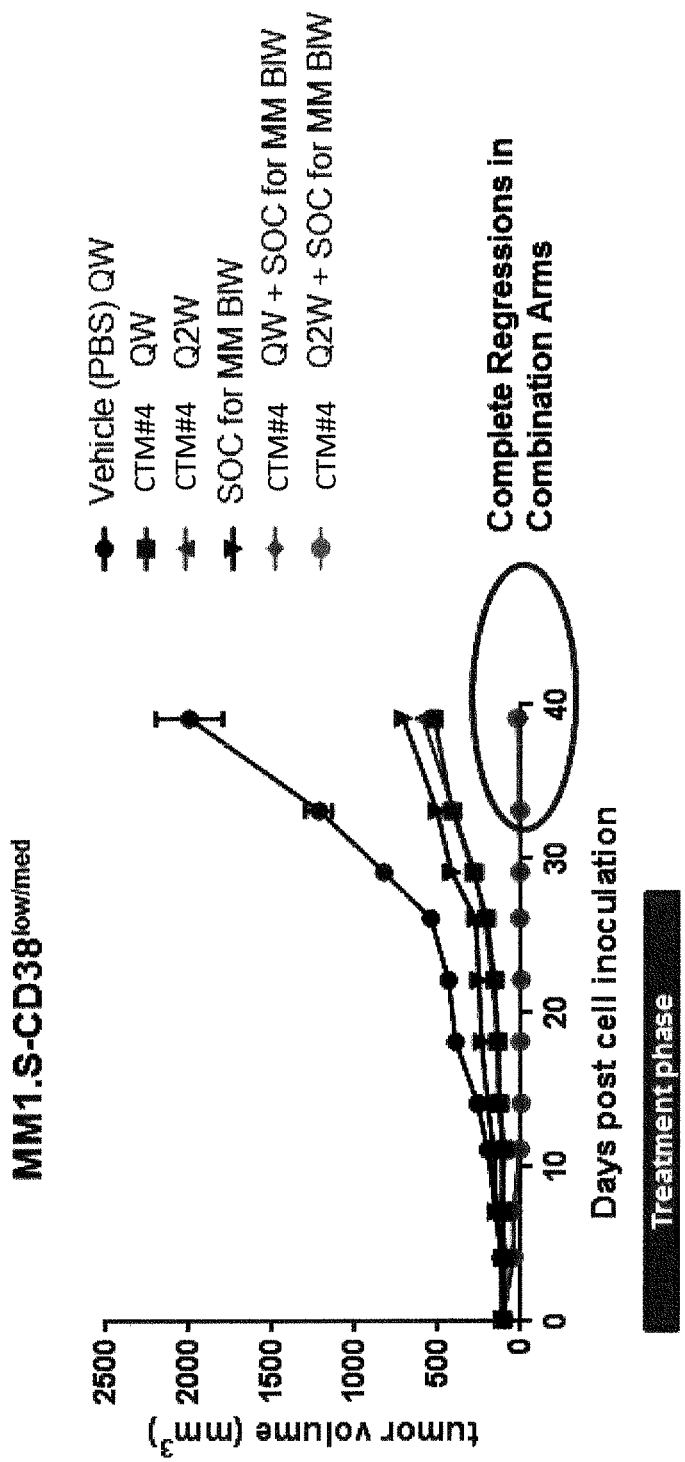

FIG. 17: FIG. 17 shows a time course of tumor volume after mice were inoculated with human multiple myeloma MM1.S cells to form a disseminated xenograft and treated with CTM#4. Mice were treated with CTM#4 once per week (QW) or every other week (Q2W), and were optionally co-treated with a current standard of care (SOC) for multiple myeloma in the U.S.A.

Figures 18A, 18B:
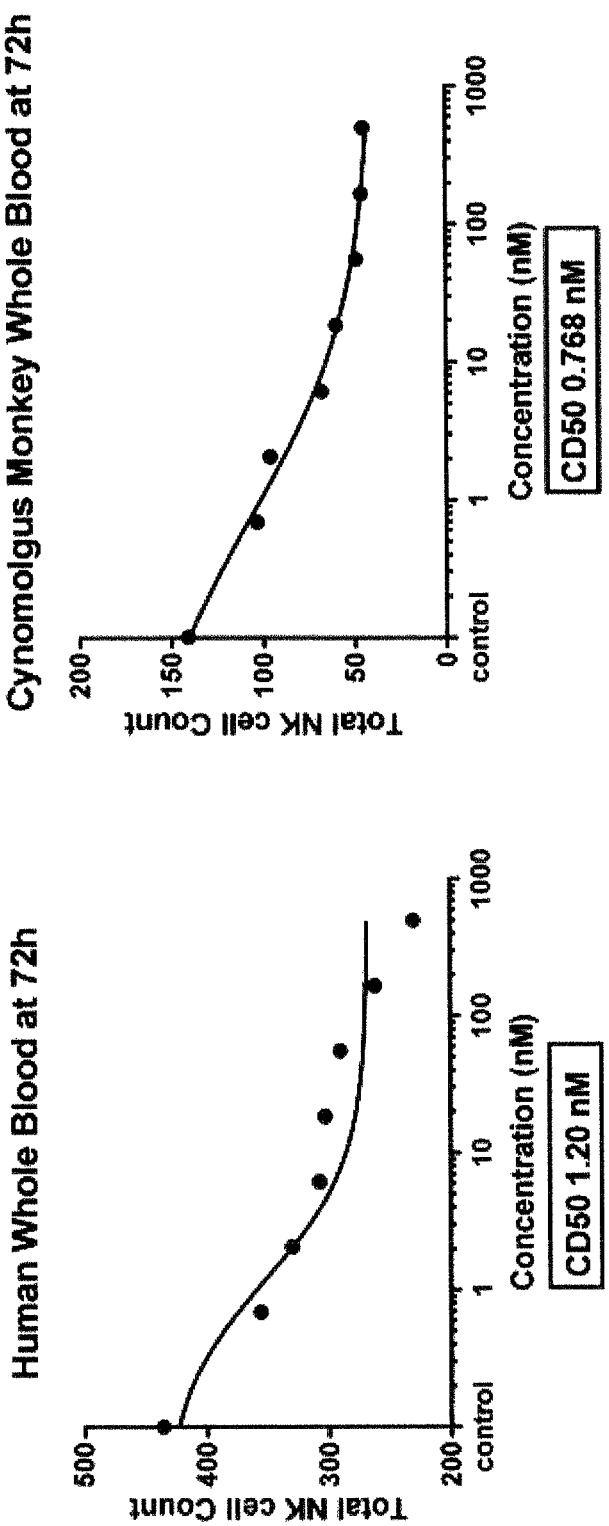

FIG. 18A-18B: FIG. 18A-18B shows an ex-vivo analysis using flow cytometry of total natural killer (NK) cell counts in human whole blood (left panel) and cynomolgus monkey whole blood after administration of a dilution series of CTM#4. The concentration of CTM#4 calculated to eliminate half of the NK population ($CD_{50}$) in this assay is shown.

Figure 19:
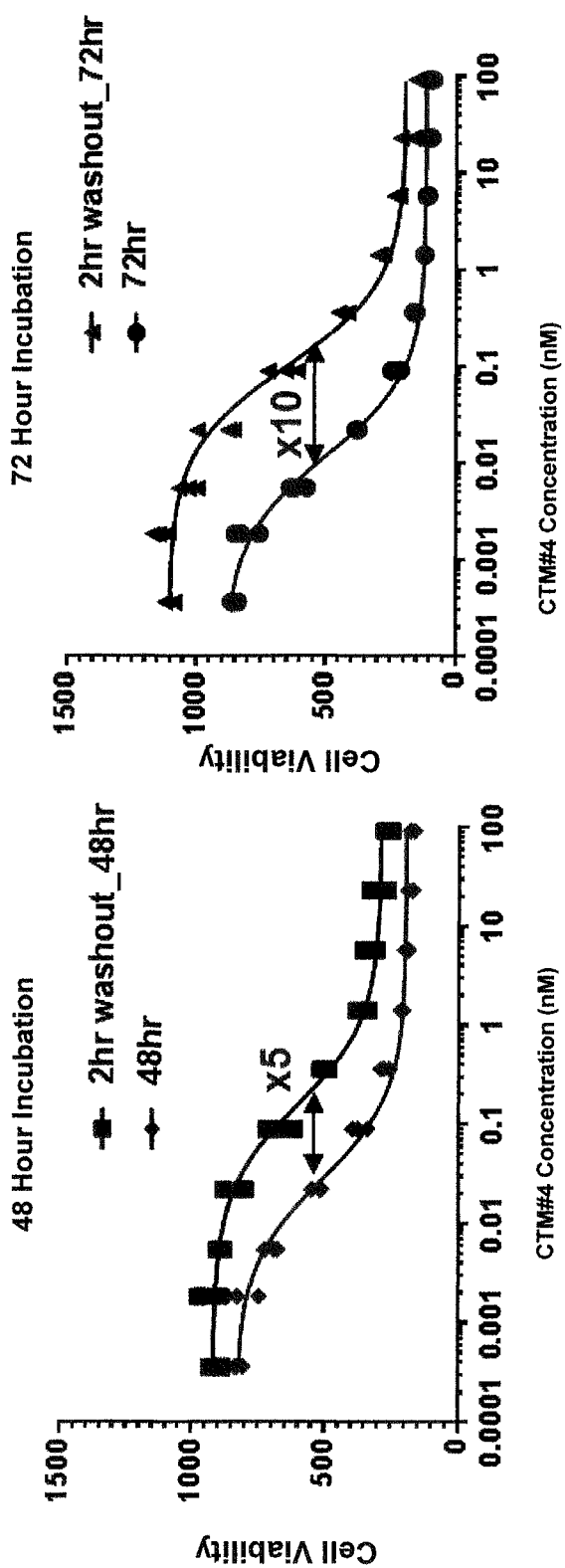

FIG. 19: FIG. 19 shows dose-response curves of human multiple myeloma ANBL-6 cells to CTM#4 administration and a tabular summary of the results. ANBL-6 cells were incubated either continuously with CTM#4 for 48 or 72 hours, or exposed for 2 hours to CTM#4, washed, and kept in CTM#4-free media until a 48- or 72-hour time-point. FIG. 19 shows $CD_{50}$ values for CTM#4 to ANBL-6 cells for the four conditions tested: at the 48-hour time-point-0.03 nM with no washout and 0.16 nM for the 2-hour washout; at the 72-hour time-point-0.01 nM with no washout and 0.1 nM for the 2-hour washout.

Figure 20:
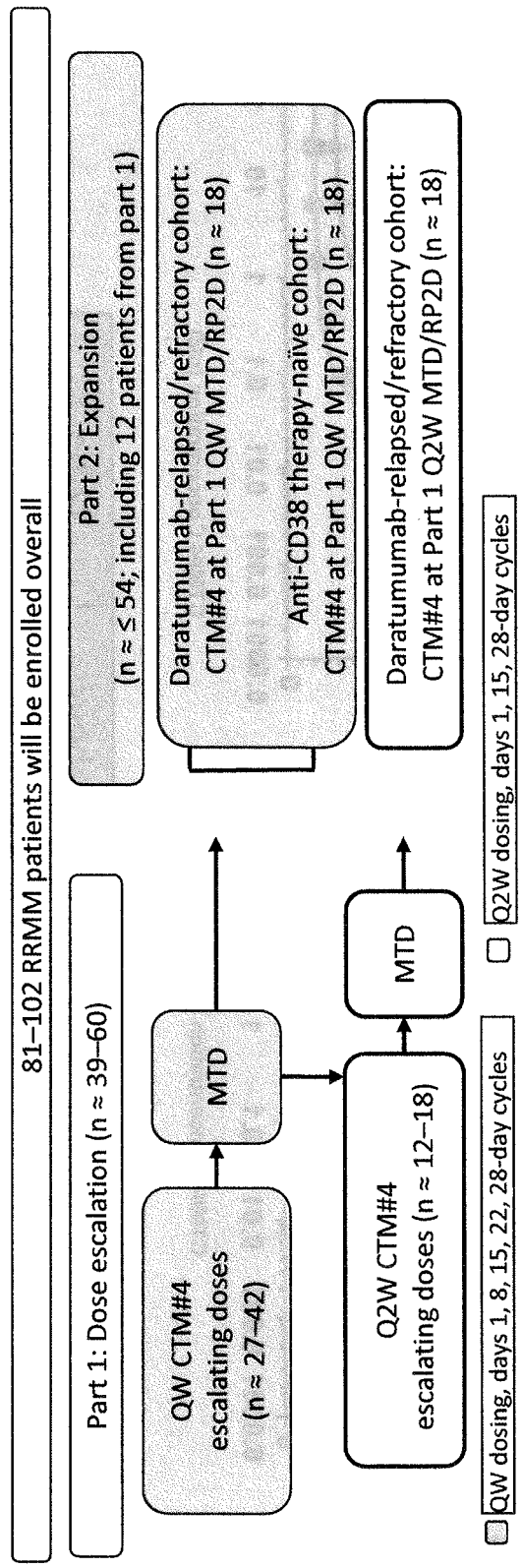

FIG. 20: FIG. 20 is a schematic showing the design of the first phase of a CTM#4 monotherapy clinical study for patients categorized as having relapsed and/or refractory multiple myeloma (RRMM). The study design comprises a dose-escalation phase (Part 1) and an expansion phase (Part 2). In both parts, patients are treated until progressive disease (PD), unacceptable toxicity, or withdrawal.

Figure 21:
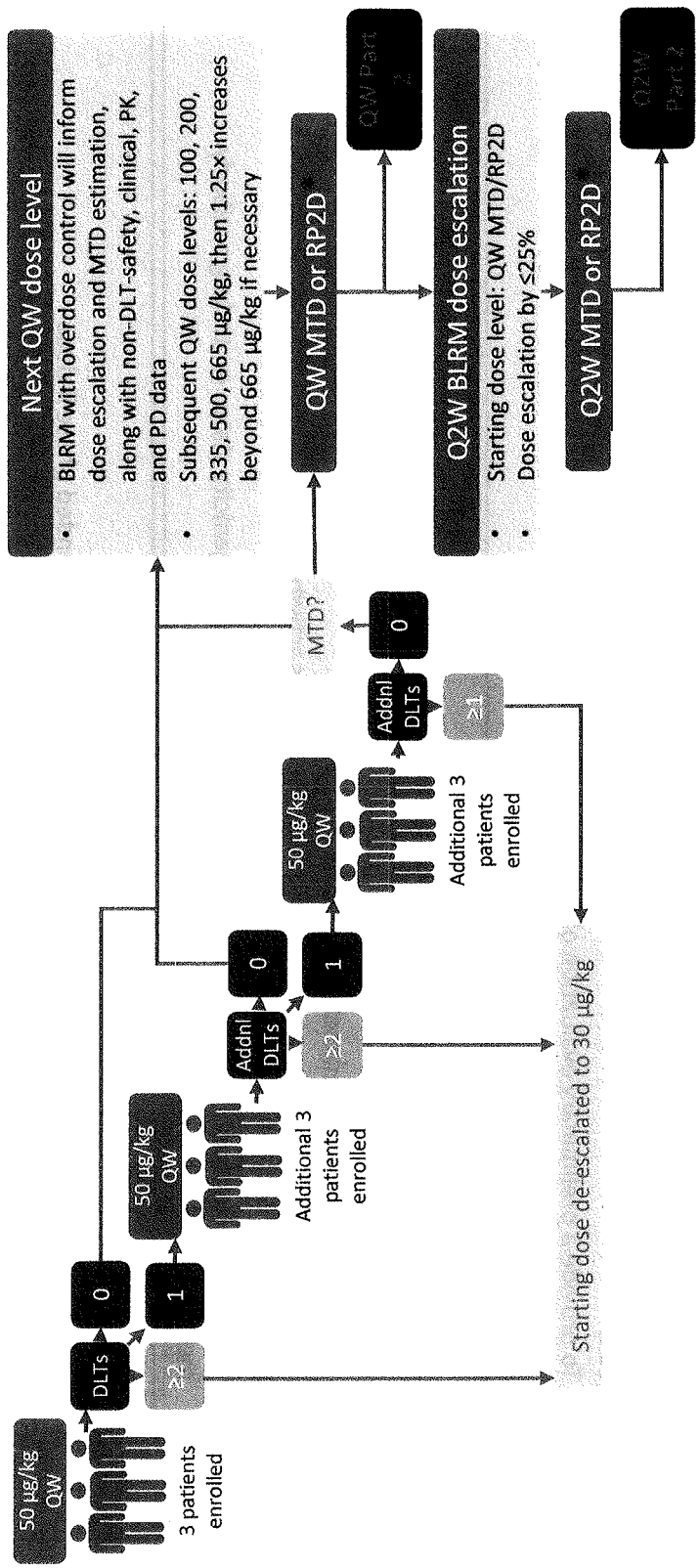

FIG. 21: FIG. 21 is a schematic illustrating a dosing scheme for a CTM#4 monotherapy clinical study. Dose escalation will start at 50 µg/kg CTM#4 and then proceed as shown in FIG. 21, according to the number of dose-limiting toxicities (DLT) observed in cycle 1 of therapy. Following evaluation of the 50 µg/kg dose, subsequent dose escalation and maximum tolerated dose (MTD) determination will be informed by Bayesian Logistical Regression Model (BLRM) with overdose control, along with consideration of other available non-DLT-safety, clinical efficacy, pharmacokinetic (PK) and pharmacodynamic (PD) data.

FIG. 22A-22B: FIG. 22A lists primary and secondary objectives of a CTM#4 monotherapy clinical study, and FIG. 22B lists exploratory objectives thereof.

Figure 23A:
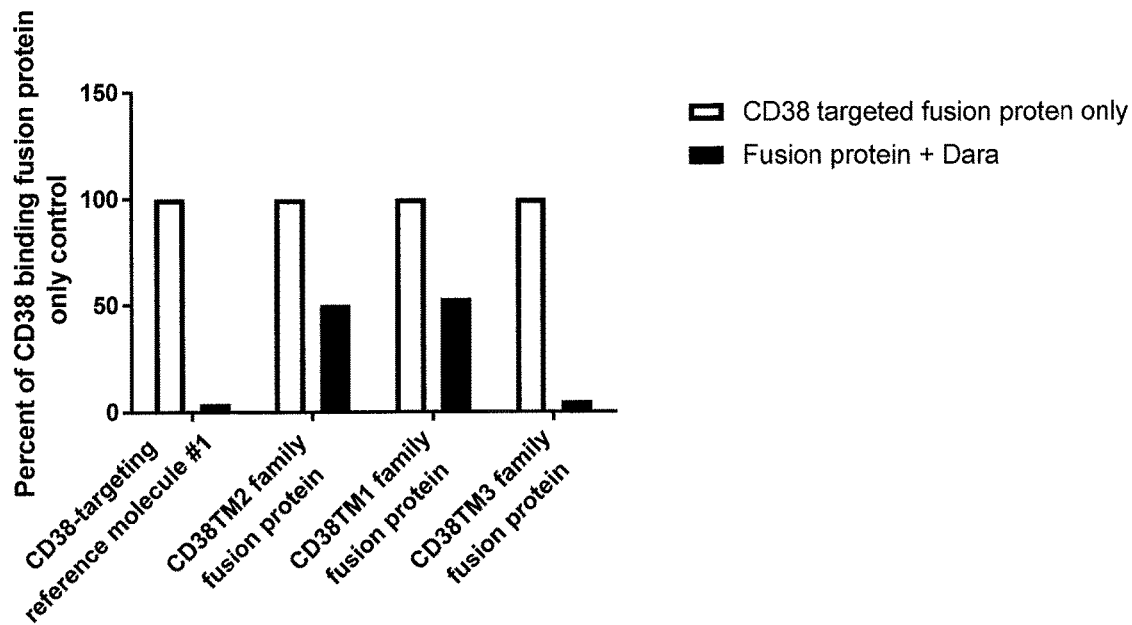
Figure 23B:
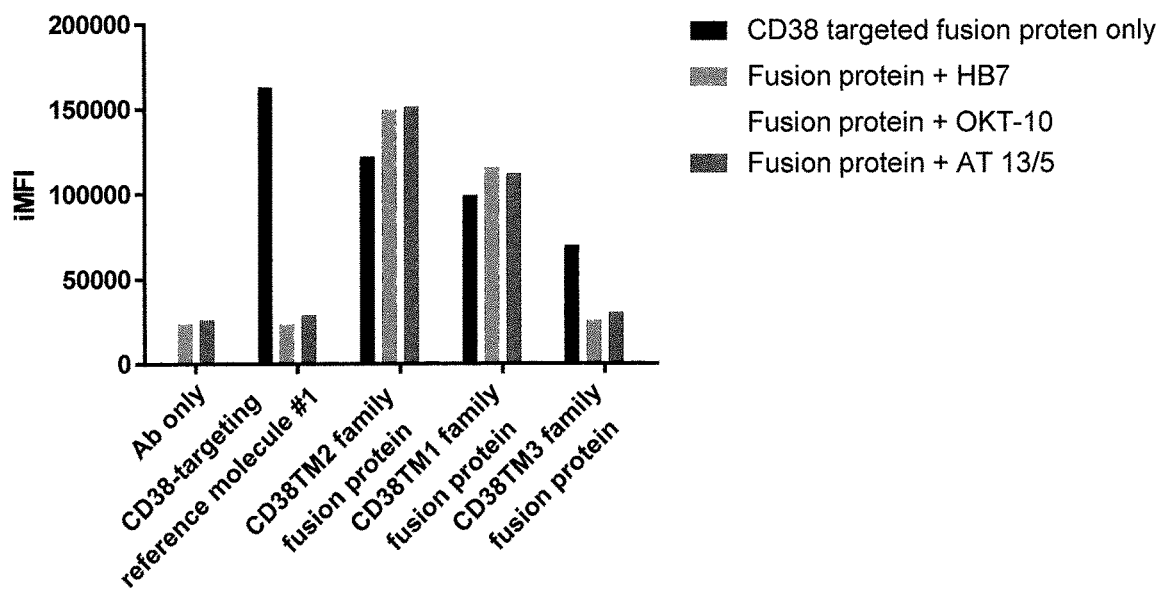
Figures 23C, 23D:
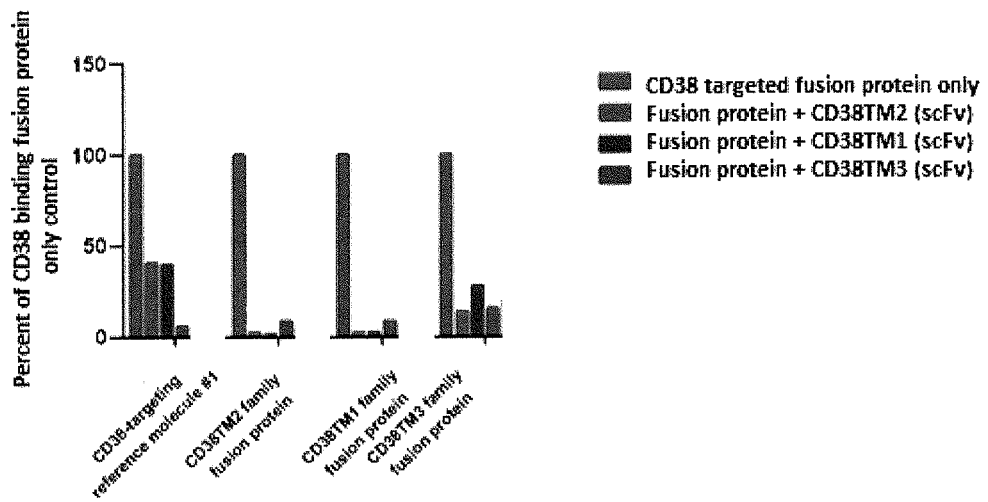

FIG. 23A-23D: FIG. 23A and FIG. 23B show binding of CD38 binding proteins (including CD38 targeting reference molecule #1 (SEQ ID NO:83)) to CD38-expressing MOLP-8 cells in the presence of anti-CD38 antibodies daratumumab, HB-7, AT13-5, and OKT-10. FIG. 23C shows competitive binding of CD38 binding proteins (including CD38 targeting reference molecule #1(SEQ ID NO:83)) to CD38-expressing MOLP-8 cells. All signals were detected by flow cytometry. FIG. 23D is a table summarizing the binding of CD38 binding proteins (top row) in the presence of anti-CD38 antibodies daratumumab, HB-7, AT13-5, OKT-10, and anti-CD38 binding scFv's (first left column). As used in FIG. 23A-D: CD38TM1-fusion protein refers to a CD38-binding fusion protein comprising the amino acid sequence of SEQ ID NO: 228; CD38TM2-fusion protein refers to a CD38-binding fusion protein comprising the sequence of SEQ ID NO: 229; and CD38TM3-fusion protein refers to a CD38-binding fusion protein comprising the sequence of SEQ ID NO: 230.

Figures 24A, 24B:
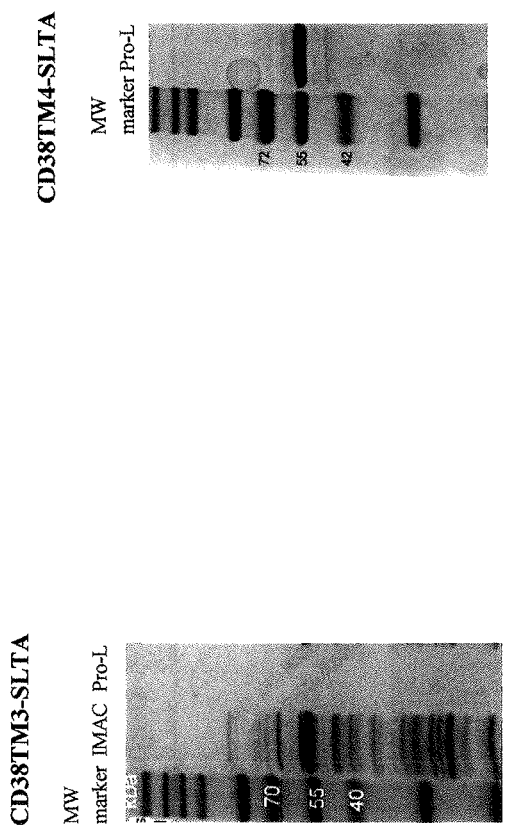
Figure 2B:
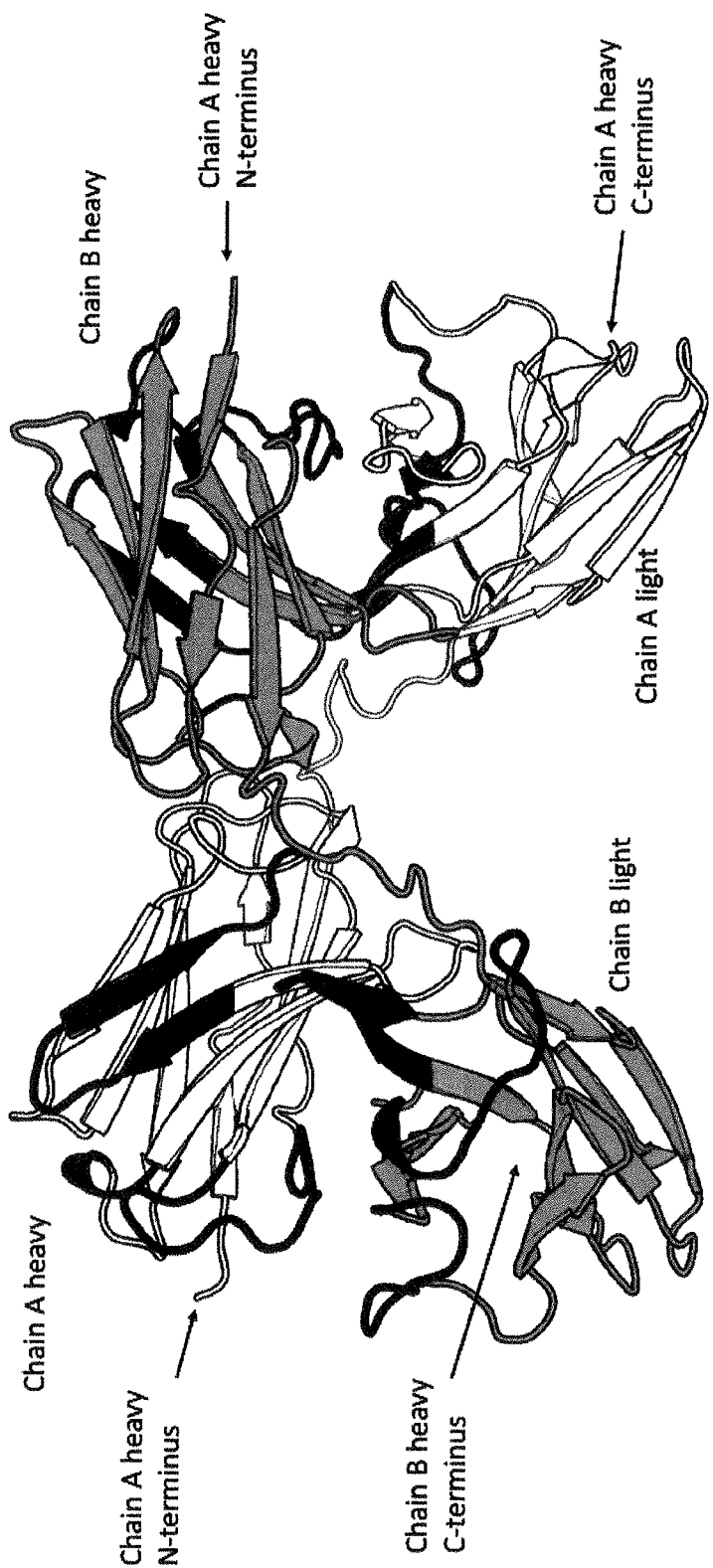

FIGS. 24A and 24B show purification of CTM #3 and CTM #4 by IMAC column and protein L (Pro-L) column respectively. MW marker indicates where molecular weight markers are located. VH and VL of CD38TM3 do not bind to standard monoclonal antibody purification resins (protein A or protein L), and it was purified using the His-tag and IMAC column (FIG. 24A). In order to render easier purification, the light chain of CD38TM3 which is a Lambda light chain was modified by framework mutations so that it is able to bind to Protein L, allowing for affinity purification without an additional tag. The resulting CD38TM4 is able to bind to protein L and thus may be purified by Protein L affinity.

FIG. 25A-25D: FIG. 25A-25D shows sequences of various illustrative CD38-targeting moieties suitable for use as a component of a CD38-targeting molecule. FIG. 25A provides sequences for CD38-Binding Region Family #1 and CD38-binding protein #1 (CD38TM1). FIG. 25B provides sequences for CD38-Binding Region Family #2 and CD38-binding protein #2 (CD38TM2). FIG. 25C provides sequences for CD38-Binding Region Family #3 and CD38-targeting moiety #3 (CD38TM3). FIG. 25D provides sequences for CD38-Binding Region Family #3 and CD38-targeting moiety #4 (CD38TM4). As shown in FIG. 25D, the first 21 amino acids of CD38TM3 VL domain was replaced with the first 22 amino acids of the VL domain of CD38TR1, which is a Kappa light chain to derive the VL domain of CD38TM4. CDR sequences are underlined.

FIG. 26: FIG. 26 shows illustration of the X-ray structure of a diabody formed by two identical scFvs, each containing VH-GGGGS-VL from N- to C-terminus, wherein the VH and VL are from CD38TM4. The VH of one scFv chain (chain A) complexes with the VL of the other scFv chain (chain B) to form a CD38 binding domain.

VII. DETAILED DESCRIPTION OF THE INVENTION

The present invention provides various embodiments of CD38-binding proteins, and compositions thereof, wherein each CD38-binding protein comprises (1) at least one Shiga toxin A Subunit effector polypeptide derived from the A Subunit of at least one member of the Shiga toxin family and (2) at least one CD38-binding region capable of specifically binding an extracellular part of a CD38 molecule, optionally with linkers, as described below. For each CD38-binding protein of the present invention, the at least one binding region is heterologous to the Shiga toxin A Subunit effector polypeptide, such as, e.g., an immunoglobulin-type binding region.

A. Definitions

These and other features, aspects and advantages of the present invention will become better understood with regard to the following description, appended claims, and accompanying figures. The aforementioned elements of the invention may be individually combined or removed freely in order to make other embodiments of the invention, without any statement to object to such combination or removal hereinafter.

In order that the present invention may be more readily understood, some terms are defined below. Additional definitions may be found within the detailed description of the invention.

As used in the specification and the appended claims, the terms “a,” “an” and “the” include both singular and the plural referents unless the context clearly dictates otherwise.

As used in the specification and the appended claims, the term “and/or” when referring to two species, A and B, means at least one of A and B. As used in the specification and the appended claims, the term “and/or” when referring to greater than two species, such as A, B, and C, means at least one of A, B, or C, or at least one of any combination of A, B, or C (with each species in singular or multiple possibility).

The term “amino acid residue” or “amino acid” includes reference to an amino acid that is incorporated into a protein, polypeptide, or peptide. The term “polypeptide” includes any polymer of amino acids or amino acid residues. The term “polypeptide sequence” refers to a series of amino acids or amino acid residues which physically comprise a polypeptide.

A “protein” is a macromolecule comprising one or more polypeptides or polypeptide “chains.” For example, a protein may comprise one, two, three, four, five, six, seven, eight, nine, ten, or more polypeptides. In embodiments wherein the protein comprises more than one polypeptide, the polypeptides of the protein may either be the same or different from one another. A protein may be a monomer, or a multimer, such as a dimer, trimer, tetramer, etc.

A “peptide” is a small polypeptide of sizes less than about a total of 15 to 20 amino acid residues. The term “amino acid sequence” refers to a series of amino acids or amino acid residues which physically comprise a peptide or polypeptide depending on the length. Sometimes “residue” as used herein is meant to indicate a position in a protein and its associated amino acid identity. Unless otherwise indicated, polypeptide and protein sequences disclosed herein are written from left to right representing their order from an amino-terminus to a carboxy-terminus.

The terms “amino acid,” “amino acid residue,” “amino acid sequence,” or polypeptide sequence include naturally occurring amino acids (including L and D isosteriomers) and, unless otherwise limited, also include known analogs of natural amino acids that can function in a similar manner as naturally occurring amino acids, such as selenocysteine, pyrrolysine, N-formylmethionine, gamma-carboxyglutamate, hydroxyprolinehypusine, pyroglutamic acid, and selenomethionine.

By “modification” herein is meant an amino acid substitution, insertion, and/or deletion in a polypeptide sequence or an alteration to a moiety chemically linked to a protein. For example, a modification may be an altered carbohydrate or PEG structure attached to a protein. By “amino acid modification” herein is meant an amino acid substitution, insertion, and/or deletion in a polypeptide sequence. For clarity, unless otherwise noted, the amino acid modification is always to an amino acid coded for by DNA, e.g. the 20 amino acids that have codons in DNA and RNA.

By “amino acid substitution” or “substitution” herein is meant the replacement of an amino acid at a particular position in a parent polypeptide sequence with a different amino acid. In particular, in some embodiments, the substitution is to an amino acid that is not naturally occurring at the particular position, either not naturally occurring within the organism or in any organism. For example, the substitution N297A refers to a variant polypeptide, in this case an Fc variant, in which the asparagine at position 297 is replaced with alanine. For clarity, a protein which has been engineered to change the nucleic acid coding sequence but not change the starting amino acid (for example exchanging CGG (encoding arginine) to CGA (still encoding arginine) to increase host organism expression levels) is not an “amino acid substitution”; that is, despite the creation of a new gene encoding the same protein, if the protein has the same amino acid at the particular position that it started with, it is not an amino acid substitution.

The phrase “conservative substitution” with regard to an amino acid residue of a peptide, peptide region, polypeptide region, protein, or molecule refers to a change in the amino acid composition of the peptide, peptide region, polypeptide region, protein, or molecule that does not substantially alter the function and structure of the overall peptide, peptide region, polypeptide region, protein, or molecule (see Creighton, Proteins: Structures and Molecular Properties (W. H. Freeman and Company, New York (2nd ed., 1992))).

By "amino acid insertion" or "insertion" as used herein is meant the addition of an amino acid sequence at a particular position in a parent polypeptide sequence. For example, -233E or 233E designates an insertion of glutamic acid after position 233 and before position 234. Additionally, 233ADE or A233ADE designates an insertion of AlaAspGlu after position 233 and before position 234.

By "amino acid deletion" or "deletion" as used herein is meant the removal of an amino acid sequence at a particular position in a parent polypeptide sequence. For example, E233- or E233#, E233( ) or E233del designates a deletion of glutamic acid at position 233. Additionally, EDA233- or EDA233# designates a deletion of the sequence GluAspAla that begins at position 233.

As used herein, "protein" means at least two covalently attached amino acids, which includes proteins, polypeptides, oligopeptides and peptides. The peptidyl group comprises naturally occurring amino acids and peptide bonds, or synthetic peptidomimetic structures, i.e. "analogs", such as peptoids (see Simon et al., PNAS USA 89(20):9367 (1992), entirely incorporated by reference). The amino acids may either be naturally occurring or synthetic (e.g. not an amino acid that is coded for by DNA); as will be appreciated by those in the art. For example, homo-phenylalanine, citrulline, ornithine and noreleucine are considered synthetic amino acids for the purposes of the invention, and both D- and L-(R or S) configured amino acids may be utilized. The variants of the present invention may comprise modifications that include the use of synthetic amino acids incorporated using, for example, the technologies developed by Schultz and colleagues, including but not limited to methods described by Cropp & Shultz, 2004, Trends Genet. 20(12): 625-30, Anderson et al., 2004, Proc Natl Acad Sci USA 101 (2):7566-71, Zhang et al., 2003, 303(5656):371-3, and Chin et al., 2003, Science 301(5635):964-7, all entirely incorporated by reference. In addition, polypeptides may include synthetic derivatization of one or more side chains or termini, glycosylation, PEGylation, circular permutation, cyclization, linkers to other molecules, fusion to proteins or protein domains, and addition of peptide tags or labels.

By "wild type or WT" herein is meant an amino acid sequence or a nucleotide sequence that is found in nature, including allelic variations. A WT protein has an amino acid sequence or a nucleotide sequence that has not been intentionally modified.

By "variant protein" or "protein variant", or "variant" as used herein is meant a protein that differs from that of a parent protein by virtue of at least one amino acid modification. Protein variant may refer to the protein itself, a composition comprising the protein, or the amino sequence that encodes it. In some embodiments, the protein variant has at least one amino acid modification compared to the parent protein, e.g. from about one to about seventy amino acid modifications, and in some embodiments, from about one to about five amino acid modifications compared to the parent. As described below, in some embodiments the parent polypeptide, for example an Fc parent polypeptide, is a human wild type sequence, such as the Fc region from IgG1, IgG2, IgG3 or IgG4, although human sequences with variants can also serve as "parent polypeptides". In some embodiments, the protein variant sequence herein will possess at least about 80% identity with a parent protein sequence, and in some embodiments will possess at least about 90% identity, at least about 95%, at least about 95%, or at least about 99% identity to the parent protein sequences. Variant protein can refer to the variant protein itself, compositions comprising the protein variant, or the DNA sequence that encodes it.

By "antigen binding domain" or "ABD" herein is meant a set of six Complementary Determining Regions (CDRs) that, when present as part of a polypeptide sequence, specifically binds a target antigen as described herein. Thus, an "anti-CD38 antigen binding domain" binds CD38 antigen as outlined herein. As is known in the art, these CDRs are generally present as a first set of variable heavy CDRs (vhCDRs or VHCDRs) and a second set of variable light CDRs (vlCDRs or VLCDRs), each comprising three CDRs: vhCDR1, vhCDR2, vhCDR3 for the heavy chain and vlCDR1, vlCDR2 and vlCDR3 for the light chain. As is understood in the art, the CDRs are separated by framework regions in each of the heavy variable and light variable regions: for the light variable region, these are (VL)FR1-vlCDR1-(VL)FR2-vlCDR2-(VL)FR3-vlCDR3-(VL)FR4, and for the heavy variable region, these are (VH)FR1-vhCDR1-(VH)FR2-vhCDR2-(VH)FR3-vhCDR3-(VH) FR4.

Antigen binding domains of the invention can be embodied in multiple formats, for example, in Fab, Fv and scFv. In an "Fab" format, the set of 6 CDRs are contributed by two different polypeptide sequences, the heavy variable region (vh or VH; containing the vhCDR1, vhCDR2 and vhCDR3) and the light variable region (vl or VL; containing the vlCDR1, vlCDR2 and vlCDR3), with the C-terminus of the VH being attached to the N-terminus of the CH1 domain of the heavy chain and the C-terminus of the VL being attached to the N-terminus of the constant light domain (and thus forming the light chain). Heavy variable regions and light variable regions together form Fvs, which can be either scFvs or Fabs, as outlined herein. Thus, in some cases, the six CDRs of the antigen binding domain are contributed by a VH and VL. In an scFv format, the VH and VL are covalently attached, generally through the use of a linker as outlined herein, into a single polypeptide sequence, which can be either (starting from the N-terminus) VH-linker-VL or VL-linker-VH.

By "Fab" or "Fab region" as used herein is meant the polypeptide that comprises the VH, CH1, VL, and CL immunoglobulin domains. Fab may refer to this region in isolation, or this region in the context of a full-length antibody or antibody fragment.

By "Fv" or "Fv fragment" or "Fv region" as used herein is meant a polypeptide that comprises the VL and VH domains of a single antibody. As will be appreciated by those in the art, these are made up of two domains, a variable heavy domain and a variable light domain.

By "single chain Fv" or "scFv" herein is meant a variable heavy domain covalently attached to a variable light domain, generally using a scFv linker as described herein, to form a scFv or scFv domain. A scFv domain can be in either orientation from N- to C-terminus (vh-linker-vl or vl-linker-vh). In general, the linker is a scFv linker as is generally known in the art, and described above.

The term "antibody" is used in the broadest sense and includes, for example, an intact immunoglobulin or an antigen binding portion of an immunoglobulin or an antigen binding protein related or derived from an immunoglobulin. Intact antibody structural units often comprise a tetramertetrameric protein. Each tetramer is typically composed of two identical pairs of polypeptide chains, each pair having one "light" chain (typically having a molecular weight of about 25 kDa) and one "heavy" chain (typically having a molecular weight of about 50- to 70 kDa). Human immunoglobulin light chains may be classified as having kappa or lambda light chains. In some embodiments, the invention provides antibody structures comprising antigen binding domains (e.g. antibody heavy and/or light chains) that generally are based on the IgG class, which has several subclasses, including, but not limited to IgG1, IgG2, IgG3, and IgG4. In general, IgG1 has different allotypes with polymorphisms at 356 (D or E), IgG2 and 358 (L or M). The sequences depicted herein use the 356D/358M allotype, however the other allotype is included herein. That is, any sequence inclusive of an IgG1 Fc domain included herein can have 356E/358L replacing the 356D/358M allotype. IgG4 are used more frequently than IgG3.

It should be noted that IgG1 has different allotypes with polymorphisms at 356 (D or E) and 358 (L or M). The sequences depicted herein use the 356D/358M allotype, however the other allotype is included herein. That is, any sequence inclusive of an IgG1 Fc domain included herein can have 356E/358L replacing the 356D/358M allotype.

Thus, "isotype" as used herein is meant any of the subclasses of immunoglobulins defined by the chemical and antigenic characteristics of their constant regions. By "IgG subclass modification" or "isotype modification" as used herein is meant an amino acid modification that converts one amino acid of one IgG isotype to the corresponding amino acid in a different, aligned IgG isotype. For example, because IgG1 comprises a tyrosine and IgG2 a phenylalanine at EU position 296, a F296Y substitution in IgG2 is considered an IgG subclass modification. Similarly, because IgG1 has a proline at position 241 and IgG4 has a serine there, an IgG4 molecule with a S241P is considered an IgG subclass modification. Note that subclass modifications are considered amino acid substitutions herein.

By "Fc" or "Fc region" or "Fc domain" as used herein is meant the polypeptide comprising the constant region of an antibody excluding the first constant region immunoglobulin domain (e.g., CH1) and in some cases, part of the hinge. For IgG, the Fc domain comprises immunoglobulin domains CH2 and CH3 (Cγ2 and Cγ3) and the lower hinge region between CH1 (Cγ1) and CH2 (Cγ2). Although the boundaries of the Fc region may vary, the human IgG heavy chain Fc region is usually defined to include residues C226 or P230 to its carboxyl-terminus, wherein the numbering is according to the EU index as in Kabat. Accordingly, "CH" domains in the context of IgG are as follows: "CH1" refers to positions 118-215 according to the EU index as in Kabat. "Hinge" refers to positions 216-230 according to the EU index as in Kabat. "CH2" refers to positions 231-340 according to the EU index as in Kabat, and "CH3" refers to positions 341-447 according to the EU index as in Kabat. Thus, the "Fc domain" includes the —CH2-CH3 domain, and optionally a hinge domain (hinge-CH2-CH3). In some embodiments, as is more fully described below, amino acid modifications are made to the Fc region, for example to alter binding to one or more Fc?R receptors or to the FcRn receptor.

By "heavy constant region" herein is meant the CH1-hinge-CH2-CH3 portion of a human IgG antibody.

By "light constant region" is meant the CL domain from kappa or lambda.

By "variable domain" as used herein is meant the region of an immunoglobulin that comprises one or more Ig domains substantially encoded by any of the V? (V.kappa), V? (V.lamda), and/or VH genes that make up the kappa, lambda, and heavy chain immunoglobulin genetic loci respectively. Thus a "variable heavy domain" comprises (VH)FR1-vhCDR1-(VH)FR2-vhCDR2-(VH)FR3-vhCDR3-(VH)FR4 and a "variable light domain" comprises (VL)FR1-vlCDR1-(VL)FR2-vlCDR2-(VL)FR3-vlCDR3-(VL)FR4.

The amino-terminal portion of each chain comprises a variable region of about 100 to 110 or more amino acids primarily responsible for antigen recognition, generally referred to in the art and herein as the "Fv domain" or "Fv region". In the variable region, three loops are gathered for each of the V domains of the heavy chain and light chain to form an antigen-binding site. Each of the loops is referred to as a complementarity-determining region (hereinafter referred to as a "CDR"), in which the variation in the amino acid sequence is most significant. "Variable" refers to the fact that some segments of the variable region differ extensively in sequence among antibodies. Variability within the variable region is not evenly distributed. Instead, the V regions consist of relatively invariant stretches called framework regions (FRs) of 15-30 amino acids separated by shorter regions of extreme variability called "hypervariable regions" that are each 9-15 amino acids long or longer.

Each VH and VL is composed of three hypervariable regions ("complementary determining regions," "CDRs") and four FRs, arranged from amino-terminus to carboxy-terminus in the following order: FR1-CDR1-FR2-CDR2-FR3-CDR3-FR4.

The hypervariable region generally encompasses amino acid residues from about amino acid residues 24-34 (LCDR1; "L" denotes light chain), 50-56 (LCDR2) and 89-97 (LCDR3) in the light chain variable region and around about 31-35B (HCDR1; "H" denotes heavy chain), 50-65 (HCDR2), and 95-102 (HCDR3) in the heavy chain variable region; Kabat et al, SEQUENCES OF PROTEINS OF IMMUNOLOGICAL INTEREST, 5th Ed. Public Health Service, National Institutes of Health, Bethesda, Md. (1991) and/or those residues forming a hypervariable loop (e.g. residues 26-32 (LCDR1), 50-52 (LCDR2) and 91-96 (LCDR3) in the light chain variable region and 26-32 (HCDR1), 53-55 (HCDR2) and 96-101 (HCDR3) in the heavy chain variable region; Chothia and Lesk (1987) J. Mol. Biol. 196:901-917. Specific CDRs of the invention are described below.

As will be appreciated by those in the art, the exact numbering and placement of the CDRs can be different among different numbering systems. However, it should be understood that the invention of a variable heavy and/or variable light sequence includes the invention of the associated (inherent) CDRs. Accordingly, the invention of each variable heavy region is a invention of the vhCDRs (e.g. vhCDR1, vhCDR2 and vhCDR3) and the invention of each variable light region is a invention of the vhCDRs (e.g. vlCDR1, vlCDR2 and vlCDR3).

A useful comparison of CDR numbering is as below (Table 4), see Lafranc et al., Dev. Comp. Immunol. 27(1): 55-77 (2003):

TABLE 1

Antibody CDR Nomenclature

|        | Kabat + Chothia | IMGT  | Kabat | AbM   | Chothia | Contact |
|--------|-----------------|-------|-------|-------|---------|---------|
| vhCDR1 | 26-35           | 27-38 | 31-35 | 26-35 | 26-32   | 30-35   |
| vhCDR2 | 50-65           | 56-65 | 50-65 | 50-58 | 52-56   | 47-58   |

TABLE 1-continued

Antibody CDR Nomenclature

| | Kabat + Chothia | IMGT | Kabat | AbM | Chothia | Contact |
|---|---|---|---|---|---|---|
| vhCDR3 | 95-102 | 105-117 | 95-102 | 95-102 | 95-102 | 93-101 |
| vlCDR1 | 24-34 | 27-38 | 24-34 | 24-34 | 24-34 | 30-36 |
| vlCDR2 | 50-56 | 56-65 | 50-56 | 50-56 | 50-56 | 46-55 |
| vlCDR3 | 89-97 | 105-117 | 89-97 | 89-97 | 89-97 | 89-96 |

In the present specification, the Kabat numbering system is generally used when referring to a residue in the variable domain (approximately, residues 1-107 of the light chain variable region and residues 1-113 of the heavy chain variable region) and the EU numbering system for Fc regions (e.g, Kabat et al., supra (1991)).

The present invention provides a large number of different CDR sets. In this case, a "full CDR set" comprises the three variable light and three variable heavy CDRs, e.g. a vlCDR1, vlCDR2, vlCDR3, vhCDR1, vhCDR2 and vhCDR3. These can be part of a larger variable light or variable heavy domain, respectfully. In addition, as more fully outlined herein, the variable heavy and variable light domains can be on separate polypeptide chains, when a heavy and light chain is used (for example when Fabs are used), or on a single polypeptide chain in the case of scFv sequences.

The CDRs contribute to the formation of the antigen-binding, or more specifically, epitope binding site of antibodies.

"Epitope" refers to a determinant that interacts with a specific antigen binding site in the variable region of an antibody molecule known as a paratope. Epitopes are groupings of molecules such as amino acids or sugar side chains and usually have specific structural characteristics, as well as specific charge characteristics. A single antigen may have more than one epitope. The epitope may comprise amino acid residues directly involved in the binding (also called immunodominant component of the epitope) and other amino acid residues, which are not directly involved in the binding, such as amino acid residues which are effectively blocked by the specifically antigen binding peptide; in other words, the amino acid residue is within the footprint of the specifically antigen binding peptide. Epitopes may be either conformational or linear. A conformational epitope is produced by spatially juxtaposed amino acids from different segments of the linear polypeptide chain. A linear epitope is one produced by adjacent amino acid residues in a polypeptide chain. Conformational and non-conformational epitopes may be distinguished in that the binding to the former but not the latter is lost in the presence of denaturing solvents.

"Specific binding" or "specifically binds to" or is "specific for" a particular antigen or an epitope means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target.

The term "Kassoc" or "Ka", as used herein, is intended to refer to the association rate of a particular antibody-antigen interaction, whereas the term "Kdis" or "Kd," as used herein, is intended to refer to the dissociation rate of a particular antibody-antigen interaction. The term "$K_D$", as used herein, is intended to refer to the dissociation constant, which is obtained from the ratio of $K_D$ to Ka (i.e., $K_D$/Ka) and is expressed as a molar concentration (M). $K_D$ values for antibodies can be determined using methods well established in the art. In some embodiments, the method for determining the $K_D$ of an antibody is by using surface plasmon resonance, for example, by using a biosensor system such as a BIACORE® system. In some embodiments, the $K_D$ of an antibody is determined by Bio-Layer Interferometry. In some embodiments, the $K_D$ is measured using flow cytometry with antigen-expressing cells. In some embodiments, the $K_D$ value is measured with the antigen immobilized. In other embodiments, the $K_D$ value is measured with the antibody (e.g., parent mouse antibody, chimeric antibody, or humanized antibody variants) immobilized. In some embodiments, the $K_D$ value is measured in a bivalent binding mode. In other embodiments, the $K_D$ value is measured in a monovalent binding mode. Specific binding for a particular antigen or an epitope can be exhibited, for example, by an antibody having a $K_D$ for an antigen or epitope of at least about $10^{-7}$ M, at least about $10^{-8}$ M, at least about $10^{-9}$ M, at least about $10^{-10}$ M, at least about $10^{-11}$ M, at least about $10^{-12}$ M, at least about $10^{-13}$ M, at least about $10^{-14}$ M. Typically, an antibody that specifically binds an antigen will have a $K_D$ that is 20-, 50-, 100-, 500-, 1000-, 5,000-, 10,000- or more times greater for a control molecule relative to the antigen or epitope.

"Percent (%) amino acid sequence identity" with respect to a protein sequence is defined as the percentage of amino acid residues in a candidate sequence that are identical with the amino acid residues in the specific (parental) sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full-length of the sequences being compared. One particular program is the ALIGN-2 program outlined at paragraphs [0279] to [0280] of US Pre-Grant Pub. No. 20160244525, hereby incorporated by reference. Another approximate alignment for nucleic acid sequences is provided by the local homology algorithm of Smith and Waterman, Advances in Applied Mathematics, 2:482-489 (1981). This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986).

An example of an implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages, the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the Internet address located by placing http:// in front of blast.ncbi.nlm.nih.gov/Blast.cgi.

The degree of identity between an amino acid sequence of the present invention ("invention sequence") and the parental amino acid sequence is calculated as the number of exact matches in an alignment of the two sequences, divided by the length of the "invention sequence," or the length of the parental sequence, whichever is the shortest. The result is expressed in percent identity.

The term "nucleic acid" includes RNA or DNA molecules having more than one nucleotide in any form including single-stranded, double-stranded, oligonucleotide or polynucleotide. The term "nucleotide sequence" includes the ordering of nucleotides in an oligonucleotide or polynucleotide in a single-stranded form of nucleic acid.

The term "promoter" as used herein includes a DNA sequence operably linked to a nucleic acid sequence to be transcribed such as a nucleic acid sequence encoding a desired molecule. A promoter is generally positioned upstream of a nucleic acid sequence to be transcribed and provides a site for specific binding by RNA polymerase and other transcription factors.

A "vector" is capable of transferring gene sequences to a target cell. Typically, "vector construct," "expression vector," and "gene transfer vector," mean any nucleic acid construct capable of directing the expression of a gene of interest and which can transfer a gene sequence to a target cell, which can be accomplished by genomic integration of all or a portion of the vector, or transient or inheritable maintenance of the vector as an extrachromosomal element. Thus, the term includes cloning, and expression vehicles, as well as integrating vectors.

The term "regulatory element" as used herein includes a nucleotide sequence which controls some aspect of the expression of a nucleic acid sequence. Examples of regulatory elements illustratively include an enhancer, an internal ribosome entry site (IRES), an intron, an origin of replication, a polyadenylation signal (pA), a promoter, an enhancer, a transcription termination sequence, and an upstream regulatory domain, which contribute to the replication, transcription, and/or post-transcriptional processing of a nucleic acid sequence. In cases, regulatory elements can also include cis-regulatory DNA elements as well as transposable elements (TEs). Those of ordinary skill in the art are capable of selecting and using these and other regulatory elements in an expression construct with no more than routine experimentation. Expression constructs can be generated using a genetic recombinant approach or synthetically using well-known methodology.

A "control element" or "control sequence" is a nucleotide sequence involved in an interaction of molecules contributing to the functional regulation of a polynucleotide, including replication, duplication, transcription, splicing, translation, or degradation of the polynucleotide. The regulation may affect the frequency, speed, or specificity of the process, and may be enhancing or inhibitory in nature. Control elements known in the art include, for example, transcriptional regulatory sequences such as promoters and enhancers. A promoter is a DNA region capable under some conditions of binding RNA polymerase and initiating transcription of a coding region usually located downstream (in the 3' direction) from the promoter.

For purposes of the present invention, the phrase "derived from" when referring to a polypeptide or polypeptide region means that the polypeptide or polypeptide region comprises amino acid sequences originally found in a "parental" protein and which may now comprise some amino acid residue additions, deletions, truncations, rearrangements, or other alterations relative to the original polypeptide or polypeptide region as long as a some function(s) and a structure(s) of the "parental" molecule are substantially conserved. The skilled worker will be able to identify a parental molecule from which a polypeptide or polypeptide region was derived using techniques known in the art, e.g., protein sequence alignment software.

For purposes of the invention, and with regard to a Shiga toxin polypeptide sequence or Shiga toxin derived polypeptide, the term "wild-type" generally refers to a naturally occurring, Shiga toxin protein sequence(s) found in a living species, such as, e.g., a pathogenic bacterium, wherein that Shiga toxin protein sequence(s) is one of the most frequently occurring variants. This is in contrast to infrequently occurring Shiga toxin protein sequences that, while still naturally occurring, are found in less than one percent of individual organisms of a given species when sampling a statistically powerful number of naturally occurring individual organisms of that species which comprise at least one Shiga toxin protein variant. A clonal expansion of a natural isolate outside its natural environment (regardless of whether the isolate is an organism or molecule comprising biological sequence information) does not alter the naturally occurring requirement as long as the clonal expansion does not introduce new sequence variety not present in naturally occurring populations of that species and/or does not change the relative proportions of sequence variants to each other.

The terms "associated," "associating," "linked," or "linking" as used herein refer to the state of two or more components of a molecule being joined, attached, connected, or otherwise coupled to form a single molecule or the act of making two molecules associated with each other to form a single molecule by creating an association, linkage, attachment, and/or any other connection between the two molecules. For example, the term "linked" may refer to two or more components associated by one or more atomic interactions such that a single molecule is formed and wherein the atomic interactions may be covalent and/or non-covalent. Non-limiting examples of covalent associations between two components include peptide bonds and cysteine-cysteine disulfide bonds. Non-limiting examples of non-covalent associations between two molecular components include ionic bonds and hydrogen bonds.

For purposes of the present invention, the term "linked" refer to two or more molecular components associated by one or more atomic interactions such that a single molecule is formed and wherein the atomic interactions includes at least one covalent bond. For purposes of the present invention, the term "linking" refers to the act of creating a linked molecule as described above.

For purposes of the present invention, the term "fused" refers to two or more proteinaceous components associated by at least one covalent bond which is a peptide bond, regardless of whether the peptide bond involves the participation of a carbon atom of a carboxyl acid group or involves another carbon atom, such as, e.g., the ?-carbon, ?-carbon, ?-carbon, ?-carbon, etc. Non-limiting examples of two proteinaceous components fused together include, e.g., an amino acid, peptide, or polypeptide fused to a polypeptide via a peptide bond such that the resulting molecule is a single, continuous polypeptide. For purposes of the present invention, the term "fusing" refers to the act of creating a fused molecule as described above, such as, e.g., a fusion protein generated from the recombinant fusion of genetic regions which when translated produces a single proteinaceous molecule.

The symbol "::" means the polypeptide regions before and after it are physically linked together to form a continuous polypeptide.

As used herein, the terms "expressed," "expressing," or "expresses," and grammatical variants thereof, refer to translation of a polynucleotide or nucleic acid into a protein. The expressed protein may remain intracellular, become a component of the cell surface membrane or be secreted into an extracellular space.

As used herein, cells which express a significant amount of an extracellular target biomolecule at least one cellular surface are "target positive cells" or "target+cells" and are cells physically coupled to the specified, extracellular target biomolecule.

As used herein, the symbol "?" is shorthand for an immunoglobulin-type binding region capable of binding to the biomolecule following the symbol. The symbol "?" is used to refer to the functional characteristic of an immunoglobulin-type binding region based on its ability to bind to the biomolecule following the symbol with a binding affinity described by a dissociation constant ($K_D$) of $10^{-5}$ or less.

As used herein, the term "heavy chain variable (VH) domain" or "light chain variable (VL) domain" respectively refer to any antibody VH or VL domain (e.g. a human VH or VL domain) as well as any derivative thereof retaining at least qualitative antigen binding ability of the corresponding native antibody (e.g. a humanized VH or VL domain derived from a native murine VH or VL domain). A VH or VL domain comprises a "framework" region interrupted by the three CDRs or antigen binding regions (ABRs). The framework regions serve to align the CDRs or ABRs for specific binding to an epitope of an antigen. From amino-terminus to carboxy-terminus, both VH and VL domains comprise the following framework (FR) and CDR regions or ABR regions: FR1, CDR1, FR2, CDR2, FR3, CDR3, and FR4; or, similarly, FR1, ABR1, FR2, ABR2, FR3, ABR3, and FR4. As used herein, the terms "HCDR1," "HCDR2," or "HCDR3" are used to refer to CDRs 1, 2, or 3, respectively, in a VH domain, and the terms "LCDR1," "LCDR2," and "LCDR3" are used to refer to CDRs 1, 2, or 3, respectively, in a VL domain. As used herein, the terms "HABR1," "HABR2," or "HABR3" are used to refer to ABRs 1, 2, or 3, respectively, in a VH domain, and the terms "LABR1," "LABR2," or "LABR3" are used to refer to CDRs 1, 2, or 3, respectively, in a VL domain. For camelid VHH fragments, IgNARs of cartilaginous fish, VNAR fragments, some single domain antibodies, and derivatives thereof, there is a single, heavy chain variable domain comprising the same basic arrangement: FR1, CDR1, FR2, CDR2, FR3, CDR3, and FR4. As used herein, the terms "HCDR1," "HCDR2," or "HCDR3" may be used to refer to CDRs 1, 2, or 3, respectively, in a single heavy chain variable domain.

For purposes of the present invention, the term "effector" means providing a biological activity, such as cytotoxicity, biological signaling, enzymatic catalysis, subcellular routing, and/or intermolecular binding resulting in an allosteric effect(s) and/or the recruitment of one or more factors.

For purposes of the present invention, the phrases "Shiga toxin effector polypeptide," "Shiga toxin effector polypeptide region," and "Shiga toxin effector region" refer to a polypeptide or polypeptide region derived from at least one Shiga toxin A Subunit of a member of the Shiga toxin family wherein the polypeptide or polypeptide region is capable of exhibiting at least one Shiga toxin function. For example, SEQ ID NOs: 45-69 are derived from StxA and SLT-1A.

For purposes of the present invention, a Shiga toxin effector function is a biological activity conferred by a polypeptide region derived from a Shiga toxin A Subunit. Non-limiting examples of Shiga toxin effector functions include promoting cell entry; lipid membrane deformation; promoting cellular internalization; stimulating clathrin-mediated endocytosis; directing intracellular routing to various intracellular compartments such as, e.g., the Golgi, endoplasmic reticulum, and cytosol; directing intracellular routing with a cargo; inhibiting a ribosome function(s); inhibition of protein synthesis, catalytic activities, such as, e.g., N-glycosidase activity and catalytically inhibiting ribosomes; reducing protein synthesis, inducing caspase activity, activating effector caspases, effectuating cytostatic effects, and cytotoxicity. Shiga toxin catalytic activities include, for example, ribosome inactivation, protein synthesis inhibition, N-glycosidase activity, polynucleotide:adenosine glycosidase activity, RNAase activity, and DNAase activity. Shiga toxins are ribosome inactivating proteins (RIPs). RIPs can depurinate nucleic acids, polynucleotides, polynucleotides, rRNA, ssDNA, dsDNA, mRNA (and polyA), and viral nucleic acids (see e.g., Barbieri L et al, Biochem J 286: 1-4 (1992); Barbieri L et al, Nature 372: 624 (1994); Ling J et al, FEBS Lett 345: 143-6 (1994); Barbieri L et al., Biochem J 319: 507-13 (1996); Roncuzzi L, Gasperi-Campani A, FEBS Lett 392: 16-20 (1996); Stirpe F et al, FEBS Lett 382: 309-12 (1996); Barbieri L et al., Nucleic Acids Res 25: 518-22 (1997); Wang P, Turner N, Nucleic Acids Res 27: 1900-5 (1999); Barbieri L et al., Biochim Biophys Acta 1480: 258-66 (2000); Barbieri L et al., J Biochem 128: 883-9 (2000); Brigotti M et al, Toxicon 39: 341-8 (2001); Brigotti M et al, FASEB J 16: 365-72 (2002); Bagga S et al, J Biol Chem 278: 4813-20 (2003); Picard D et al, J Biol Chem 280: 20069-75 (2005)). Some RIPs show antiviral activity and superoxide dismutase activity (Erice A et al., Antimicrob Agents Chemother 37: 835-8 (1993); Au T et al, FEBS Lett 471: 169-72 (2000); Parikh B, Turner N, Mini Rev Med Chem 4: 523-43 (2004); Sharma N et al, Plant Physiol 134: 171-81 (2004)). Shiga toxin catalytic activities have been observed both in vitro and in vivo. Non-limiting examples of assays for Shiga toxin effector activity measure various activities, such as, e.g., protein synthesis inhibitory activity, depurination activity, inhibition of cell growth, cytotoxicity, supercoiled DNA relaxation activity, and nuclease activity.

As used herein, the retention of Shiga toxin effector function refers to being capable of exhibiting a level of Shiga toxin functional activity, as measured by an appropriate quantitative assay with reproducibility, comparable to a wild-type, Shiga toxin effector polypeptide control (e.g. a Shiga toxin A1 fragment) or CD38-binding protein comprising a wild-type Shiga toxin effector polypeptide (e.g. a Shiga toxin A1 fragment) under the same conditions. For the Shiga toxin effector function of ribosome inactivation or ribosome inhibition, retained Shiga toxin effector function is exhibiting an IC50 of 10,000 pM or less in an in vitro setting, such as, e.g., by using an assay known to the skilled worker and/or described herein. For the Shiga toxin effector function of cytotoxicity in a target positive cell-kill assay, retained Shiga toxin effector function is exhibiting a $CD_{50}$ of 1,000 nM or less, depending on the cell type and its expression of the appropriate extracellular target biomolecule, as shown, e.g., by using an assay known to the skilled worker and/or described herein.

For purposes of the instant invention, the term "equivalent" with regard to ribosome inhibition means an empirically measured level of ribosome inhibitory activity, as measured by an appropriate quantitative assay with reproducibility, which is reproducibly within 10% or less of the activity of the reference molecule (e.g., a second CD38-binding protein or third CD38-binding protein) under the same conditions.

For purposes of the instant invention, the term "equivalent" with regard to cytotoxicity means an empirically measured level of cytotoxicity, as measured by an appropriate quantitative assay with reproducibility, which is reproducibly within 10% or less of the activity of the reference molecule (e.g., a second CD38-binding protein or third binding protein) under the same conditions.

As used herein, the term "attenuated" with regard to cytotoxicity means a molecule exhibits or exhibited a $CD_{50}$ between 10-fold to 100-fold of a $CD_{50}$ exhibited by a reference molecule under the same conditions.

Inaccurate $IC_{50}$ and $CD_{50}$ values should not be considered when determining a level of Shiga toxin effector function activity. For some samples, accurate values for either $IC_{50}$ or $CD_{50}$ might be unobtainable due to the inability to collect the required data points for an accurate curve fit. For example, theoretically, neither an $IC_{50}$ nor $CD_{50}$ can be determined if greater than 50% ribosome inhibition or cell death, respectively, does not occur in a concentration series for a given sample. Data insufficient to accurately fit a curve as described in the analysis of the data from illustrative Shiga toxin effector function assays, such as, e.g., assays described in the Examples below, should not be considered as representative of actual Shiga toxin effector function.

A failure to detect activity in Shiga toxin effector function may be due to improper expression, polypeptide folding, and/or protein stability rather than a lack of cell entry, subcellular routing, and/or enzymatic activity. Assays for Shiga toxin effector functions may not require much polypeptide of the invention to measure significant amounts of Shiga toxin effector function activity. To the extent that an underlying cause of low or no effector function is determined empirically to relate to protein expression or stability, one of skill in the art may be able to compensate for such factors using protein chemistry and molecular engineering techniques known in the art, such that a Shiga toxin functional effector activity may be restored and measured. As examples, improper cell-based expression may be compensated for by using different expression control sequences; and improper polypeptide folding and/or stability may benefit from stabilizing terminal sequences, or compensatory mutations in non-effector regions which stabilize the three-dimensional structure of the molecule.

Some Shiga toxin effector functions are not easily measurable, e.g. subcellular routing functions. For example, there is no routine, quantitative assay to distinguish whether the failure of a Shiga toxin effector polypeptide to be cytotoxic and/or deliver a heterologous epitope is due to improper subcellular routing, but at a time when tests are available, then Shiga toxin effector polypeptides may be analyzed for any significant level of subcellular routing as compared to the appropriate wild-type Shiga toxin effector polypeptide. However, if a Shiga toxin effector polypeptide component of a binding protein of the present invention exhibits cytotoxicity comparable or equivalent to a wild-type Shiga toxin A Subunit construct, then the subcellular routing activity level is inferred to be comparable or equivalent, respectively, to the subcellular routing activity level of a wild-type Shiga toxin A Subunit construct at least under the conditions tested.

When new assays for individual Shiga toxin functions become available, Shiga toxin effector polypeptides and/or binding proteins comprising Shiga toxin effector polypeptides may be analyzed for any level of those Shiga toxin effector functions, such as a being within 1000-fold or 100-fold or less the activity of a wild-type Shiga toxin effector polypeptide or exhibiting 3-fold to 30-fold or greater activity as compared to a functional knockout, Shiga toxin effector polypeptide.

Sufficient subcellular routing may be merely deduced by observing a molecule's cytotoxic activity levels in cytotoxicity assays, such as, e.g., cytotoxicity assays based on T-cell epitope presentation or based on a toxin effector function involving a cytosolic and/or endoplasmic reticulum-localized, target substrate.

As used herein, the retention of "significant" Shiga toxin effector function refers to a level of Shiga toxin functional activity, as measured by an appropriate quantitative assay with reproducibility comparable to a wild-type Shiga toxin effector polypeptide control (e.g. a Shiga toxin A1 fragment). For in vitro ribosome inhibition, significant Shiga toxin effector function is exhibiting an IC50 of 300 pM or less depending on the source of the ribosomes used in the assay (e.g. a bacterial, archaeal, or eukaryotic (algal, fungal, plant, or animal) source). This is significantly greater inhibition as compared to the approximate $IC_{50}$ of 100,000 pM exhibited by the catalytically disrupted SLT-1A 1-251 double mutant (Y77S/E167D). For cytotoxicity in a target-positive cell-kill assay in laboratory cell culture, significant Shiga toxin effector function is exhibiting a $CD_{50}$ of 100, 50, 30 nM, or less, depending on the target biomolecule(s) of the binding region and the cell type, particularly that cell type's expression and/or cell-surface representation of the appropriate extracellular target biomolecule(s) and/or the extracellular epitope(s) targeted by the molecule being evaluated. This is significantly greater cytotoxicity to the appropriate, target-positive cell population as compared to a Shiga toxin A Subunit alone (or a wild-type Shiga toxin A1 fragment), without a cell targeting binding region, which has a $CD_{50}$ of 100-10,000 nM, depending on the cell line.

For purposes of the present invention and with regard to the Shiga toxin effector function of a molecule of the present invention, the term "reasonable activity" refers to exhibiting at least a moderate level (e.g. within 11-fold to 1,000-fold) of Shiga toxin effector activity as defined herein in relation to a molecule comprising a naturally occurring (or wild-type) Shiga toxin, wherein the Shiga toxin effector activity is selected from: internalization efficiency, subcellular routing efficiency to the cytosol, delivered epitope presentation by a target cell(s), ribosome inhibition, and cytotoxicity. For cytotoxicity, a reasonable level of Shiga toxin effector activity includes being within 1,000-fold of a wild-type, Shiga toxin construct, such as, e.g., exhibiting a $CD_{50}$ of 500 nM or less when a wild-type Shiga toxin construct exhibits a $CD_{50}$ of 0.5 nM (e.g. a binding protein comprising a wild-type Shiga toxin A1 fragment).

For purposes of the present invention and with regard to the cytotoxicity of a molecule of the present invention, the term "optimal" refers to a level of Shiga toxin catalytic domain mediated cytotoxicity that is within 2, 3, 4, 5, 6, 7, 8, 9, or 10-fold of the cytotoxicity of a molecule comprising wild-type Shiga toxin A1 fragment (e.g. a Shiga toxin A Subunit or some truncated variants thereof) and/or a naturally occurring (or wild-type) Shiga toxin.

It should be noted that even if the cytotoxicity of a Shiga toxin effector polypeptide is reduced relative to a wild-type Shiga toxin A Subunit or fragment thereof, in practice, applications using attenuated, Shiga toxin effector polypeptides might be equally or more effective than using wild-type Shiga toxin effector polypeptides because the highest potency variants might exhibit undesirable effects which are minimized or reduced in reduced cytotoxic-potency variants. Wild-type Shiga toxins are very potent, being able to kill an intoxicated cell after only one toxin molecule has reached the cytosol of the intoxicated cell or perhaps after only forty toxin molecules have been internalized into the intoxicated cell. Shiga toxin effector polypeptides with even considerably reduced Shiga toxin effector functions, such as, e.g., subcellular routing or cytotoxicity, as compared to wild-type Shiga toxin effector polypeptides might still be potent enough for practical applications, such as, e.g., applications involving targeted cell-killing, cargo molecule delivery, and/or detection of specific cells and their subcellular compartments. In addition, some reduced-activity Shiga toxin effector polypeptides may be particularly useful for delivering molecular cargos (e.g. an additional exogenous material) to some intracellular locations or subcellular compartments of CD38-positive target cells.

The term "selective cytotoxicity" with regard to the cytotoxic activity of a molecule refers to the relative level of cytotoxicity between a CD38 target positive cell population (e.g. a targeted cell-type) and a non-targeted bystander cell population (e.g. a CD38 target negative cell-type), which can be expressed as a ratio of the half-maximal cytotoxic concentration ($CD_{50}$) for a targeted cell type over the $CD_{50}$ for an untargeted cell type to provide a metric of cytotoxic selectivity or indication of the selectivity of killing of a targeted cell versus an untargeted cell.

The cell surface representation and/or density of a given extracellular target biomolecule (or extracellular epitope of a given target biomolecule) may influence the applications for which some binding proteins may be most suitably used. Differences in cell surface representation and/or density of a given target biomolecule between cells may alter, both quantitatively and qualitatively, the efficiency of cellular internalization and/or cytotoxicity potency of a given binding protein. The cell surface representation and/or density of a given target biomolecule can vary greatly among target biomolecule positive cells or even on the same cell at different points in the cell cycle or cell differentiation. The total cell surface representation of a given target biomolecule and/or of some extracellular epitopes of a given target biomolecule on a particular cell or population of cells may be determined using methods known to the skilled worker, such as methods involving fluorescence-activated cell sorting (FACS) flow cytometry.

As used herein, the terms "disrupted," "disruption," or "disrupting," and grammatical variants thereof, with regard to a polypeptide region or feature within a polypeptide refers to an alteration of at least one amino acid within the region or composing the disrupted feature. Amino acid alterations include various mutations, such as, e.g., a deletion, inversion, insertion, or substitution which alter the amino acid sequence of the polypeptide. Amino acid alterations also include chemical changes, such as, e.g., the alteration one or more atoms in an amino acid functional group or the addition of one or more atoms to an amino acid functional group.

As used herein, "de-immunized" means reduced antigenic and/or immunogenic potential after administration to a subject (e.g., a human subject) as compared to a reference molecule, such as, e.g., a wild-type peptide region, polypeptide region, or polypeptide. This includes a reduction in overall antigenic and/or immunogenic potential despite the introduction of one or more, de novo, antigenic and/or immunogenic epitopes as compared to a reference molecule. For some embodiments, "de-immunized" means a molecule exhibited reduced antigenicity and/or immunogenicity after administration to a mammal as compared to a "parental" molecule from which it was derived, such as, e.g., a wild-type Shiga toxin A1 fragment or binding protein comprising the aforementioned. In some embodiments, the de-immunized, Shiga toxin effector polypeptide is capable of exhibiting a relative antigenicity compared to a reference "parental" molecule which is reduced by about 10%, about 20%, about 30%, about 40%, about 50%, about 60%, about 70%, about 80%, about 90%, or greater than the antigenicity of the reference molecule under the same conditions measured by the same assay, such as, e.g., an assay known to the skilled worker and/or described herein like a quantitative ELISA or Western blot analysis. In some embodiments, the de-immunized, Shiga toxin effector polypeptide is capable of exhibiting a relative immunogenicity compared to a reference "parental" molecule which is reduced by about 10%, about 20%, about 30%, about 40%, about 50%, about 60%, about 70%, about 80%, about 90%, about 95%, about 97%, about 99%, or greater than the immunogenicity of the reference molecule under the same conditions measured by the same assay, such as, e.g., an assay known to the skilled worker and/or described herein like a quantitative measurement of anti-molecule antibodies produced in a mammal(s) after receiving parenteral administration of the molecule at a given time-point.

The relative immunogenicities of illustrative binding proteins were determined using an assay for in vivo antibody responses to the binding proteins after repeat, parenteral administrations over periods of time.

For purposes of the present invention, the phrase "B-cell and/or CD4+ T-cell de-immunized" means that the molecule has a reduced antigenic and/or immunogenic potential after administration to a mammal regarding either B-cell antigenicity or immunogenicity and/or CD4+ T-cell antigenicity or immunogenicity. For some embodiments, "B-cell de-immunized" means a molecule exhibited reduced B-cell antigenicity and/or immunogenicity after administration to a mammal as compared to a "parental" molecule from which it was derived, such as, e.g., a wild-type Shiga toxin A1 fragment. For some embodiments, "CD4+ T-cell de-immunized" means a molecule exhibited reduced CD4 T-cell antigenicity and/or immunogenicity after administration to a mammal as compared to a "parental" molecule from which it was derived, such as, e.g., a wild-type Shiga toxin A1 fragment.

The term "endogenous" with regard to a B-cell epitope, CD4+ T-cell epitope, B-cell epitope region, or CD4+ T-cell epitope region in a Shiga toxin effector polypeptide refers to an epitope present in a wild-type Shiga toxin A Subunit.

For purposes of the present invention, the phrase "CD8+ T-cell hyper-immunized" means that the molecule, when present inside a nucleated cell within a living subject (e.g., a human subject), has an increased antigenic and/or immunogenic potential regarding CD8+ T-cell antigenicity or immunogenicity. Commonly, CD8+ T-cell immunized molecules are capable of cellular internalization to an early endosomal compartment of a nucleated, cell due either to an inherent feature(s) or as a component of a CD38-binding protein of the invention.

For purposes of the present invention, the term "heterologous" means of a different source, e.g., a heterologous Shiga A Subunit polypeptide is not naturally found as part of any A Subunit of a native Shiga toxin, as opposed to endogenous, for example. The fusion proteins of the invention comprise non-heterologous components, e.g. the Shiga toxin and an anti-CD38 antigen binding domain.

The term "embedded" and grammatical variants thereof with regard to a polypeptide component of a binding protein of the present invention refers to the internal replacement of one or more amino acids within a polypeptide region with different amino acids in order to generate a new polypeptide sequence sharing the same total number of amino acid residues with the starting polypeptide region. Thus, the term "embedded" does not include any external, terminal fusion of any additional amino acid, peptide, or polypeptide component to the starting polypeptide nor any additional internal insertion of any additional amino acid residues, but rather includes only substitutions for existing amino acids. The internal replacement may be accomplished merely by amino acid residue substitution or by a series of substitutions, deletions, insertions, and/or inversions. If an insertion of one or more amino acids is used, then the equivalent number of proximal amino acids must be deleted next to the insertion to result in an embedded peptide. This is in contrast to use of the term "inserted" with regard to a a polypeptide component of a binding protein of the present invention to refer to the insertion of one or more amino acids internally within a polypeptide resulting in a new polypeptide having an increased number of amino acids residues compared to the starting polypeptide.

The term "inserted" and grammatical variants thereof with regard to a polypeptide component of a binding protein of the present invention refers to the insertion of one or more amino acids within a polypeptide resulting in a new polypeptide sequence having an increased number of amino acids residues compared to the starting polypeptide. The phrases "partially inserted," "embedded and inserted," and grammatical variants thereof with regard to a polypeptide component of a binding protein of the present invention, refers to when the resulting polypeptide increased in length, but by less than the number of amino acid residues equivalent to the length of the entire, inserted polypeptide. Insertions, whether "pure" or "partial," include any of the previously described insertions even if other regions of the polypeptide not proximal to the insertion site within the polypeptide are deleted thereby resulting in a decrease in the total length of the final polypeptide because the final polypeptide still comprises an internal insertion of one or more amino acids of a T-cell epitope-peptide within a polypeptide region.

For purposes of the present invention, the phrase "proximal to an amino-terminus" with reference to the position of a Shiga toxin effector polypeptide region of a binding protein of the present invention refers to a distance wherein at least one amino acid residue of the Shiga toxin effector polypeptide region is within 1, 2, 3, 4, 5, 6, 7, 8, 9, 10, 11, 12 or more, e.g., up to 18-20 amino acid residues, of an amino-terminus of the binding protein as long as the binding protein is capable of exhibiting the appropriate level of Shiga toxin effector functional activity noted herein (e.g., a some level of cytotoxic potency). Thus for some embodiments of the present invention, any amino acid residue(s) fused amino-terminal to the Shiga toxin effector polypeptide should not reduce any Shiga toxin effector function (e.g., by sterically hindering a structure(s) near the amino-terminus of the Shiga toxin effector polypeptide region) such that a functional activity of the Shiga toxin effector polypeptide is reduced below the appropriate activity level required herein.

For purposes of the present invention, the phrase "more proximal to an amino-terminus" with reference to the position of a Shiga toxin effector polypeptide region within a binding protein of the present invention as compared to another component (e.g., a cell-targeting, binding region, molecular moiety, and/or additional exogenous material) refers to a position wherein at least one amino acid residue of the amino-terminus of the Shiga toxin effector polypeptide is closer to the amino-terminus of a linear, polypeptide component of the binding protein of the present invention as compared to the other referenced component.

For purposes of the present invention, the phrase "active enzymatic domain derived from one A Subunit of a member of the Shiga toxin family" refers to having the ability to inhibit protein synthesis via a catalytic ribosome inactivation mechanism. The enzymatic activities of naturally occurring Shiga toxins may be defined by the ability to inhibit protein translation using assays known to the skilled worker, such as, e.g., in vitro assays involving RNA translation in the absence of living cells or in vivo assays involving RNA translation in a living cell. Using assays known to the skilled worker and/or described herein, the potency of a Shiga toxin enzymatic activity may be assessed directly by observing N-glycosidase activity toward ribosomal RNA (rRNA), such as, e.g., a ribosome nicking assay, and/or indirectly by observing inhibition of ribosome function and/or protein synthesis.

For purposes of the present invention, the term "Shiga toxin A1 fragment region" refers to a polypeptide region consisting essentially of a Shiga toxin A1 fragment and/or derived from a Shiga toxin A1 fragment of a Shiga toxin.

For purposes of the present invention, the terms "terminus," "amino-terminus," or "carboxy-terminus" with regard to a binding protein refers generally to the last amino acid residue of a polypeptide chain of the binding protein (e.g., a single, continuous polypeptide chain). A binding protein may comprise more than one polypeptides or proteins, and, thus, a binding protein of the present invention may comprise multiple amino-terminals and carboxy-terminals. For example, the "amino-terminus" of a binding protein may be defined by the first amino acid residue of a polypeptide chain representing the amino-terminal end of the polypeptide, which is generally characterized by a starting, amino acid residue which does not have a peptide bond with any amino acid residue involving the primary amino group of the starting amino acid residue or involving the equivalent nitrogen for starting amino acid residues which are members of the class of N-alkylated alpha amino acid residues. Similarly, the "carboxy-terminus" of a binding protein may be defined by the last amino acid residue of a polypeptide chain representing the carboxyl-terminal end of the polypeptide, which is generally characterized by a final, amino acid residue which does not have any amino acid residue linked by a peptide bond to the alpha-carbon of its primary carboxyl group.

For purposes of the present invention, the terms "terminus," "amino-terminus," or "carboxy-terminus" with regard to a polypeptide region refers to the regional boundaries of that region, regardless of whether additional amino acid residues are linked by peptide bonds outside of that region. In other words, the terminals of the polypeptide region regardless of whether that region is fused to other peptides or polypeptides. For example, a fusion protein comprising two proteinaceous regions, e.g., a binding region comprising a peptide or polypeptide and a Shiga toxin effector polypeptide, may have a Shiga toxin effector polypeptide region with a carboxy-terminus ending at amino acid residue 251 of the Shiga toxin effector polypeptide region despite a peptide bond involving residue 251 to an amino acid residue at position 252 representing the beginning of another proteinaceous region, e.g., the binding region. In this example, the carboxy-terminus of the Shiga toxin effector polypeptide region refers to residue 251, which is not a terminus of the fusion protein but rather represents an internal, regional boundary. Thus, for polypeptide regions, the terms "terminus," "amino-terminus," and "carboxy-terminus" are used to refer to the boundaries of polypeptide regions, whether the boundary is a physically terminus or an internal, position embedded within a larger polypeptide chain.

For purposes of the present invention, the phrase "carboxy-terminus region of a Shiga toxin A1 fragment" refers to a polypeptide region derived from a naturally occurring Shiga toxin A1 fragment, the region beginning with a hydrophobic residue (e.g., V236 of StxA-A1 and SLT-1A1, and V235 of SLT-2A1) that is followed by a hydrophobic residue and the region ending with the furin-cleavage site conserved among Shiga toxin A1 fragment polypeptides and ending at the junction between the A1 fragment and the A2 fragment in native, Shiga toxin A Subunits. For purposes of the present invention, the carboxy-terminal region of a Shiga toxin A1 fragment includes a peptidic region derived from the carboxy-terminus of a Shiga toxin A1 fragment polypeptide, such as, e.g., a peptidic region comprising or consisting essentially of the carboxy-terminus of a Shiga toxin A1 fragment. Non-limiting examples of peptidic regions derived from the carboxy-terminus of a Shiga toxin A1 fragment include the amino acid residue sequences natively positioned from position 236 to position 239, 240, 241, 242, 243, 244, 245, 246, 247, 248, 249, 250, or 251 in Stx1A (SEQ ID NO:2) or SLT-1A (SEQ ID NO:1); and from position 235 to position 239, 240, 241, 242, 243, 244, 245, 246, 247, 248, 249, or 250 in SLT-2A (SEQ ID NO:3).

For purposes of the present invention, the phrase "proximal to the carboxy-terminus of an A1 fragment polypeptide" with regard to a linked molecular moiety and/or binding region refers to being within 1, 2, 3, 4, 5, 6, 7, 8, 9, 10, 11, or 12 amino acid residues from the amino acid residue defining the last residue of the Shiga toxin A1 fragment polypeptide.

For purposes of the present invention, the phrase "sterically covers the carboxy-terminus of the A1 fragment-derived region" includes any molecular moiety of a size of 4.5 kDa or greater (e.g., an immunoglobulin-type binding region) linked and/or fused to an amino acid residue in the carboxy-terminus of the A1 fragment-derived region, such as, e.g., the amino acid residue derived from the amino acid residue natively positioned at any one of positions 236 to 251 in Stx1A (SEQ ID NO:2) or SLT-1A (SEQ ID NO:1) or from 235 to 250 in SLT-2A (SEQ ID NO:3). For purposes of the present invention, the phrase "sterically covers the carboxy-terminus of the A1 fragment-derived region" also includes any molecular moiety of a size of 4.5 kDa or greater (e.g., an immunoglobulin-type binding region) linked and/or fused to an amino acid residue in the carboxy-terminus of the A1 fragment-derived region, such as, e.g., the amino acid residue carboxy-terminal to the last amino acid A1 fragment-derived region and/or the Shiga toxin effector polypeptide. For purposes of the present invention, the phrase "sterically covers the carboxy-terminus of the A1 fragment-derived region" also includes any molecular moiety of a size of 4.5 kDa or greater (e.g., an immunoglobulin-type binding region) physically preventing cellular recognition of the carboxy-terminus of the A1 fragment-derived region, such as, e.g. recognition by the ERAD machinery of a eukaryotic cell.

For purposes of the present invention, a binding region, such as, e.g., an immunoglobulin-type binding region, that comprises a polypeptide comprising at least forty amino acids and that is linked (e.g., fused) to the carboxy-terminus of the Shiga toxin effector polypeptide region comprising an A1 fragment-derived region is a molecular moiety which is "sterically covering the carboxy-terminus of the A1 fragment-derived region."

For purposes of the present invention, a binding region, such as, e.g., an immunoglobulin-type binding region, that comprises a polypeptide comprising at least forty amino acids and that is linked (e.g., fused) to the carboxy-terminus of the Shiga toxin effector polypeptide region comprising an A1 fragment-derived region is a molecular moiety "encumbering the carboxy-terminus of the A1 fragment-derived region."

For purposes of the present invention, the term "A1 fragment of a member of the Shiga toxin family" refers to the remaining amino-terminal fragment of a Shiga toxin A Subunit after proteolysis by furin at the furin-cleavage site conserved among Shiga toxin A Subunits and positioned between the A1 fragment and the A2 fragment in wild-type Shiga toxin A Subunits.

For purposes of the instant invention, the phrase "furin-cleavage motif at the carboxy-terminus of the A1 fragment region" refers to a specific, furin-cleavage motif conserved among Shiga toxin A Subunits and bridging the junction between the A1 fragment and the A2 fragment in naturally occurring, Shiga toxin A Subunits.

For purposes of the present invention, the phrase "furin-cleavage site proximal to the carboxy-terminus of the A1 fragment region" refers to any identifiable, furin-cleavage site having an amino acid residue within a distance of less than 1, 2, 3, 4, 5, 6, 7, or more amino acid residues of the amino acid residue defining the last amino acid residue in the A1 fragment region or A1 fragment derived region, including a furin-cleavage motif located carboxy-terminal of an A1 fragment region or A1 fragment derived region, such as, e.g., at a position proximal to the linkage of the A1 fragment-derived region to another component of the molecule, such as, e.g., a molecular moiety of a binding protein of the present invention.

As used herein, the term "additional CD38-targeting therapeutic agent" means an additional therapeutic agent (e.g., a molecule) that targets CD38 to produce a therapeutic effect or benefit. This additional CD38-targeting therapeutic agent is complementary to the binding protein and does not compete directly with the binding protein in its CD38-targeting activity. The additional CD38-targeting therapeutic agent may comprise, consist essentially of, or consist of an anti-CD38 antibody or small molecule inhibitor that interferes with CD38 signaling. For example, additional CD38-targeting therapeutic agent may comprise, consist essentially of, or consist of an anti-CD38 antibody therapy that binds to an antigenic determinant that does not overlap with the antigenic determinant bound by the binding protein or that binds a CD38 molecule in such a manner that when bound the additional CD38-targeting therapeutic does not prevent the binding of that CD38 molecule by the binding protein of the invention. For example, the additional CD38-targeting therapeutic agent may comprise, consist essentially of, or consist of anti-CD38 monoclonal antibody therapy, such as, e.g., daratumumab.

For purposes of the present invention, the phrase "disrupted furin-cleavage motif" refers to (i) a specific furin-cleavage motif as described herein in Section I-B and (ii) which comprises a mutation and/or truncation that can confer a molecule with a reduction in furin-cleavage as compared to a reference molecule, such as, e.g., a reduction in furin-cleavage reproducibly observed to be 30%, 40%, 50%, 60%, 70%, 80%, 90%, 95%, 97%, 98%, 99%, or less (including 100% for no cleavage) than the furin-cleavage of a reference molecule observed in the same assay under the same conditions. The percentage of furin-cleavage as compared to a reference molecule can be expressed as a ratio of cleaved:uncleaved material of the molecule of interest divided by the cleaved:uncleaved material of the reference molecule (see e.g. WO 2015/191764; WO 2016/196344). Non-limiting examples of suitable reference molecules include some molecules comprising a wild-type Shiga toxin furin-cleavage motif and/or furin-cleavage site as described herein.

For purposes of the present invention, the phrase "furin-cleavage resistant" means a molecule or specific polypeptide region thereof exhibits reproducibly less Turin cleavage than (i) the carboxy-terminus of a Shiga toxin A1 fragment in a wild-type Shiga toxin A Subunit or (ii) the carboxy-terminus of the Shiga toxin A1 fragment derived region of construct wherein the naturally occurring furin-cleavage site natively positioned at the junction between the A1 and A2 fragments is not disrupted; as assayed by any available means to the skilled worker, including by using a method described herein.

For purposes of the present invention, the phrase "active enzymatic domain derived form an A Subunit of a member of the Shiga toxin family" refers to a polypeptide structure having the ability to inhibit protein synthesis via catalytic inactivation of a ribosome based on a Shiga toxin enzymatic activity. The ability of a molecular structure to exhibit inhibitory activity of protein synthesis and/or catalytic inactivation of a ribosome may be observed using various assays known to the skilled worker, such as, e.g., in vitro assays involving RNA translation assays in the absence of living cells or in vivo assays involving the ribosomes of living cells. For example, using assays known to the skilled worker, the enzymatic activity of a molecule based on a Shiga toxin enzymatic activity may be assessed directly by observing N-glycosidase activity toward ribosomal RNA (rRNA), such as, e.g., a ribosome nicking assay, and/or indirectly by observing inhibition of ribosome function, RNA translation, and/or protein synthesis.

As used herein with respect to a Shiga toxin effector polypeptide, a "combination" describes a Shiga toxin effector polypeptide comprising two or more sub-regions wherein each sub-region comprises at least one of the following, e.g., (1) a disruption in an endogenous epitope or epitope region; and (2) a disrupted furin-cleavage motif at the carboxy-terminus of an A1 fragment region.

As used herein with respect to a molecule of the present invention, a "binding protein" is used interchangeably with a "CD38-binding protein" or "CD38-binding molecule" or "CD38-binding fusion protein". All of the aforementioned molecule types include various "CD38-binding proteins". Generally, the proteins of the invention are referred to herein as "CD38-binding fusion proteins" that comprise a CD38-binding domain (also referred to herein as an "anti-CD38 antigen binding domain" (ABD) and optional linkers as more fully described herein) and a Shiga toxin A subunit effector polypeptide", with optional linkers as more fully described herein.

B. Introduction

The present invention provides a genus of binding proteins which bind CD38 and comprise a Shiga toxin A Subunit effector polypeptide (with optional linkers; referred to herein as "CD38-binding fusion proteins"). The CD38-binding fusion proteins of the present invention are useful, for e.g., (1) as molecules for inhibiting the growth of CD38-expressing cells, (2) as cytotoxic molecules for killing CD38-expressing cells, (3) for selectively killing specific CD38-positive cell type(s) amongst other cells, (4) as nontoxic delivery vehicles for delivering a cargo molecule to the interior of a CD38 expressing cell, (5) as diagnostic molecules for the diagnosis, prognosis, or characterization of diseases and conditions involving CD38-expressing cells, and (6) as therapeutic molecules for treating a variety of diseases, disorders, and conditions involving CD38-expressing cells, such as some blood cancers, including hematopoietic cancers like multiple myeloma and CD38-positive cell growth disorders. In some embodiments, the CD38-binding proteins may be used to treat non-Hodgkin's lymphoma (NHL), Burkitt's lymphoma (BL), B chronic lymphocytic leukemia (B-CLL), B and T acute lymphocytic leukemia (ALL), T cell lymphoma (TCL), acute myeloid leukemia (AML), hairy cell leukemia (HCL), Hodgkin's Lymphoma (HL), and chronic myeloid leukemia (CML) in a subject in need thereof. In some embodiments, the CD38-binding proteins of the present invention may be used to treat relapsed or refractory multiple myeloma in a subject in need thereof. In some embodiments, the CD-38 binding proteins of the present invention may be used to treat melanoma in a subject in need thereof.

Shiga toxin A Subunit effector polypeptides provide robust and powerful scaffolds for engineering novel binding proteins (see e.g. WO 2014/164680, WO 2014/164693, WO 2015/138435, WO 2015/138452, WO 2015/113005, WO 2015/113007, WO 2015/191764, WO 2016/196344, WO 2017/019623, WO 2018/106895, and WO 2018/140427). The association of CD38-binding immunoglobulin-derived fragments as cell-targeting moieties with Shiga toxin A Subunit effector polypeptides enables the engineering of therapeutic and diagnostic molecules that target CD38 expressing cells.

C. The General Structure of the CD38 Binding Fusion Proteins

A CD38-binding fusion protein of the present invention may comprise (1) a binding region capable of specifically binding an extracellular part of CD38 associated with a cell surface; and (2) a Shiga toxin effector polypeptide region comprising a Shiga toxin A Subunit effector polypeptide (referred to herein as a "Shiga toxin effector polypeptide"). In some embodiments, a binding protein of the present invention comprises two or more of the same CD38-binding regions, and two or more Shiga toxin effector polypeptide regions, whether the same or different. One non-limiting example of a CD38-binding fusion protein of the present invention is a Shiga toxin effector polypeptide fused to an immunoglobulin-type binding region comprising a single-chain variable fragment that binds specifically to an extracellular part of CD38 when associated with a cell surface, or a homodimer of the aforementioned, as is more fully described below.

In some embodiments, the Shiga toxin A Subunit effector polypeptide of the binding protein of the present invention combines structural elements resulting in two or more properties in a single molecule, such as, e.g., the ability to 1) exhibit reduced antigenicity and/or immunogenicity as compared to molecular variants lacking that particular combination of elements, 2) exhibit reduced protease-cleavage as compared to molecular variants lacking that particular combination of elements, 3) exhibit reduced non-specific toxicity to a multicellular organism at some dosages as compared to molecular variants lacking that particular combination of elements and/or 4) exhibit potent cytotoxicity.

In some embodiments, the CD38-binding fusion proteins of the invention are monomers. In some embodiments, the CD38-binding fusion proteins are homodimers. In some embodiments, the CD38-binding fusion proteins are homodimers comprising two identical polypeptides. In some embodiments, a monomeric CD38-binding fusion protein comprises the sequence of SEQ ID NO: 233, or a sequence at least 90%, at least 95%, at least 96%, at least 97%, at least 98%, at least 99% identical thereto.

1. CD38 Binding Regions

In some embodiments, a CD38-binding protein of the present invention comprises a binding region (also referred to as a "binding domain" or an "antigen binding domain (ABD)) comprising an immunoglobulin-type polypeptide (e.g. VH and VL) capable of exhibiting specific and high-affinity binding to CD38 and/or CD38 present on a cellular surface of a cell, such as, e.g., a CD38 expressing cell or CD38 positive cell in a mammal (e.g., human, non-human primate, mouse, etc.).

The invention provides a number of CD38-binding domains. Specific CDRs of CD38-binding domains are described below. As described above, the exact numbering and placement of the CDRs can be different among different numbering systems. However, it should be understood that the invention of a heavy variable and/or light variable region includes the invention of the CDRs present therein. Accordingly, the invention of each heavy variable region is an invention of the vhCDRs (e.g. vhCDR1, vhCDR2 and vhCDR3) and the invention of each light variable region is an invention of the vlCDRs (e.g. vlCDR1, vlCDR2 and vlCDR3).

The present invention provides binding proteins comprising novel CD38-binding domains. Such antigen binding domains (ABDs) can bind human and cynomolgus CD38 proteins. FIG. 25A-D depicts four different binding proteins comprising four different anti-CD38 ABDs that can bind to both human and cynomolgus CD38. In some embodiments, the heavy chain variable region and the light chain variable region are arranged in a Fab format, e.g. on two different polypeptide chains, In some embodiments, the heavy chain variable region and the light chain variable region are fused together to form an scFv as generally outlined herein. Alternatively, as shown in FIG. 1 and more fully described below, the CD-38 binding domains from two CD-38 binding fusion protein monomers that have dimerized then associate with each other; that is one VH from one monomeric polypeptide chain associates with the VL from the other monomeric polypeptide chain, and vice versa, such that two anti-CD38 binding domains are formed in the non-covalently associated homodimer, which also contains two Shiga components.

Also included herein are anti-CD38 ABDs that have amino acid modifications in one or more of the CDRs and/or the framework regions. as outlined herein, in some embodiments the set of 6 CDRs can have from 0, 1, 2, 3, 4, 5 or 6 amino acid modifications (with amino acid substitutions finding particular use). The CDRs can have amino acid modifications (e.g. from 1, 2, 3, 4, 5 or 6 amino acid modifications in the set of CDRs (that is, the CDRs can be modified as long as the total number of changes in the set of 6 CDRs is less than 6 amino acid modifications, with any combination of CDRs being changed; e.g. there may be one change in vlCDR1, two in vhCDR2, none in vhCDR3, etc.). In some embodiments, each CDR has no more than a single amino acid substitution. In some embodiments, amino acid substitutions in the vhCDR3 are avoided. In some cases, the binding affinity for either or both of human and cyno CD38 may be increased, while in other embodiments the binding affinity may be reduced. In these embodiments, binding to human and cyno CD38 is retained. Suitable assays for testing whether an anti-CD38 antigen binding domain that contains mutations as compared to the VH and VL sequences outlined herein are known in the art, such as Biacore assays or the binding assay outlined in Examples 1, 2 or 3.

In some embodiments, the anti-CD38 ABDs outlined herein may also have amino acid modifications (again, with amino acid substitutions finding particular use) in the framework regions of either or both of the variable heavy and variable light framework regions, as long as the frameworks (excluding the CDRs) retain at least about 80%, about 85% or about 90% identity to a human germline sequence. Thus, for example, the identical CDRs as described herein can be combined with different framework sequences from human germline sequences, as long as the framework regions retain at least 80%, at least 85% or at least 90% identity to a human germline sequence.

In another aspect, the invention provides CD38-binding domains that include variants of the above listed heavy chain variable and light chain variable regions. The heavy chain variable regions can be at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to "VH" sequences herein, and/or contain from 1, 2, 3, 4, 5, 6, 7, 8, 9, 10 amino acid changes. The light chain variable regions can be at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to "VL" sequences herein, and/or contain 1, 2, 3, 4, 5, 6, 7, 8, 9, 10 amino acid changes. In these embodiments, the invention includes these variants as long as the antigen binding domains still bind to human and cynomolgus CD38. Suitable assays for testing whether an anti-CD38 antigen binding domain that contains mutations as compared to the VH and VL sequences outlined herein are known in the art, such as Biacore assays and those of Examples 1, 2 and 3.

In some embodiments, the CD38-binding domain is CD38TM1 (FIG. 25A) and includes a heavy chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:109 and a light chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:113.

In some embodiments, the CD38-binding domain is CD38TM1 (FIG. 25A) and includes a vhCDR1 comprising SEQ ID NO:110, a vhCDR2 comprising SEQ ID NO:111, a vhCDR3 comprising SEQ ID NO:112, a vlCDR1 comprising SEQ ID NO:114, a vlCDR2 comprising SEQ ID NO:115, and a vlCDR3 comprising SEQ ID NO:116. In some embodiments, one or more of such 6 CDRs have 1, 2, 3, 4 or 5 amino acid modifications. In embodiments, any single CDR contains no more than 1 or 2 amino acid substitutions, and the modified anti-CD38 antigen binding domain retain binding to human CD38.

In some embodiments the CD38-binding domain of CD38TM1 (FIG. 25A) has a VH domain that has no more than 1, 2, 3, 4 or 5 amino acid changes in SEQ ID NO:109.

In some embodiments the CD38-binding domain of CD38TM1 (FIG. 25A) has a VL domain that has no more than 1, 2, 3, 4 or 5 amino acid changes in SEQ ID NO:113.

In some embodiments the CD38-binding domain of CD38TM1 (FIG. 25A) has a VH domain that has no more than 1, 2, 3, 4 or 5 amino acid changes in SEQ ID NO:109 and a VL domain that has no more than 1, 2, 3, 4 or 5 amino acid changes in SEQ ID NO:113.

In some embodiments the CD38-binding domain is CD38TM1 (FIG. 25A) and has a VH with SEQ ID NO:109 and a VL with SEQ ID NO:113.

In some embodiments, the CD38-binding domain is CD38TM2 (FIG. 25B) and includes a heavy chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:117 and a light chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:121.

In some embodiments, the CD38-binding domain is CD38TM2 (FIG. 25B) and includes a vhCDR1 comprising SEQ ID NO:118, a vhCDR2 comprising SEQ ID NO:119, a vhCDR3 comprising SEQ ID NO:120, a vlCDR1 comprising SEQ ID NO:122, a vlCDR2 comprising SEQ ID NO:23, and a vlCDR3 comprising SEQ ID NO:124. In some embodiments, one or more of such 6 CDRs have 1, 2, 3, 4 or 5 amino acid modifications. In embodiments, a single CDR contains no more than 1 or 2 amino acid substitutions, and the modified anti-CD38 antigen binding domain retain binding to human and/or cynomolgus CD38.

In some embodiments the CD38-binding domain of CD38TM2 (FIG. 25B) has a VH domain that has no more than 1, 2, 3, 4 or 5 amino acid changes in SEQ ID NO:117.

In some embodiments the CD38-binding domain of CD38TM1 (FIG. 25A) has a VL domain that has no more than 1, 2, 3, 4 or 5 amino acid changes in SEQ ID NO:121.

In some embodiments the CD38-binding domain of CD38TM2 (FIG. 25B) has a VH domain that has no more than 1, 2, 3, 4 or 5 amino acid changes in SEQ ID NO:117 and a VL domain that has no more than 1, 2, 3, 4 or 5 amino acid changes in SEQ ID NO:121.

In some embodiments the CD38-binding domain is CD38TM2 (FIG. 25B) and has a VH with SEQ ID NO:117 and a VL with SEQ ID NO:121.

In some embodiments, the CD38-binding domain is CD38TM3 (FIG. 25C) and includes a heavy chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:101 and a light chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:105.

In some embodiments, the CD38-binding domain is CD38TM3 (FIG. 25C) and includes a vhCDR1 comprising SEQ ID NO:102, a vhCDR2 comprising SEQ ID NO:103, a vhCDR3 comprising SEQ ID NO:104, a vlCDR1 comprising SEQ ID NO:106, a vlCDR2 comprising SEQ ID NO:7, and a vlCDR3 comprising SEQ ID NO:108. In some embodiments, one or more of such 6 CDRs have from 1, 2, 3, 4 or 5 amino acid modifications. In embodiments, a single CDR contains 1 or 2 amino acid substitutions, and the modified anti-CD38 antigen binding domain retain binding to human and/or cynomolgus CD38.

In some embodiments the CD38-binding domain of CD38TM3 (FIG. 25C) has a VH domain that has no more than 1, 2, 3, 4 or 5 amino acid changes in SEQ ID NO:101.

In some embodiments the CD38-binding domain of CD38TM3 (FIG. 25C) has a VL domain that has no more than 1, 2, 3, 4 or 5 amino acid changes in SEQ ID NO:105.

In some embodiments the CD38-binding domain of CD38TM3 (FIG. 25C) has a VH domain that has no more than 1, 2, 3, 4 or 5 amino acid changes in SEQ ID NO:101 and a VL domain that has no more than 1, 2, 3, 4 or 5 amino acid changes in SEQ ID NO:105.

In some embodiments the CD38-binding domain is CD38TM3 (FIG. 25C) and has a VH with SEQ ID NO:101 and a VL with SEQ ID NO:105.

In some embodiments, the CD38-binding domain is CD38TM4 (FIG. 25D) in the present invention include a heavy chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:101 and a light chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:125.

In some embodiments, the CD38-binding domain is CD38TM4 (FIG. 25D) and includes a vhCDR1 comprising SEQ ID NO:102, a vhCDR2 comprising SEQ ID NO:3, a vhCDR3 comprising SEQ ID NO:104, a vlCDR1 comprising SEQ ID NO:106, a vlCDR2 comprising SEQ ID NO:107, and a vlCDR3 comprising SEQ ID NO:108. In some embodiments, one or more of such 6 CDRs have 1, 2, 3, 4 or 5 amino acid modifications. In embodiments, a single CDR contains 1 or 2 amino acid substitutions, and the modified anti-CD38 antigen binding domain retain binding to human and/or cynomolgus CD38.

In some embodiments the CD38-binding domain of CD38TM4 (FIG. 25D) has a VH domain that has no more than 1, 2, 3, 4 or 5 amino acid changes in SEQ ID NO:101.

In some embodiments the CD38-binding domain of CD38TM1 (FIG. 25A) has a VL domain that has no more than 1, 2, 3, 4 or 5 amino acid changes in SEQ ID NO:125.

In some embodiments the CD38-binding domain of CD38TM4 (FIG. 25D) has a VH domain that has no more than 1, 2, 3, 4 or 5 amino acid changes in SEQ ID NO:101 and a VL domain that has no more than 1, 2, 3, 4 or 5 amino acid changes in SEQ ID NO:125.

In some embodiments the CD38-binding domain is CD38TM4 (FIG. 25D) and has a VH with SEQ ID NO:101 and a VL with SEQ ID NO:125.

In addition to the sequence variants described herein in the heavy chain and light chain variable regions and/or CDRs for each CD38-binding domain, changes in the framework region(s) of the heavy and/or light variable region(s) can be made. In some embodiments, variations are made in the framework regions that retain at least 80, 85, 90 or 95% identity to the framework region sequences described in Table 4, while keeping 6 CDRs unchanged and retaining the binding to human and/or cynomolgus CD38.

In some embodiments, variations are made in both the framework regions and the 6 CDRs while retaining the binding of the CD38-binding domains to human and/or cynomolgus CD38. In these embodiments, the CDRs can have amino acid modifications (e.g., from 1, 2, 3, 4 or 5 amino acid modifications in the set of 6 CDRs, that is, the CDRs can be modified as long as the total number of changes in the set of 6 CDRs is less than 6 amino acid modifications, with any combination of CDRs being changed; e.g., there may be one change in vlCDR1, two in vhCDR2, none in vhCDR3, etc.).

a. Formats of the CD38 Binding Domains

As shown in FIG. 1 and described herein, the CD38 binding domains of the invention comprises a VH and VL domains that can either be resident on different polypeptide chains or on a single polypeptide chain. It should be noted that the VH and VL can form a scFv in some embodiments, where the CD38-binding fusion protein is a monomer, for example. In some cases as described herein and shown in FIG. 1, the VH and the VL are on a single polypeptide chain but the linker between them is too short to allow intramolecular association, and thus a homodimer forms, that contains two anti-CD38 binding regions and 2 Shiga components. In other embodiments, the linker between the VH and the VL is long enough to allow for scFv formation, and thus the protein fusion is a monomer.

In some embodiments, the composition comprises an scFv that comprises a CD38-binding domain described herein. The scFvs binds to human and cynomolgus CD38, and comprises a heavy chain variable region (VH) and a light chain variable region (VL) linked by an scFv linker. In some embodiments, the CD38-binding domain comprises, from its N- to C-terminus, VH—linker-VL. In some embodiments, the CD38-binding domain comprises, from its N- to C-terminus, VL—linker-VH.

2. Shiga Toxin Effector Polypeptide Components

The binding proteins of the present invention comprise at least one Shiga toxin effector polypeptide derived from a Shiga toxin A Subunit. A Shiga toxin effector polypeptide is a polypeptide derived from a Shiga toxin A Subunit member of the Shiga toxin family that is capable of exhibiting one or more Shiga toxin functions (see e.g., Cheung M et al., *Mol Cancer* 9: 28 (2010); WO 2014/164680, WO 2014/164693, WO 2015/138435, WO 2015/138452, WO 2015/113005, WO 2015/113007, WO 2015/191764, WO 2016/196344, WO 2017/019623, WO 2018/106895, and WO 2018/140427). Shiga toxin functions include, e.g., increasing cellular internalization, directing subcellular routing from an endosomal compartment to the cytosol, avoiding intracellular degradation, catalytically inactivating ribosomes (preventing protein synthesis) and effectuating cytostatic and/or cytotoxic effects.

The Shiga toxin family of protein toxins is composed of various naturally occurring toxins which are structurally and functionally related, e.g., Shiga toxin, Shiga-like toxin 1, and Shiga-like toxin 2 (Johannes L, Römer W, *Nat Rev Microbiol* 8: 105-16 (2010)). Holotoxin members of the Shiga toxin family contain targeting domains that selectively bind a specific glycosphingolipid present on the surface of some host cells and an enzymatic domain capable of permanently inactivating ribosomes once inside a cell (Johannes L, Römer W, *Nat Rev Microbiol* 8: 105-16 (2010)). Members of the Shiga toxin family share the same overall structure and mechanism of action (Engedal N et al., *Microbial Biotech* 4: 32-46 (2011)). For example, Stx, SLT-1 and SLT-2 display indistinguishable enzymatic activity in cell free systems (Head S et al, *J Biol Chem* 266: 3617-21 (1991); Tesh V et al., Infect Immun 61: 3392-402 (1993); Brigotti M et al, *Toxicon* 35:1431-1437 (1997)).

The Shiga toxin family encompasses true Shiga toxin (Stx) isolated from *S. dysenteriae* serotype 1, Shiga-like toxin 1 variants (SLT1 or Stx1 or SLT-1 or Slt-I) isolated from serotypes of enterohemorrhagic *E. coli*, and Shiga-like toxin 2 variants (SLT2 or Stx2 or SLT-2) isolated from serotypes of enterohemorrhagic *E. coli*. SLT1 differs by only one amino acid residue from Stx, and both have been referred to as Verocytotoxins or Verotoxins (VTs) (O'Brien A, *Curr Top Microbiol Immunol* 180: 65-94 (1992)). Although SLT1 and SLT2 variants are only about 53-60% similar to each other at the primary amino acid sequence level, they share mechanisms of enzymatic activity and cytotoxicity common to the members of the Shiga toxin family (Johannes L, Römer W, *Nat Rev Microbiol* 8: 105-16 (2010)). Over 39 different Shiga toxins have been described, such as the defined subtypes Stx1a, Stx1c, Stx1d, and Stx2a-g (Scheutz F et al, *J Clin Microbiol* 50: 2951-63 (2012)). Members of the Shiga toxin family are not naturally restricted to any bacterial species because Shiga-toxin-encoding genes can spread among bacterial species via horizontal gene transfer (Strauch E et al., *Infect Immun* 69: 7588-95 (2001); Bielaszewska M et al, *Appl Environ Micrbiol* 73: 3144-50 (2007); Zhaxybayeva O, Doolittle W, *Curr Biol* 21: R242-6 (2011)). As an example of interspecies transfer, a Shiga toxin was discovered in a strain of *A. haemolyticus* isolated from a human subject (Grotiuz G et al, *J Clin Microbiol* 44: 3838-41 (2006)). Once a Shiga toxin encoding polynucleotide enters a new subspecies or species, the Shiga toxin amino acid sequence is presumed to be capable of developing slight sequence variations due to genetic drift and/or selective pressure while still maintaining a mechanism of cytotoxicity common to members of the Shiga toxin family (see Scheutz F et al, *J Clin Microbiol* 50: 2951-63 (2012)).

In some embodiments of the CD38-binding proteins of the present invention as more fully described below, the Shiga toxin A Subunit effector polypeptide component comprises a combination of at least the following Shiga toxin effector polypeptide sub-regions: (1) a de-immunized sub-region and (2) a protease-cleavage resistant sub-region near the carboxy-terminus of a Shiga toxin A1 fragment region.

In some embodiments, a CD38-binding protein comprise a Shiga toxin A subunit effector polypeptide comprising the sequence of any one of SEQ ID NOS: 45-69, or a sequence having at least 95%, at least 96%, at least 97%, at least 95%, at least 99% amino acid sequence identity thereto. In some embodiments, the Shiga toxin A subunit effector polypeptide comprises the sequence of SEQ ID NO: 46.

a. Useful Shiga Toxin Components in Particular Embodiments

As has been described in the art, there are a number of Shiga Toxin components that find use for combination with the CD38 binding regions of the invention as generally described below. Specifically, Embodiments #1 to #11 from U.S. Provisional Application No. 62/795,633, filed Jan. 23, 2019 are specifically incorporated by reference in their entirety.

(i) Wild-Type Shiga Toxin Component

In some embodiments, a wild-type Shiga toxin effector polypeptide such as depicted in SEQ ID NO:1, SEQ ID NO:2 or SEQ ID NO:3 of Table 20 can be used, (see e.g. WO 2014/164693, WO 2015/138435, WO 2015/138452, WO 2017/019623, all of which are incorporated by reference in their entirety, and in particular for the sequences and fragments of the wild type sequences, such as those referenced in paragraph [21] of WO2017/019623).

(ii) Shiga Toxin Component with Disrupted, Furin-Cleavage Motif

In some embodiments, the Shiga toxin effector polypeptide comprises a disrupted furin-cleavage motif at the carboxy-terminus of its Shiga toxin A1 fragment region (see e.g. WO 2015/191764, hereby expressly incorporated by reference in its entirety, and specifically paragraphs [8], [9] and the sequences of the disrupted motifs and the toxin polypeptides including the disrupted motifs). A particularly useful embodiment in this regard is SEQ ID NO:46.

Shiga toxin A Subunits of members of the Shiga toxin family comprise a conserved, furin-cleavage site at the carboxy-terminal of their A1 fragment regions important for Shiga toxin function. Furin-cleavage site motifs and furin-cleavage sites can be identified by the skilled worker using standard techniques and/or by using the information herein.

The model of Shiga toxin cytotoxicity is that intracellular proteolytic processing of Shiga toxin A Subunits by furin in intoxicated cells is essential for 1) liberation of the A1 fragment from the rest of the Shiga holotoxin, 2) escape of the A1 fragment from the endoplasmic reticulum by exposing a hydrophobic domain in the carboxy-terminus of the A1 fragment, and 3) enzymatic activation of the A1 fragment (see Johannes L, Römer W, *Nat Rev Microbiol* 8: 105-16 (2010)). The efficient liberation of the Shiga toxin A1 fragment from the A2 fragment and the rest of the components of the Shiga holotoxin in the endoplasmic reticulum of intoxicated cells is essential for efficient intracellular routing to the cytosol, maximal enzymatic activity, efficient ribosome inactivation, and achieving optimal cytotoxicity, i.e. comparable to a wild-type Shiga toxin (see e.g. WO 2015/191764 and references therein).

During Shiga toxin intoxication, the A Subunit is proteolytically cleaved by furin at the carboxy bond of a conserved arginine residue (e.g. the arginine residue at position 251 in StxA and SLT-1A and the arginine residue at position 250 in Stx2A and SLT-2A). Furin cleavage of Shiga toxin A Subunits occurs in endosomal and/or Golgi compartments. Furin is a specialized serine endoprotease which is expressed by a wide variety of cell types, in all human tissues examined, and by most animal cells. Furin cleaves polypeptides comprising accessible motifs often centered on the minimal, dibasic, consensus motif R-x-(R/K/x)-R (SEQ ID NO: 181). The A Subunits of members of the Shiga toxin family comprise a conserved, surface-exposed, extended loop structure (e.g. 242-261 in StxA and SLT-1A, and 241-260 in SLT-2) with a conserved S-R/Y-x-x-R (SEQ ID NO: 182) motif which is cleaved by furin. The surface exposed, extended loop structure positioned at amino acid residues 242-261 in StxA is required for furin-induced cleavage of StxA, including features flanking the minimal, furin-cleavage motif R-x-x-R (SEQ ID NO: 183).

Furin-cleavage motifs and furin-cleavage sites in Shiga toxin A Subunits and Shiga toxin effector polypeptides can be identified by the skilled worker using standard methods and/or by using the information herein. Furin cleaves the minimal, consensus motif R-x-x-R (SEQ ID NO: 183) (Schalken J et al., *J Clin Invest* 80: 1545-9 (1987); Bresnahan P et al., *J Cell Biol* 111: 2851-9 (1990); Hatsuzawa K et al., *J Biol Chem* 265: 22075-8 (1990); Wise R et al., Proc *Natl Acad Sci USA* 87: 9378-82 (1990); Molloy S et al., *J Biol Chem* 267: 16396-402 (1992)). Consistent with this, many furin inhibitors comprise peptides comprising the motif R-x-x-R (SEQ ID NO: 183). An example of a synthetic inhibitor of furin is a molecule comprising the peptide R-V-K-R (SEQ ID NO: 190) (Henrich S et al., *Nat Struct Biol* 10: 520-6 (2003)). In general, a peptide or protein comprising a surface accessible, dibasic amino acid motif with two positively charged, amino acids separated by two amino acid residues can be predicted to be sensitive to furin-cleavage with cleavage occurring at the carboxy bond of the last basic amino acid in the motif.

Consensus motifs in substrates cleaved by furin have been identified with some degree of specificity. A furin-cleavage site motif has been described that comprises a region of twenty, continuous, amino acid residues, which can be labeled P14 through P6' (Tian Set al., *Int J Mol Sci* 12: 1060-5 (2011)) using the nomenclature described in Schechter I, Berger, *A, Biochem Biophys Res Commun* 32: 898-902 (1968). According to this nomenclature, the furin-cleavage site is at the carboxy bond of the amino acid residue designated P1, and the amino acid residues of the furin-cleavage motif are numbered P2, P3, P4, etc., in the direction going toward the amino-terminus from this reference P1 residue. The amino acid residues of the motif going toward the carboxy-terminus from the P1 reference residue are numbered with the prime notation P2', P3', P4', etc. Using this nomenclature, the P6 to P2' region delineates the core substrate of the furin cleavage motif which is bound by the enzymatic domain of furin. The two flanking regions P14 to P7 and P3' to P6' are often rich in polar, amino acid residues to increase the accessibility to the core furin cleavage site located between them.

A general, furin-cleavage site is often described by the consensus motif R-x-x-R (SEQ ID NO: 183) which corresponds to P4-P3-P2-P1 (SEQ ID NO: 192); where “R” represents an arginine residue (see Table 1 supra), a dash “-” represents a peptide bond, and a lowercase “x” represents any amino acid residue. However, other residues and positions may help to further define furin-cleavage motifs. A slightly more refined furin-cleavage site, consensus motif is often reported as the consensus motif R-x-[K/R]-R (SEQ ID NO: 191) (where a forward slash “/” means “or” and divides alternative amino acid residues at the same position), which corresponds to P4-P3-P2-P1 (SEQ ID NO: 192), because it was observed that furin has a strong preference for cleaving substrates containing this motif.

In addition to the minimal, furin-cleavage site R-x-x-R (SEQ ID NO: 183), a larger, furin-cleavage motif has been described with certain amino acid residue preferences at certain positions. By comparing various known furin substrates, certain physicochemical properties have been characterized for the amino acids residues in a 20 amino acid residue long, furin-cleavage site motif. The P6 to P2' region of the furin-cleavage motif delineates the core furin-cleavage site which physically interacts with the enzymatic domain of furin. The two flanking regions P14 to P7 and P3' to P6' are often hydrophilic being rich in polar, amino acid residues to increase the surface accessibility of the core furin-cleavage site located between them.

In general, the furin-cleavage motif region from position P5 to P1 tends to comprise amino acid residues with a positive charge and/or high isoelectric points. In particular, the P1 position, which marks the position of furin proteolysis, is generally occupied by an arginine but other positively charged, amino acid residues can occur in this position. Positions P2 and P3 tend to be occupied by flexible, amino acid residues, and in particular P2 tends to be occupied by arginine, lysine, or sometimes by very small and flexible amino acid residues like glycine. The P4 position tends to be occupied by positively charged, amino acid residues in furin substrates. However, if the P4 position is occupied by an aliphatic, amino acid residue, then the lack of a positively charged, functional group can be compensated for by a positively charged residue located at position(s) P5 and/or P6. Positions P1' and P2' are commonly occupied by aliphatic and/or hydrophobic amino acid residues, with the P1' position most commonly being occupied by a serine.

The two, hydrophilic, flanking regions tend to be occupied by amino acid residues which are polar, hydrophilic, and have smaller amino acid functional groups; however, in certain verified furin substrates, the flanking regions do not contain any hydrophilic, amino acid residues (see Tian S, *Biochem Insights* 2: 9-20 (2009)).

The twenty amino acid residue, furin-cleavage motif and furin-cleavage site found in native, Shiga toxin A Subunits at the junction between the Shiga toxin A1 fragment and A2 fragment is well characterized in certain Shiga toxins. For example in StxA (SEQ ID NO:2) and SLT-1A (SEQ ID NO:1), this furin-cleavage motif is natively positioned from L238 to F257, and in SLT-2A (SEQ ID NO:3), this furin-cleavage motif is natively positioned from V237 to Q256. Based on amino acid homology, experiment, and/or furin-cleavage assays described herein, the skilled worker can identify furin-cleavage motifs in other native, Shiga toxin A Subunits or Shiga toxin effector polypeptides, where the motifs are actual furin-cleavage motifs or are predicted to result in the production of A1 and A2 fragments after furin cleavage of those molecules within a eukaryotic cell.

In some embodiments, the Shiga toxin effector polypeptide comprises (1) a Shiga toxin A1 fragment derived polypeptide having a carboxy-terminus and (2) a disrupted furin-cleavage motif at the carboxy-terminus of the Shiga toxin A1 fragment derived polypeptide. The carboxy-terminus of a Shiga toxin A1 fragment derived polypeptide may be identified by the skilled worker by using techniques known in the art, such as, e.g., by using protein sequence alignment software to identify (i) a furin-cleavage motif conserved with a naturally occurring Shiga toxin, (ii) a surface exposed, extended loop conserved with a naturally occurring Shiga toxin, and/or (iii) a stretch of amino acid residues which are predominantly hydrophobic (i.e. a hydrophobic "patch") that may be recognized by the ERAD system.

A protease-cleavage resistant, Shiga toxin effector polypeptide of the binding protein of the present invention (1) may be completely lacking any furin-cleavage motif at a carboxy-terminus of its Shiga toxin A1 fragment region and/or (2) comprise a disrupted furin-cleavage motif at the carboxy-terminus of its Shiga toxin A1 fragment region and/or region derived from the carboxy-terminus of a Shiga toxin A1 fragment. A disruption of a furin-cleavage motif include various alterations to an amino acid residue in the furin-cleavage motif, such as, e.g., a post-translation modification(s), an alteration of one or more atoms in an amino acid functional group, the addition of one or more atoms to an amino acid functional group, the association to a non-proteinaceous moiety(ies), and/or the linkage to an amino acid residue, peptide, polypeptide such as resulting in a branched proteinaceous structure.

Protease-cleavage resistant, Shiga toxin effector polypeptides may be created from a Shiga toxin effector polypeptide and/or Shiga toxin A Subunit polypeptide, whether naturally occurring or not, using a method described herein, described in WO 2015/191764, and/or known to the skilled worker, wherein the resulting molecule still retains one or more Shiga toxin A Subunit functions.

For purposes of the present invention with regard to a furin-cleavage site or furin-cleavage motif, the term "disruption" or "disrupted" refers to an alteration from the naturally occurring furin-cleavage site and/or furin-cleavage motif, such as, e.g., a mutation, that results in a reduction in furin-cleavage proximal to the carboxy-terminus of a Shiga toxin A1 fragment region, or identifiable region derived thereof, as compared to the furin-cleavage of a wild-type Shiga toxin A Subunit or a polypeptide derived from a wild-type Shiga toxin A Subunit comprising only wild-type polypeptide sequences. An alteration to an amino acid residue in the furin-cleavage motif includes a mutation in the furin-cleavage motif, such as, e.g., a deletion, insertion, inversion, substitution, and/or carboxy-terminal truncation of the furin-cleavage motif, as well as a post-translation modification, such as, e.g., as a result of glycosylation, albumination, and the like which involve conjugating or linking a molecule to the functional group of an amino acid residue. Because the furin-cleavage motif is comprised of about twenty, amino acid residues, in theory, alterations, modifications, mutations, deletions, insertions, and/or truncations involving one or more amino acid residues of any one of these twenty positions might result in a reduction of furin-cleavage sensitivity (Tian S et al., *Sci Rep* 2: 261 (2012)). The disruption of a furin-cleavage site and/or furin-cleavage motif might or might not increase resistance to cleavage by other proteases, such as, e.g., trypsin and extracellular proteases common in the vascular system of mammals. The effects of a given disruption to cleavage sensitivity of a given protease may be tested by the skilled worker using techniques known in the art.

For purposes of the present invention, a "disrupted furin-cleavage motif" is furin-cleavage motif comprising an alteration to one or more amino acid residues derived from the 20 amino acid residue region representing a conserved, furin-cleavage motif found in native, Shiga toxin A Subunits at the junction between the Shiga toxin A1 fragment and A2 fragment regions and positioned such that furin cleavage of a Shiga toxin A Subunit results in the production of the A1 and A2 fragments; wherein the disrupted furin-cleavage motif exhibits reduced furin cleavage in an experimentally reproducible way as compared to a reference molecule comprising a wild-type, Shiga toxin A1 fragment region fused to a carboxy-terminal polypeptide of a size large enough to monitor furin cleavage using the appropriate assay known to the skilled worker and/or described herein.

Examples of types of mutations which can disrupt a furin-cleavage site and furin-cleavage motif are amino acid residue deletions, insertions, truncations, inversions, and/or substitutions, including substitutions with non-standard amino acids and/or non-natural amino acids. In addition, furin-cleavage sites and furin-cleavage motifs can be disrupted by mutations comprising the modification of an amino acid by the addition of a covalently-linked structure which masks at least one amino acid in the site or motif, such as, e.g., as a result of PEGylation, the coupling of small molecule adjuvants, and/or site-specific albumination.

If a furin-cleavage motif has been disrupted by mutation and/or the presence of non-natural amino acid residues, certain disrupted furin-cleavage motifs may not be easily recognizable as being related to any furin-cleavage motif; however, the carboxy-terminus of the Shiga toxin A1 fragment derived region will be recognizable and will define where the furin-cleavage motif would be located were it not disrupted. For example, a disrupted furin-cleavage motif may comprise less than the twenty, amino acid residues of the furin-cleavage motif due to a carboxy-terminal truncation as compared to a Shiga toxin A Subunit and/or Shiga toxin A1 fragment.

In some embodiments, the Shiga toxin effector polypeptide comprises (1) a Shiga toxin A1 fragment derived polypeptide having a carboxy-terminus and (2) a disrupted furin-cleavage motif at the carboxy-terminus of the Shiga toxin A1 fragment polypeptide region; wherein the Shiga toxin effector polypeptide (and any binding protein comprising it) is more furin-cleavage resistant as compared to a reference molecule, such as, e.g., a wild-type Shiga toxin polypeptide comprising the carboxy-terminus of an A1 fragment and/or the conserved, furin-cleavage motif between A1 and A2 fragments. For example, a reduction in furin cleavage of one molecule compared to a reference molecule may be determined using an in vitro, furin-cleavage assay described in WO 2015/191764, conducted using the same conditions, and then performing a quantitation of the band density of any fragments resulting from cleavage to quantitatively measure in change in furin cleavage.

In some embodiments, the Shiga toxin effector polypeptide is more resistant to Turin-cleavage in vitro and/or in vivo as compared to a wild-type, Shiga toxin A Subunit.

In general, the protease-cleavage sensitivity of a binding protein of the present invention is tested by comparing it to the same molecule having its furin-cleavage resistant, Shiga toxin effector polypeptide replaced with a wild-type, Shiga toxin effector polypeptide comprising a Shiga toxin A1 fragment. In some embodiments, the CD38-binding fusion protein of the invention comprising a disrupted furin-cleavage motif exhibits a reduction in in vitro furin cleavage of at least 30%, at least 40%, at least 50%, at least 60%, at least 70%, at least 80%, at least 90%, at least 95%, at least 97%, at least 98% or greater compared to a reference molecule comprising a wild-type, Shiga toxin A1 fragment fused at its carboxy-terminus to a peptide or polypeptide.

Several furin-cleavage motif disruptions have been described. For example, mutating the two conserved arginines to alanines in the minimal R-x-x-R motif (SEQ ID NOL: 183) completely blocked processing by furin and/or furin-like proteases (see e.g Duda A et al, *J Virology* 78: 13865-70 (2004)). Because the furin-cleavage site motif is comprised of about twenty amino acid residues, in theory, certain mutations involving one or more of any one of these twenty, amino acid residue positions might abolish furin cleavage or reduce furin cleavage efficiency (see e.g. Tian S et al., *Sci Rep* 2: 261 (2012)).

In some embodiments, the CD38-binding fusion protein of the invention comprise a Shiga toxin effector polypeptide derived from at least one A Subunit of a member of the Shiga toxin family wherein the Shiga toxin effector polypeptide comprises a disruption in one or more amino acids derived from the conserved, highly accessible, protease-cleavage sensitive loop of Shiga toxin A Subunits. For example, in StxA and SLT-1A, this highly accessible, protease-sensitive loop is natively positioned from amino acid residues 242 to 261, and in SLT-2A, this conserved loop is natively positioned from amino acid residues 241 to 260. Based on polypeptide sequence homology, the skilled worker can identify this conserved, highly accessible loop structure in other Shiga toxin A Subunits. Certain mutations to the amino acid residues in this loop can reduce the accessibility of certain amino acid residues within the loop to proteolytic cleavage and this might reduce furin-cleavage sensitivity.

In some embodiments, a molecule of the present invention comprises a Shiga toxin effector polypeptide comprising a disrupted furin-cleavage motif comprising a mutation in the surface-exposed, protease sensitive loop conserved among Shiga toxin A Subunits. In some embodiments, a molecule of the present invention comprises a Shiga toxin effector polypeptide comprising a disrupted furin-cleavage motif comprising a mutation in this protease-sensitive loop of Shiga toxin A Subunits, the mutation which reduce the surface accessibility of certain amino acid residues within the loop such that furin-cleavage sensitivity is reduced.

In some embodiments, the disrupted furin-cleavage motif of a Shiga toxin effector polypeptide comprises a disruption in terms of existence, position, or functional group of one or both of the consensus amino acid residues P1 and P4, such as, e.g., the amino acid residues in positions 1 and 4 of the minimal furin-cleavage motif R/Y-x-x-R (SEQ ID NO: 180). For example, mutating one or both of the two arginine residues in the minimal, furin consensus site R-x-x-R (SEQ ID NO: 183) to alanine will disrupt a furin-cleavage motif and prevent furin-cleavage at that site. Similarly, amino acid residue substitutions of one or both of the arginine residues in the minimal furin-cleavage motif R-x-x-R (SEQ ID NO: 183) to any non-conservative amino acid residue known to the skilled worker will reduced the furin-cleavage sensitivity of the motif. In particular, amino acid residue substitutions of arginine to any non-basic amino acid residue which lacks a positive charge, such as, e.g., A, G, P, S, T, D, E, Q, N, C, I, L, M, V, F, W, and Y, will result in a disrupted furin-cleavage motif.

In some embodiments, the disrupted furin-cleavage motif of a Shiga toxin effector polypeptide comprises a disruption in the spacing between the consensus amino acid residues P4 and P1 in terms of the number of intervening amino acid residues being other than two, and, thus, changing either P4 and/or P1 into a different position and eliminating the P4 and/or P1 designations. For example, deletions within the furin-cleavage motif of the minimal furin-cleavage site or the core, furin-cleavage motif will reduce the furin-cleavage sensitivity of the furin-cleavage motif.

In some embodiments, the disrupted furin-cleavage motif comprises one or more amino acid residue substitutions, as compared to a wild-type, Shiga toxin A Subunit. In some embodiments, the disrupted furin-cleavage motif comprises one or more amino acid residue substitutions within the minimal furin-cleavage site R/Y-x-x-R (SEQ ID NO: 180), such as, e.g., for StxA and SLT-1A derived Shiga toxin effector polypeptides, the natively positioned amino acid residue 8248 substituted with any non-positively charged, amino acid residue and/or R251 substituted with any non-positively charged, amino acid residue; and for SLT-2A derived Shiga toxin effector polypeptides, the natively positioned amino acid residue Y247 substituted with any non-positively charged, amino acid residue and/or R250 substituted with any non-positively charged, amino acid residue.

In some embodiments, the disrupted furin-cleavage motif comprises an un-disrupted, minimal furin-cleavage site R/Y-x-x-R (SEQ ID NO: 180) but instead comprises a disrupted flanking region, such as, e.g., amino acid residue substitutions in one or more amino acid residues in the furin-cleavage motif flanking regions natively position at, e.g., 241-247 and/or 252-259. In some embodiments, the disrupted furin cleavage motif comprises a substitution of one or more of the amino acid residues located in the P1-P6 region of the furin-cleavage motif; mutating P1' to a bulky amino acid, such as, e.g., R, W, Y, F, and H; and mutating P2' to a polar and hydrophilic amino acid residue; and substituting one or more of the amino acid residues located in the P1'-P6' region of the furin-cleavage motif with one or more bulky and hydrophobic amino acid residues In some embodiments, the disruption of the furin-cleavage motif comprises a deletion, insertion, inversion, and/or mutation of at least one amino acid residue within the furin-cleavage motif. In some embodiments, a protease-cleavage resistant, Shiga toxin effector polypeptide comprises a disruption of the amino acid sequence natively positioned at amino acids 249-251 of the A Subunit of Shiga-like toxin 1 (SEQ ID NO:1) or Shiga toxin (SEQ ID NO:2), or at amino acids 247-250 of the A Subunit of Shiga-like toxin 2 (SEQ ID NO:3) or the equivalent position in a conserved Shiga toxin effector polypeptide and/or non-native Shiga toxin effector polypeptide sequence. In some embodiments, protease-cleavage resistant, Shiga toxin effector polypeptides comprise a disruption which comprises a deletion of at least one amino acid within the furin-cleavage motif. In some embodiments, protease-cleavage resistant, Shiga toxin effector polypeptides comprise a disruption which comprises an insertion of at least one amino acid within the protease-cleavage motif region. In some embodiments, the protease-cleavage resistant, Shiga toxin effector polypeptides comprise a disruption which comprises an inversion of amino acids, wherein at least one inverted amino acid is within the protease motif region. In some embodiments, the protease-cleavage resistant, Shiga toxin effector polypeptides comprise a disruption which comprises a mutation, such as an amino acid substitution to a non-standard amino acid or an amino acid with a chemically modified side chain.

In some embodiments of the CD38-binding fusion proteins of the invention, the disrupted furin-cleavage motif comprises the deletion of nine, ten, eleven, or more of the carboxy-terminal amino acid residues within the furin-cleavage motif. In these embodiments, the disrupted furin-cleavage motif will not comprise a furin-cleavage site or a minimal furin-cleavage motif. In other words, some embodiments lack a furin-cleavage site at the carboxy-terminus of the A1 fragment region.

In some embodiments, the disrupted furin-cleavage motif comprises both an amino acid residue deletion and an amino acid residue substitution as compared to a wild-type, Shiga toxin A Subunit. In some embodiments, the disrupted furin-cleavage motif comprises one or more amino acid residue deletions and substitutions within the minimal furin-cleavage site R/Y-x-x-R (SEQ ID NO: 180), such as, e.g., for StxA and SLT-1A derived Shiga toxin effector polypeptides, the natively positioned amino acid residue R248 substituted with any non-positively charged, amino acid residue and/or R251 substituted with any non-positively charged, amino acid residue; and for SLT-2A derived Shiga toxin effector polypeptides, the natively positioned amino acid residue Y247 substituted with any non-positively charged, amino acid residue and/or R250 substituted with any non-positively charged, amino acid residue.

In some embodiments, the disrupted furin-cleavage motif comprises an amino acid residue deletion and an amino acid residue substitution as well as a carboxy-terminal truncation as compared to a wild-type, Shiga toxin A Subunit. In some embodiments, the disrupted Turin-cleavage motif comprises one or more amino acid residue deletions and substitutions within the minimal Turin-cleavage site R/Y-x-x-R (SEQ ID NO: 180), such as, e.g., for StxA and SLT-1A derived Shiga toxin effector polypeptides, the natively positioned amino acid residue R248 substituted with any non-positively charged, amino acid residue and/or R251 substituted with any non-positively charged, amino acid residue; and for SLT-2A derived Shiga toxin effector polypeptides, the natively positioned amino acid residue Y247 substituted with any non-positively charged, amino acid residue and/or R250 substituted with any non-positively charged, amino acid residue.

In some embodiments, the disrupted furin-cleavage motif comprises both an amino acid substitution within the minimal Turin-cleavage site R/Y-x-x-R (SEQ ID NO: 180) and a carboxy-terminal truncation as compared to a wild-type, Shiga toxin A Subunit, such as, e.g., for StxA and SLT-1A derived Shiga toxin effector polypeptides, truncations ending at the natively amino acid position 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, or greater and comprising the natively positioned amino acid residue R248 and/or R251 substituted with any non-positively charged, amino acid residue where appropriate; and for SLT-2A derived Shiga toxin effector polypeptides, truncations ending at the natively amino acid position 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, or greater and comprising the natively positioned amino acid residue Y247 and/or R250 substituted with any non-positively charged, amino acid residue where appropriate.

In some embodiments, the disrupted furin-cleavage motif comprises an insertion of one or more amino acid residues as compared to a wild-type, Shiga toxin A Subunit as long as the inserted amino residue(s) does not create a de novo furin-cleavage site. In some embodiments, the insertion of one or more amino acid residues disrupts the natural spacing between the arginine residues in the minimal, furin-cleavage site R/Y-x-x-R (SEQ ID NO: 180), such as, e.g., StxA and SLT-1A derived polypeptides comprising an insertion of one or more amino acid residues at 249 or 250 and thus between R248 and 8251; or SLT-2A derived polypeptides comprising an insertion of one or more amino acid residues at 248 or 249 and thus between Y247 and R250.

In some embodiments, the disrupted furin-cleavage motif comprises both an amino acid residue insertion and a carboxy-terminal truncation as compared to a wild-type, Shiga toxin A Subunit. In some embodiments, the disrupted furin-cleavage motif comprises both an amino acid residue insertion and an amino acid residue substitution as compared to a wild-type, Shiga toxin A Subunit. In some embodiments, the disrupted furin-cleavage motif comprises both an amino acid residue insertion and an amino acid residue deletion as compared to a wild-type, Shiga toxin A Subunit.

In some embodiments, the disrupted furin-cleavage motif comprises an amino acid residue deletion, an amino acid residue insertion, and an amino acid residue substitution as compared to a wild-type, Shiga toxin A Subunit.

In some embodiments, the disrupted furin-cleavage motif comprises an amino acid residue deletion, insertion, substitution, and carboxy-terminal truncation as compared to a wild-type, Shiga toxin A Subunit.

In some embodiments, the Shiga toxin effector polypeptide comprising a disrupted furin-cleavage motif is directly fused by a peptide bond to a molecular moiety comprising an amino acid, peptide, and/or polypeptide wherein the fused structure involves a single, continuous polypeptide. In these fusion embodiments, the amino acid sequence following the disrupted furin-cleavage motif should not create a de novo, furin-cleavage site at the fusion junction.

Any of the above protease-cleavage resistant, Shiga toxin effector polypeptide sub-regions and/or disrupted furin-cleavage motifs may be used alone or in combination with each individual embodiment of the present invention, including methods of the present invention.

In some embodiments, the Shiga toxin effector polypeptide may comprise a disrupted, furin cleavage motif and/or furin cleavage site at the carboxy-terminus of a Shiga toxin A1 fragment derived region. In some embodiments, the Shiga toxin effector polypeptide does not comprise any known compensatory structure which may provide furin cleavage proximal to the carboxy-terminus of the Shiga toxin A1 fragment derived region. Non-limiting examples of disrupted furin cleavage motifs and furin cleave sites suitable for use in the present invention are described in WO 2015/191764.

Certain furin-cleavage motif disruptions are indicated herein by reference to specific amino acid positions of native Shiga toxin A Subunits provided in the Sequence Listing, noting that naturally occurring Shiga toxin A Subunits includes precursor forms containing signal sequences of about 22 amino acids at their amino-terminals which are removed to produce mature Shiga toxin A Subunits and are recognizable to the skilled worker. Further, certain furin-cleavage motif disruptions comprising mutations are indicated herein by reference to specific amino acids (e.g. R for an arginine residue) natively present at specific positions within native Shiga toxin A Subunits (e.g. R251 for the arginine residue at position 251 from the amino-terminus) followed by the amino acid with which that residue has been substituted in the particular mutation under discussion (e.g. R251A represents the amino acid substitution of alanine for arginine at amino acid residue 251 from the amino-terminus).

In some embodiments, the Shiga toxin effector polypeptide comprises a disrupted furin-cleavage motif at the carboxy-terminus of a Shiga toxin A1 fragment derived region, and such embodiments are referred to herein as "furin-cleavage resistant" or "protease-cleavage resistant," Shiga toxin effector polypeptides to describe their property(ies) relative to wild-type, Shiga toxin A Subunits and/or wild-type, Shiga toxin A1 fragment fusion proteins.

In some embodiments, the protease-cleavage resistant, Shiga toxin effector polypeptide consists essentially of a truncated Shiga toxin A Subunit having two or more mutations.

In some embodiments, the protease-cleavage resistant, Shiga toxin effector polypeptide comprises the disrupted furin-cleavage motif comprising the amino acid residue substitution (relative to a wild-type Shiga toxin polypeptide) of one or both of the arginine residues in the minimal, furin-cleavage site consensus motif with A, G, or H. In some embodiments, the protease-cleavage resistant, Shiga toxin effector polypeptide comprises a disruption which comprises an amino acid substitution within a furin-cleavage motif region, where in the substitution occurs at the natively positioned amino acid selected from the group consisting of: amino acid 247 of SEQ ID NO:3, amino acid 248 of SEQ ID NO:1 or SEQ ID NO:2, amino acid 250 of SEQ ID NO:3, amino acid 251 of SEQ ID NO:1 or SEQ ID NO:2, or the equivalent position in a conserved Shiga toxin effector polypeptide and/or non-native Shiga toxin effector polypeptide sequence. In some embodiments, the substitution is to any non-conservative amino acid and the substitution occurs at the natively positioned amino acid residue position. In some embodiments, the mutation comprises an amino acid substitution selected from the group consisting of: R247A, R248A, R250A R251A, or the equivalent position in a conserved Shiga toxin effector polypeptide and/or non-native Shiga toxin effector polypeptide sequence.

In some embodiments, the protease-cleavage resistant Shiga toxin effector polypeptide comprises the disrupted furin-cleavage motif comprising the mutation which is a deletion. In some embodiments, the disrupted furin-cleavage motif comprises a mutation which is a deletion of the region natively positioned at 247-252 in StxA (SEQ ID NO:2) and SLT-1A (SEQ ID NO:3), or the region natively positioned at 246-251 in SLT-2A (SEQ ID NO:3); a deletion of the region natively positioned at 244-246 in StxA (SEQ ID NO:2) and SLT-1A (SEQ ID NO:3), or the region natively positioned at 243-245 in SLT-2A (SEQ ID NO:3); or a deletion of the region natively positioned at 253-259 in StxA (SEQ ID NO:2) and SLT-1A (SEQ ID NO:3), or the region natively positioned at 252-258 in SLT-2A (SEQ ID NO:3).

In some embodiments, the protease-cleavage resistant Shiga toxin effector polypeptide comprises the disrupted furin-cleavage motif comprising the mutation which is a carboxy-terminal truncation as compared to a wild-type Shiga toxin A Subunit, the truncation which results in the deletion of one or more amino acid residues within the furin-cleavage motif. In some embodiments, the disrupted furin-cleavage motif comprises the carboxy-terminal truncation which deletes one or more amino acid residues within the minimal cleavage site Y/R-x-x-R (SEQ ID NO: 180), such as, e.g., for StxA and SLT-1A derived Shiga toxin effector polypeptides, truncations ending at the natively amino acid residue position 250, 249, 248, 247, 246, 245, 244, 243, 242, 241, 240, or less; and for SLT-2A derived Shiga toxin effector polypeptides, truncations ending at the natively amino acid residue position 249, 248, 247, 246, 245, 244, 243, 242, 241, or less. Some embodiments comprise the disrupted furin-cleavage motif comprising a combination of any of the aforementioned mutations, where possible.

In some embodiments, the disrupted furin-cleavage motif comprises the mutation(s) that is a partial, carboxy-terminal truncation of the furin-cleavage motif; however, some CD38-binding fusion proteins of the invention do not comprise the disrupted furin-cleavage motif which is a complete, carboxy-terminal truncation of the entire 20 amino acid residue, furin-cleavage motif. For example, some Shiga toxin effector polypeptides comprise the disrupted furin-cleavage motif comprising a partial, carboxy-terminal truncation of the Shiga toxin A1 fragment region up to native position 240 in StxA (SEQ ID NO:2) or SLT-1A (SEQ ID NO:1) but not a carboxy-terminal truncation at position 239 or less. Similarly, certain Shiga toxin effector polypeptides comprise the disrupted furin-cleavage motif comprising a partial, carboxy-terminal truncation of the Shiga toxin A1 fragment region up to native position 239 in SLT-2A (SEQ ID NO:3) but not a carboxy-terminal truncation at position 238 or less. In the largest carboxy-terminal truncation of the furin-cleavage resistant, Shiga toxin effector polypeptide, mutations comprising the disrupted furin-cleavage motif, positions P14 and P13 of the furin-cleavage motif are still present.

In some other embodiments, the disrupted furin-cleavage motif comprises the mutation(s) that is a complete or partial, carboxy-terminal truncation of the furin-cleavage motif. For example, certain Shiga toxin effector polypeptides comprise the disrupted furin-cleavage motif comprising a complete carboxy-terminal truncation of the Shiga toxin A1 fragment region up to native position 236 in StxA (SEQ ID NO:2) or SLT-1A (SEQ ID NO:1) or 235 in SLT-2A (SEQ ID NO:3).

For example, certain reduced cytotoxicitiy Shiga toxin effector polypeptides comprise the disrupted furin-cleavage motif comprising a complete carboxy-terminal truncation of the Shiga toxin A1 fragment region beyond native position 240 in StxA (SEQ ID NO:2) or SLT-1A (SEQ ID NO:1) or 239 in SLT-2A (SEQ ID NO:3). Reduced cytotoxicity Shiga toxin effector polypeptides are useful for delivering exogenous materials into cells and/or specific subcellular compartments.

In some embodiments, the disrupted furin-cleavage motif comprises both an amino acid residue substitution within the minimal furin-cleavage site R/Y-x-x-R (SEQ ID NO: 180) and a carboxy-terminal truncation as compared to a wild-type, Shiga toxin A Subunit, such as, e.g., for StxA and SLT-1A derived Shiga toxin effector polypeptides, truncations ending at the natively amino acid residue position 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, or greater and comprising the natively positioned amino acid residue R248 and/or R251 substituted with any non-positively charged, amino acid residue where appropriate; and for SLT-2A derived Shiga toxin effector polypeptides, truncations ending at the natively amino acid residue position 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, or greater and comprising the natively positioned amino acid residue Y247 and/or R250 substituted with any non-positively charged, amino acid residue where appropriate. In some embodiments, the truncated Shiga toxin effector polypeptide comprising a disrupted Turin-cleavage motif also comprises the Turin-cleavage motif, amino acid residues at positions P9, P8, and/or P7 in order to maintain optimal cytotoxicity.

In some embodiments, the disrupted furin-cleavage motif comprises a mutation(s) which is one or more internal, amino acid residue deletions, as compared to a wild-type, Shiga toxin A Subunit. In some embodiments, the disrupted furin-cleavage motif comprises a mutation(s) which has one or more amino acid residue deletions within the minimal furin-cleavage site R/Y-x-x-R (SEQ ID NO: 180). For example, StxA and SLT-1A derived Shiga toxin effector polypeptides comprising internal deletions of the natively positioned amino acid residues R248 and/or R251, which may be combined with deletions of surrounding residues such as, e.g., 249, 250, 247, 252, etc.; and SLT-2A derived Shiga toxin effector polypeptides comprising internal deletions of the natively positioned amino acid residues Y247 and/or R250, which may be combined with deletions of surrounding residues such as, e.g., 248, 249, 246, 251, etc. In some embodiments, the disrupted furin-cleavage motif comprises a mutation which is a deletion of four, consecutive, amino acid residues which deletes the minimal furin-cleavage site R/Y-x-x-R (SEQ ID NO: 180), such as, e.g., StxA and SLT-1A derived Shiga toxin effector polypeptides lacking R248-R251 and SLT-2A derived Shiga toxin effector polypeptides lacking Y247-R250. In some embodiments, the disrupted furin-cleavage motif comprises a mutation(s) having one or more amino acid residue deletions in the amino acid residues flanking the core furin-cleavage motif, such as, e.g., a deletion of amino acids 244-247 and/or amino acids 252-255 in SLT-1A or StxA. In some embodiments, the disrupted furin-cleavage motif comprises a mutation which is an internal deletion of the entire surface-exposed, protease-cleavage sensitive loop as compared to a wild-type, Shiga toxin A Subunit, such as, e.g., for StxA and SLT-1A derived Shiga toxin effector polypeptides, a deletion of natively positioned amino acid residues 241-262; and for SLT-2A derived Shiga toxin effector polypeptides, a deletion of natively positioned amino acid residues 240-261.

In some embodiments, the disrupted furin-cleavage motif comprises both a mutation which is an internal, amino acid residue deletion within the furin-cleavage motif and a mutation which is carboxy-terminal truncation as compared to a wild-type, Shiga toxin A Subunit. In some embodiments, the disrupted furin-cleavage motif comprises both a mutation which is an amino acid residue deletion within the minimal furin-cleavage site R/Y-x-x-R (SEQ ID NO: 180) and a mutation which is a carboxy-terminal truncation as compared to a wild-type, Shiga toxin A Subunit. For example, protease-cleavage resistant, Shiga toxin effector polypeptides may comprise a disrupted furin-cleavage motif comprising mutation(s) which are deletions of the natively positioned amino acid residues 248-249 and/or 250-251 in a truncated StxA or SLT-1A polypeptide which still has amino acid residue 247 and/or 252, or the amino acid residues 247-248 and/or 249-250 in a truncated SLT-2A which still has amino acid residue 246 and/or 251. In some embodiments, the disrupted furin-cleavage motif comprises a mutation having a deletion of four, consecutive, amino acid residues which deletes the minimal furin-cleavage site R/Y-x-x-R (SEQ ID NO: 180) and a carboxy-terminal truncation as compared to a wild-type, Shiga toxin A Subunit, such as, e.g., for StxA and SLT-1A derived Shiga toxin effector polypeptides, truncations ending at the natively amino acid residue position 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, or greater and lacking R248-R251; and for SLT-2A derived Shiga toxin effector polypeptides, truncations ending at the natively amino acid residue position 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, or greater and lacking Y247-R250.

In some embodiments, the disrupted furin-cleavage motif comprises one or more mutations, relative to a wild-type Shiga toxin A Subunit, the one or more mutations altering at least one amino acid residue in a region natively positioned at amino acids 248-251 of the A Subunit of Shiga toxin (SEQ ID NOs: 1-2 and 4-6), or at amino acids 247-250 of the A Subunit of Shiga-like toxin 2 (SEQ ID NOs: 3 and 7-18), or the equivalent region in a Shiga toxin A Subunit or derivative thereof. In some embodiments, the disrupted furin-cleavage motif comprises one or more mutations, relative to a wild-type Shiga toxin A Subunit, in a minimal furin cleavage site of the furin-cleavage motif. In some embodiments, the minimal furin cleavage site is represented by the consensus amino acid sequence R/Y-x-x-R (SEQ ID NO: 180) and/or R-x-x-R (SEQ ID NO: 183).

(iii) Shiga Toxin Component with Carboxy-Terminal Endoplasmic Reticulum Retention/Retrieval Signal Motif In some embodiments, the Shiga toxin effector polypeptide comprises a carboxy-terminal endoplasmic reticulum retention/retrieval signal motif of a member of the KDEL family, such as recited in paragraph [52] of WO2018/140427, and paragraphs [28], [107] to [113] of WO2015/138435, all of which are expressly incorporated by reference.

(iv) De-Immunized, Shiga Toxin A Subunit Effector Polypeptides

In some embodiments, the Shiga toxin effector polypeptide of the binding protein is de-immunized, such as, e.g., as compared to a wild-type Shiga toxin, wild-type Shiga toxin polypeptide, and/or Shiga toxin effector polypeptide comprising only wild-type polypeptide sequences. A Shiga toxin effector polypeptide and/or Shiga toxin A Subunit polypeptide, whether naturally occurring or not, can be de-immunized by a method described herein, described in WO 2015/113005, WO 2015/113007, WO 2016/196344, and WO 2018/140427, and/or known to the skilled worker, wherein the resulting molecule retains one or more Shiga toxin A Subunit functions. The de-immunized, Shiga toxin effector polypeptide may comprise a disruption of at least one, putative, endogenous, epitope region in order to reduce the antigenic and/or immunogenic potential of the Shiga toxin effector polypeptide after administration of the polypeptide to a subject, such as a human subject.

In some embodiments, the Shiga toxin effector polypeptide comprises a disruption of an endogenous epitope or epitope region, such as, e.g., a B-cell and/or CD4+ T-cell epitope. In some embodiments, the Shiga toxin effector polypeptide comprises a disruption of at least one, endogenous, epitope region described herein, wherein the disruption reduces the antigenic and/or immunogenic potential of the Shiga toxin effector polypeptide after administration of the polypeptide to a subject, and wherein the Shiga toxin effector polypeptide is capable of exhibiting one or more Shiga toxin A Subunit functions, such as, e.g., a significant level of Shiga toxin cytotoxicity.

The term "disrupted" or "disruption" as used herein with regard to an epitope region refers to the deletion of at least one amino acid residue in an epitope region, inversion of two or more amino acid residues where at least one of the inverted amino acid residues is in an epitope region, insertion of at least one amino acid into an epitope region, and a substitution of at least one amino acid residue in an epitope region. An epitope region disruption by mutation includes amino acid substitutions with non-standard amino acids and/or non-natural amino acids. Epitope regions may alternatively be disrupted by mutations comprising the modification of an amino acid by the addition of a covalently-linked chemical structure which masks at least one amino acid in an epitope region, see, e.g. PEGylation (see Zhang C et al., *BioDrugs* 26: 209-15 (2012), small molecule adjuvants (Flower D, *Expert Opin Drug Discov* 7: 807-17 (2012), and site-specific albumination (Lim S et al., *J Control Release* 207-93 (2015)).

Some epitope regions and disruptions are indicated herein by reference to specific amino acid positions of native Shiga toxin A Subunits provided in the Sequence Listing, noting that naturally occurring Shiga toxin A Subunits may comprise precursor forms containing signal sequences of about 22 amino acids at their amino-terminals which are removed to produce mature Shiga toxin A Subunits and are recognizable to the skilled worker. Further, some epitope region disruptions are indicated herein by reference to specific amino acids (e.g. S for a serine residue) natively present at specific positions within native Shiga toxin A Subunits (e.g. S33 for the serine residue at position 33 from the amino-terminus) followed by the amino acid with which that residue has been substituted in the particular mutation under discussion (e.g. S33I represents the amino acid substitution of isoleucine for serine at amino acid residue 33 from the amino-terminus).

In some embodiments, the de-immunized, Shiga toxin effector polypeptide comprises a disruption of at least one epitope region provided herein. In some embodiments, the de-immunized, Shiga toxin effector polypeptide comprises a disruption of at least one epitope region described in WO 2015/113005 or WO 2015/113007.

In some embodiments, the de-immunized, Shiga toxin effector polypeptide comprises a full-length Shiga toxin A Subunit (e.g. SLT-1A (SEQ ID NO:1), StxA (SEQ ID NO:2), or SLT-2A (SEQ ID NO:3)) comprising at least one disruption of the amino acid sequence selected from the group of natively positioned amino acids consisting of: amino acids 1-15 of SEQ ID NO:1 or SEQ ID NO:2; amino acids 3-14 of SEQ ID NO:3; amino acids 26-37 of SEQ ID NO:3; amino acids 27-37 of SEQ ID NO:1 or SEQ ID NO:2; amino acids 39-48 of SEQ ID NO:1 or SEQ ID NO:2; amino acids 42-48 of SEQ ID NO:3; amino acids 53-66 of SEQ ID NO:1, SEQ ID NO:2, or SEQ ID NO:3; amino acids 94-115 of SEQ ID NO:1, SEQ ID NO:2, or SEQ ID NO:3; amino acids 141-153 of SEQ ID NO:1 or SEQ ID NO:2; amino acids 140-156 of SEQ ID NO:3; amino acids 179-190 of SEQ ID NO:1 or SEQ ID NO:2; amino acids 179-191 of SEQ ID NO:3; amino acid 204 of SEQ ID NO:3; amino acid 205 of SEQ ID NO:1 or SEQ ID NO:2; amino acids 210-218 of SEQ ID NO:3; amino acids 240-258 of SEQ ID NO:3; amino acids 243-257 of SEQ ID NO:1 or SEQ ID NO:2; amino acids 254-268 of SEQ ID NO:1 or SEQ ID NO:2; amino acids 262-278 of SEQ ID NO:3; amino acids 281-297 of SEQ ID NO:3; and amino acids 285-293 of SEQ ID NO:1 or SEQ ID NO:2, or the equivalent position in a Shiga toxin A Subunit polypeptide, conserved Shiga toxin effector polypeptide sub-region, and/or non-native, Shiga toxin effector polypeptide sequence.

In some embodiments, the Shiga toxin effector polypeptide comprises a truncated Shiga toxin A Subunit. Truncations of Shiga toxin A Subunits might result in the deletion of an entire epitope region(s) without affecting Shiga toxin effector function(s). The smallest Shiga toxin A Subunit fragment shown to exhibit significant enzymatic activity was a polypeptide composed of residues 75-247 of StxA (Al-Jaufy A et al., Infect Immun 62: 956-60 (1994)). Truncating the carboxy-terminus of SLT-1A, StxA, or SLT-2A to amino acids 1-251 removes two predicted B-cell epitope regions, two predicted CD4 positive (CD4+) T-cell epitopes, and a predicted, discontinuous, B-cell epitope. Truncating the amino-terminus of SLT-1A, StxA, or SLT-2A to 75-293 removes at least three, predicted, B-cell epitope regions and three predicted CD4+ T-cell epitopes. Truncating both amino- and carboxy-terminals of SLT-1A, StxA, or SLT-2A to 75-251 deletes at least five, predicted, B-cell epitope regions; four, putative, CD4+ T-cell epitopes; and one, predicted, discontinuous, B-cell epitope.

In some embodiments, a Shiga toxin effector polypeptide of the invention comprises a full-length or truncated Shiga toxin A Subunit with at least one mutation, e.g. deletion, insertion, inversion, or substitution, in a B- or T-cell epitope region. In some embodiments, the polypeptides comprise a disruption which comprises a deletion of at least one amino acid within the epitope region. In some embodiments, the polypeptides comprise a disruption which comprises an insertion of at least one amino acid within the epitope region. In some embodiments, the polypeptides comprise a disruption which comprises an inversion of amino acids, wherein at least one inverted amino acid is within the epitope region. In some embodiments, the polypeptides comprise a disruption which comprises a mutation, such as an amino acid substitution to a non-standard amino acid or an amino acid with a chemically modified side chain.

In some embodiments, the Shiga toxin effector polypeptides of the invention comprise or consist essentially of a full-length or truncated Shiga toxin A Subunit with one or more mutations as compared to the native sequence which comprises at least one amino acid substitution selected from the group consisting of: A, G, V, L, I, P, C, M, F, S, D, N, Q, H, and K. In some embodiments, the polypeptide comprises a full-length or truncated Shiga toxin A Subunit with a single mutation as compared to the native sequence wherein the substitution is selected from: D to A, D to G, D to V, D to L, D to I, D to F, D to S, D to Q, E to A, E to G, E to V, E to L, E to I, E to F, E to S, E to Q, E to N, E to D, E to M, E to R, G to A, H to A, H to G, H to V, H to L, H to I, H to F, H to M, K to A, K to G, K to V, K to L, K to I, K to M, K to H, L to A, L to G, N to A, N to G, N to V, N to L, N to I, N to F, P to A, P to G, P to F, R to A, R to G, R to V, R to L, R to I, R to F, R to M, R to Q, R to S, R to K, R to H, S to A, S to G, S to V, S to L, S to I, S to F, S to M, T to A, T to G, T to V, T to L, T to I, T to F, T to M, T to S, Y to A, Y to G, Y to V, Y to L, Y to I, Y to F, and Y to M.

In some embodiments, the Shiga toxin effector polypeptides of the invention comprise or consist essentially of a full-length or truncated Shiga toxin A Subunit with one or more mutations as compared to the native amino acid residue sequence which comprises at least one amino acid substitution of an immunogenic residue and/or within an epitope region, wherein at least one substitution occurs at the natively positioned group of amino acids selected from: 1 of SEQ ID NO:1 or SEQ ID NO:2; 4 of SEQ ID NO:1, SEQ ID NO:2, or SEQ ID NO:3; 8 of SEQ ID NO:1, SEQ ID NO:2, or SEQ ID NO:3; 9 of SEQ ID NO:1, SEQ ID NO:2, or SEQ ID NO:3; 11 of SEQ ID NO:1, SEQ ID NO:2, or SEQ ID NO:3; 33 of SEQ ID NO:1 or SEQ ID NO:2; 43 of SEQ ID NO:1 or SEQ ID NO:2; 44 of SEQ ID NO:1 or SEQ ID NO:2; 45 of SEQ ID NO:1 or SEQ ID NO:2; 46 of SEQ ID NO:1 or SEQ ID NO:2; 47 of SEQ ID NO:1 or SEQ ID NO:2; 48 of SEQ ID NO:1, SEQ ID NO:2, or SEQ ID NO:3; 49 of SEQ ID NO:1 or SEQ ID NO:2; 50 of SEQ ID NO:1 or SEQ ID NO:2; 51 of SEQ ID NO:1 or SEQ ID NO:2; 53 of SEQ ID NO:1 or SEQ ID NO:2; 54 of SEQ ID NO:1 or SEQ ID NO:2; 55 of SEQ ID NO:1 or SEQ ID NO:2; 56 of SEQ ID NO:1 or SEQ ID NO:2; 57 of SEQ ID NO:1 or SEQ ID NO:2; 58 of SEQ ID NO:1, SEQ ID NO:2, or SEQ ID NO:3; 59 of SEQ ID NO:1, SEQ ID NO:2, or SEQ ID NO:3; 60 of SEQ ID NO:1 or SEQ ID NO:2; 61 of SEQ ID NO:1 or SEQ ID NO:2; 62 of SEQ ID NO:1 or SEQ ID NO:2; 84 of SEQ ID NO:1 or SEQ ID NO:2; 88 of SEQ ID NO:1 or SEQ ID NO:2; 94 of SEQ ID NO:1, SEQ ID NO:2, or SEQ ID NO:3; 96 of SEQ ID NO:1, SEQ ID NO:2, or SEQ ID NO:3; 104 of SEQ ID NO:1 or SEQ ID NO:2; 105 of SEQ ID NO:1 or SEQ ID NO:2; 107 of SEQ ID NO:1 or SEQ ID NO:2; 108 of SEQ ID NO:1 or SEQ ID NO:2; 109 of SEQ ID NO:1, SEQ ID NO:2, or SEQ ID NO:3; 110 of SEQ ID NO:1 or SEQ ID NO:2; 111 of SEQ ID NO:1 or SEQ ID NO:2; 112 of SEQ ID NO:1, SEQ ID NO:2, or SEQ ID NO:3; 141 of SEQ ID NO:1 or SEQ ID NO:2; 147 of SEQ ID NO:1, SEQ ID NO:2, or SEQ ID NO:3; 154 of SEQ ID NO:1 or SEQ ID NO:2; 179 of SEQ ID NO:1, SEQ ID NO:2, or SEQ ID NO:3; 180 of SEQ ID NO:1 or SEQ ID NO:2; 181 of SEQ ID NO:1 or SEQ ID NO:2; 183 of SEQ ID NO:1, SEQ ID NO:2, or SEQ ID NO:3; 184 of SEQ ID NO:1, SEQ ID NO:2, or SEQ ID NO:3; 185 of SEQ ID NO:1 or SEQ ID NO:2; 186 of SEQ ID NO:1, SEQ ID NO:2, or SEQ ID NO:3; 187 of SEQ ID NO:1 or SEQ ID NO:2; 188 of SEQ ID NO:1 or SEQ ID NO:2; 189 of SEQ ID NO:1 or SEQ ID NO:2; 198 of SEQ ID NO:1 or SEQ ID NO:2; 204 of SEQ ID NO:3; 205 of SEQ ID NO:1 or SEQ ID NO:2; 241 of SEQ ID NO:3; 242 of SEQ ID NO:1 or SEQ ID NO:2; 247 of SEQ ID NO:1 or SEQ ID NO:2; 247 of SEQ ID NO:3; 248 of SEQ ID NO:1 or SEQ ID NO:2; 250 of SEQ ID NO:3; 251 of SEQ ID NO:1 or SEQ ID NO:2; 264 of SEQ ID NO:1, SEQ ID NO:2, or SEQ ID NO:3; 265 of SEQ ID NO:1 or SEQ ID NO:2; and 286 of SEQ ID NO:1 or SEQ ID NO:2.

In some embodiments, the Shiga toxin effector polypeptides of the invention comprise or consist essentially of a full-length or truncated Shiga toxin A Subunit with at least one substitution of an immunogenic residue and/or within an epitope region, wherein at least one amino acid substitution is to a non-conservative amino acid (see, e.g., Table 3, infra) relative to a natively occurring amino acid positioned at one of the following native positions: 1 of SEQ ID NO:1 or SEQ ID NO:2; 4 of SEQ ID NO:1, SEQ ID NO:2, or SEQ ID NO:3; 8 of SEQ ID NO:1, SEQ ID NO:2, or SEQ ID NO:3; 9 of SEQ ID NO:1, SEQ ID NO:2, or SEQ ID NO:3; 11 of SEQ ID NO:1, SEQ ID NO:2, or SEQ ID NO:3; 33 of SEQ ID NO:1 or SEQ ID NO:2; 43 of SEQ ID NO:1 or SEQ ID NO:2; 44 of SEQ ID NO:1 or SEQ ID NO:2; 45 of SEQ ID NO:1 or SEQ ID NO:2; 46 of SEQ ID NO:1 or SEQ ID NO:2; 47 of SEQ ID NO:1 or SEQ ID NO:2; 48 of SEQ ID NO:1, SEQ ID NO:2, or SEQ ID NO:3; 49 of SEQ ID NO:1 or SEQ ID NO:2; 50 of SEQ ID NO:1 or SEQ ID NO:2; 51 of SEQ ID NO:1 or SEQ ID NO:2; 53 of SEQ ID NO:1 or SEQ ID NO:2; 54 of SEQ ID NO:1 or SEQ ID NO:2; 55 of SEQ ID NO:1 or SEQ ID NO:2; 56 of SEQ ID NO:1 or SEQ ID NO:2; 57 of SEQ ID NO:1 or SEQ ID NO:2; 58 of SEQ ID NO:1, SEQ ID NO:2, or SEQ ID NO:3; 59 of SEQ ID NO:1, SEQ ID NO:2, or SEQ ID NO:3; 60 of SEQ ID NO:1 or SEQ ID NO:2; 61 of SEQ ID NO:1 or SEQ ID NO:2; 62 of SEQ ID NO:1 or SEQ ID NO:2; 84 of SEQ ID NO:1 or SEQ ID NO:2; 88 of SEQ ID NO:1 or SEQ ID NO:2; 94 of SEQ ID NO:1, SEQ ID NO:2, or SEQ ID NO:3; 96 of SEQ ID NO:1, SEQ ID NO:2, or SEQ ID NO:3; 104 of SEQ ID NO:1 or SEQ ID NO:2; 105 of SEQ ID NO:1 or SEQ ID NO:2; 107 of SEQ ID NO:1 or SEQ ID NO:2; 108 of SEQ ID NO:1 or SEQ ID NO:2; 109 of SEQ ID NO:1, SEQ ID NO:2, or SEQ ID NO:3; 110 of SEQ ID NO:1 or SEQ ID NO:2; 111 of SEQ ID NO:1 or SEQ ID NO:2; 112 of SEQ ID NO:1, SEQ ID NO:2, or SEQ ID NO:3; 141 of SEQ ID NO:1 or SEQ ID NO:2; 147 of SEQ ID NO:1, SEQ ID NO:2, or SEQ ID NO:3; 154 of SEQ ID NO:1 or SEQ ID NO:2; 179 of SEQ ID NO:1, SEQ ID NO:2, or SEQ ID NO:3; 180 of SEQ ID NO:1 or SEQ ID NO:2; 181 of SEQ ID NO:1 or SEQ ID NO:2; 183 of SEQ ID NO:1, SEQ ID NO:2, or SEQ ID NO:3; 184 of SEQ ID NO:1, SEQ ID NO:2, or SEQ ID NO:3; 185 of SEQ ID NO:1 or SEQ ID NO:2; 186 of SEQ ID NO:1, SEQ ID NO:2, or SEQ ID NO:3; 187 of SEQ ID NO:1 or SEQ ID NO:2; 188 of SEQ ID NO:1 or SEQ ID NO:2; 189 of SEQ ID NO:1 or SEQ ID NO:2; 198 of SEQ ID NO:1 or SEQ ID NO:2; 204 of SEQ ID NO:3; 205 of SEQ ID NO:1 or SEQ ID NO:2; 241 of SEQ ID NO:3; 242 of SEQ ID NO:1 or SEQ ID NO:2; 247 of SEQ ID NO:1 or SEQ ID NO:2; 247 of SEQ ID NO:3; 248 of SEQ ID NO:1 or SEQ ID NO:2; 250 of SEQ ID NO:3; 251 of SEQ ID NO:1 or SEQ ID NO:2; 264 of SEQ ID NO:1, SEQ ID NO:2, or SEQ ID NO:3; 265 of SEQ ID NO:1 or SEQ ID NO:2; and 286 of SEQ ID NO:1 or SEQ ID NO:2.

In some embodiments, the Shiga toxin effector polypeptides of the invention comprise or consist essentially of a full-length or truncated Shiga toxin A Subunit with at least one amino acid substitution selected from: K1 to A, G, V, L, I, F, M or H; T4 to A, G, V, L, I, F, M, or S; D6 to A, G, V, L, I, F, S, Q or R; S8 to A, G, V, I, L, F, or M; T8 to A, G, V, I, L, F, or M; T9 to A, G, V, I, L, F, M, or S; S9 to A, G, V, L, I, F, or M; K11 to A, G, V, L, I, F, M or H; T12 to A, G, V, I, L, F, M, S, or K; S12 to A, G, V, I, L, F, or M; S33 to A, G, V, L, I, F, M, or C; S43 to A, G, V, L, I, F, or M; G44 to A or L; S45 to A, G, V, L, I, F, or M; T45 to A, G, V, L, I, F, or M; G46 to A or P; D47 to A, G, V, L, I, F, S, M, or Q; N48 to A, G, V, L, M or F; L49 to A, V, C, or G; Y49 to A, G, V, L, I, F, M, or T; F50 to A, G, V, L, I, or T; A51 to V; D53 to A, G, V, L, I, F, S, or Q; V54 to A, G, I, or L; R55 to A, G, V, L, I, F, M, Q, S, K, or H; G56 to A or P; I57 to A, G, V, or M; L57 to A, V, C, G, M, or F; D58 to A, G, V, L, I, F, S, or Q; P59 to A, G, or F; E60 to A, G, V, L, I, F, S, Q, N, D, M, T, or R; E61 to A, G, V, L, I, F, S, Q, N, D, M, or R; G62 to A; R84 to A, G, V, L, I, F, M, Q, S, K, or H; V88 to A or G; I88 to A, V, C, or G; D94 to A, G, V, L, I, F, S, or Q; S96 to A, G, V, I, L, F, or M; T104 to A, G, V, L, I, F, M; or N; A105 to L; T107 to A, G, V, L, I, F, M, or P; S107 to A, G, V, L, I, F, M, or P; L108 to A, V, C, or G; S109 to A, G, V, I, L, F, or M; T109 to A, G, V, I, L, F, M, or S; G110 to A; S112 to A, G, V, L, I, F, or M; D111 to A, G, V, L, I, F, S, Q, or T; S112 to A, G, V, L, I, F, or M; D141 to A, G, V, L, I, F, S, or Q; G147 to A; V154 to A or G. R179 to A, G, V, L, I, F, M, Q, S, K, or H; T180 to A, G, V, L, I, F, M, or S; T181 to A, G, V, L, I, F, M, or S; D183 to A, G, V, L, I, F, S, or Q; D184 to A, G, V, L, I, F, S, or Q; L185 to A, G, V or C; S186 to A, G, V, I, L, F, or M; G187 to A; R188 to A, G, V, L, I, F, M, Q, S, K, or H; S189 to A, G, V, I, L, F, and M; D197 to A, G, V, L, I, F, S, or Q; D198 to A, G, V, L, I, F, S, or Q; R204 to A, G, V, L, I, F, M, Q, S, K, or H; R205 to A, G, V, L, I, F, M, Q, S, K or H; C242 to A, G or V; R247 to A, G, V, L, I, F, M, Q, S, K, or H; S247 to A, G, V, I, L, F, or M; Y247 to A, G, V, L, I, F, or M; R248 to A, G, V, L, I, F, M, Q, S, K, or H; R250 to A, G, V, L, I, F, M, Q, S, K, or H; R251 to A, G, V, L, I, F, M, Q, S, K, or H; D264 to A, G, V, L, I, F, S, or Q; G264 to A; and T286 to A, G, V, L, I, F, M, or S.

In some embodiments, the Shiga toxin effector polypeptides of the invention comprise or consist essentially of a full-length or truncated Shiga toxin A Subunit with at least one of the following amino acid substitutions: K1A, K1M, T4I, D6R, S8I, T8V, T9I, S9I, K11A, K11H, T12K, S33I, S33C, S43N, G44L, S45V, S45I, T45V, T45I, G46P, D47M, D47G, N48V, N48F, L49A, F50T, A51V, D53A, D53N, D53G, V54L, V54I, R55A, R55V, R55L, G56P, I57F, I57M, D58A, D58V, D58F, P59A, P59F, E60I, E60T, E60R, E61A, E61V, E61L, G62A, R84A, V88A, D94A, S96I, T104N, A105L, T107P, L108M, S109V, T109V, G110A, D111T, S112V, D141A, G147A, V154A, R179A, T180G, T181I, D183A, D183G, D184A, D184A, D184F, L185V, L185D, S186A, S186F, G187A, G187T, R188A, R188L, S189A, D198A, R204A, R205A, C242S, S247I, Y247A, R248A, R250A, R251A, or D264A, G264A, T286A, and/or T286I. These epitope disrupting substitutions may be combined to form a de-immunized, Shiga toxin effector polypeptide with multiple substitutions per epitope region and/or multiple epitope regions disrupted while still retaining Shiga toxin effector function. For example, substitutions at the natively positioned K1A, K1M, T4I, D6R, S8I, T8V, T9I, S9I, K11A, K11H, T12K, S33I, S33C, S43N, G44L, S45V, S45I, T45V, T45I, G46P, D47M, D47G, N48V, N48F, L49A, F50T, A51V, D53A, D53N, D53G, V54L, V54I, R55A, R55V, R55L, G56P, I57F, I57M, D58A, D58V, D58F, P59A, P59F, E60I, E60T, E60R, E61A, E61V, E61L, G62A, R84A, V88A, D94A, S96I, T104N, A105L, T107P, L108M, S109V, T109V, G110A, D111T, S112V, D141A, G147A, V154A, R179A, T180G, T181I, D183A, D183G, D184A, D184A, D184F, L185V, L185D, S186A, S186F, G187A, G187T, R188A, R188L, S189A, D198A, R204A, R205A, C242S, S247I, Y247A, R248A, R250A, R251A, or D264A, G264A, T286A, and/or T286I to create de-immunized, Shiga toxin effector polypeptides of the invention.

Any of the de-immunized, Shiga toxin effector polypeptide sub-regions and/or epitope disrupting mutations described herein may be used alone or in combination and further in combination with each individual embodiment of the CD38-binding proteins of the present invention, including their uses in methods of the present invention.

In some embodiments, the de-immunized, Shiga toxin effector polypeptide of the CD38-binding protein of the present invention may consist essentially of a truncated Shiga toxin A Subunit having two or more mutations. Truncations of Shiga toxin A Subunits might result in the deletion of an entire epitope(s) and/or epitope region(s), B-cell epitopes, CD4+ T-cell epitopes, and/or furin-cleavage sites without affecting Shiga toxin effector functions, such as, e.g., catalytic activity and cytotoxicity. Truncating the carboxy-terminus of SLT-1A, StxA, or SLT-2A to amino acids 1-251 removes two predicted B-cell epitope regions, two predicted CD4 positive (CD4+) T-cell epitopes, and a predicted discontinuous B-cell epitope. Truncating the amino-terminus of SLT-1A, StxA, or SLT-2A to 75-293 removes at least three predicted B-cell epitope regions and three predicted CD4+ T-cell epitopes. Truncating both amino- and carboxy-terminals of SLT-1A, StxA, or SLT-2A to 75-251 deletes at least five predicted B-cell epitope regions, four putative CD4+ T-cell epitopes and one predicted discontinuous B-cell epitope.

In some embodiments, a de-immunized, Shiga toxin effector polypeptide may comprise or consist essentially of a full-length or truncated Shiga toxin A Subunit with at least one mutation (relative to a wild-type Shiga toxin polypeptide), e.g. deletion, insertion, inversion, or substitution, in a provided, endogenous, B-cell and/or CD4+ T-cell epitope region. In some embodiments, the Shiga toxin effector polypeptide comprises a disruption which comprises a mutation (relative to a wild-type Shiga toxin polypeptide) which includes a deletion of at least one amino acid residue within the endogenous, B-cell and/or CD4+ T-cell epitope region. In some embodiments, the Shiga toxin effector polypeptide comprises a disruption which comprises an insertion of at least one amino acid residue within the endogenous, B-cell and/or CD4+ T-cell epitope region. In some embodiments, the Shiga toxin effector polypeptide comprises a disruption which comprises an inversion of amino acid residues, wherein at least one inverted amino acid residue is within the endogenous, B-cell and/or CD4+ T-cell epitope region. In some embodiments, the Shiga toxin effector polypeptide comprises a disruption which comprises a mutation (relative to a wild-type Shiga toxin polypeptide), such as, e.g., an amino acid substitution, an amino acid substitution to a non-standard amino acid, and/or an amino acid residue with a chemically modified side chain. Non-limiting examples of de-immunized, Shiga toxin effector sub-regions suitable for use as described herein are described in WO 2015/113005, WO 2015/113007, WO 2015/191764, WO 2016/196344, and WO 2018/140427.

In other embodiments, the de-immunized, Shiga toxin effector polypeptide comprises a truncated Shiga toxin A Subunit which is shorter than a full-length Shiga toxin A Subunit wherein at least one amino acid residue is disrupted in a natively positioned, B-cell and/or CD4+ T-cell epitope region.

To create a de-immunized, Shiga toxin effector polypeptide, in principle modifying any amino acid residue in a provided epitope region by various means can result in a disruption of an epitope, such as, e.g., a modification which represents a deletion, insertion, inversion, rearrangement, substitution, and chemical modification of a side chain relative to a wild-type Shiga toxin polypeptide. However, modifying certain amino acid residues and using certain amino acid modifications are more likely to successfully reduce antigenicity and/or immunogenicity while maintaining a certain level of a Shiga toxin effector function(s). For example, terminal truncations and internal amino acid substitutions are preferred because these types of modifications maintain the overall spacing of the amino acid residues in a Shiga toxin effector polypeptide and thus are more likely to maintain Shiga toxin effector polypeptide structure and function.

Among some embodiments of the present invention, the de-immunized, Shiga toxin effector polypeptide comprising or consisting essentially of amino acids 75 to 251 of SLT-1A (SEQ ID NO:1), StxA (SEQ ID NO:2), and/or SLT-2A (SEQ ID NO:3) wherein at least one amino acid residue is disrupted in a natively positioned, epitope region. Among some other embodiments are de-immunized, Shiga toxin effector polypeptides which comprise or consist essentially of amino acids 1 to 241 of SLT-1A (SEQ ID NO:1), StxA (SEQ ID NO:2), and/or SLT-2A (SEQ ID NO:3) wherein at least one amino acid residue is disrupted in a natively positioned, epitope region. Embodiments are de-immunized, Shiga toxin effector polypeptides which comprise or consist essentially of amino acids 1 to 251 of SLT-1A (SEQ ID NO:1), StxA (SEQ ID NO:2), and/or SLT-2A (SEQ ID NO:3) wherein at least one amino acid residue is disrupted in a natively positioned, epitope region provided. Embodiments are Shiga toxin effector polypeptides comprising amino acids 1 to 261 of SLT-1A (SEQ ID NO:1), StxA (SEQ ID NO:2), and/or SLT-2A (SEQ ID NO:3) wherein at least one amino acid residue is disrupted in a natively positioned, epitope region.

There are numerous, diverse, internal amino acid substitutions that can be used to create de-immunized, Shiga toxin effector polypeptides of the invention. Of the possible substitute amino acids to use within an epitope region, the following substitute amino acid residues are predicted to be the most likely to reduce the antigenicity and/or immunogenicity of an epitope—G, D, E, S, T, R, K, and H. Except for glycine, these amino acid residues may all be classified as polar and/or charged residues. Of the possible amino acids to substitute with, the following amino acids A, G, V, L, I, P, C, M, F, S, D, N, Q, H, and K are predicted to be the most likely to reduce antigenicity and/or immunogenicity while providing the retention of a significant level of a Shiga toxin effector function(s), depending on the amino acid substituted for. Generally, the substitution should change a polar and/or charged amino acid residue to a non-polar and uncharged residue (see e.g. WO 2015/113007). In addition, it may be beneficial to epitope disruption to reduce the overall size and/or length of the amino acid residue's R-group functional side chain (see e.g. WO 2015/113007). However despite these generalities of substitutions most likely to confer epitope disruption, because the aim is to preserve significant Shiga toxin effector function(s), the substitute amino acid might be more likely to preserve Shiga toxin effector function(s) if it resembles the amino acid substituted for, such as, e.g., a nonpolar and/or uncharged residue of similar size substituted for a polar and/or charged residue.

In WO 2015/113007, many mutations were empirically tested for effect(s) on the Shiga toxin effector function of various Shiga toxin effector polypeptides and binding proteins. Table 2 summarizes the results described in WO 2015/113007 and WO 2016/196344 where an amino acid substitution, alone or in combination with one or more other substitutions, did not prevent the exhibition of a potent level of a Shiga toxin effector function(s). Table 2 uses the epitope region numbering scheme described in WO 2016/196344.

TABLE 2

Amino Acid Substitutions in Shiga Toxin Effector Polypeptides

| Epitope Region Disrupted | Substitution | natively positioned amino acid positions B-Cell Epitope Region | T-Cell Epitope |
|---|---|---|---|
| 1 | K1A | 1-15 | |
| 1 | K1M | 1-15 | |
| 1 | T4I | 1-15 | 4-33 |
| 1 | D6R | 1-15 | 4-33 |
| 1 | S8I | 1-15 | 4-33 |
| 1 | T9V | 1-15 | 4-33 |
| 1 | T9I | 1-15 | 4-33 |
| 1 | K11A | 1-15 | 4-33 |
| 1 | K11H | 1-15 | 4-33 |
| 1 | T12K | 1-15 | 4-33 |
| 2 | S33I | 27-37 | 4-33 |
| 2 | S33C | 27-37 | 4-33 |
| 3 | S43N | 39-48 | 34-78 |
| 3 | G44L | 39-48 | 34-78 |
| 3 | T45V | 39-48 | 34-78 |
| 3 | T45I | 39-48 | 34-78 |
| 3 | S45V | 39-48 | 34-78 |
| 3 | S45I | 39-48 | 34-78 |
| 3 | G46P | 39-48 | 34-78 |
| 3 | D47G | 39-48 | 34-78 |
| 3 | D47M | 39-48 | 34-78 |
| 3 | N48V | 39-48 | 34-78 |
| 3 | N48F | 39-48 | 34-78 |
| — | L49A | immunogenic residue | 34-78 |
| — | F50T | | 34-78 |
| — | A51V | | 34-78 |
| 4 | D53A | 53-66 | 34-78 |
| 4 | D53G | 53-66 | 34-78 |
| 4 | D53N | 53-66 | 34-78 |
| 4 | V54L | 53-66 | 34-78 |
| 4 | V54I | 53-66 | 34-78 |
| 4 | R55A | 53-66 | 34-78 |
| 4 | R55V | 53-66 | 34-78 |
| 4 | R55L | 53-66 | 34-78 |
| 4 | G56P | 53-66 | 34-78 |
| 4 | I57M | 53-66 | 34-78 |
| 4 | I57F | 53-66 | 34-78 |
| 4 | D58A | 53-66 | 34-78 |
| 4 | D58V | 53-66 | 34-78 |
| 4 | D58F | 53-66 | 34-78 |
| 4 | P59A | 53-66 | 34-78 |
| 4 | P59F | 53-66 | 34-78 |
| 4 | E60I | 53-66 | 34-78 |

TABLE 2-continued

Amino Acid Substitutions in Shiga Toxin Effector Polypeptides

| Epitope Region Disrupted | Substitution | natively positioned amino acid positions B-Cell Epitope Region | T-Cell Epitope |
|---|---|---|---|
| 4 | E60T | 53-66 | 34-78 |
| 4 | E60R | 53-66 | 34-78 |
| 4 | E61A | 53-66 | 34-78 |
| 4 | E61V | 53-66 | 34-78 |
| 4 | E61L | 53-66 | 34-78 |
| 4 | G62A | 53-66 | 34-78 |
| — | R84A | | 77-103 |
| — | V88A | | 77-103 |
| 5 | D94A | 94-115 | 77-103 |
| 5 | S96I | 94-115 | 77-103 |
| 5 | T104N | 94-115 | |
| 5 | A105L | 94-115 | |
| 5 | T107P | 94-115 | |
| 5 | L108M | 94-115 | |
| 5 | S109V | 94-115 | |
| 5 | G110A | 94-115 | |
| 5 | D111T | 94-115 | |
| 5 | S112V | 94-115 | |
| 6 | D141A | 141-153 | 128-168 |
| 6 | G147A | 141-153 | 128-168 |
| — | V154A | | 128-168 |
| 7 | R179A | 179-190 | 160-183 |
| 7 | T180G | 179-190 | 160-183 |
| 7 | T181I | 179-190 | 160-183 |
| 7 | D183A | 179-190 | 160-183 |
| 7 | D183G | 179-190 | 160-183 |
| 7 | D184A | 179-190 | |
| 7 | D184F | 179-190 | |
| 7 | L185V | 179-190 | |
| 7 | S186A | 179-190 | |
| 7 | S186F | 179-190 | |
| 7 | G187A | 179-190 | |
| 7 | G187T | 179-190 | |
| 7 | R188A | 179-190 | |
| 7 | R188L | 179-190 | |
| 7 | S189A | 179-190 | |
| — | D198A | immunogenic residue | |
| — | R205A | immunogenic residue | |
| — | C242S | | 236-258 |
| 8 | R248A | 243-257 | 236-258 |
| 8 | R251A | 243-257 | 236-258 |

Based on the empirical evidence in WO 2015/113007 and WO 2016/196344, certain amino acid positions in the A Subunits of Shiga toxins are predicted to tolerate epitope disruptions while still retaining significant Shiga toxin effector functions. For example, the following natively occurring positions tolerate amino acid substitutions, either alone or in combination, while retaining a Shiga toxin effector function (s) such as cytotoxicity—amino acid 1 of SEQ ID NO:1 or SEQ ID NO:2; 4 of SEQ ID NO:1, SEQ ID NO:2, or SEQ ID NO:3; 8 of SEQ ID NO:1, SEQ ID NO:2, or SEQ ID NO:3; 9 of SEQ ID NO:1, SEQ ID NO:2, or SEQ ID NO:3; 11 of SEQ ID NO:1, SEQ ID NO:2, or SEQ ID NO:3; 33 of SEQ ID NO:1 or SEQ ID NO:2; 43 of SEQ ID NO:1 or SEQ ID NO:2; 44 of SEQ ID NO:1 or SEQ ID NO:2; 45 of SEQ ID NO:1 or SEQ ID NO:2; 46 of SEQ ID NO:1 or SEQ ID NO:2; 47 of SEQ ID NO:1 or SEQ ID NO:2; 48 of SEQ ID NO:1, SEQ ID NO:2, or SEQ ID NO:3; 49 of SEQ ID NO:1 or SEQ ID NO:2; 50 of SEQ ID NO:1 or SEQ ID NO:2; 51 of SEQ ID NO:1 or SEQ ID NO:2; 53 of SEQ ID NO:1 or SEQ ID NO:2; 54 of SEQ ID NO:1 or SEQ ID NO:2; 55 of SEQ ID NO:1 or SEQ ID NO:2; 56 of SEQ ID NO:1 or SEQ ID NO:2; 57 of SEQ ID NO:1 or SEQ ID NO:2; 58 of SEQ ID NO:1, SEQ ID NO:2, or SEQ ID NO:3; 59 of SEQ ID NO:1, SEQ ID NO:2, or SEQ ID NO:3; 60 of SEQ ID NO:1 or SEQ ID NO:2; 61 of SEQ ID NO:1 or SEQ ID NO:2; 62 of SEQ ID NO:1 or SEQ ID NO:2; 84 of SEQ ID NO:1 or SEQ ID NO:2; 88 of SEQ ID NO:1 or SEQ ID NO:2; 94 of SEQ ID NO:1, SEQ ID NO:2, or SEQ ID NO:3; 96 of SEQ ID NO:1, SEQ ID NO:2, or SEQ ID NO:3; 104 of SEQ ID NO:1 or SEQ ID NO:2; 105 of SEQ ID NO:1 or SEQ ID NO:2; 107 of SEQ ID NO:1 or SEQ ID NO:2; 108 of SEQ ID NO:1 or SEQ ID NO:2; 109 of SEQ ID NO:1, SEQ ID NO:2, or SEQ ID NO:3; 110 of SEQ ID NO:1 or SEQ ID NO:2; 111 of SEQ ID NO:1 or SEQ ID NO:2; 112 of SEQ ID NO:1, SEQ ID NO:2, or SEQ ID NO:3; 141 of SEQ ID NO:1 or SEQ ID NO:2; 147 of SEQ ID NO:1, SEQ ID NO:2, or SEQ ID NO:3; 154 of SEQ ID NO:1 or SEQ ID NO:2; 179 of SEQ ID NO:1, SEQ ID NO:2, or SEQ ID NO:3; 180 of SEQ ID NO:1 or SEQ ID NO:2; 181 of SEQ ID NO:1 or SEQ ID NO:2; 183 of SEQ ID NO:1, SEQ ID NO:2, or SEQ ID NO:3; 184 of SEQ ID NO:1, SEQ ID NO:2, or SEQ ID NO:3; 185 of SEQ ID NO:1 or SEQ ID NO:2; 186 of SEQ ID NO:1, SEQ ID NO:2, or SEQ ID NO:3; 187 of SEQ ID NO:1 or SEQ ID NO:2; 188 of SEQ ID NO:1 or SEQ ID NO:2; 189 of SEQ ID NO:1 or SEQ ID NO:2; 198 of SEQ ID NO:1 or SEQ ID NO:2; 204 of SEQ ID NO:3; 205 of SEQ ID NO:1 or SEQ ID NO:2; 241 of SEQ ID NO:3; 242 of SEQ ID NO:1 or SEQ ID NO:2; 247 of SEQ ID NO:1 or SEQ ID NO:2; 247 of SEQ ID NO:3; 248 of SEQ ID NO:1 or SEQ ID NO:2; 250 of SEQ ID NO:3; 251 of SEQ ID NO:1 or SEQ ID NO:2; 264 of SEQ ID NO:1, SEQ ID NO:2, or SEQ ID NO:3; 265 of SEQ ID NO:1 or SEQ ID NO:2; and 286 of SEQ ID NO:1 or SEQ ID NO:2.

The empirical data in WO 2015/113007 and WO 2016/196344 point towards other epitope disrupting substitutions and combinations of epitope disrupting substitutions that can reduce antigenicity and/or immunogenicity of a Shiga toxin effector polypeptide while retaining the ability of the Shiga toxin effector polypeptide to exhibit a significant Shiga toxin effector function such as, e.g., new combinations of the aforementioned truncations and positions tolerating substitutions as well as new substitutions at identical positions or conserved positions in related Shiga toxin A Subunits.

It is predictable that other amino acid substitutions to amino acid residues of a conservative functional group of a substitution tested herein may reduce antigenicity and/or immunogenicity while preserving a significant Shiga toxin effector function. For example, other substitutions known to the skilled worker to be similar to any of K1A, K1M, T4I, D6R, S8I, T8V, T9I, S9I, K11A, K11H, T12K, S33I, S33C, S43N, G44L, S45V, S45I, T45V, T45I, G46P, D47M, D47G, N48V, N48F, L49A, F50T, A51V, D53A, D53N, D53G, V54L, V54I, R55A, R55V, R55L, G56P, I57F, I57M, D58A, D58V, D58F, P59A, P59F, E60I, E60T, E60R, E61A, E61V, E61L, G62A, R84A, V88A, D94A, S96I, T104N, A105L, T107P, L108M, S109V, T109V, G110A, D111T, S112V, D141A, G147A, V154A, R179A, T180G, T181I, D183A, D183G, D184A, D184A, D184F, L185V, L185D, S186A, S186F, G187A, G187T, R188A, R188L, S189A, D198A, R204A, R205A, C242S, S247I, Y247A, R248A, R250A, R251A, or D264A, G264A, T286A, and/or T286I may disrupt an endogenous epitope while maintaining at least one Shiga toxin effector function. In particular, amino acid substitutions to conservative amino acid residues similar to K1A, K1M, T4I, S8I, T8V, T9I, S9I, K11A, K11H, S33I, S33C, S43N, G44L, S45V, S45I, T45V, T45I, G46P, D47M, N48V, N48F, L49A, A51V, D53A, D53N, V54L, V54I, R55A, R55V, R55L, G56P, I57F, I57M, D58A, D58V, D58F, P59A, E60I, E60T, E61A, E61V, E61L, G62A, R84A, V88A, D94A, S96I, T104N, T107P, L108M, S109V, T109V, G110A, D111T, S112V, D141A, G147A, V154A, R179A, T180G, T181I, D183A, D183G, D184A, D184F, L185V, S186A, S186F, G187A, R188A, R188L, S189A, D198A, R204A, R205A, C242S, S247I, Y247A, R248A, R250A, R251A, D264A, G264A, T286A, and T286I may have the same or similar effects. In certain embodiments, a Shiga toxin effector polypeptide of the invention may comprise similar conservative amino acid substitutions to empirically tested ones, such as, e.g., K1 to G, V, L, I, F, and H; T4 to A, G, V, L, F, M, and S; S8 to A, G, V, L, F, and M; T9 to A, G, L, F, M, and S; S9 to A, G, L, I, F, and M; K11 to G, V, L, I, F, and M; S33 to A, G, V, L, F, and M; S43 to A, G, V, L, I, F, and M; S45 to A, G, L, F, and M; T45 to A, G, L, F, and M; D47 to A, V, L, I, F, S, and Q; N48 to A, G, L, and M; L49 to G; Y49 to A; D53 to V, L, I, F, S, and Q; R55 to G, I, F, M, Q, S, K, and H; D58 to G, L, I, S, and Q; P59 to G; E60 to A, G, V, L, F, S, Q, N, D, and M; E61 to G, I, F, S, Q, N, D, M, and R; R84 to G, V, L, I, F, M, Q, S, K, and H; V88 to G; I88 to G; D94 to G, V, L, I, F, S, and Q; S96 to A, G, V, L, F, and M; T107 to A, G, V, L, I, F, M, and S; S107 to A, G, V, L, I, F, and M; S109 to A, G, I, L, F, and M; T109 to A, G, I, L, F, M, and S; S112 to A, G, L, I, F, and M; D141 to V, L, I, F, S, and Q; V154 to G; R179 to G, V, L, I, F, M, Q, S, K, and H; T180 to A, V, L, I, F, M, and S; T181 to A, G, V, L, F, M, and S; D183 to V, L, I, F, S, and Q; D184 to G, V, L, I, S, and Q; S186 to G, V, I, L, and M; R188 to G, V, I, F, M, Q, S, K, and H; S189 to G, V, I, L, F, and M; D197 to V, L, I, F, S, and Q; D198 to A, V, L, I, F, S. and Q; R204 to G, V, L, I, F, M, Q, S, K, and H; R205 to G, V, L, I, F, M, Q, S, K and H; S247 to A, G, V, I, L, F, and M; Y247 to A, G, V, L, I, F, and M; R248 to G, V, L, I, F, M, Q, S, K, and H; R250 to G, V, L, I, F, M, Q, S, K, and H; R251 to G, V, L, I, F, M, Q, S, K, and H; D264 to A, G, V, L, I, F, S, and Q; and T286 to A, G, V, L, I, F, M, and S.

Similarly, amino acid substitutions which remove charge, polarity, and/or reduce side chain length can disrupt an epitope while maintaining at least one Shiga toxin effector function. In some embodiments, a Shiga toxin effector polypeptide of the invention may comprise one or more epitopes disrupted by substitutions such that side chain charge is removed, polarity is removed, and/or side chain length is reduced such as, e.g., substituting the appropriate amino acid selected from the following group A, G, V, L, I, P, C, M, F, S, D, N, Q, H, or K for the amino acid residue at position 1 of SEQ ID NO:1 or SEQ ID NO:2; 4 of SEQ ID NO:1, SEQ ID NO:2, or SEQ ID NO:3; 6 of SEQ ID NO:1 or SEQ ID NO:2; 8 of SEQ ID NO:1, SEQ ID NO:2, or SEQ ID NO:3; 9 of SEQ ID NO:1, SEQ ID NO:2, or SEQ ID NO:3; 11 of SEQ ID NO:1, SEQ ID NO:2, or SEQ ID NO:3; 12 of SEQ ID NO:1, SEQ ID NO:2, or SEQ ID NO:3; 33 of SEQ ID NO:1 or SEQ ID NO:2; 43 of SEQ ID NO:1 or SEQ ID NO:2; 44 of SEQ ID NO:1 or SEQ ID NO:2; 45 of SEQ ID NO:1 or SEQ ID NO:2; 46 of SEQ ID NO:1 or SEQ ID NO:2; 47 of SEQ ID NO:1 or SEQ ID NO:2; 48 of SEQ ID NO:1, SEQ ID NO:2, or SEQ ID NO:3; 49 of SEQ ID NO:1 or SEQ ID NO:2; 50 of SEQ ID NO:1 or SEQ ID NO:2; 51 of SEQ ID NO:1 or SEQ ID NO:2; 53 of SEQ ID NO:1 or SEQ ID NO:2; 54 of SEQ ID NO:1 or SEQ ID NO:2; 55 of SEQ ID NO:1 or SEQ ID NO:2; 56 of SEQ ID NO:1 or SEQ ID NO:2; 57 of SEQ ID NO:1, SEQ ID NO:2, or SEQ ID NO:3; 58 of SEQ ID NO:1, SEQ ID NO:2, or SEQ ID NO:3; 59 of SEQ ID NO:1, SEQ ID NO:2, or SEQ ID NO:3; 60 of SEQ ID NO:1 or SEQ ID NO:2; 61 of SEQ ID NO:1 or SEQ ID NO:2; 62 of SEQ ID NO:1 or SEQ ID NO:2; 84 of SEQ ID NO:1 or SEQ ID NO:2; 88 of SEQ ID NO:1, SEQ ID NO:2, or SEQ ID NO:3; 94 of SEQ ID NO:1, SEQ ID NO:2, or SEQ ID NO:3; 96 of SEQ ID NO:1, SEQ ID NO:2, or SEQ ID NO:3; 104 of SEQ ID NO:1 or SEQ ID NO:2; 105 of SEQ ID NO:1 or SEQ ID NO:2; 107 of SEQ ID NO:1, SEQ ID NO:2, or SEQ ID NO:3; 108 of SEQ ID NO:1 or SEQ ID NO:2; 109 of SEQ ID NO:1, SEQ ID NO:2, or SEQ ID NO:3; 110 of SEQ ID NO:1 or SEQ ID NO:2; 111 of SEQ ID NO:1 or SEQ ID NO:2; 112 of SEQ ID NO:1, SEQ ID NO:2, or SEQ ID NO:3; 141 of SEQ ID NO:1 or SEQ ID NO:2; 147 of SEQ ID NO:1, SEQ ID NO:2, or SEQ ID NO:3; 154 of SEQ ID NO:1 or SEQ ID NO:2; 179 of SEQ ID NO:1, SEQ ID NO:2, or SEQ ID NO:3; 180 of SEQ ID NO:1 or SEQ ID NO:2; 181 of SEQ ID NO:1 or SEQ ID NO:2; 183 of SEQ ID NO:1, SEQ ID NO:2, or SEQ ID NO:3; 184 of SEQ ID NO:1, SEQ ID NO:2, or SEQ ID NO:3; 185 of SEQ ID NO:1 or SEQ ID NO:2; 186 of SEQ ID NO:1, SEQ ID NO:2, or SEQ ID NO:3; 187 of SEQ ID NO:1 or SEQ ID NO:2; 188 of SEQ ID NO:1 or SEQ ID NO:2; 189 of SEQ ID NO:1 or SEQ ID NO:2; 197 of SEQ ID NO:3; 198 of SEQ ID NO:1 or SEQ ID NO:2; 204 of SEQ ID NO:3; 205 of SEQ ID NO:1 or SEQ ID NO:2; 241 of SEQ ID NO:3; 242 of SEQ ID NO:1 or SEQ ID NO:2; 247 of SEQ ID NO:1 or SEQ ID NO:2; 247 of SEQ ID NO:3; 248 of SEQ ID NO:1 or SEQ ID NO:2; 250 of SEQ ID NO:3; 251 of SEQ ID NO:1 or SEQ ID NO:2; 264 of SEQ ID NO:1, SEQ ID NO:2, or SEQ ID NO:3; 265 of SEQ ID NO:1 or SEQ ID NO:2; and 286 of SEQ ID NO:1 or SEQ ID NO:2. In some embodiments, a Shiga toxin effector polypeptide may comprise one or more of the following amino acid substitutions: K1 to A, G, V, L, I, F, M or H; T4 to A, G, V, L, I, F, M, or S; D6 to A, G, V, L, I, F, S, or Q; S8 to A, G, V, I, L, F, or M; T8 to A, G, V, I, L, F, M, or S; T9 to A, G, V, I, L, F, M, or S; S9 to A, G, V, L, I, F, or M; K11 to A, G, V, L, I, F, M or H; T12 to A, G, V, I, L, F, M, or S; S33 to A, G, V, L, I, F, or M; S43 to A, G, V, L, I, F, or M; G44 to A or L; S45 to A, G, V, L, I, F, or M; T45 to A, G, V, L, I, F, or M; G46 to A or P; D47 to A, G, V, L, I, F, S. or Q; N48 to A, G, V, L, or M; L49 to A or G; F50; A51 to V; D53 to A, G, V, L, I, F, S, or Q; V54 to A, G, or L; R55 to A, G, V, L, I, F, M, Q, S, K, or H; G56 to A or P; I57 to A, G, M, or F; L57 to A, G, M, or F; D58 to A, G, V, L, I, F, S, or Q; P59 to A, G, or F; E60 to A, G, V, L, I, F, S, Q, N, D, M, or R; E61 to A, G, V, L, I, F, S, Q, N, D, M, or R; G62 to A; D94 to A, G, V, L, I, F, S. or Q; R84 to A, G, V, L, I, F, M, Q, S, K, or H; V88 to A or G; I88 to A, G, or V; D94; S96 to A, G, V, I, L, F, or M; T104 to A, G, V, I, L, F, or M; A105 to L; T107 to A, G, V, I, L, F, M, or S; S107 to A, G, V, L, I, F, or M; L108 to A, G, or M; S109 to A, G, V, I, L, F, or M; T109 to A, G, V, I, L, F, M, or S; G110 to A; D111 to A, G, V, L, I, F, S, or Q; S112 to A, G, V, L, I, F, or M; D141 to A, G, V, L, I, F, S, or Q; G147 to A; V154 to A or G; R179 to A, G, V, L, I, F, M, Q, S, K, or H; T180 to A, G, V, L, I, F, M, or S; T181 to A, G, V, L, I, F, M, or S; D183 to A, G, V, L, I, F, S, or Q; D184 to A, G, V, L, I, F, S, or Q; L185 to A, G, or V; S186 to A, G, V, I, L, F, or M; G187 to A; R188 to A, G, V, L, I, F, M, Q, S, K, or H; S189 to A, G, V, I, L, F, or M; D197 to A, G, V, L, I, F, S, or Q; D198 to A, G, V, L, I, F, S, or Q; R204 to A, G, V, L, I, F, M, Q, S, K, or H; R205 to A, G, V, L, I, F, M, Q, S, K or H; C242 to A, G, V, or S; S247 to A, G, V, I, L, F, or M; Y247 to A, G, V, L, I, F, or M; R248 to A, G, V, L, I, F, M, Q, S, K, or H; R250 to A, G, V, L, I, F, M, Q, S, K, or H; R251 to A, G, V, L, I, F, M, Q, S, K, or H; C262 to A, G, V, or S; D264 to A, G, V, L, I, F, S, or Q; G264 to A; or T286 to A, G, V, L, I, F, M, or S.

In addition, any amino acid substitution in one epitope region of a Shiga toxin effector polypeptide which disrupts an epitope while retaining significant Shiga toxin effector function is combinable with any other amino acid substitution in the same or a different epitope region which disrupts an epitope while retaining significant Shiga toxin effector function to form a de-immunized, Shiga toxin effector polypeptide with multiple epitope regions disrupted while still retaining a significant level of Shiga toxin effector function. In some embodiments, a Shiga toxin effector polypeptide of the invention may comprise a combination of two or more of the aforementioned substitutions and/or the combinations of substitutions described in WO 2015/113007, WO 2016/196344, and/or WO 2018/140427.

Based on work described in WO 2015/113007, WO 2016/196344, and WO 2018/140427, certain amino acid regions in the A Subunits of Shiga toxins are predicted to tolerate epitope disruptions while still retaining significant Shiga toxin effector functions. For example, the epitope regions natively positioned at 1-15, 39-48, 53-66, 55-66, 94-115, 180-190, 179-190, and 243-257 tolerated multiple amino acid substitution combinations simultaneously without compromising Shiga toxin enzymatic activity and cytotoxicity.

(v) De-Immunized Shiga Toxin with Disrupted, Furin Cleavage Motif

A combination Shiga toxin effector polypeptide comprises two or more sub-regions (i.e. non-overlapping sub-regions) wherein each sub-region comprises at least one of the following: (1) a disruption in an endogenous epitope or epitope region, and (2) a disrupted furin-cleavage motif at the carboxy-terminus of an A1 fragment derived region.

Some embodiments of the combination Shiga toxin effector polypeptides comprise both (1) a disruption in an endogenous epitope or epitope region and (2) a disrupted furin-cleavage motif at the carboxy-terminus of an A1 fragment derived region. It is predicted that any of the individual, de-immunized, Shiga toxin effector sub-regions described in WO 2015/113007, WO 2016/196344, and WO 2018/140427 (see e.g. Table 2, supra) may generally be combined with any Shiga toxin effector sub-region comprising a disrupted furin-cleavage motif described herein, described in WO 2015/191764, and/or known in the art in order to create a Shiga toxin effector polypeptide for use as a component of a binding protein.

In combination, Shiga toxin effector polypeptide may combine the features of their respective sub-regions, such as, e.g., a furin-cleavage motif disruption, one or more individual epitope disruptions, and/or a heterologous molecular cargo, and these combinations sometimes result in Shiga toxin effector polypeptides with synergistic reductions in immunogenicity as compared to the sum of their partially de-immunized sub-regions.

De-immunized, Shiga toxin effector polypeptides which exhibit no cytotoxicity or reduced cytotoxicity at certain concentrations, e.g. Shiga toxin effector polypeptides comprising Y77S, R179A, and/or E167D or truncated at the carboxy-terminus beyond native position 240, may still be useful as de-immunized, Shiga toxin effector polypeptides for delivering exogenous materials into cells.

In some embodiments, the Shiga toxin effector polypeptide comprises: (i) a disrupted furin-cleavage motif at the carboxy-terminus of its Shiga toxin A1 fragment region (see e.g. WO 2015/191764, hereby expressly incorporated by reference in its entirety, and specifically paragraphs [8], [9] and the sequences of the disrupted motifs and the toxin polypeptides including the disrupted motifs) and (ii) is de-immunized; see for example WO2018/140427, "Embodiment Set #5" at paragraph [80] et seq, as well as paragraph [81] and [82], expressly incorporated herein by reference.

b. Other Structural Variations

The skilled worker will recognize that variations may be made to the Shiga toxin effector polypeptides and binding proteins of the present invention, and polynucleotides encoding any of the former, without diminishing their biological activities, e.g., by maintaining the overall structure and function of the Shiga toxin effector polypeptide, such as in conjunction with one or more 1) endogenous epitope disruptions which reduce antigenic and/or immunogenic potential and/or 2) furin-cleavage motif disruptions which reduce proteolytic cleavage. For example, some modifications may facilitate expression, facilitate purification, improve pharmacokinetic properties, and/or improve immunogenicity. Such modifications are well known to the skilled worker and include, for example, a methionine added at the amino-terminus to provide an initiation site, additional amino acids placed on either terminus to create conveniently located restriction sites or termination codons, and biochemical affinity tags fused to either terminus to provide for convenient detection and/or purification. A common modification to improve the immunogenicity of a polypeptide produced using a microbial system (e.g. a prokaryotic cell) is to remove, after the production of the polypeptide, the starting methionine residue, which may be formylated during production, such as, e.g., in a bacterial host system, because, e.g., the presence of N-formylmethionine (fMet) might induce undesirable immune responses in subjects such as in human subjects.

Also provided herein is the inclusion of additional amino acid residues at the amino and/or carboxy termini of a binding protein of the present invention, or a proteinaceous component of a binding protein of the present invention, such as sequences for epitope tags or other moieties. The additional amino acid residues may be used for various purposes including, e.g., facilitating cloning, facilitating expression, post-translational modification, facilitating synthesis, purification, facilitating detection, and administration. Non-limiting examples of epitope tags and moieties are chitin binding protein domains, enteropeptidase cleavage sites, Factor Xa cleavage sites, FlAsH tags, FLAG tags, green fluorescent proteins (GFP), glutathione-S-transferase moieties, HA tags, maltose binding protein domains, myc tags, polyhistidine tags, ReAsH tags, strep-tags, strep-tag II, TEV protease sites, thioredoxin domains, thrombin cleavage site, and V5 epitope tags.

In some of the above embodiments, the polypeptide sequence of the Shiga toxin effector polypeptides and/or binding proteins of the present invention are varied by one or more conservative amino acid substitutions introduced into the polypeptide region(s) as long as all required structural features are still present and the Shiga toxin effector polypeptide is capable of exhibiting any required function (s), either alone or as a component of a binding protein. As used herein, the term "conservative substitution" denotes that one or more amino acids are replaced by another, biologically similar amino acid residue. Examples include substitution of amino acid residues with similar characteristics, e.g. small amino acids, acidic amino acids, polar amino acids, basic amino acids, hydrophobic amino acids and aromatic amino acids (see, for example, Table 3). An example of a conservative substitution with a residue normally not found in endogenous, mammalian peptides and proteins is the conservative substitution of an arginine or lysine residue with, for example, ornithine, canavanine, aminoethylcysteine, or another basic amino acid. For further information concerning phenotypically silent substitutions in peptides and proteins see, e.g., Bowie J et al., *Science* 247: 1306-10 (1990).

In some embodiments, the Shiga toxin effector polypeptides and binding proteins of the present invention may comprise functional fragments or variants of a polypeptide region of the present invention described herein that have, at most, 20, 15, 10, 9, 8, 7, 6, 5, 4, 3, 2, or 1 amino acid substitutions compared to a polypeptide sequence recited herein, as long as it comprises (1) a disrupted furin-cleavage motif at the carboxy-terminus of a Shiga toxin A1 fragment derived region and (2) at least one amino acid disrupted in an endogenous, B-cell and/or CD4+ T-cell epitope region, wherein the disrupted amino acid does not overlap with the disrupted furin-cleavage motif. Variants of the Shiga toxin effector polypeptides and binding proteins of the invention are within the scope of the present invention as a result of changing a polypeptide described herein by altering one or more amino acid residues or deleting or inserting one or more amino acid residues, such as within the binding region or Shiga toxin effector polypeptide region, in order to achieve desired properties, such as changed cytotoxicity, changed cytostatic effects, changed immunogenicity, and/or changed serum half-life. The Shiga toxin effector polypeptides and CD38-binding proteins of the present invention may further be with or without a signal sequence.

Accordingly, in some embodiments, the Shiga toxin effector polypeptide comprises or consists essentially of amino acid sequences having at least 55%, at least 60%, at least 65%, at least 70%, at least 75%, at least 80%, at least 85%, at least 90%, at least 95%, at least 97%, at least 98%, or at least 99%, overall sequence identity to a naturally occurring Shiga toxin A Subunit or fragment thereof, such as, e.g., Shiga toxin A Subunit, such as SLT-1A (SEQ ID NO:1), StxA (SEQ ID NO:2), and/or SLT-2A (SEQ ID NO:3), wherein the Shiga toxin effector polypeptide has one or more activity associated with a naturally occurring SLT-1A subunit, e.g., target mediated internalization, catalytic activity and/or cytotoxic activity.

In some embodiments, the Shiga toxin effector polypeptide has one or more amino acid residues which are mutated, inserted, or deleted in order to increase the enzymatic activity of the Shiga toxin effector polypeptide. In some embodiments, the Shiga toxin effector polypeptide has one or more amino acid residues which are mutated or deleted in order to reduce or eliminate catalytic and/or cytotoxic activity of the Shiga toxin effector polypeptide. For example, the catalytic and/or cytotoxic activity of the A Subunits of members of the Shiga toxin family may be diminished or eliminated by mutation or truncation.

The cytotoxicity of the A Subunits of members of the Shiga toxin family may be altered, reduced, or eliminated by mutation and/or truncation. The positions labeled tyrosine-77, glutamate-167, arginine-170, tyrosine-114, and tryptophan-203 have been shown to be important for the catalytic activity of Stx, Stx1, and Stx2 (Hovde C et al., *Proc Natl Acad Sci USA* 85: 2568-72 (1988); Deresiewicz R et al., *Biochemistry* 31: 3272-80 (1992); Deresiewicz R et al., *Mol Gen Genet* 241: 467-73 (1993); Ohmura M et al., *Microb Pathog* 15: 169-76 (1993); Cao C et al., *Microbiol Immunol* 38: 441-7 (1994); Suhan M, Hovde C, *Infect Immun* 66: 5252-9 (1998)). Mutating both glutamate-167 and arginine-170 eliminated the enzymatic activity of Slt-I A1 in a cell-free ribosome inactivation assay (LaPointe P et al., *J Biol Chem* 280: 23310-18 (2005)). In another approach using de novo expression of Slt-I A1 in the endoplasmic reticulum, mutating both glutamate-167 and arginine-170 eliminated Slt-I A1 fragment cytotoxicity at that expression level (LaPointe P et al., *J Biol Chem* 280: 23310-18 (2005)). A truncation analysis demonstrated that a fragment of StxA from residues 75 to 268 still retains significant enzymatic activity in vitro (Haddad J et al., *J Bacteriol* 175: 4970-8 (1993)). A truncated fragment of Slt-I A1 containing residues 1-239 displayed significant enzymatic activity in vitro and cytotoxicity by de novo expression in the cytosol (LaPointe P et al., *J Biol Chem* 280: 23310-18 (2005)). Expression of a Slt-I A1 fragment truncated to residues 1-239 in the endoplasmic reticulum was not cytotoxic because it could not retrotranslocate to the cytosol (LaPointe P et al., *J Biol Chem* 280: 23310-18 (2005)).

The most critical residues for enzymatic activity and/or cytotoxicity in the Shiga toxin A Subunits were mapped to the following residue-positions: asparagine-75, tyrosine-77, tyrosine-114, glutamate-167, arginine-170, arginine-176, and tryptophan-203 among others (Di R et al., *Toxicon* 57: 525-39 (2011)). In particular, a double-mutant construct of Stx2A containing glutamate-E167-to-lysine and arginine-176-to-lysine mutations was completely inactivated; whereas, many single mutations in Stx1 and Stx2 showed a 10-fold reduction in cytotoxicity. Further, truncation of Stx1A to 1-239 or 1-240 reduced its cytotoxicity, and similarly, truncation of Stx2A to a conserved hydrophobic residue reduced its cytotoxicity. The most critical residues for binding eukaryotic ribosomes and/or eukaryotic ribosome inhibition in the Shiga toxin A Subunit have been mapped to the following residue-positions arginine-172, arginine-176, arginine-179, arginine-188, tyrosine-189, valine-191, and leucine-233 among others (McCluskey A et al., *PLoS One* 7: e31191 (2012). However, certain modification may increase a Shiga toxin functional activity exhibited by a Shiga toxin effector polypeptide. For example, mutating residue-position alanine-231 in Stx1A to glutamate increased Stx1 A's enzymatic activity in vitro (Suhan M, Hovde C, *Infect Immun* 66: 5252-9 (1998)).

In some embodiments, the Shiga toxin effector polypeptide derived from SLT-1A (SEQ ID NO:1) or StxA (SEQ ID NO:2) has one or more amino acid residues mutated include substitution of the asparagine at position 75, tyrosine at position 77, tyrosine at position 114, glutamate at position 167, arginine at position 170, arginine at position 176, and/or substitution of the tryptophan at position 203. Examples of such substitutions will be known to the skilled worker based on the prior art, such as asparagine at position 75 to alanine, tyrosine at position 77 to serine, substitution of the tyrosine at position 114 to serine, substitution of the glutamate position 167 to glutamate, substitution of the arginine at position 170 to alanine, substitution of the arginine at position 176 to lysine, substitution of the tryptophan at position 203 to alanine, and/or substitution of the alanine at 231 with glutamate. Other mutations which either enhance or reduce Shiga toxin enzymatic activity and/or cytotoxicity are within the scope of the present invention and may be determined using well known techniques and assays disclosed herein.

3. Linkers Connecting Components and/or Their Subcomponents

Individual CD38-binding regions, Shiga toxin effector polypeptides, and/or components of the binding proteins may be suitably linked to each other via one or more linkers well known in the art and/or described herein. Individual polypeptide subcomponents of the binding regions, e.g. heavy chain variable regions ($V_H$), light chain variable regions ($V_L$), CDR, and/or ABR regions, may be suitably linked to each other via one or more linkers well known in the art and/or described herein. Proteinaceous components of the invention, e.g., multi-chain binding regions, may be suitably linked to each other or other polypeptide components via one or more linkers well known in the art. Peptide components, e.g., KDEL family endoplasmic reticulum retention/retrieval signal motifs, may be suitably linked to another component of the invention via one or more linkers, such as a proteinaceous linker, which are well known in the art.

By "linker" herein is meant a domain linker that joins two protein domains together, such as are used in scFv and/or other protein and protein fusion structures. Generally, there are a number of suitable linkers that can be used, including traditional peptide bonds, generated by recombinant techniques that allows for recombinant attachment of the two domains with sufficient length and flexibility to allow each domain to retain its biological function. The linker peptide may predominantly include the following amino acid residues: Gly, Ser, Ala, or Thr. The linker peptide should have a length that is adequate to link two molecules in such a way that they assume the correct conformation relative to one another so that they retain the desired activity. In some embodiments, the linker is from about 1 to about 50 amino acids in length. In some embodiments, the linker is from about 1 to about 30 amino acids in length. In one embodiment, linkers of 1 to 20 amino acids in length may be used, with from about 5 to about 10 amino acids or 8 to 15 amino acids finding use in some embodiments. Useful linkers include glycine-serine polymers, including for example (GS)n (SEQ ID NO: 193), (GSGGS)n (SEQ ID NO: 194), (GGGGS)n (SEQ ID NO: 195), and (GGGS)n (SEQ IDNO: 196), where n is an integer of at least one (and generally from 3 to 4), glycine-alanine polymers, alanine-serine polymers, and other flexible linkers. Alternatively, a variety of non-proteinaceous polymers, including but not limited to polyethylene glycol (PEG), polypropylene glycol, polyoxyalkylenes, or copolymers of polyethylene glycol and polypropylene glycol, may find use as linkers. Other linker sequences may include any sequence of any length of CL/CH1 domain but not all residues of CL/CH1 domain; for example, the first 5-12 amino acid residues of the CL/CH1 domains. Linkers can also be derived from immunoglobulin light chain, for example C or C. Linkers can be derived from immunoglobulin heavy chains of any isotype, including for example C1, C2, C3, C4, C1, C2, C, C, and C. Linker sequences may also be derived from other proteins such as Ig-like proteins (e.g., TCR, FcR, KIR), hinge region-derived sequences, and other natural sequences from other proteins. While any suitable linker can be used, many embodiments utilize a glycine-serine polymer, including for example (GS)n (SEQ ID NO: 193), (GSGGS)n (SEQ ID NO: 194), (GGGGS)n (SEQ ID NO: 195), and (GGGS)n (SEQ ID NO: 196), where n is an integer of at least one (and generally from 2 to 3 to 4 to 5). "scFv linkers" generally include these glycine-serine polymers.

Suitable linkers are generally those which allow each polypeptide component of the present invention to fold with a three-dimensional structure very similar to the polypeptide components produced individually without any linker or other component. Suitable linkers include single amino acids, peptides, polypeptides, and linkers lacking any of the aforementioned, such as various non-proteinaceous carbon chains, whether branched or cyclic.

Suitable linkers may be non-proteinaceous, such as, e.g. chemical linkers. Various non-proteinaceous linkers known in the art may be used to link cell-targeting binding regions to the Shiga toxin effector polypeptide components of the binding proteins of the present invention, such as linkers commonly used to conjugate immunoglobulin polypeptides to heterologous polypeptides. For example, polypeptide regions may be linked using the functional side chains of their amino acid residues and carbohydrate moieties such as, e.g., a carboxy, amine, sulfhydryl, carboxylic acid, carbonyl, hydroxyl, and/or cyclic ring group. For example, disulfide bonds and thioether bonds may be used to link two or more polypeptides. In addition, non-natural amino acid residues may be used with other functional side chains, such as ketone groups. Examples of non-proteinaceous chemical linkers include but are not limited to N-succinimidyl (4-iodoacetyl)-aminobenzoate, S-(N-succinimidyl) thioacetate (SATA), N-succinimidyl-oxycarbonyl-cu-methyl-a-(2-pyridyldithio) toluene (SMPT), N-succinimidyl4-(2-pyridyldithio)-pentanoate (SPP), succinimidyl4-(N-maleimidomethyl) cyclohexane carboxylate (SMCC or MCC), sulfosuccinimidyl (4-iodoacetyl)-aminobenzoate, 4-succinimidyl-oxycarbonyl-α-(2-pyridyldithio) toluene, sulfosuccinimidyl-6-(α-methyl-α-(pyridyldithiol)-toluamido) hexanoate, N-succinimidyl-3-(-2-pyridyldithio)-proprionate (SPDP), succinimidyl 6(3(-(-2-pyridyldithio)-proprionamido) hexanoate, sulfosuccinimidyl 6(3(-(-2-pyridyldithio)-propionamido) hexanoate, maleimidocaproyl (MC), maleimidocaproyl-valine-citrulline-p-aminobenzyloxycarbonyl (MC-vc-PAB), 3-maleimidobenzoic acid N-hydroxysuccinimide ester (MBS), alpha-alkyl derivatives, sulfoNHS-ATMBA (sulfosuccinimidyl N-[3-(acetylthio)-3-methylbutyryl-beta-alanine]), sulfodichlorophenol, 2-iminothiolane, 3-(2-pyridyldithio)-propionyl hydrazide, Ellman's reagent, dichlorotriazinic acid, and S-(2-thiopyridyl)-L-cysteine.

Proteinaceous linkers may be chosen for incorporation into recombinant fusion binding proteins of the present invention. For recombinant fusion cell-targeting proteins of the invention, linkers typically comprise about 1 to about 50 amino acid residues. In some embodiments, the linker may comprise about 5 to 30 amino acid residues. Commonly, proteinaceous linkers comprise a majority of amino acid residues with polar, uncharged, and/or charged residues, such as, e.g., threonine, proline, glutamine, glycine, and alanine. Non-limiting examples of proteinaceous linkers include alanine-serine-glycine-glycine-proline-glutamate (ASGGPE, SEQ ID NO: 197), valine-methionine (VM), alanine-methionine (AM), AM($G_2$ to $_4S)_x$AM where G is glycine, S is serine, and x is an integer from 1 to 10 (SEQ ID NO: 198).

Proteinaceous linkers may be selected based upon the properties desired. Proteinaceous linkers may be chosen by the skilled worker with specific features in mind, such as to optimize one or more of the fusion molecule's folding, stability, expression, solubility, pharmacokinetic properties, pharmacodynamic properties, and/or the activity of the fused domains in the context of a fusion construct as compared to the activity of the same domain by itself. For example, proteinaceous linkers may be selected based on flexibility, rigidity, and/or cleavability. The skilled worker may use databases and linker design software tools when choosing linkers. In some instances, certain linkers may be chosen to optimize expression. Certain linkers may be chosen to promote intermolecular interactions between identical polypeptides or proteins to form homomultimers such as homodimers Flexible proteinaceous linkers are often greater than 12 amino acid residues long and rich in small, non-polar amino acid residues, polar amino acid residues, and/or hydrophilic amino acid residues, such as, e.g., glycines, serines, and threonines. Flexible proteinaceous linkers may be chosen to increase the spatial separation between components and/or to allow for intramolecular interactions between components. For example, various "GS" linkers are known to the skilled worker and are composed of multiple glycines and/or one or more serines, sometimes in repeating units, such as, e.g., $(G_xS)_n$ (SEQ ID NO:199), $(S_xG)_n$ (SEQ ID NO:200), $(GGGGS)_n$ (SEQ ID NO:195), and $(G)_n$ (SEQ ID NO:201), in which x is 1 to 6 and n is 1 to 30. Non-limiting examples of flexible proteinaceous linkers include GKSSGSGSESKS (SEQ ID NO: 202), EGKSSGSGSESKEF (SEQ ID NO: 203), GSTSGSGKSSEGKG (SEQ ID NO: 204), GSTSGSGKSSEGSGSTKG (SEQ ID NO: 205), GSTSGSGKPGSGEGSTKG (SEQ ID NO: 206), SRSSG (SEQ ID NO: 207), and SGSSC (SEQ ID NO: 208).

Rigid proteinaceous linkers are often stiff alpha-helical structures and rich in proline residues and/or one or more strategically placed prolines. Rigid linkers may be chosen to prevent intramolecular interactions between linked components.

In some embodiments of the CD38-binding proteins of the present invention, a linker may be used which comprises one or more protease sensitive sites to provide for cleavage by a protease present within a target cell. In some embodiments of the binding proteins of the invention, a linker may be used which is not cleavable to reduce unwanted toxicity after administration to a vertebrate organism.

In some embodiments of the CD38-binding proteins of the present invention, a CD38-binding region is linked to a Shiga toxin effector polypeptide using any number of means known to the skilled worker, including both covalent and noncovalent linkages.

In some embodiments of the CD38-binding proteins of the present invention, the molecule comprises a binding region which is a scFv with a linker connecting a heavy chain variable ($V_H$) domain and a light chain variable ($V_L$) domain. There are numerous linkers known in the art suitable for this purpose, such as, e.g., the 15-residue $(Gly_4Ser)_3$ peptide (SEQ ID NO: 183). Suitable scFv linkers which may be used in forming non-covalent homodimeric structures include GGGS (SEQ ID NO: 185), GGGGS (SEQ ID NO: 186), GGGGSGGG (SEQ ID NO: 187), GGSGGGG (SEQ ID NO: 188), GSTSGGGSGGGGSS (SEQ ID NO: 189), and GSTSGSGKPGSSEGSTKG (SEQ ID NO: 190).

Suitable methods for linkage of the components of the CD38-binding proteins may be by any method presently known in the art for accomplishing such, so long as the attachment does not substantially impede the binding capability of the binding region, the cellular internalization of the Shiga toxin effector polypeptide component, and/or when appropriate the desired Shiga toxin effector function(s) as measured by an appropriate assay, including assays described herein.

The components of the binding protein, e.g. a Shiga toxin A Subunit effector polypeptide and/or immunoglobulin-type CD38-binding region, may be engineered to provide a suitable attachment moiety for the linkage of additional components, e.g. an additional exogenous material (see WO 2018/106895).

In some embodiments, a CD38-binding protein comprises or consists of Shiga toxin A subunit effector polypeptide, a linker, and a CD38-binding domain. The linker may be a proteinaceous linker, and may comprise or about 1 to about 50 amino acid residues. In some embodiments, the proteinaceous linker consists of 1 to 50 amino acid residues. In some embodiments, the linker comprises or consists of the sequence of any one of SEQ ID NOS: 70-75, or a sequence having at least 95%, at least 96%, at least 97%, at least 98%, or at least 99% amino acid sequence identity thereto. In some embodiments, the linker comprises or consists of the sequence of SEQ ID NO: 70.

D. For the purposes of the CD38-binding proteins of the present invention, the specific order or orientation is not fixed for the components: the Shiga toxin effector polypeptide(s), the binding region(s), and any optional linker(s), may vary in relation to each other or the entire binding protein (see e.g. FIG. 1) unless specifically noted. The components of the binding proteins of the present invention may be arranged in any order provided that the desired activity(ies) of the binding region and Shiga toxin effector polypeptide are not eliminated. In some embodiments, a CD38-binding protein comprises, from its N- to C-terminus, the Shiga toxin A subunit effector polypeptide-first linker-VH-second linker-VL. In some embodiments, a CD38-binding protein comprises, from its N- to C-terminus, the Shiga toxin A subunit effector polypeptide-first linker-VL-second linker-VH. Useful Embodiments of the CD-38 Binding Fusion Proteins As will be appreciated by those in the art, the CD38-binding fusion proteins of the invention can be in a variety of formats, as depicted generally in FIG. 1.

In some embodiments, a wild-type Shiga toxin effector polypeptide component such as depicted in SEQ ID NO:1, SEQ ID NO:2 or SEQ ID NO:3 can be linked using a linker to any one of the CD38 targeting moieties (also referred to herein as CD38-binding regions or domains) selected from CD38TM1, CD38TM2, CD38TM3 and CD38TM4, as depicted in FIG. 13.

In certain embodiments, the Shiga toxin effector polypeptide component is SLT-1A-D1-1 (SEQ ID NO:47) linked to a CD38-binding domain selected from CD38TM1, CD38TM2, CD38TM3 and CD38TM4, as depicted in FIG. 13.

In certain embodiments, the Shiga toxin effector polypeptide component is SLT-1A-D1 (SEQ ID NO:45) linked to a CD38-binding domain selected from CD38TM1, CD38TM2, CD38TM3 and CD38TM4, as depicted in FIG. 13.

In certain embodiments, the Shiga toxin effector polypeptide component is SLT-1A-D1-2 (SEQ ID NO:47) linked to a CD38-binding domain selected from CD38TM1, CD38TM2, CD38TM3 and CD38TM4, as depicted in FIG. 13.

In certain embodiments, the Shiga toxin effector polypeptide component is SLT-1A-D1-3 (SEQ ID NO:48) linked to a CD38-binding domain selected from CD38TM1, CD38TM2, CD38TM3 and CD38TM4, as depicted in FIG. 13.

In certain embodiments, the Shiga toxin effector polypeptide component is SLT-1A-D1-4 (SEQ ID NO:49) linked to a CD38-binding domain selected from CD38TM1, CD38TM2, CD38TM3 and CD38TM4, as depicted in FIG. 13.

In certain embodiments, the Shiga toxin effector polypeptide component is SLT-1A-combo variant 1 (SEQ ID NO:55) linked to a CD38-binding domain selected from CD38TM1, CD38TM2, CD38TM3 and CD38TM4, as depicted in FIG. 13.

In certain embodiments, the Shiga toxin effector polypeptide component is SLT-1A-combo variant 2 (SEQ ID NO:56) linked to a CD38-binding domain selected from CD38TM1, CD38TM2, CD38TM3 and CD38TM4, as depicted in FIG. 13.

In certain embodiments, the Shiga toxin effector polypeptide component is SLT-1A-combo variant 3 (SEQ ID NO:57) linked to a CD38-binding domain selected from CD38TM1, CD38TM2, CD38TM3 and CD38TM4, as depicted in FIG. 13.

In certain embodiments, the Shiga toxin effector polypeptide component is SLT-1A-combo variant 4 (SEQ ID NO:58) linked to a CD38-binding domain selected from CD38TM1, CD38TM2, CD38TM3 and CD38TM4, as depicted in FIG. 13.

In certain embodiments, the Shiga toxin effector polypeptide component is SLT-1A-combo variant 5 (SEQ ID NO:59) linked to a CD38-binding domain selected from CD38TM1, CD38TM2, CD38TM3 and CD38TM4, as depicted in FIG. 13.

In certain embodiments, the Shiga toxin effector polypeptide component is SLT-1A-combo variant 6 (SEQ ID NO:60) linked to a CD38-binding domain selected from CD38TM1, CD38TM2, CD38TM3 and CD38TM4, as depicted in FIG. 13.

In certain embodiments, the Shiga toxin effector polypeptide component is SLT-1A-combo variant 7 (SEQ ID NO:61) linked to a CD38-binding domain selected from CD38TM1, CD38TM2, CD38TM3 and CD38TM4, as depicted in FIG. 13.

In certain embodiments, the Shiga toxin effector polypeptide component is SLT-1A-combo variant 8 (SEQ ID NO:62) linked to a CD38-binding domain selected from CD38TM1, CD38TM2, CD38TM3 and CD38TM4, as depicted in FIG. 13.

In certain embodiments, the Shiga toxin effector polypeptide component is SLT-1A-combo variant 9 (SEQ ID NO:63) linked to a CD38-binding domain selected from CD38TM1, CD38TM2, CD38TM3 and CD38TM4, as depicted in FIG. 13.

In certain embodiments, the Shiga toxin effector polypeptide component is SLT-1A-combo variant 10 (SEQ ID NO:64) linked to a CD38-binding domain selected from CD38TM1, CD38TM2, CD38TM3 and CD38TM4, as depicted in FIG. 13.

In certain embodiments, the Shiga toxin effector polypeptide component is SLT-1A-combo variant 11 (SEQ ID NO:65) linked to a CD38-binding domain selected from CD38TM1, CD38TM2, CD38TM3 and CD38TM4, as depicted in FIG. 13.

In certain embodiments, the Shiga toxin effector polypeptide component is SLT-1A-combo variant 12 (SEQ ID NO:66) linked to a CD38-binding domain selected from CD38TM1, CD38TM2, CD38TM3 and CD38TM4, as depicted in FIG. 13.

In certain embodiments, the Shiga toxin effector polypeptide component is SLT-1A-combo variant 13 (SEQ ID NO:67) linked to a CD38-binding domain selected from CD38TM1, CD38TM2, CD38TM3 and CD38TM4, as depicted in FIG. 13.

In certain embodiments, the Shiga toxin effector polypeptide component is SLT-1A-combo variant 14 (SEQ ID NO:68) linked to a CD38-binding domain selected from CD38TM1, CD38TM2, CD38TM3 and CD38TM4, as depicted in FIG. 13.

In certain embodiments, the Shiga toxin effector polypeptide component is SLT-1A-combo variant 15 (SEQ ID NO:69) linked to a CD38-binding domain selected from CD38TM1, CD38TM2, CD38TM3 and CD38TM4, as depicted in FIG. 13.

The following embodiments describe in more detail certain structures of illustrative CD38-binding proteins, including CD38-binding fusion proteins, which target cells physically coupled to CD38 at a cellular surface, including cells which express CD38.

As will be appreciated in the art, the CD38-binding fusion proteins of the invention comprise, at a minimum, a Shiga toxin A subunit effector polypeptide and a CD38 binding domain, with appropriate linkers as needed. The CD38 binding domain generally comprises a VH and a VL that when correctly associated, will bind human CD38.

Particularly useful CD38 binding proteins of the invention include, but are not limited to, CD38-Binding protein #1 (SEQ ID NO:76), CD38-Binding protein #2 (SEQ ID NO:77), CD38-Binding protein #3 (SEQ ID NO:78), CD38-Binding protein #4 (SEQ ID NO:79), CD38-Binding protein #5 (SEQ ID NO:80), CD38-Binding protein #6 (SEQ ID NO:81) and CD38-Binding protein #7 (SEQ ID NO:82).

In particularly useful embodiments, the CD38-binding proteins of the invention comprise, from N- to C-terminal, a Shiga toxin A subunit effector polypeptide-linker-VH-linker-VL. In this embodiment, the Shiga toxin polypeptide has SEQ ID NO:46, and the VH and VL are selected from the pairs SEQ ID NOs:101 and 105; SEQ ID NOs:101 and 125; SEQ ID NOs:109 and 113 and SEQ ID NOs:117 and 121.

In particularly useful embodiments, the CD38-binding proteins of the invention comprise, from N- to C-terminal, a Shiga toxin A subunit effector polypeptide-linker-VH-linker-VL. In this embodiment, the Shiga toxin polypeptide has SEQ ID NO:46, and the VH and VL are selected from the pairs SEQ ID NOs:101 and 105; SEQ ID NOs:101 and 125; SEQ ID NOs:109 and 113 and SEQ ID NOs:117 and 121.

In some embodiments, a CD38-binding fusion protein comprises from N-terminus to C-terminus or from C-terminus to N-terminus, a Shiga toxin A subunit effector polypeptide and a CD38-binding domain. The CD-38 binding fusion protein may further comprise a first linker that links the Shiga toxin A subunit effector polypeptide and the CD38-binding domain.

In some embodiments, a CD38-binding fusion protein comprises, from N-terminus to C-terminus or from C-terminus to N-terminus, a Shiga toxin A subunit effector polypeptide, a heavy chain variable domain (VH) and a light chain variable domain (VL).

In some embodiments, a CD38-binding fusion protein comprises, from N-terminus to C-terminus or from C-terminus to N-terminus, a Shiga toxin A subunit effector polypeptide, a first linker, a VH, and a VL.

In some embodiments, a CD38-binding fusion protein comprises, from N-terminus to C-terminus or from C-terminus to N-terminus, a Shiga toxin A subunit effector polypeptide, a first linker, a VH, a second linker, and a VL.

In some embodiments, a CD38-binding fusion protein comprises, from N-terminus to C-terminus or from C-terminus to N-terminus, a Shiga toxin A subunit effector polypeptide, a VL, and a VH.

In some embodiments, a CD38-binding fusion protein comprises, from N-terminus to C-terminus or from C-terminus to N-terminus, a Shiga toxin A subunit effector polypeptide, a first linker, a VL, and a VH.

In some embodiments, a CD38-binding fusion protein comprises, from N-terminus to C-terminus or from C-terminus to N-terminus, a Shiga toxin A subunit effector polypeptide, a first linker, a VL, a second linker, and a VH.

In some embodiments, a CD38-binding fusion protein comprises (i) a Shiga toxin A subunit effector polypeptide; (ii) a VH comprising a vHCDR1 that comprises the sequence of SEQ ID NO: 34, a vHCDR2 that comprises the sequence of SEQ ID NO: 35, and a vHCDR3 that comprises the sequence of SEQ ID NO: 36; and (iii) a VL comprising a vLCDR1 that comprises the sequence of SEQ ID NO: 31, a vLCDR2 that comprises the sequence of SEQ ID NO: 32, and a vLCDR3 that comprises the sequence of SEQ ID NO: 33. In some embodiments, the CD38-binding fusion protein further comprises a first linker that links (i) the Shiga toxin subunit effector polypeptide and (ii) the VH or (iii) the VL. In some embodiments, the CD38-binding protein further comprises a second linker that links (ii) the VH and (iii) the VL. In some embodiments, the first linker comprises the sequence of SEQ ID NO: 70. In some embodiments, the second linker comprises the sequence of SEQ ID NO: 75.

In some embodiments, the VL comprises the sequence of SEQ ID NO: 43, or a sequence having at least 95%, at least 96%, at least 97%, at least 98%, or at least 99% amino acid identity thereto. In some embodiments, the VH comprises the sequence of SEQ ID NO: 44, or a sequence having at least 95%, at least 96%, at least 97%, at least 98%, or at least 99% amino acid identity thereto. In some embodiments, the VL comprises the sequence of SEQ ID NO: 43, or a sequence having at least 95%, at least 96%, at least 97%, at least 98%, or at least 99% amino acid identity thereto, and the VH comprises the sequence of SEQ ID NO: 44, or a sequence having at least 95%, at least 96%, at least 97%, at least 98%, or at least 99% amino acid sequence identity thereto. In some embodiments, the VH comprises the sequence of SEQ ID NO: 43, and the VL comprises the sequence of SEQ ID NO: 44.

In some embodiments, the VL comprises the sequence of SEQ ID NO: 41, or a sequence having at least 95%, at least 96%, at least 97%, at least 98%, or at least 99% amino acid sequence identity thereto. In some embodiments, the VH comprises the sequence of SEQ ID NO: 44, or a sequence having at least 95%, at least 96%, at least 97%, at least 98%, or at least 99% amino acid sequence identity thereto. In some embodiments, the VL comprises or consists of the sequence of SEQ ID NO: 41, or a sequence having at least 95%, at least 96%, at least 97%, at least 98%, or at least 99% amino acid sequence identity thereto, and the VH comprises the sequence of SEQ ID NO: 44, or a sequence having at least 95%, at least 96%, at least 97%, at least 98%, or at least 99% amino acid sequence identity thereto. In some embodiments, the VL comprises the sequence of SEQ ID NO: 41, and the VH comprises or consists of the sequence of SEQ ID NO: 44.

In some embodiments, a CD38-binding fusion protein comprises (i) a Shiga toxin A subunit effector polypeptide; (ii) a VH comprising a vHCDR1 comprising the sequence of SEQ ID NO: 22, a vHCDR2 comprising the sequence of SEQ ID NO: 23, and a vHCDR3 comprising the sequence of SEQ ID NO: 24; and (iii) a VL comprising a vLCDR1 comprising the sequence of SEQ ID NO: 19, a vLCDR2 comprising the sequence of SEQ ID NO: 20, and a vLCDR3 comprising the sequence of SEQ ID NO: 21. In some embodiments, the VL comprises or consists of the sequence of SEQ ID NO: 37, and the VH comprises the sequence of SEQ ID NO: 38. In some embodiments, the VL comprises the sequence of SEQ ID NO: 37, or a sequence having at least 95%, at least 96%, at least 97%, at least 98%, or at least 99% amino acid sequence identity thereto, and the VH comprises the sequence of SEQ ID NO: 37, or a sequence having at least 95%, at least 96%, at least 97%, at least 98%, or at least 99% amino acid sequence identity thereto. In some embodiments, the CD38-binding fusion protein further comprises a first linker that links (i) the Shiga toxin subunit effector polypeptide and (ii) the VH or (iii) the VL. In some embodiments, the CD38-binding fusion protein further comprises a second linker that links (ii) the VH and (iii) the VL.

In some embodiments, a CD38-binding fusion protein comprises (i) a CD38-binding protein comprising (i) a Shiga toxin A subunit effector polypeptide; (ii) a VH comprising a vHCDR1 comprising the sequence of SEQ ID NO: 28, a vHCDR2 comprising the sequence of SEQ ID NO: 29, and a vHCDR3 comprising the sequence of SEQ ID NO: 30; and (iii) VL comprising a vLCDR1 comprising the sequence of SEQ ID NO: 25, a vLCDR2 comprising the sequence of SEQ ID NO: 26, and a vLCDR3 comprising the sequence of SEQ ID NO: 27. In some embodiments, the VL comprises of the sequence of SEQ ID NO: 39, and the VH comprises the sequence of SEQ ID NO: 40. In some embodiments, the VL comprises the sequence of SEQ ID NO: 39, or a sequence having at least 95%, at least 96%, at least 97%, at least 98%, or at least 99% amino acid sequence identity thereto, and the VH comprises the sequence of SEQ ID NO: 40, or a sequence having at least 95%, at least 96%, at least 97%, at least 98%, or at least 99% amino acid sequence identity thereto. In some embodiments, the CD38-binding fusion protein further comprises a first linker that links (i) the Shiga toxin subunit effector polypeptide and (ii) the VH or (iii) the VL. In some embodiments, the CD38-binding protein further comprises a second linker that links (ii) the VH and (iii) the VL.

In some embodiments, the CD38-binding fusion protein of the present invention comprises the polypeptide shown in any one of SEQ ID NOs: 76-82 and 228-232. Optionally, the CD38-binding fusion protein comprises an amino-terminal methionine residue. In some embodiments, the CD38-binding fusion protein has at least 95%, at least 96%, at least 97%, at least 98%, at least 99% amino acid sequence identity to any one of SEQ ID NO: 79-82. In some embodiments, the CD38-binding fusion protein comprises the sequence of SEQ ID NO: 79. In some embodiments, the CD38-binding fusion protein comprises two identical polypeptides, each polypeptide comprising a sequence at least 95%, at least 96%, at least 97%, at least 98%, at least 99% amino acid sequence identity to SEQ ID NO: 79. In some embodiments, the CD38-binding fusion protein comprises two identical polypeptides, each polypeptide comprising the sequence of SEQ ID NO: 79. In some embodiments, the CD38-binding fusion protein consists of two identical polypeptides, each polypeptide consisting of the sequence of SEQ ID NO: 79.General Functions of the CD38-binding Fusion Proteins The CD38-binding proteins of the present invention are useful in diverse applications involving, e.g., cell-killing; cell growth inhibition; intracellular, cargo delivery; biological information gathering; immune response stimulation, and/or remediation of a health condition. In some embodiments, the CD38-binding proteins of the invention target CD38 (i.e., are CD38-targeting molecules). The CD38-binding proteins of the present invention are useful as therapeutic and/or diagnostic molecules, such as, e.g., as cell-targeting, cytotoxic, therapeutic molecules; cell-targeting, nontoxic, delivery vehicles; and/or cell-targeting, diagnostic molecules; for examples in applications involving the in vivo targeting of specific CD38 expressing cell types for the diagnosis or treatment of a variety of diseases, including cancers and immune disorders associated with CD38 expression.

In some embodiments, the CD38-binding proteins of the present invention are capable of binding an extracellular part of CD38 molecules associated with cell surfaces of particular cell types and entering those cells. Once internalized within a targeted cell type, some embodiments of the binding proteins of the invention are capable of routing an enzymatically active, cytotoxic, Shiga toxin effector polypeptide fragment into the cytosol of the target cell and eventually killing the cell. Alternatively, nontoxic or reduced-toxicity variants of the binding proteins of the present invention may be used to deliver additional exogenous materials into CD38 positive target cells. This system is modular, in that any number of diverse Shiga toxin effector polypeptides may be associated with a CD38-binding region(s) to produce variants of the binding protein of the present invention with different functional characterstics, such as, e.g. de-immunized effectors for applications involving administration of the CD38-binding protein to a subject such as a human subject, and reduced protease-cleavage sensitive effectors to improve stability particularly in vivo.

E. CD38 Positive Cell-Kill Via Shiga Toxin A Subunit Cytotoxicity

Some embodiments of the Shiga toxin effector polypeptides and binding proteins of the present invention are cytotoxic. Some embodiments of the CD38-binding proteins of the present invention are cytotoxic only due to the presence of one or more Shiga toxin effector polypeptide components. The A Subunits of members of the Shiga toxin family each comprise an enzymatically active polypeptide region capable of killing a eukaryotic cell once in the cell's cytosol. Because members of the Shiga toxin family are adapted to killing eukaryotic cells, molecules derived from Shiga toxins, such as, e.g., CD38-binding proteins comprising some embodiments of the Shiga toxin effector polypeptides can exhibit potent cell-kill activities.

For some embodiments of the binding proteins of the present invention, upon contacting a cell physically coupled with CD38 bound by the binding region of the binding protein (e.g. a CD38 positive cell), the binding protein is capable of causing death of the cell. For some embodiments, the $CD_{50}$ value of the binding protein is less than 5, less than 2.5, less than 1, less than 0.5, or less than 0.25 nM, which is vastly more potent than an untargeted, wild-type, Shiga toxin effector polypeptide (e.g. SEQ ID NOs: 1-18). For example, CD38-binding protein comprising, consisting essentially of, or consisting of any one of SEQ ID NOs: 76, 78-81, and 228-232 potently kills CD38-expressing cells, including cells expressing attenuated levels of CD38 (see Examples, infra, Tables 7-9 and FIG. 3), such those as characterized by $CD_{50}$ values of about 0.1 to about 0.2 nM.

For some embodiments, the $CD_{50}$ value of the binding protein is less than 50, less than 30, less than 20, less than 15, less than 10, less than 5, less than 1, less than 0.5, less than 0.4, less than 0.3, less than 0.2, less than 0.1 ng/mL. For example, CD38-binding protein comprising, consisting essentially of, or consisting of any one of SEQ ID NOs: 76, 78-81 and 228-232 potently kill CD38-expressing cells, including cells expressing attenuated levels of CD38 (see Examples, infra, Tables 7-9 and FIG. 3), such as those characterized by $CD_{50}$ values of about 0.05 or 0.1 ng/mL.

Cell-kill may be accomplished using a molecule of the present invention under varied conditions of target cells, such as, e.g., an ex vivo manipulated target cell, a target cell cultured in vitro, a target cell within a tissue sample cultured in vitro, or a target cell in an in vivo setting like within a multicellular organism.

In some embodiments, the Shiga toxin effector polypeptides and binding proteins of the present invention comprise (1) a de-immunized, Shiga toxin effector sub-region, (2) a protease-cleavage resistant region near the carboxy-terminus of a Shiga toxin A1 fragment derived region, (3) a carboxy-terminal, endoplasmic reticulum retention/retrieval signal motif; and/or (4) a heterologous molecular cargo; however, for some embodiments, these structural modifications do not significantly alter the potency of Shiga toxin cytotoxicity as compared to reference molecules comprising a wild-type Shiga toxin A Subunit polypeptide, such as, e.g., a wild-type Shiga toxin A1 fragment. Thus, Shiga toxin effector polypeptides and CD38-binding proteins of the present invention which are de-immunized, protease cleavage resistant, and/or carrying molecular cargo can maintain potent cytotoxicity while providing one or more various other functionalities or properties.

The binding protein components may be chosen from the prior art or created using routine methods known to the skilled worker (see e.g. WO 2014/164680, WO 2014/164693, WO 2015/138435, WO 2015/138452, WO 2015/113005, WO 2015/113007, WO 2015/191764, WO 2016/196344, PCT/US2017/065074, and WO 2018/106895). For example, de-immunized and furin-cleavage resistant, Shiga toxin effector polypeptides have been described previously in WO 2015/113007, WO 2015/191764, and WO 2016/196344. Shiga toxin effector polypeptides and Shiga toxin effector scaffolds comprising site-specific conjugation sites have been described previously in WO 2018/106895.

F. Selective Cytotoxicity Among Cell Types

Some CD38-binding proteins of the present invention have uses in the selective killing of specific target cells in the presence of untargeted, bystander cells. By targeting the delivery of Shiga toxin effector polypeptides to specific CD38 positive cells via a cell-targeting binding region(s), the binding proteins of the present invention can exhibit cell-type specific, restricted cell-kill activities resulting in the exclusive or selective killing of selected cell types in the presence of untargeted cells. In addition, the cell-targeted delivery of a cytotoxic, Shiga toxin effector polypeptide region using a CD38-binding protein of the present invention delivers cytotoxic components restricted exclusively or selectively to CD38 positive target cells in the presence of untargeted cells.

For some embodiments, the binding protein of the present invention is cytotoxic at certain concentrations. In some embodiments, upon administration of the binding protein of the present invention to a mixture of cell types, the cytotoxic binding protein is capable of selectively killing those cells which are physically coupled with extracellular CD38 bound by the binding region compared to cell types not physically coupled with any extracellular CD38. For some embodiments, the cytotoxic binding protein of the present invention is capable of selectively or preferentially causing the death of a specific cell type within a mixture of two or more different cell types. This enables targeting cytotoxic activity to specific cell types with a high preferentiality, such as a 3-fold cytotoxic effect, over "bystander" cell types that do not express the target biomolecule. Alternatively, the expression of the target biomolecule of the binding region may be non-exclusive to one cell type if the target biomolecule is expressed in low enough amounts and/or physically coupled in low amounts with cell types that are not to be targeted. This enables the targeted cell-killing of specific cell types with a high preferentiality, such as a 3-fold cytotoxic effect, over "bystander" cell types that do not express significant amounts of the target biomolecule or are not physically coupled to significant amounts of the target biomolecule.

For some embodiments, upon administration of the cytotoxic binding protein to two different populations of cell types, the cytotoxic binding protein is capable of causing cell death as defined by the half-maximal cytotoxic concentration ($CD_{50}$) on a population of target cells, whose members express an extracellular target biomolecule of the binding region of the cytotoxic binding protein, at a dose at least three-times lower than the $CD_{50}$ dose of the same cytotoxic binding protein to a population of cells whose members do not express an extracellular target biomolecule of the binding region of the cytotoxic binding protein.

For some embodiments, the cytotoxic activity of a binding protein of the present invention toward populations of cell types physically coupled with an extracellular CD38 bound by the binding region is at least 3-fold higher than the cytotoxic activity toward populations of cell types not physically coupled with any extracellular CD38 bound by the binding region. According to the present invention, selective cytotoxicity may be quantified in terms of the ratio (a/b) of (a) cytotoxicity towards a population of cells of a specific cell type physically coupled with extracellular CD38 bound by the binding region to (b) cytotoxicity towards a population of cells of a cell type not physically coupled with any extracellular CD38 bound by binding region. In some embodiments, the cytotoxicity ratio is indicative of selective cytotoxicity which is at least 3-fold, at least 5-fold, at least 10-fold, at least 15-fold, at least 20-fold, at least 25-fold, at least 30-fold, at least 40-fold, at least 50-fold, at least 75-fold, at least 100-fold, at least 250-fold, at least 500-fold, at least 750-fold, or at least 1000-fold higher for populations of cells or cell types physically coupled with a target biomolecule of the binding region compared to populations of cells or cell types not physically coupled with a target biomolecule of the binding region.

This preferential cell-killing function allows a targeted cell to be killed by certain cytotoxic, binding proteins of the present invention under varied conditions and in the presence of non-targeted bystander cells, such as ex vivo manipulated mixtures of cell types, in vitro cultured tissues with mixtures of cell types, or in vivo in the presence of multiple cell types (e.g. in situ or in a native location within a multicellular organism).

G. Production, Manufacture, and Purification of Shiga Toxin Effector Polypeptides and CD38-Binding Proteins The Shiga toxin effector polypeptides and CD38-binding proteins disclosed herein may be produced using techniques well known to those of skill in the art. For example, Shiga toxin effector polypeptides and CD38-binding proteins of the invention may be manufactured by standard synthetic methods, by use of recombinant expression systems, or by any other suitable method. Thus, Shiga toxin effector polypeptides and binding proteins of the invention may be synthesized in a number of ways, including, e.g. methods comprising: (1) synthesizing a polypeptide or polypeptide component of a binding protein using standard solid-phase or liquid-phase methodology, either stepwise or by fragment assembly, and isolating and purifying the final polypeptide compound product; (2) expressing a polynucleotide that encodes a protein or protein component of a binding protein of the invention in a host cell and recovering the expression product from the host cell or host cell culture; or (3) cell-free, in vitro expression of a polynucleotide encoding a polypeptide or polypeptide component of a binding protein of the invention, and recovering the expression product; or by any combination of the methods of (1), (2) or (3) to obtain fragments of the protein component, subsequently joining (e.g. ligating) the peptide or polypeptide fragments to obtain a polypeptide component, and recovering the polypeptide component.

In some embodiments, a CD38-binding protein of the present invention, or a protein component of a binding protein of the invention, may be synthesized by means of solid-phase or liquid-phase peptide synthesis. Polypeptides and binding proteins of the present invention may suitably be manufactured by standard synthetic methods. Thus, peptides may be synthesized by, e.g. methods comprising synthesizing the peptide by standard solid-phase or liquid-phase methodology, either stepwise or by fragment assembly, and isolating and purifying the final peptide product. In this context, reference may be made to WO 1998/011125 or, inter alia, Fields G et al., *Principles and Practice of Solid-Phase Peptide Synthesis* (Synthetic Peptides, Grant G, ed., Oxford University Press, U.K., 2nd ed., 2002) and the synthesis examples therein.

Shiga toxin effector polypeptides and CD38-binding proteins of the present invention may be prepared (produced and purified) using recombinant techniques well known in the art. In general, methods for preparing proteins by culturing host cells transformed or transfected with a vector comprising the encoding polynucleotide and purifying or recovering the protein from cell culture are described in, e.g., Sambrook J et al., *Molecular Cloning: A Laboratory Manual* (Cold Spring Harbor Laboratory Press, NY, U.S., 1989); Dieffenbach C et al., *PCR Primer: A Laboratory Manual* (Cold Spring Harbor Laboratory Press, N.Y., U.S., 1995). Any suitable host cell may be used to produce a polypeptide and/or binding protein of the invention. Host cells may be cells stably or transiently transfected, transformed, transduced or infected with one or more expression vectors which drive expression of a polypeptide of the invention. In addition, a Shiga toxin effector polypeptide and/or binding protein of the invention may be produced by modifying the polynucleotide encoding a polypeptide or binding protein of the invention that result in altering one or more amino acids or deleting or inserting one or more amino acids in order to achieve desired properties, such as changed cytotoxicity, changed cytostatic effects, and/or changed serum half-life.

There are a wide variety of expression systems which may be chosen to produce a polypeptide or CD38-binding protein of the present invention. For example, host organisms for expression of binding proteins of the invention include prokaryotes, such as *E. coli* and *B. subtilis*, eukaryotic cells, such as yeast and filamentous fungi (like *S. cerevisiae, P. pastoris, A. awamori*, and *K. lactis*), algae (like *C. reinhardtii*), insect cell lines, mammalian cells (like CHO cells), plant cell lines, and eukaryotic organisms such as transgenic plants (like *A. thaliana* and *N. benthamiana*).

Accordingly, the present invention also provides methods for producing a Shiga toxin effector polypeptide and/or binding protein of the present invention according to above recited methods and using a polynucleotide encoding part or all of a polypeptide of the invention or a protein component of a binding protein of the invention, an expression vector comprising at least one polynucleotide of the invention capable of encoding part or all of a polypeptide or binding protein of the invention when introduced into a host cell, and/or a host cell comprising a polynucleotide or expression vector of the invention.

In some embodiments, nucleic acids encoding a CD38-binding protein are prepared, for use in methods of making a CD38-binding protein of the invention. In some embodiments, a method of making a CD38-binding protein of the invention comprises contacting a host cell with the nucleic acid encoding the CD38-binding protein. The CD38-binding protein may be produced by culturing the host cell under conditions under which the CD38-binding protein is expressed, and recovering the protein. Culture conditions for producing recombinant proteins using various host cells are known to those of skill in the art. For example, in some embodiments, the host cell may be maintained in culture medium at 95° C. with 5% $CO_2$ atmosphere for a period of time sufficient to express the protein.

When a protein is expressed using recombinant techniques in a host cell or cell-free system, it is advantageous to separate (or purify) the desired protein away from other components, such as host cell factors, in order to obtain preparations that are of high purity or are substantially homogeneous. Purification can be accomplished by methods well known in the art, such as centrifugation techniques, extraction techniques, chromatographic and fractionation techniques (e.g. size separation by gel filtration, charge separation by ion-exchange column, hydrophobic interaction chromatography, reverse phase chromatography, chromatography on silica or cation-exchange resins such as DEAE and the like, chromatofocusing, and Protein A Sepharose chromatography to remove contaminants), and precipitation techniques (e.g. ethanol precipitation or ammonium sulfate precipitation). Any number of biochemical purification techniques may be used to increase the purity of a polypeptide and/or binding protein of the present invention. In some embodiments, the polypeptides and binding proteins of the invention may optionally be purified in homo-multimeric forms (e.g. a molecular complex comprising two or more polypeptides or binding proteins of the invention).

In embodiments, provided herein is a method of making a CD38-binding protein as described herein, the method comprising culturing a host cell as described herein under conditions wherein the CD38-binding protein is expressed, and recovering the protein. In some embodiments, the method comprises contacting the CD38-binding protein with protein L. In some embodiments, protein L is *Peptostreptococcus magnus* protein L. In some embodiments, protein L is produced recombinantly. In some embodiments, a protein L fragment or variant may be used, wherein the fragment or variant maintains the binding of protein L to kappa light chain variable domains (e.g., human VκI, VκIII and VκIV subtypes). In some embodiment, protein L is conjugated to a resin. In some embodiments, protein L is a matrix. Examples of protein L purification of antibody fragments are described in Royce, BioProcess International 2015; 13:6.

In the Examples below are descriptions of non-limiting examples of methods for producing illustrative Shiga toxin effector polypeptides and CD38-binding proteins of the present invention, as well as specific but non-limiting aspects of production methods.

Production or Manufacture of Pharmaceutical and/or Diagnostic Compositions comprising CD38-binding Fusion proteins Provided herein are compositions comprising a CD38-binding protein of the invention. In some embodiments, the CD38-binding protein may be in the form of a dimer (e.g., a homodimer). In some embodiments, the CD-38 binding proteins are members of a population of CD38-binding proteins, wherein at least about 50%, at least about 55%, at least about 60%, at least about 70%, at least about 75%, at least about 80%, at least about 85%, at least about 90%, at least about 95%, at least about 96%, at least about 97%, at least about 98%, at least about 99%, or 100% of the CD38-binding proteins of the population are in the form of a homodimer. In some embodiments, at least about 90% of the CD38-binding proteins of the population are in the form of a homodimer. In some embodiments, at least about 95% of the CD38-binding proteins of the population are in the form of a homodimer.

In some embodiments, the CD38-binding proteins are in the form of a dimer (e.g., a homodimer). In some embodiments, the CD38-binding proteins are members of a population of CD38-binding proteins, wherein the population is substantially free of monomers and multimers of higher order than dimers (e.g., trimers, tetramers, etc.). In some embodiments, a population that is "substantially free of" monomers and multimers of higher order than dimers (e.g., trimers, tetramers, etc.) has a ratio of dimers to monomers or to multimers of higher order than dimers of no more than about 2:1 to about 9:1. In some embodiments, the ratio is about 2:1, about 3:1, about 4:1, about 5:1, about 6:1, about 7:1, about 8:1, or about 9:1.

Pharmaceutically acceptable salts or solvates of any of the Shiga toxin effector polypeptides and CD38-binding proteins of the present invention are within the scope of the present invention.

The term "solvate" in the context of the present invention refers to a complex of defined stoichiometry formed between a solute (in casu, a proteinaceous compound or pharmaceutically acceptable salt thereof according to the invention) and a solvent. When the solvent in question is water, such a solvate is normally referred to as a hydrate.

Polypeptides and proteins of the present invention, or salts thereof, may be formulated as pharmaceutical compositions prepared for storage or administration, which typically comprise an effective amount of a molecule of the present invention, or a salt thereof, in a pharmaceutically acceptable carrier. The term "pharmaceutically acceptable carrier" includes any of the standard pharmaceutical carriers. Pharmaceutically acceptable carriers for therapeutic molecule use are well known in the pharmaceutical art, and are described, for example, in *Remington's Pharmaceutical Sciences* (Mack Publishing Co. (A. Gennaro, ed., 1985). As used herein, "pharmaceutically acceptable carrier" includes any and all physiologically acceptable, i.e. compatible, solvents, dispersion media, coatings, antimicrobial agents, isotonic, and absorption delaying agents, and the like.

VIII. POLYNUCLEOTIDES, EXPRESSION VECTORS, AND HOST CELLS

Beyond the polypeptides and binding proteins of the present invention, the polynucleotides that encode the polypeptide components and binding proteins of the invention, or functional portions thereof, are also encompassed within the scope of the present invention. The term "polynucleotide" is equivalent to the term "nucleic acid," each of which includes one or more of: polymers of deoxyribonucleic acids (DNAs), polymers of ribonucleic acids (RNAs), analogs of these DNAs or RNAs generated using nucleotide analogs, and derivatives, fragments and homologs thereof. The polynucleotide of the present invention may be single-, double-, or triple-stranded. Such polynucleotides are specifically disclosed to include all polynucleotides capable of encoding an illustrative protein, for example, taking into account the wobble known to be tolerated in the third position of RNA codons, yet encoding for the same amino acid as a different RNA codon (see Stothard P, *Biotechniques* 28: 1102-4 (2000)).

In one aspect, the present invention provides polynucleotides which encode a Shiga toxin effector polypeptide and/or binding protein of the present invention, or a fragment or derivative thereof. The polynucleotides may include, e.g., a nucleic acid sequence encoding a polypeptide at least 50%, at least 55%, at least 60%, at least 65%, at least 70%, at least 75%, at least 80%, at least 85%, at least 90%, at least 95%, at least 99% or more, identical to a polypeptide comprising one of the amino acid sequences of a polypeptide or binding protein of the present invention. The invention also includes polynucleotides comprising nucleotide sequences that hybridize under stringent conditions to a polynucleotide which encodes a Shiga toxin effector polypeptide component and/or binding protein of the invention, or a fragment or derivative thereof, or the antisense or complement of any such sequence.

Derivatives or analogs of the molecules of the present invention (e.g., CD38-binding proteins) include, inter alia, polynucleotide (or polypeptide) molecules having regions that are substantially homologous to the polynucleotides (or binding proteins of the present invention), e.g. by at least about 45%, about 50%, about 70%, about 80%, about 95%, about 98%, or even about 99% identity (e.g., an identity of 80-99%) over a polynucleotide (or polypeptide) sequence of the same size or when compared to an aligned sequence in which the alignment is done by a computer homology program known in the art. An illustrative program is the GAP program (Wisconsin Sequence Analysis Package, Version 8 for UNIX, Genetics Computer Group, University Research Park, Madison, Wis., U.S.) using the default settings, which uses the algorithm of Smith T, Waterman M, *Adv Appl Math* 2: 482-9 (1981). Also included are polynucleotides capable of hybridizing to the complement of a sequence encoding the binding proteins of the invention under stringent conditions (see e.g. Ausubel F et al., *Current Protocols in Molecular Biology* (John Wiley & Sons, New York, N.Y., U.S., 1993)), and below. Stringent conditions are known to those skilled in the art and may be found, e.g., in *Current Protocols in Molecular Biology* (John Wiley & Sons, NY, U.S., Ch. Sec. 6.3.1-6.3.6 (1989)).

The present invention additionally provides expression vectors that comprise the polynucleotides within the scope of the present invention. The polynucleotides capable of encoding the Shiga toxin effector polypeptide components and/or binding proteins of the invention may be inserted into known vectors, including bacterial plasmids, viral vectors and phage vectors, using material and methods well known in the art to produce expression vectors. Such expression vectors will include the polynucleotides necessary to support production of Shiga toxin effector polypeptides and/or binding proteins of the invention within any host cell of choice or cell-free expression systems (e.g. pTxb1 and pIVEX2.3). The specific polynucleotides comprising expression vectors for use with specific types of host cells or cell-free expression systems are well known to one of ordinary skill in the art, can be determined using routine experimentation, and/or may be purchased.

The term "expression vector," as used herein, refers to a polynucleotide, linear or circular, comprising one or more expression units. The term "expression unit" denotes a polynucleotide segment encoding a polypeptide of interest and capable of providing expression of the nucleic acid segment in a host cell. An expression unit typically comprises a transcription promoter, an open reading frame encoding the polypeptide of interest, and a transcription terminator, all in operable configuration. An expression vector contains one or more expression units. Thus, in the context of the present invention, an expression vector encoding a Shiga toxin effector polypeptide and/or binding protein of the invention comprising a single polypeptide chain includes at least an expression unit for the single polypeptide chain, whereas a protein comprising, e.g. two or more polypeptide chains (e.g. one chain comprising a $V_L$ domain and a second chain comprising a $V_H$ domain linked to a toxin effector polypeptide) includes at least two expression units, one for each of the two polypeptide chains of the protein. For expression of multi-chain binding proteins of the invention, an expression unit for each polypeptide chain may also be separately contained on different expression vectors (e.g. expression may be achieved with a single host cell into which expression vectors for each polypeptide chain has been introduced).

Expression vectors capable of directing transient or stable expression of polypeptides and proteins are well known in the art. The expression vectors generally include, but are not limited to, one or more of the following: a heterologous signal sequence or peptide, an origin of replication, one or more marker genes, an enhancer element, a promoter, and a transcription termination sequence, each of which is well known in the art. Optional regulatory control sequences, integration sequences, and useful markers that can be employed are known in the art.

The term "host cell" refers to a cell which can support the replication or expression of the expression vector. Host cells may be prokaryotic cells, such as *E. coli* or eukaryotic cells (e.g. yeast, insect, amphibian, bird, or mammalian cells). Creation and isolation of host cell lines comprising a polynucleotide of the invention or capable of producing a polypeptide and/or binding protein of the present invention can be accomplished using standard techniques known in the art.

Shiga toxin effector polypeptides and/or proteins within the scope of the present invention may be variants or derivatives of the polypeptides and molecules described herein that are produced by modifying the polynucleotide encoding a polypeptide and/or proteinaceous component of a binding protein by altering one or more amino acids or deleting or inserting one or more amino acids that may render it more suitable to achieve desired properties, such as more optimal expression by a host cell.

IX. MOLECULES IMMOBILIZED ON SOLID SUBSTRATES

Some embodiments of the present invention include a molecule of the present invention (e.g. a binding protein, fusion protein, or polynucleotide of the present invention), or any effector fragment thereof, immobilized on a solid substrate. Solid substrates disclosed herein include, but are not limited to, microbeads, nanoparticles, polymers, matrix materials, microarrays, microtiter plates, or any solid surface known in the art (see e.g. U.S. Pat. No. 7,771,955). In accordance with these embodiments, a molecule of the present invention may be covalently or non-covalently linked to a solid substrate, such as, e.g., a bead, particle, or plate, using techniques known to the skilled worker (see e.g. Jung Y et al., *Analyst* 133: 697-701 (2008)). Immobilized molecules of the invention may be used for screening applications using techniques known in the art (see e.g. Bradbury A et al., *Nat Biotechnol* 29: 245-54 (2011); Sutton C, *Br J Pharmacol* 166: 457-75 (2012); Diamante L et al., *Protein Eng Des Sel* 26: 713-24 (2013); Houlihan G et al., *J Immunol Methods* 405: 47-56 (2014)).

Non-limiting examples of solid substrates to which a CD38-binding fusion protein of the invention may be immobilized on include: microbeads, nanoparticles, polymers, nanopolymers, nanotubes, magnetic beads, paramagnetic beads, superparamagnetic beads, streptavidin coated beads, reverse-phase magnetic beads, carboxy terminated beads, hydrazine terminated beads, silica (sodium silica) beads and iminodiacetic acid (IDA)-modified beads, aldehyde-modified beads, epoxy-activated beads, diaminodipropylamine (DADPA)-modified beads (beads with primary amine surface group), biodegradable polymeric beads, polystyrene substrates, amino-polystyrene particles, carboxyl-polystyrene particles, epoxy-polystyrene particles, dimethylaminopolystyrene particles, hydroxy-polystyrene particles, colored particles, flow cytometry particles, sulfonate-polystyrene particles, nitrocellulose surfaces, reinforced nitrocellulose membranes, nylon membranes, glass surfaces, activated glass surfaces, activated quartz surfaces, polyvinylidene difluoride (PVDF) membranes, polyacrylamide-based substrates, poly-vinyl chloride substrates, poly-methyl methacrylate substrates, poly(dimethyl siloxane) substrates, and photopolymers which contain photoreactive species (such as nitrenes, carbenes, and ketyl radicals) capable of forming covalent linkages. Other examples of solid substrates to which a CD38-binding fusion protein of the invention may be immobilized on are commonly used in molecular display systems, such as, e.g., cellular surfaces, phages, and virus particles.

X. DELIVERY DEVICES AND KITS

In some embodiments, the invention relates to a device comprising one or more compositions of matter of the present invention, such as a pharmaceutical composition or a diagnostic composition, for delivery to a subject in need thereof. Thus, a delivery device comprising one or more compositions of the present invention can be used to administer to a subject a composition of matter of the present invention by various delivery methods, including: intravenous, subcutaneous, intramuscular or intraperitoneal injection; or by other suitable means recognized by a person of skill in the art.

Also within the scope of the present invention are kits comprising at least one composition of matter of the invention, and optionally, packaging and instructions for use. Kits may be useful for drug administration and/or diagnostic information gathering. A kit of the invention may optionally comprise at least one additional reagent (e.g., standards, markers and the like). Kits typically include a label indicating the intended use of the contents of the kit. The kit may further comprise reagents and other tools for detecting a cell type (e.g. a tumor cell) in a sample or in a subject, or for diagnosing whether a subject belongs to a group that responds to a therapeutic strategy which makes use of a compound, composition, or related method of the present invention, e.g., such as a method described herein.

XI. METHODS FOR USING CD38-BINDING PROTEINS AND/OR PHARMACEUTICAL AND/OR DIAGNOSTIC COMPOSITIONS THEREOF

Generally, it is an object of the present invention to provide pharmacologically active agents, as well as compositions comprising the same, that can be used in the prevention and/or treatment of a disease or condition associated with CD38 overexpression, such as in certain hematopoietic cancers, e.g., multiple myeloma, and other conditions associated with loss of growth control in CD38 positive cells. Accordingly, the present invention provides methods of using the polypeptides, CD38-binding proteins, and pharmaceutical compositions of the invention for the targeted killing of CD38 expressing cells, for delivering additional exogenous materials into such CD38 targeted cells, for labeling of the interiors of targeted cells, for collecting diagnostic information.

In particular, it is an object of the invention to provide such pharmacologically active agents, compositions, and/or methods that have certain advantages compared to the agents, compositions, and/or methods that are currently known in the art. Accordingly, the present invention provides methods of using Shiga toxin effector polypeptides and binding proteins with specified protein sequences and pharmaceutical compositions thereof. For example, any of the amino acid sequences described herein may be specifically utilized as a component of the binding protein used in the following methods or any method for using a binding protein known to the skilled worker, such as, e.g., various methods described in WO 2014/164680, WO 2014/164693, WO 2015/138435, WO 2015/138452, WO 2015/113005, WO 2015/113007, WO 2015/191764, US20150259428, WO 2016/196344, WO 2017/019623, WO 2018/106895, and WO 2018/140427.

The present invention provides methods of inhibiting the growth of a CD38 positive cell or a population of CD38 positive cells comprising the step of contacting the cell or the population, either in vitro, ex vivo, or in vivo, with a CD38-binding protein comprising a cytotoxic Shiga toxin effector polypeptide, or a pharmaceutical composition comprising a CD38 cell binding protein of the present invention. The present invention also provides methods of killing a CD38 positive cell comprising the step of contacting the cell, either in vitro, ex vivo, or in vivo, with a CD38-binding protein comprising a cytotoxic Shiga toxin effector polypeptide, or a pharmaceutical composition comprising a CD38 cell binding protein of the present invention. The Shiga CD38-binding proteins and pharmaceutical compositions of the present invention can be used to kill a CD38 expressing cell type upon contacting a cell or cells with one of the claimed compositions of matter. In some embodiments, a CD38-binding protein or pharmaceutical composition of the present invention can be used to kill a CD38 overexpressing cell types in a mixture of different cell types. In some embodiments, a CD38-binding protein, or pharmaceutical composition of the present invention can be used to kill CD38 positive hematopoietic cancer cells, such as myeloma cells, in a mixture of different cell types. One of skill in the art may determine the therapeutic concentration or dosage amount of CD38-binding proteins using one or more of a variety of methods well known in the art.

In some embodiments, certain CD38-binding proteins and pharmaceutical compositions of the present invention can show potent cell-kill activity when administered to a population of cells, in vitro, ex vivo or in vivo in a subject such as in a human subject in need of such treatment. By targeting the delivery of enzymatically active Shiga toxin A Subunit effector polypeptides using high-affinity binding regions to specific CD38-expressing cell types, cell-kill activities can be restricted to specifically and selectively killing those CD38-expressing cells within an organism.

The present invention provides a method of killing a CD38 positive blood cancer cell in a subject in need thereof, the method comprising the step of administering to the subject at least one CD38-binding protein of the present invention or a pharmaceutical composition thereof. In some embodiments, the subject has not previously received a CD38-based therapy, such as an anti-CD38 antibody (e.g., daratumumab). In some embodiments, the subject is immunocompetent. In some embodiments, the subject is immunocompromised. In some embodiments, the subject has not previously received an autologous stem cell transplant.

In some embodiments, the subject has previously received one or more CD38-based therapies, such as an anti-CD38 antibody (e.g., daratumumab) prior to administration of CTM#4. In some embodiments, the methods further comprise administering a CD38-based therapy, such as an anti-CD38 antibody (e.g., daratumumab) in addition to CTM#4.

In some embodiments, the subject has multiple myeloma and the CD38-binding protein is the first treatment administered to the subject. In some embodiments, the subject has multiple myeloma and the CD38-binding protein is administered subsequent or concurrently with another treatment.

In some embodiments, the CD38-binding protein of the present invention or pharmaceutical compositions thereof can be used to kill a cancer cell in a subject by targeting an extracellular CD38 found physically coupled with a cancer cell. The terms "cancer cell" or "cancerous cell" refer to various neoplastic cells which grow and divide in an abnormally accelerated and/or unregulated fashion and will be clear to the skilled person. The CD38 positive hematopoietic cancers (either malignant or non-malignant) that may benefit from methods and compositions of the invention will be clear to the skilled person. Neoplastic cells are often associated with one or more of the following: unregulated growth, lack of differentiation, local tissue invasion, angiogenesis, and metastasis.

It is within the scope of the present invention to utilize the CD38-binding protein of the present invention, or pharmaceutical composition thereof, for the purposes of ex vivo depletion of CD38 positive blood cells, e.g., T cells and/or B-cells, from isolated cell populations removed from a subject.

Administration of an "effective dosage" of a composition of the present invention can result in a decrease in severity of disease symptoms, an increase in frequency and duration of disease symptom-free periods, or a prevention of impairment or disability due to the disease affliction. The effective amount of a composition of the present invention will depend on the route of administration, the type of organism being treated, and the physical characteristics of the specific subject under consideration. These factors and their relationship to determining this amount are well known to skilled practitioners in the medical arts. This amount and the method of administration can be tailored to achieve optimal efficacy, and may depend on such factors as weight, diet, concurrent medication and other factors, well known to those skilled in the medical arts. The dosage sizes and dosing regimen most appropriate for human use may be guided by the results obtained by the present invention, and may be confirmed in properly designed clinical trials. An effective dosage and treatment protocol may be determined by conventional means, starting with a low dose in laboratory animals and then increasing the dosage while monitoring the effects, and systematically varying the dosage regimen as well. Numerous factors may be taken into consideration by a clinician when determining an optimal dosage for a given subject. Dosages may be selected and readjusted by the skilled health care professional as required to maximize therapeutic benefit for a particular subject. Such considerations are known to the skilled person.

In some embodiments, the invention provides a method of treating a blood cancer, comprising administering to a subject in need thereof a CD38-binding protein or composition comprising the same. In some embodiments, the invention provides a method of treating a blood cancer, comprising administering to a subject in need thereof an effective amount of a CD38-binding protein or composition comprising the same. The blood cancer may be, for example, multiple myeloma, non-Hodgkin's lymphoma (NHL), Burkitt's lymphoma (BL), B chronic lymphocytic leukemia (B-CLL), B and T acute lymphocytic leukemia (ALL), T cell lymphoma (TCL), acute myeloid leukemia (AML), hairy cell leukemia (HCL), Hodgkin's Lymphoma (HL), chronic myeloid leukemia (CML). In some embodiments, the blood cancer is multiple myeloma. In some embodiments, the myeloma is relapsed or refractory.

In some embodiments, the invention provides a method of treating a condition related to multiple myeloma, comprising administering to a subject in need thereof a CD38-binding protein or composition comprising the same. In some embodiments, the invention provides a method of treating a condition related to multiple myeloma, comprising administering to a subject in need thereof an effective amount of a CD38-binding protein or composition comprising the same.

In some embodiments, the invention provides a method of treating melanoma, comprising administering to a subject in need thereof a CD38-binding protein or composition comprising the same. In some embodiments, the invention provides a method of treating melanoma, comprising administering to a subject in need thereof an effective amount of a CD38-binding protein or composition comprising the same.

In some embodiments, the present methods do not comprise transplanting into the subject an autologous stem cell.

A pharmaceutical composition of the present invention may be administered via one or more suitable routes of administration, using one or more of a variety of methods known in the art. As will be appreciated by the skilled worker, the route and/or mode of administration will vary depending upon the desired results. An acceptable route of administration may refer to any administration pathway known in the art which may be taken into consideration by a clinician in conjunction with the intended therapeutic or diagnostic use, such as by parenteral administration which is typically associated with injection at or in communication with the intended site of action (e.g., intravenous administration).

Pharmaceutical compositions of the present invention will typically be administered to the same subject on multiple occasions. Intervals between single dosages can vary and may be on regular or irregular cycles, based on regulating blood levels or other markers in the subject.

In some embodiments, the present invention provides methods for treating blood cell cancers associated with CD38 overexpression in a mammalian subject, such as a human subject, the method comprising the step of administering to a subject in need thereof an effective amount of a cytotoxic CD38-binding protein or pharmaceutical composition of the present invention. In some embodiments, the blood cell cancer is multiple myeloma (MM).

H. Formulations of the CD38-Binding Fusion Proteins

The present invention provides CD38-binding proteins for use in a pharmaceutical composition, for treatment or prophylaxis of cancer, and/or conditions, diseases, or symptoms associated with CD38 overexpression described in further detail below (e.g. blood cancers including hematopoietic cancers of CD38 positive cells, such as multiple myeloma). The present invention provides pharmaceutical compositions comprising a CD38-binding protein of the present invention, or a pharmaceutically acceptable salt or solvate thereof, according to the invention, together with at least one pharmaceutically acceptable carrier, excipient, or vehicle. In some embodiments, the pharmaceutical composition of the present invention may comprise homo-dimeric forms of a binding protein of the present invention. Each such disease, condition, disorder, or symptom is envisioned to be a separate embodiment with respect to uses of a pharmaceutical composition according to the invention. The invention also provides pharmaceutical compositions for use in at least one method of treatment according to the invention, as described in more detail below.

As used herein, the term "subject" refers to any organism, commonly mammalian subjects, such as humans and animals. The terms "subject" and "patient" are used interchangeably. In some embodiments, the subject may be a mammal, such as a primate (e.g., a human or non-human primate), a livestock animal (e.g. cow, horse, pig, sheep, goat, etc.), a companion animal (e.g. cat, dog, etc.) and a laboratory animal (e.g. mouse, rabbit, rat, etc.). In some embodiments, the subject may present symptoms, signs, and/or indications of at least one condition associated with CD38 cell overexpression.

As used herein, the terms "treat," "treating," or "treatment", and grammatical variants thereof, have the same meaning as commonly understood by those of ordinary skill in the art. In some embodiments, these terms may refer to an approach for obtaining beneficial or desired clinical results. The terms may refer to slowing the onset or rate of development of a condition, disorder or disease, reducing or alleviating symptoms associated with it, generating a complete or partial regression of the condition, or some combination of any of the above. For the purposes of this invention, beneficial or desired clinical results include, but are not limited to, reduction or alleviation of symptoms, diminishment of extent of disease, stabilization (e.g. not worsening) of state of disease, delay or slowing of disease progression, amelioration or palliation of the disease state, and remission (whether partial or total), whether detectable or undetectable. "Treat," "treating," or "treatment" can also mean prolonging survival relative to expected survival time if not receiving treatment. A subject (e.g. a human) in need of treatment may thus be a subject already afflicted with the disease or disorder in question. The terms "treat," "treating," or "treatment" includes inhibition or reduction of an increase in severity of a pathological state or symptoms relative to the absence of treatment, and is not necessarily meant to imply complete cessation of the relevant disease or condition.

As used herein, the terms "prevent," "preventing," "prevention" and grammatical variants thereof refer to an approach for preventing the development of, or altering the pathology of, a condition or disease. Accordingly, "prevention" may refer to prophylactic or preventive measures. For the purposes of this invention, beneficial or desired clinical results include, but are not limited to, prevention or slowing of symptoms, progression or development of a disease, whether detectable or undetectable. A subject (e.g. a human) in need of prevention may thus be a subject not yet afflicted with the disease or disorder in question. The term "prevention" includes slowing the onset of disease relative to the absence of treatment, and is not necessarily meant to imply permanent prevention of the relevant disease, disorder or condition. Thus "preventing" or "prevention" of a condition may in certain contexts refer to reducing the risk of developing the condition, or preventing or delaying the development of symptoms associated with the condition.

As used herein, an "effective amount" is an amount effective for treating and/or preventing a disease, disorder, or condition as disclosed herein. In some embodiments, an effective amount is an amount or dose of a composition (e.g. a therapeutic composition, compound, or agent) that produces at least one desired therapeutic effect in a subject, such as preventing or treating a target condition or beneficially alleviating a symptom associated with the condition. The most desirable effective amount is an amount that will produce a desired efficacy of a particular treatment selected by one of skill in the art for a given subject in need thereof. This amount will vary depending upon a variety of factors understood by the skilled worker, including but not limited to the characteristics of the therapeutic composition (including activity, pharmacokinetics, pharmacodynamics, and bioavailability), the physiological condition of the subject (including age, sex, disease type, disease stage, general physical condition, responsiveness to a given dosage, and type of medication), the nature of the pharmaceutically acceptable carrier or carriers in the formulation, and the route of administration. One skilled in the clinical and pharmacological arts will be able to determine an effective amount through routine experimentation, namely by monitoring a subject's response to administration of a composition and adjusting the dosage accordingly (see e.g. *Remington: The Science and Practice of Pharmacy* (Gennaro A, ed., Mack Publishing Co., Easton, Pa., U.S., 19th ed., 1995)).

In some embodiments, the CD38-binding proteins described herein are intended for intraveneous infusion. In some embodiments, the CD38-binding proteins are formulated in an aqueous buffer solution containing a cryogenic protectant and a surfactant. In some embodiments, the CD38-binding proteins described herein are formulated in an aqueous sodium citrate buffer solution containing sucrose as a cryogenic protectant and polysorbate 80 as a surfactant and having a pH ranging from 4.8-5.2. In some embodiments, the CD38-binding proteins are formulated in a solution comprising between about 1 mM and about 100 mM sodium citrate. In some embodiments, the CD38-binding proteins are formulated in a solution comprising between about 1 mM and about 300 mM sucrose. In some embodiments, the CD38-binding proteins are formulated in a solution comprising an aqueous solution of between about 0.01% and about 0.15% % Polysorbate 80. In some embodiments, the aqueous solution has a pH ranging from about 4.3 to about 5.5. In some embodiments, the composition comprises an aqueous solution of about 20 mM sodium citrate, about 200 mM sucrose, and about 0.02% Polysorbate 80, wherein the aqueous solution has a pH ranging from about 4.8 to about 5. In some embodiments, the CD38-binding proteins described herein are formulated in 20 mM sodium citrate buffer, pH 5.0, with 200 mM sucrose and 0.02% (volume/volume) polysorbate 80. An exemplary formulation is listed below:

| Ingredient | Amount per ml | Function |
| --- | --- | --- |
| CTM#4 | 0.50 mg | Active Ingredient |
| Sodium Citrate, dihydrate | 3.82 mg | Buffering agent, conjugated base |
| Citric Acid, monohydrate | 1.47 mg | Buffering agent, acid |
| Sucrose | 68.4 mg | Cryogenic protectant |
| Polysorbate 80 | 0.2 mg | Surfactant stabilizer |
| Water for Injection (WFI) | q.s. to 1 mL | Solvent |
| Sodium Hydroxide | As needed to adjust to pH 4.8 to 5.2 | Base, adjust pH |
| Hydrochloric Acid | As needed to adjust to pH 4.8 to 5.2 | Acid, adjust pH |

The formulations of the pharmaceutical compositions of the invention may conveniently be presented in unit dosage form and may be prepared by any of the methods well known in the art of pharmacy. In such form, the composition is divided into unit doses containing appropriate quantities of the active component. Compositions may be formulated for any suitable route and means of administration.

In some embodiments, a pharmaceutical composition comprises: (i) a CD38-binding protein comprising: (A) a cytotoxic Shiga toxin A subunit effector polypeptide; and (B) a binding region capable of specifically binding an extracellular part of human CD38, wherein the binding region comprises: (a) an immunoglobulin light chain variable region comprising a CDR1 comprising the amino acid sequence of SEQ ID NO: 31; a CDR2 comprising the amino acid sequence of SEQ ID NO: 32; and a CDR3 comprising the amino acid sequence of SEQ ID NO: 33; and; (b) an immunoglobulin heavy chain variable region comprising: a CDR1 comprising the amino acid sequence of SEQ ID NO: 34; a CDR2 comprising the amino acid sequence of SEQ ID NO: 35; and a CDR3 comprising the amino acid sequence of SEQ ID NO: 36; and (ii) a pharmaceutically acceptable carrier, excipient or buffer.

Diagnostic compositions of the present invention comprise a CD38-binding protein of the present invention and one or more detection promoting agents. When producing or manufacturing a diagnostic composition of the present invention, a binding protein of the present invention may be directly or indirectly linked to one or more detection promoting agents. There are numerous standard techniques known to the skilled worker for incorporating, affixing, and/or conjugating various detection promoting agents to proteins or proteinaceous components of molecules, especially to immunoglobulins and immunoglobulin-derived domains.

There are numerous detection promoting agents known to the skilled worker, such as isotopes, dyes, colorimetric agents, contrast enhancing agents, fluorescent agents, bioluminescent agents, and magnetic agents, which can be operably linked to the polypeptides or binding proteins of the invention for information gathering methods, such as for diagnostic and/or prognostic applications to diseases or conditions of an organism (see e.g. Cai W et al., *J Nucl Med* 48: 304-10 (2007); Nayak T, Brechbiel M, *Bioconjug Chem* 20: 825-41 (2009); Paudyal P et al., *Oncol Rep* 22: 115-9 (2009); Qiao J et al., *PLoS ONE* 6: e18103 (2011); Sano K et al., *Breast Cancer Res* 14: R61 (2012)). The incorporation of the agent is in such a way to enable the detection of the presence of the diagnostic composition in a screen, assay, diagnostic procedure, and/or imaging technique.

Similarly, there are numerous imaging approaches known to the skilled worker, such as non-invasive in vivo imaging techniques commonly used in the medical arena, for example: computed tomography imaging (CT scanning), optical imaging (including direct, fluorescent, and bioluminescent imaging), magnetic resonance imaging (MRI), positron emission tomography (PET), single-photon emission computed tomography (SPECT), ultrasound, and x-ray computed tomography imaging.

1. Dosing of CTM#4

In some embodiments, the effective amount is a first effective amount and the methods of the present invention further comprise administering to a subject a second effective amount. In some embodiments, the second effective amount is a subsequent dose. In some embodiments, the starting dose of CTM#4 is about 665 μg/kg body weight, and the subsequent dose is about 831 μg/kg body weight. In some embodiments, the starting dose is about 831 μg/kg body weight, and the subsequent dose is about 1039 μg/kg body weight. In some embodiments, the starting dose is about 1039 μg/kg body weight, and the subsequent dose is about 1299 μg/kg body weight. In some embodiments, the starting dose is about 1299 μg/kg body weight, and the subsequent dose is about 1624 μg/kg body weight.

In some embodiments, 50 μg/kg of the CTM#4 CD38-binding fusion protein is administered to a subject once per week. For example, the CTM#4 CD38-binding protein may be administered to a subject for 1, 2, 3, 4 weeks, or more. In some embodiments, the CD38 molecule is administered to the subject on days 1, 8, 15 and/or 22.

In some embodiments, 100 μg/kg of the CTM#4 CD38 targeting molecule is administered to a subject once per week. For example, the CD38-binding protein may be administered to a subject for 1, 2, 3, 4 weeks, or more. In some embodiments, the CD38 molecule is administered to the subject on days 1, 8, 15 and/or 22.

In some embodiments, 200 μg/kg of the CTM#4 CD38-binding protein is administered to a subject once per week. For example, the CD38-binding protein may be administered to a subject for 1, 2, 3, 4 weeks, or more. In some embodiments, the CD38 molecule is administered to the subject on days 1, 8, 15 and/or 22.

In some embodiments, 335 μg/kg of the CTM#4 CD38-binding protein is administered to a subject once per week. For example, the CD38-binding protein may be administered to a subject for 1, 2, 3, 4 weeks, or more. In some embodiments, the CD38 molecule is administered to the subject on days 1, 8, 15 and/or 22.

In some embodiments, 500 μg/kg of the CTM#4 CD38-binding protein is administered to a patient once per week. For example, the CD38-binding protein may be administered to a subject for 1, 2, 3, 4 weeks, or more. In some embodiments, the CD38 molecule is administered to the subject on days 1, 8, 15 and/or 22.

In some embodiments, 550 μg/kg of the CTM#4 CD38-binding protein is administered to a patient once per week. For example, the CTM#4 CD38-binding protein may be administered to a subject for 1, 2, 3, 4 weeks, or more. In some embodiments, the CD38 molecule is administered to the subject on days 1, 8, 15 and/or 22.

In some embodiments, 665 μg/kg of the CTM#4 CD38-binding protein is administered to a subject once per week. For example, the CD38-binding protein may be administered to a subject for 1, 2, 3, 4 weeks, or more. In some embodiments, the CD38 molecule is administered to the subject on days 1, 8, 15 and/or 22.

In some embodiments, 50 μg/kg of the CTM#4 CD38-binding protein is administered to a subject every other week. In some embodiments, the CTM#4 CD38 molecule is administered to the subject on days 1 and 15.

In some embodiments, 100 μg/kg of the CTM#4 CD38-binding protein is administered to a subject every other week. In some embodiments, the CD38 molecule is administered to the subject on days 1 and 15.

In some embodiments, 200 μg/kg of the CTM#4 CD38-binding protein is administered to a subject every other week. In some embodiments, the CTM#4 CD38 molecule is administered to the subject on days 1 and 15.

In some embodiments, 335 μg/kg of the CTM#4 CD38-binding protein is administered to a subject every other week. In some embodiments, the CTM#4 CD38 molecule is administered to the subject on days 1 and 15.

In some embodiments, 500 μg/kg of the CTM#4 CD38-binding protein is administered to a subject every other week. In some embodiments, the CTM#4 CD38 molecule is administered to the subject on days 1 and 15.

In some embodiments, 550 μg/kg of the CTM#4 CD38-binding protein is administered to a subject every other week. In some embodiments, the CTM#4 CD38 molecule is administered to the subject on days 1 and 15.

In some embodiments, 665 μg/kg of the CTM#4 CD38-binding protein is administered to a subject every other week. In some embodiments, the CTM#4 CD38 molecule is administered to the subject on days 1 and 15.

2. Methods of Treating Blood Cancers Including Multiple Myeloma

In some embodiments, a method of treating a blood cancer (e.g., multiple myeloma) comprises administering to a subject in need thereof the CTM#4 CD38-binding protein in an amount of 50 μg/kg, 100 μg/kg, 200 μg/kg, 335 μg/kg, 500 μg/kg, or 665 μg/kg of the subject's body weight.

In some embodiments, a method of treating a blood cancer (e.g., multiple myeloma) comprises administering to a subject in need thereof the CTM#4 CD38-binding protein in an amount of 50 μg/kg of the subject's body weight on each of days 1, 8, 15, and 22, wherein day 8 is one week later than day 1; day 15 is one week later than day 8; and day 22 is one week later than day 15.

In some embodiments, a method of treating a blood cancer (e.g., multiple myeloma) comprises administering to a subject in need thereof the CTM#4 CD38-binding protein in an amount of 100 μg/kg of the subject's body weight on each of days 1, 8, 15, and 22, wherein day 8 is one week later than day 1; day 15 is one week later than day 8; and day 22 is one week later than day 15.

In some embodiments, a method of treating a blood cancer (e.g., multiple myeloma) comprises administering to a subject in need thereof the CTM#4 CD38-binding protein in an amount of 200 μg/kg of the subject's body weight on each of days 1, 8, 15, and 22, wherein day 8 is one week later than day 1; day 15 is one week later than day 8; and day 22 is one week later than day 15.

In some embodiments, a method of treating a blood cancer (e.g., multiple myeloma) comprises administering to a subject in need thereof the CTM#4 CD38-binding protein in an amount of 335 μg/kg of the subject's body weight on each of days 1, 8, 15, and 22, wherein day 8 is one week later than day 1; day 15 is one week later than day 8; and day 22 is one week later than day 15.

In some embodiments, a method of treating a blood cancer (e.g., multiple myeloma) comprises administering to a subject in need thereof the CTM#4 CD38-binding protein in an amount of 500 μg/kg of the subject's body weight on each of days 1, 8, 15 and 22, wherein day 8 is one week later than day 1; day 15 is one week later than day 8; and day 22 is one week later than day 15.

In some embodiments, a method of treating a blood cancer (e.g., multiple myeloma) comprises administering to a subject in need thereof the CTM#4 CD38-binding protein in an amount of 550 μg/kg of the subject's body weight on each of days 1, 8, 15, and 22, wherein day 8 is one week later than day 1; day 15 is one week later than day 8; and day 22 is one week later than day 15.

In some embodiments, a method of treating the CTM#4 a blood cancer (e.g., multiple myeloma) comprises administering to a subject in need thereof a CD38-binding protein in an amount of 665 μg/kg of the subject's body weight on each of days 1, 8, 15, and 22, wherein day 8 is one week later than day 1; day 15 is one week later than day 8; and day 22 is one week later than day 15.

In some embodiments, invention provides the CTM#4 method of treating a human subject (generally with a confirmed diagnosis of MM) by administering the CTM#4 cytotoxic CD38-binding proteins or pharmaceutical compositions comprising the CTM#4 cytotoxic CD38-binding fusion protein described herein.

In some embodiments, the subject is an adult human patient (e.g., greater than or equal to 18 years of age). In some embodiments, the subject is a juvenile subject (e.g., less than 18 year of age). In some embodiments, the subject is a male. In some embodiments, the subject is a female. In some embodiments, the subject has a confirmed diagnosis of multiple myeloma.

In some embodiments, the subject suffers from Relapsed or Refractory Multiple Myeloma (RRMM). In some embodiments, the RRMM human subject has failed treatment with, is intolerant to, or is not a candidate for available therapies that are known to confer clinical benefit in RRMM patients.

In some embodiments, the RRMM subject has received at least three prior lines of MM therapy and is refractory or intolerant to at least one proteasome inhibitor (PI) based therapy, at least one immunomodulatory drug (IMiD) based therapy, and optionally at least one steroid based therapy. The prior lines of MM therapy can include one or more anti-CD38 therapy, including but not limited to daratumumab.

In some embodiments, the RRMM subject has received at least three prior lines of MM therapy including daratumumab, and is relapsed or refractory to daratumumab, at least one proteasome inhibitor (PI) based therapy, at least one immunomodulatory drug (IMiD) based therapy, and optionally at least one steroid based therapy.

In some embodiments, the RRMM subject has received at least three prior lines of MM therapy, and is refractory to at least one proteasome inhibitor (PI) based therapy, at least one immunomodulatory drug (IMiD) based therapy, and optionally at least one steroid based therapy. The prior lines of MM therapy do not include any anti-CD38 therapy.

In some embodiments, the RRMM subject has received at least two prior lines of MM therapy if one of these two lines includes a combination of a PI based therapy and an IMiD based therapy, and the subject is refractory to at least one PI based therapy, at least one IMiD based therapy, and optionally at least one steroid based therapy. One or more of the prior lines of MM therapy can include an anti-CD38 therapy, including but not limited to daratumumab.

In some embodiments, the RRMM subject has received at least two prior lines of MM therapy, wherein one of these two lines includes a combination of a PI based therapy and an IMiD based therapy, and the other line includes daratumumab, and the subject is relapsed or refractory to daratumumab, at least one PI based therapy, at least one IMiD based therapy, and optionally at least one steroid based therapy.

In some embodiments, the RRMM subject has received at least two prior lines of MM therapy if one of these two lines includes a combination of a PI based therapy and an IMiD based therapy, and the subject is refractory to at least one PI based therapy, at least one IMiD based therapy, and optionally at least one steroid based therapy. The prior lines of MM therapy do not include any anti-CD38 therapy.

In some embodiments, the RRMM subject has received prior lines of anti-CD38 therapy, including but not limited to daratumumab, and the subject is relapsed or refractory to the anti_CD38 therapy at any time during treatment with the CTM#4 CD38-binding protein described herein.

In some embodiments, the subject has not received any prior lines of MM therapy. In some embodiments, the subject has not received any prior anti-CD38-based therapies.

In some embodiments, the RRMM subject contains at least one of the following critia, including the serum concentration of M-protein >=500 mg/dL (>=5 g/L) on serum protein electrophoresis (SPEP); the urine concentration of M-protein >=200 mg/24 h on urine protein electrophoresis (UPEP); and an involved free light chain (FLC) level >=10 mg/dL (>=100 milligram per liter [mg/L]) measured by serum FLC assay provided the serum FLC ratio is abnormal.

In some embodiments, the RRMM subject has Eastern Cooperative Oncology Group (ECOG) performance status score of 0 or 1.

In some embodiments, the RRMM subject has normal QT interval corrected by the Fridericia method (QTcF) on screening electrocardiogram (ECG), defined as QTcF of <=450 millisecond (ms) in males or <=470 ms in females.

In some embodiments, the RRMM subject meets or substantially meets the following clinical laboratory criteria, including total bilirubin <=1.5*the upper limit of the normal range (ULN), except for participant with Gilbert's syndrome, in whom the direct bilirubin must be <2.0*ULN; serum alanine aminotransferase (ALT) and aspartate aminotransferase (AST) <=2.5*ULN; estimated glomerular filtration rate (eGFR) >=30 milliliters per minute (mL/min/1.73 square meter [m^2], using the modification of diet in renal disease (MDRD) equation; absolute neutrophil count (ANC) >=750 per cubic millimeter (/mm^3) (>=1.0*10^9 per liter [/L]); platelet count >=50,000/mm^3 (>=75*10^9/L); hemoglobin >=7.5 g/dL.

In some embodiments, the RRMM subject does not have one or more of the conditions including (1) polyneuropathy, organomegaly, endocrinopathy, monoclonal gammopathy and skin changes (POEMS) syndrome, monoclonal gammopathy of unknown significance, smoldering myeloma, solitary plasmacytoma, amyloidosis, Waldenström macroglobulinemia, or Immunoglobulin M (IgM) myeloma; (2) sensory or motor neuropathy of NCI CTCAE Grade >=3; (3) a final dose of any of the following treatments/procedures including myeloma-specific therapy including PIs and IMiDs within 14 days, corticosteroid therapy for myeloma within 7 days, radiation therapy for localized bone lesions within 14 days, major surgery within 30 days, autologous stem cell transplant within 90 days; (4) having received allogeneic stem cell transplant or organ transplantation; (5) having not recovered, to NCI CTCAE V5 Grade <=1 or baseline, from adverse reactions to prior myeloma treatment or procedures (chemotherapy, immunotherapy, radiation therapy) excluding alopecia; (6) clinical signs of central nervous system (CNS) involvement of MM; (7) known or suspected light chain amyloidosis of any organ (the presence of amyloid on the bone marrow biopsy without other evidence of amyloidosis is acceptable); (8) congestive heart failure (New York Heart Association) class >=II or left ventricular ejection fraction (LVEF <40%, cardiac myopathy, active ischemia, or any other uncontrolled cardiac condition such as angina pectoris or myocardial infarction within the past 6 months, clinically significant arrhythmia requiring therapy including anticoagulants, or clinically significant uncontrolled hypertension; (9) chronic or active infection requiring systemic therapy, as well as a history of symptomatic viral infection that has not been fully cured (example, human immunodeficiency viruses (HIV) or viral hepatitis B or C); (10) a history of systemic inflammatory response syndrome (SIRS)/cytokine release syndrome (CRS) reactions following infusion with any monoclonal antibodies or Chimeric Antigen Receptor (CAR) T-cell therapy; and (11) a chronic condition requiring the use of systemic corticosteroids at a dose of >10 milligram per day (mg/day) of prednisone or equivalent. In some embodiments, the subject does not have a history of significant pleural or pericardial effusions. In some embodiments, the subject does not have a history of hypersensitivity or serious toxic reactions to kanamycin or other aminoglycosides.

In some embodiments, the subject described herein is infused intravenously with 1 to 1500 μg of a CD38-binding protein per kilogram body weight once or twice a week for three or more consecutive weeks, such as for four, five, or six weeks. Illustrative dosage includes 50, 100, 200, 335, 500, 550 and 665 μg of a CD38-binding protein per kilogram body weight. Illustrative administration regime includes once a week for 4 weeks on days 1, 8, 15, and 28; or once every two weeks for 4 weeks on day 1 and 15.

In some embodiments of the methods of the present invention, the cancer being treated is multiple myeloma (MM).

VIII. EXAMPLES

The Examples below describe illustrative CD38-binding proteins of the present invention comprising (1) an immunoglobulin-type, CD38-binding region; and (2) a de-immunized and furin-cleavage resistant Shiga toxin A Subunit effector polypeptide. Each CD38-binding region of the illustrative binding proteins exhibits high-affinity binding to an extracellular part of a human CD38 target molecule physically-coupled to the surface of one or more specific cell-type(s). Each Shiga toxin A Subunit effector polypeptide of the illustrative binding protein exhibits catalytic activity resulting in eukaryotic ribosome inhibition. These illustrative binding proteins of the present invention bind to CD38 expressed by target cells and associated with the cell surface and subsequently enter target cells by internalization. Then, the internalized binding proteins effectively route a Shiga toxin A Subunit effector polypeptide component to the cytosol and kill target cells directly via ribosome inhibition as a result of the catalytic activity of a Shiga toxin effector. Illustrative CD38-binding proteins are capable of killing CD38-expressing cells in the presence of the anti-CD38 antibody daratumumab.

A. Example 1

CD38-Binding Proteins Comprising De-Immunized and Furin-Cleavage Resistant, Shiga Toxin A Subunit Derived Polypeptides Binding proteins were created and tested—the binding proteins each comprising 1) a cell-targeting binding region which binds human CD38, and 2) a de-immunized Shiga toxin effector polypeptide which is furin-cleavage resistant.

Previously, Shiga toxin A Subunit derived, binding proteins have been constructed and shown to promote cellular internalization and direct intracellular routing of their Shiga toxin effector polypeptide components to the cytosol (see e.g. WO 2014/164680, WO 2014/164693, WO 2015/138435, WO 2015/138452, WO 2015/113005, WO 2015/113007, WO 2015/191764, WO 2016/196344, PCT/US2017/065074, and WO 2018/106895). In this Example, binding proteins targeting cell-surface CD38 were created. As demonstrated below, these CD38-binding proteins were capable, upon exogenous administration, of specifically binding and killing CD38-expressing human cancer cells.

1. Construction of Illustrative CD38-Binding Proteins

Figure 1B:
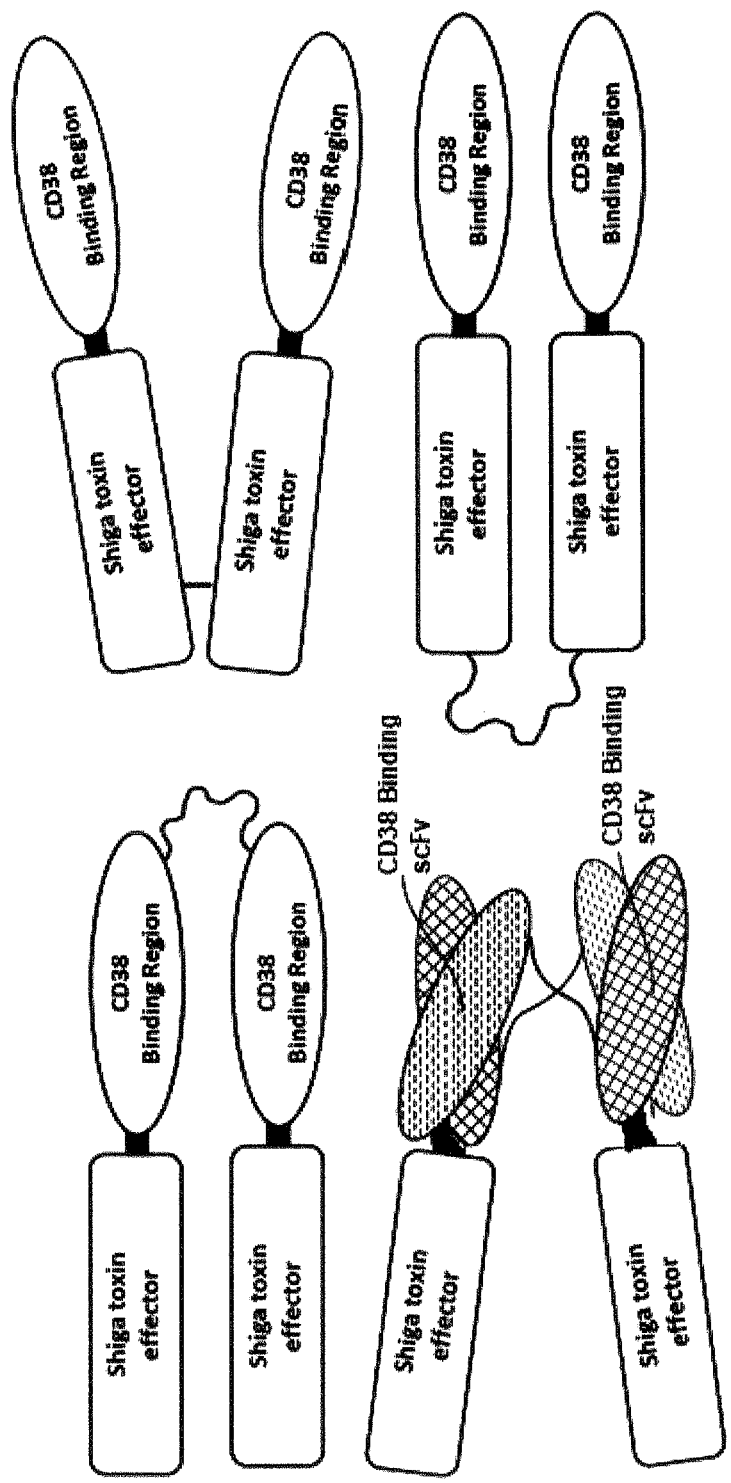

Using techniques known in the art, illustrative CD38-binding proteins were created comprising 1) a de-immunized and furin-cleavage resistant Shiga toxin A Subunit effector polypeptide, and 2) a CD38-binding immunoglobulin-derived polypeptide separated by a proteinaceous linker (see, e.g., FIG. 1A-1B). The resulting cell-targeting fusion proteins were constructed such that each comprised a continuous polypeptide comprising the CD38-binding immunoglobulin-derived polypeptide fused to a de-immunized and furin-cleavage resistant Shiga toxin A Subunit effector polypeptide.

In this Example, all the Shiga toxin effector polypeptide components of the binding proteins are derived from amino acids 1-251 of SLT-1A (SEQ ID NO:1) or StxA (SEQ ID NO:2), and certain of them contained two or more amino acid residue substitutions relative to a wild-type Shiga toxin A Subunit, such as, e.g., de-immunizing substitutions and/or furin-cleavage motif disrupting substitutions (see e.g. WO 2015/113007, WO 2015/191764, and WO 2016/196344) or an insertion of three amino acid residues to aid in purification. Illustrative Shiga toxin effector polypeptide components of the binding proteins are provided in SEQ ID NOs: 45-69. For each illustrative CD38-binding protein, the Shiga toxin effector polypeptide was linked to a CD38-binding region using a proteinaceous linker.

A library of CD38-targeting antibodies fused to de-immunized Shiga toxin effectors was screened in a variety of efficacy and safety models to identify candidates. First, over fifty different CD38-binding proteins were constructed and screened for targeted cytotoxicity to CD38 positive myeloma and lymphoma cells in vitro. All of the binding proteins tested in the experiments of this Example were produced in a bacterial system and purified by column chromatography using techniques known to the skilled worker, such as, e.g., intein mediated purification via a chitin-binding tag (see e.g. WO 2016/126950 at Example 1), using a polyhistidine-tag in the binding protein, and/or using a bacterial protein bound by an immunoglobulin domain in the binding protein, for instance, using a bacterial protein such as Protein A or Protein L.

Illustrative binding proteins that were produced and tested in this Example include CD38-binding protein #1 (SEQ ID NO:76, FIG. 25A), CD38-binding protein #2 (SEQ ID NO:77, FIG. 25B), CD38-binding protein #3 (SEQ ID NO:78, FIG. 25C), CD38-binding protein #4 (SEQ ID NO:79, FIG. 25D), CD38-binding protein #5 (SEQ ID NO:80), and CD38-binding protein #6 (SEQ ID NO:81).

Initially, fifty CD38-binding proteins derived from twenty-five sets of anti-CD38 antibody variable domain sequences were created. For each of the anti-CD38 antibodies, single-chain variable fragments (scFv's) were generated wherein the CD38-binding domain variable regions of the antibody were arranged in one of two orientations, either the light chain (VL) is closer to the amino terminus (VL-VH) or the heavy chain (VH) closer to the amino terminus (VH-VL). The scFvs were fused to a de-immunized Shiga toxin A Subunit effector polypeptide to create over fifty different CD38-binding proteins for screening, analysis, and comparison. Each CD38-binding protein comprises at least one single-chain variable fragment as a potential CD38-binding region.

The fifty CD38-binding proteins were produced in $E.\ coli$ with an intein-chitin binding domain (CBD) tag and then purified with chitin affinity and dithiothreitol (DTT) elution (as described previously in WO 2016/126950). The resulting CD38-binding proteins were screened for cytotoxicity to CD38 positive cells. A reference molecule referred to herein as CD38-targeting reference molecule #1 (SEQ ID NO:83) was also used to evaluate the screening results, e.g. by setting a cytotoxic potency benchmark.

2. II. Screening CD38-Binding Proteins for Cytotoxicity to CD38 Positive Cells

The cytotoxic activities of illustrative binding proteins are measured using a tissue culture cell-based toxicity assay. The concentration of exogenously administered binding protein which kills half the cells in a homogenous cell population (half-maximal cytotoxic concentration) was determined for certain binding proteins. The cytotoxicities of illustrative binding proteins are tested using cell-kill assays involving either target biomolecule positive or target biomolecule negative cells with respect to the target biomolecule of each binding protein's binding region.

Certain CD38-expression target cells used in this Example (MOLP-8, H929, ST486, Daudi, ANBL6, MM.1S, LP-1, and RPMI8226) are immortalized tumor cells available from the ATCC (Manassas Va., U.S.) or the DSMZ (The Leibniz Deutsche Sammlung von Mikroorganismen and Zellkulture) (Braunschweig, DE)).

The cell-kill assays were performed as follows. Human tumor cell line cells were plated (typically at 2×103 cells per well) in 20 μL cell culture medium in 384-well plates. A series of (typically 10-fold dilutions) of the protein to be tested was prepared in an appropriate buffer, and 5 μL of the dilutions or only buffer as a negative control were added to the cells. Control wells containing only cell culture medium were used for baseline correction. The cell samples were incubated with the proteins or just buffer for 2 to 3 days at 37° C. and in an atmosphere of 5% carbon dioxide ($CO_2$). The total cell survival or percent viability was determined using a luminescent readout using the CellTiter-Glo® Luminescent Cell Viability Assay 2.0 (G924A Promega Madison, Wis., U.S.) according to the manufacturer's instructions as measured in relative light units (RLU).

The Percent Viability of experimental wells was calculated using the following equation: (Test RLU−Average Media RLU)÷(Average Cells RLU−Average Media RLU)× 100. Log protein concentration versus Percent Viability was plotted in Prism (GraphPad Prism, San Diego, Calif., U.S.)

and log (inhibitor) versus response (3 parameter) analysis were used to determine the half-maximal cytotoxic concentration ($CD_{50}$) value for the tested proteins. The $CD_{50}$ values for each illustrative cell-targeting protein tested was calculated when possible. When $CD_{50}$ values could not be calculated based on the shape of the curve over the concentrations tested, then a maximum $CD_{50}$ value was noted as being beyond the maximum tested value. In some experiments, biomolecule target negative cells treated with the maximum concentration of the binding protein did not show any change in viability as compared to a buffer only control.

The specificity of the cytotoxic activity of a given CD38-binding protein was determined by comparing cell kill activities toward cells expressing a significant amount of CD38 (target positive cells) with cell-kill activities toward cells which do not exhibit any significant amount of CD38 physically coupled to any cellular surface (target negative cells). This was accomplished by determining the half-maximal cytotoxic concentrations of a given binding protein toward cell populations which were positive for cell surface expression of the target biomolecule of the binding protein being analyzed, and, then, using the same binding protein concentration range to attempt to determine the half-maximal cytotoxic concentrations toward cell populations which were negative for cell surface expression of the target biomolecule of the CD38-binding protein. In some experiments, the target negative cells treated with the maximum amount of the Shiga-toxin containing molecule did not show any change in viability as compared to a "buffer only" negative control. In addition, an isolated Shiga toxin effector region polypeptide was used as untargeted, negative control.

Figure 2:
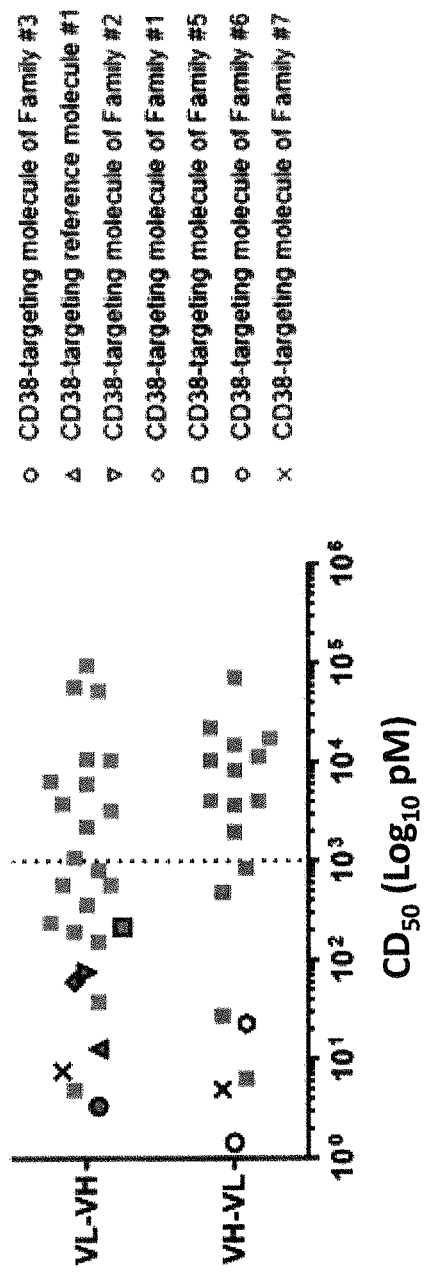

The data in Table 5 shows the cytotoxicity results using the cell-kill assay described above for fifty CD38-binding proteins derived from twenty-five anti-CD38 antibody variable domain sequences toward CD38 positive tumor cells. The cytotoxicity for each compared to the cytotoxicity of CD38-targeting reference molecule #1 (SEQ ID NO:83) is shown in the right-hand columns. For each cell-type tested, the cytotoxicity of CD38-targeting reference molecule #1 (SEQ ID NO:80) was analyzed in six different experiments and the mean was calculated and used for the comparison (e.g. the fold-change calculation shown in Table 5). FIG. 2 shows the results of screening the cytotoxic activities of these fifty-one CD38-binding proteins toward CD38 positive H929 myeloma cells, as determined using a Cell Titer-Glo viability assay. Additional cytotoxicity data is reported in Tables 7-9 and 13-14 and in FIGS. 3A-3C, 4A-4B and 8A-8E. Representative $CD_{50}$ values in this assay for the CD38-targeting reference molecule #1 (SEQ ID NO:83) are 37 pM to ST486 cells and 44 pM to Daudi cells.

TABLE 5

Cytotoxic Activities of CD38-binding proteins

| Protein | $CD_{50}$ (ng/mL) | | | | Fold change in $CD_{50}$ relative to CD38-Targeting Reference Molecule #1 | | | |
|---|---|---|---|---|---|---|---|---|
| | MOLP-8 | H929 | ST486 | Daudi | MOLP-8 | H929 | ST486 | Daudi |
| 1 | 32.4 | 2.53 | 14.03 | 22.88 | 3.6 | 3.0 | 8.6 | 8.8 |
| 2 | 25.7 | 4.2 | 9.1 | 6.9 | 2.9 | 5.1 | 5.6 | 2.7 |
| 3 | >20,000 | 1,918 | 1,661 | >20,000 | N/A | 2310.8 | 1019.0 | N/A |
| 4 | 19.9 | 6.7 | 1.9 | 6.8 | 2.2 | 8.1 | 1.2 | 2.6 |
| 5 | 8.9 | 0.7 | 1.1 | 5.3 | 1.0 | 0.8 | 0.7 | 2.0 |
| 6 | 232.7 | 63.4 | 302.6 | 253.3 | 26.0 | 76.4 | 185.6 | 97.4 |
| 7 | 3023 | 914.1 | 1126 | >20,000 | 337.4 | 1101.3 | 690.8 | N/A |
| 8 | 165 | 23.7 | 18.2 | 267.3 | 18.4 | 28.6 | 11.2 | 102.8 |
| 9 | 8090 | 2476 | 1768 | 13052 | 902.9 | 2983.1 | 1084.7 | 5020.0 |
| 10 | 35 | 17 | 3.9 | 41 | 3.9 | 20.5 | 2.4 | 15.8 |
| 11 | 8.54 | 0.55 | 4.13 | 0.88 | 1.0 | 0.7 | 2.5 | 0.3 |
| 12 | 8.26 | 0.84 | 0.25 | 5.47 | 0.9 | 1.0 | 0.2 | 2.1 |
| 13 | 91.8 | 53.6 | 9.5 | 93.2 | 10.2 | 64.6 | 5.8 | 35.8 |
| 14 | >20,000 | 1,156 | 498 | >20,000 | N/A | 1392.8 | 305.5 | N/A |
| 15 | >20,000 | >20,000 | >20,000 | >20,000 | N/A | N/A | N/A | N/A |
| 16 | 57 | 40 | 13 | 66 | 6.4 | 48.2 | 8.0 | 25.4 |
| 17 | 1436 | 217.6 | 507.7 | 2593 | 160.3 | 262.2 | 311.5 | 997.3 |
| 18 | 55.57 | 21.14 | 3.34 | 56.16 | 6.2 | 25.5 | 2.0 | 21.6 |
| 19 | >20,000 | >20,000 | >20,000 | >20,000 | N/A | N/A | N/A | N/A |
| 20 | 772 | 356 | 248 | 2,719 | 86.2 | 428.9 | 152.1 | 1045.8 |
| 21 | 30.66 | 3.03 | 9.86 | 2.18 | 3.4 | 3.7 | 6.0 | 0.8 |
| 22 | 2.26 | 0.54 | ~0.014 | ~0.2 | 0.3 | 0.7 | NC | NC |
| 23 | >20,000 | >20,000 | >20,000 | >20,000 | N/A | N/A | N/A | N/A |
| 24 | 73.76 | 63.48 | 7.94 | 119.5 | 8.2 | 76.5 | 4.9 | 46.0 |
| 25 | >20,000 | >20,000 | >20,000 | >20,000 | N/A | N/A | N/A | N/A |
| 26 | >20,000 | 10,635 | 6,056 | >20,000 | N/A | 1281.3 | 3715.3 | N/A |
| 27 | 10,300 | 1,661 | 1,782 | >20,000 | 1149.6 | 2001.2 | 1093.3 | N/A |
| 28 | >20,000 | 6,411.0 | >20,000 | >20,000 | N/A | 7724.1 | N/A | N/A |
| 29 | 6072 | 1270 | 1366 | 9346 | 677.7 | 1530.1 | 838.0 | 3594.6 |
| 30 | 160 | 119 | 28 | 208 | 17.9 | 143.4 | 17.2 | 80.0 |
| 31 | 266.8 | 93.22 | 110.1 | 120.3 | 29.8 | 112.3 | 67.5 | 46.3 |
| 32 | 730.2 | 88.2 | 238.8 | 602.1 | 81.5 | 106.3 | 146.5 | 231.6 |
| 33 | >20,000 | >20,000 | >20,000 | dnt | N/A | N/A | N/A | N/A |
| 34 | 249.3 | 244.8 | 34.4 | 137.2 | 27.8 | 294.9 | 21.1 | 52.8 |
| 35 | >20,000 | >20,000 | 8,856 | >20,000 | N/A | N/A | 5433.1 | N/A |
| 36 | 4,395 | 1,189 | 3,516 | >20,000 | 490.5 | 1432.5 | 2157.1 | N/A |
| 37 | 148.7 | 406.6 | 89.7 | 566.6 | 16.6 | 489.9 | 55.0 | 217.9 |
| 38 | 12,585.0 | 707.4 | 2,752.0 | 9,111.0 | 1404.6 | 852.3 | 1688.3 | 3504.2 |

TABLE 5-continued

Cytotoxic Activities of CD38-binding proteins

| Protein | CD$_{50}$ (ng/mL) | | | | Fold change in CD$_{50}$ relative to CD38-Targeting Reference Molecule #1 | | | |
|---|---|---|---|---|---|---|---|---|
| | MOLP-8 | H929 | ST486 | Daudi | MOLP-8 | H929 | ST486 | Daudi |
| 39 | >20,000 | >20,000 | >20,000 | >20,000 | N/A | N/A | N/A | N/A |
| 40 | >20,000 | 5,846.0 | 7,902.0 | >20,000 | N/A | 7043.4 | 4847.9 | N/A |
| 41 | >20,000 | >20,000 | >20,000 | >20,000 | N/A | N/A | N/A | N/A |
| 42 | 2,528 | 421 | 551 | 4,741 | 282.1 | 507.2 | 338.0 | 1823.5 |
| 43 | 6,029.0 | 445.5 | 2,414.0 | 7,613.0 | 672.9 | 536.7 | 1481.0 | 2928.1 |
| 44 | 188.8 | 26.4 | 16.4 | 751.6 | 21.1 | 31.8 | 10.1 | 289.1 |
| 45 | 6.18 | 0.16 | 0.62 | 1.72 | 0.7 | 0.2 | 0.4 | 0.7 |
| 46 | 8.49 | 0.37 | 2.95 | 1.52 | 0.9 | 0.4 | 1.8 | 0.6 |
| 47 | >20,000 | 7,925 | 12,282 | >20,000 | N/A | 9548.0 | 7535.0 | N/A |
| 48 | 151 | 663 | 621 | >20,000 | 16.9 | 798.8 | 381.0 | N/A |
| 49 | 844.7 | 452 | 286.35 | 698.25 | 94.3 | 544.6 | 175.7 | 268.6 |
| 50 | 12.4 | 8.4 | 1.3 | 5.5 | 1.4 | 10.1 | 0.8 | 2.1 |
| reference molecule | 8.96 | 0.83 | 1.63 | 2.6 | 1.0 | 1.0 | 1.0 | 1.0 |

*"dnt" (did not test) denotes that data was not collected for that cell-type
"N/A" denotes that a relative change compared to reference was not applicable when a precise CD$_{50}$ value was not obtained, e.g. >20,000.

The initial pool of fifty CD38-binding proteins was narrowed down to eighteen molecules by cytotoxic potency using this cell-kill assay. Then, a subset of these eighteen were selected for further testing. In Table 6, sets of proteins from the screening library that share the same CDR sequences are grouped into families, for example, Family #1 includes proteins 3 and 4, Family #2 includes proteins 49 and 50, Family #3 includes proteins 45 and 46, Family #5 includes proteins 1 and 2, and Family #6 includes proteins 7 and 8 (see Table 2). For each of these families, the CD38-binding regions are structurally similar, having identical CDR sequences. Each family can be defined by its set of CDRs: Family #1 comprises a set of 6 CDRs represented by SEQ ID NOs: 19-24, Family #2 comprises a set of 6 CDRs represented by SEQ ID NOs:25-30, Family #3 comprises a set of 6 CDRs represented by SEQ ID NOs: 31-36, etc.

TABLE 6

Molecules Comprising the Same CDR Sets Form Families

| CD38-Binding Region Family | heavy chain CDR1 | heavy chain CDR2 | heavy chain CDR3 | light chain CDR1 | light chain CDR2 | light chain CDR3 |
|---|---|---|---|---|---|---|
| #1 | GFTFSDYY (SEQ ID NO: 110) | ISGSGGST (SEQ ID NO: 111) | AREHSNY FYGMDV (SEQ ID NO: 112) | SSNIGSNY (SEQ ID NO: 114) | GNS (SEQ ID NO: 115) | QSYDSSLS GSG (SEQ ID NO: 116) |
| #2 | GFTFSSYW (SEQ ID NO: 118) | ISGSGGGT (SEQ ID NO: 119) | AREGETS FGLDV (SEQ ID NO: 120) | SSNIGGNY (SEQ ID NO: 122) | RNN (SEQ ID NO: 123) | QSYDSSLS VS (SEQ ID NO: 124) |
| #3 | GYSFTSYW (SEQ ID NO: 102) | IYPGDSDT (SEQ ID NO: 103) | ARGPSTG FWSGNY FDY (SEQ ID NO: 104) | TGAVTSG FY (SEQ ID NO: 106) | ATN (SEQ ID NO: 107) | LVYYDGAW (SEQ ID NO: 108) |
| #5 | GFTFNNYD (SEQ ID NO: 210) | ISYDGSDK (SEQ ID NO: 211) | ARVYYY GFSGPSM DV (SEQ ID NO: 212) | NSNIGSNT (SEQ ID NO: 213) | SDS (SEQ ID NO: 214) | QSYDSSLS GSR (SEQ ID NO: 215) |
| #6 | GFTFSDYY (SEQ ID NO: 216) | ISSSSSYI (SEQ ID NO: 217) | ATEGPYY LYGFDI (SEQ ID NO: 218) | SSNIGSNY (SEQ ID NO: 219) | GNS (SEQ ID NO: 220) | QSYDNTLS GV (SEQ ID NO: 221) |

TABLE 6-continued

Molecules Comprising the Same CDR Sets Form Families

| CD38-Binding Region Family | heavy chain CDR1 | heavy chain CDR2 | heavy chain CDR3 | light chain CDR1 | light chain CDR2 | light chain CDR3 |
|---|---|---|---|---|---|---|
| #7 | GFTFDDYG (SEQ ID NO: 222) | INWNGGST (SEQ ID NO: 223) | ARGGLFHDSSGYYFGH (SEQ ID NO: 224) | SSNIGNSY (SEQ ID NO: 225) | RNN (SEQ ID NO: 226) | SAWDDNLSV (SEQ ID NO: 227) |

FIG. 2 shows representative $CD_{50}$ values toward CD38 positive H929 myeloma cells for various molecules in the pool with certain molecules marked: A screening cutoff of 1 nM is represented by a vertical dashed line—with $CD_{50}$ values to the left being more potent than the cutoff and $CD_{50}$ values to the right being less potent than the cutoff. Any molecule that did not exhibit a $CD_{50}$ of 20,000 ng/mL or less was not included in FIG. 2.

FIG. 2 shows that proteins from Families 1-3 and 5-6 exhibited potent cytotoxicity to CD38 positive myeloma cells in vitro and these were more potent than many of the other molecules in the pool. CD38-binding proteins from Families 1-3 and 5-6 were further characterized below.

3. Selecting Candidates and Further Testing of Best Hits from Screen

The library of fifty candidates was narrowed by considering, inter alia, cytotoxic potency to CD38 positive cells in vitro, binding affinity to both human and cynomolgus CD38, competition with monoclonal CD38 antibodies, and manufacturability. As the screening pool was narrowed down by various criteria, the CD38-binding regions in Families 1-3 and 5-6 were studied in more detail using the following molecules: CD38-binding protein #1 (SEQ ID NO:76), CD38-binding protein #2 (SEQ ID NO:77), CD38-binding protein #3 (SEQ ID NO:78), CD38-binding protein #4 (SEQ ID NO:79), CD38-binding protein #5 (SEQ ID NO:80), and CD38-binding protein #6 (SEQ ID NO:81). Table 7 shows initial $CD_{50}$ values for these five illustrative CD38-binding proteins derived from the screen. Family #1 includes CD38-binding protein #1 (SEQ ID NO:76), Family #2 includes CD38-binding protein #2 (SEQ ID NO:77), Family #3 includes CD38-binding protein #3 (SEQ ID NO:78) and CD38-binding protein #4 (SEQ ID NO:79), Family #5 includes CD38-binding protein #5 (SEQ ID NO:80), and Family #6 includes CD38-binding protein #6 (SEQ ID NO:81).

TABLE 7

Cytotoxic Potency of Selected CD38-binding proteins to Various CD38 Positive Cell Types

| CD38-binding protein | Cytotoxicity $CD_{50}$ (ng/mL) | | | | |
|---|---|---|---|---|---|
| | MOLP-8 | H929 | ST486 | Daudi | U266 |
| CD38-binding protein #1 | 4.7 | 12.6 | 3.4 | 10.3 | >20,000 |
| CD38-binding protein #2 | 7.3 | 13.8 | 2.4 | 8 | >20,000 |
| CD38-binding protein #3 | 2.2 | 0.2 | <0.1 | 0.8 | >20,000 |
| CD38-binding protein #5 | 16.8 | 17.9 | 3.9 | 26.8 | >20,000 |

TABLE 7-continued

Cytotoxic Potency of Selected CD38-binding proteins to Various CD38 Positive Cell Types

| CD38-binding protein | Cytotoxicity $CD_{50}$ (ng/mL) | | | | |
|---|---|---|---|---|---|
| | MOLP-8 | H929 | ST486 | Daudi | U266 |
| CD38-binding protein #6 | 17.1 | 42.6 | 7.2 | 109 | >20,000 |
| CD38-targeting reference molecule #1 | 3.5 | 0.8 | 2.3 | 2.2 | >20,000 |

After optimizing protein production and purification of certain candidates from the screen, additional cell-kill assays were performed to further evaluate and compare candidate CD38-binding proteins. CD38-binding proteins were purified via different methods, such as using Protein A or Protein L chromatography. Some CD38-binding proteins were altered by the introduction of additional amino acid residues in the Shiga toxin effector polypeptide or amino acid substitutions in the light chain of the CD38-binding scFv region.

Cytotoxicity assays were performed using various CD38-binding proteins as described above and reported in Table 8 and FIG. 3A-3C. Additionally, specificity of cytotoxicity to CD38-expressing cells was shown by performing the cytotoxicity assay with cells from the CD38 negative cell line U266. There was no significant cytotoxic activity exhibited toward the CD38 negative cells under the conditions tested (see e.g. FIG. 3C and Tables 7-8, last columns).

TABLE 8

Cytotoxicity of Selected CD38-binding proteins to Human Myeloma Cell Lines

| CD38-binding protein | Cytotoxicity $CD_{50}$ (ng/mL) | | |
|---|---|---|---|
| | MOLP-8 | H929 | U266 |
| CD38-binding protein #3 | 0.27 | 0.015 | >2,000 |
| CD38-binding protein #4 | 0.17 | 0.005 | >2,000 |
| CD38-targeting reference molecule #1 | 6.97 | 0.19 | >2,000 |
| Shiga toxin effector polypeptide only control | >2,000 | >2,000 | >2,000 |

Although CD38-binding protein #6 (SEQ ID NO:81) showed CD38 specificity and high cytotoxic potency, the relative cytotoxic activity of CD38-binding protein #6 (SEQ ID NO:81) was not as high as many other candidates.

CD38-binding proteins were tested for cytotoxic activity in primate cells, either human or non-human primate cells. BLCL-C162 is a rhesus cell line that expresses CD38. Results are shown in Table 9A-9B, FIG. 4A (Human), and FIG. 4B (Monkey).

TABLE 9A

Cytotoxicity of Selected CD38-binding proteins to CD38 Positive Primate Cell Lines

| | Cytotoxicity $CD_{50}$ (ng/mL) | |
|---|---|---|
| CD38-Tageting Molecule | human MOLP-8 | rhesus BLCL-C162 |
| CD38-binding protein #1 | 18.3 | 4,619 |
| CD38-binding protein #2 | 10.5 | 1,126 |
| CD38-binding protein #4 | 0.23 | 26 |
| CD38-targeting reference molecule #1 | 1.4 | >2,000 |
| Shiga toxin effector polypeptide only control | >2,000 | >2,000 |

TABLE 9B

Cytotoxicity of CD38-binding protein #4 to CD38 Positive Human Cell Lines

| | Cytotoxicity $CD_{50}$ (pM) | | | |
|---|---|---|---|---|
| CD38-Tageting Molecule | MOLP8 | RPMI8226 | ANBL6 | NCI-H929 |
| CD38-binding protein #4 | 0.7 | 1.2 | 17.7 | <0.34 |

A 2-hour exposure of CD38-binding protein #4 (SEQ ID NO:79) to ANBL6 cells was measured to result in cytotoxicities characterized by $CD_{50}$ values of about 0.1 and 0.16 nM.

A 2-hour exposure of CD38-binding protein #4 (SEQ ID NO:79) to ANBL6 cells was measured to result in cytotoxicities characterized by $CD_{50}$ values of about 0.1 and 0.16 nM.

CD38-binding protein #4 (SEQ ID NO:79) was cytotoxic in vitro to CD38 positive target cells in whole blood and PBMCs, indicating that the presence of red blood cells did not inhibit cytoxicity in this assay.

CD38-binding protein #4 (SEQ ID NO:79) was cytotoxic in vitro to multiple myeloma subject derived samples.

The catalytic (ribosomal inhibition) and cytotoxic activities for the certain CD38-binding proteins were tested to investigate the mechanism of action of these cytotoxic molecules. The ribosome inactivation capabilities of CD38-binding proteins were determined using a cell-free, in vitro protein translation assay using the TNT® Quick Coupled Transcription/Translation kit (L1170 Promega Madison, Wis., U.S.). The kit includes Luciferase T7 Control DNA (L4821 Promega Madison, Wis., U.S.) and TNT® Quick Master Mix. The ribosome activity reaction was prepared according to manufacturer instructions. A series (typically 10-fold) of dilutions were prepared in appropriate buffer and a series of identical TNT reaction mixture components were created for each dilution. The molecule to be tested was combined with each of the TNT reaction mixtures along with the Luciferase T7 Control DNA. The test samples were incubated for 1.5 hours at 30° C. After the incubation, Luciferase Assay Reagent (E1483 Promega, Madison, Wis., U.S.) was added to all test samples and the amount of luciferase protein translation was measured by luminescence according to the manufacturer instructions. The level of translational inhibition was determined by non-linear regression analysis of log-transformed concentrations of total protein versus relative luminescence units. Using software (GraphPad Prism, San Diego, Calif., U.S.), the half maximal inhibitory concentration (IC50) value was calculated for each sample using the Prism software function of log (inhibitor) vs. response (three parameters) [Y=Bottom+((Top-Bottom)/(1+10^(X−LogIC50)))] under the heading dose-response-inhibition. The results are shown in Table 10 and FIG. 5.

TABLE 10

Ribosome Inhibition Activities of Selected CD38-binding proteins

| CD38-binding protein | Protein Synthesis Inhibition $IC_{50}$ (ng/mL) |
|---|---|
| CD38-binding protein #4 | 1.45 |
| CD38-targeting reference molecule #1 | 1.16 |
| Shiga toxin effector polypeptide only control | 1.97 |

The catalytic activity of the CD38-binding protein #4 (SEQ ID NO: 79) was comparable to the SLTA effector polypetide alone and the CD38 targeting reference control molecule #1 (Table 10).

4. Testing Binding proteins for CD38 Targeting Using Cell Binding and Purified CD38-Binding Assays Cell binding affinity assays were performed to quantitate the binding affinity for certain CD38-binding proteins to CD38-expressing cells.

The binding of the CD38-binding proteins to recombinant human CD38 protein or recombinant cynomolgus CD38 protein (Sino Biological, Wayne, Pa., U.S.) was determined with an enzyme-linked immunosorbent assay (ELISA) binding assay. Nunc® Maxisorp™ plates were coated with of recombinant, human or cynomolgus monkey CD38 in PBS overnight at 4° C. The wells were washed and blocked, and then incubated with a dilution series of the CD38-binding protein being tested. The bound CD38-binding proteins are detected in a two-step method with a murine monoclonal antibody which detects the deimmunized toxin domain, then an anti-mouse horseradish peroxidase (HRP) conjugated secondary antibody. After detecting the HRP signal with TMB Ulttra and stopping the reaction with acid, the ELISA signal (absorbance at 450 nanometers (nm) ("Abs 450")) was read with a plate reader. The molecules CD38-binding protein #2 (SEQ ID NO:77), CD38-binding protein #3 (SEQ ID NO:78), and CD38-binding protein #4 (SEQ ID NO:79) each bound to both human and monkey CD38, whereas CD38-targeting reference molecule #1 (SEQ ID NO:83) bound to human CD38 (FIG. 6A) but not cynomolgus CD38 (FIG. 6B) in this assay (Table 11). In other experiments, CD38-binding protein #1 (SEQ ID NO:76) was also shown to bind to human and cynomolgus CD38 protein.

TABLE 11

CD38-Binding Affinity of Selected CD38-binding proteins

| | $K_D$ of CD38-Binding (ng/mL) | |
|---|---|---|
| CD38-binding protein | human CD38 | cynomolgous CD38 |
| CD38-binding protein #2 | 10.6 | 644 |
| CD38-binding protein #3 | 13.3 | 247 |
| CD38-binding protein #4 | 16.4 | 670 |
| CD38-targeting reference molecule #1 | 7.7 | No binding |

All the CD38-binding proteins tested in this experiment bound to human CD38 with a similar binding affinity; however, binding to cynomolgus CD38 differed among the molecules. The molecules CD38-binding protein #1 (SEQ ID NO:76), CD38-binding protein #2 (SEQ ID NO:77), CD38-binding protein #3 (SEQ ID NO:78), and CD38-binding protein #4 (SEQ ID NO:79) each bound to cynomolgus CD38. Binding to both human and cynomolgus CD38 is useful because cynomolgus animals may be used as a model for human subjects to help determine, estimate, and understand the in vivo effects and behavior of the CD38-binding protein, such as, e.g., regarding pharmacokinetics, pharmacodynamics, and toxicology; wherein the model may have target binding and target cell killing by the binding protein which is translatable to a related species such as human.

In another experiment, the binding characteristics of CD38-targeting reference molecule #1 (SEQ ID NO:83) were analyzed using a fluorescence-based, flow-cytometry assay. Samples containing CD38 positive (CD38+) cells (of either the cell line A or F) were suspended in 1× PBS containing one percent bovine serum albumin (BSA) (Calbiochem, San Diego, Calif., U.S.), hereinafter referred to as "1× PBS+1%BSA", and incubated for one hour at 4° C. with 100 µL of various dilutions of CD38-targeting reference molecule #1 (SEQ ID NO:83). After the one-hour incubation, the cell samples were washed twice with 1× PBS+1%BSA. The cell samples were incubated for one hour at 4° C. with 100 µL of 1× PBS+1%BSA containing α-SLT-1A pAb1, then washed again and incubated for one hour at 4° C. with 100 µL of 1× PBS+1%BSA solution containing an anti-rabbit secondary antibody conjugated to fluorescein isothiocyanate (FITC). The cell samples were washed twice with 1× PBS+1%BSA, resuspended in 200 µL of 1× PBS and subjected to fluorescence-based, flow cytometry to assay the percentage of cells bound by sufficient secondary antibody, indicative of the binding levels of CD38-targeting reference molecule #1 (SEQ ID NO:83) to the cells in each sample. The data for all the samples in mean fluorescence intensity units (MFI), in relative fluorescence units, was obtained by gating the data using a negative control sample of cells which was not treated with any cell-targeting molecule but which was incubated with a rabbit polyclonal antibody α-SLT-1A (pAb1) (Harlan Laboratories, Inc. Indianapolis, Ind., U.S.) and then an anti-rabbit secondary antibody. The integrated MFI (iMFI) was calculated by multiplying the percentage of positive cells with the MFI. Using the Prism software function of one-site binding [Y=Bmax*X/(KD+X)] under the heading binding-saturation, the Bmax and KD were calculated using baseline corrected data. The Bmax measured for CD38-targeting reference molecule #1 binding to two CD38+ cell types were measured to be approximately 100,000 iMFI, and the KD values of the CD38-targeting reference molecule #1 (SEQ ID NO:83) binding those CD38+ cells were measured to be approximately 2-7 nM. CD38-targeting reference molecule #1 (SEQ ID NO:83) did not exhibit binding to CD38 negative in this assay under the conditions described.

5. Mapping CD38-Binding Epitopes of Binding Proteins

To help characterize CD38-binding protein candidates from the pool, further CD38-binding studies were conducted. An epitope mapping service (by shotgun mutagenesis) was performed by Integral Molecular, Inc. (Philadelphia, Pa., U.S.) (standard assay setup with alanine scanning and additional mutations to change the amino acids from the human to cynomolgus residue as appropriate) to identify the contact residues for binding to the CD38 extracellular domain (ECD).

The assay was performed as follows. Wildtype or mutated CD38 ECD was expressed on the cell surface of HEK293 cells, and then the ability of a CD38-binding protein of interest to bind to the CD38 ECD when certain amino acids were mutated was compared to the binding of the same CD38-binding protein of interest to wildtype CD38 ECD by flow cytometry. The assay was controlled for mutations that affect expression or general folding of the molecule with a series of control molecules that also target CD38. Table 12 shows the binding to a surface expressed CD38 ECD protein with a specific mutation as a percentage of binding of that CD38-binding protein to wildtype CD38. Values marked in bold indicate the amino acids that are critical for binding and surface accessible (based on published CD38 structure details) for the binding proteins.

TABLE 12

Epitope Mapping: Effects of CD38 mutations on binding by selected CD38-binding protein

| CD38 ECD | | CD38-binding protein | | | CD38-targeting reference molecule #1 | daratumumab |
|---|---|---|---|---|---|---|
| position | mutation | #1 % wildtype | #2 % wildtype | #4 % wildtype | % wildtype | % wildtype |
| 78 | R78A | 2% | 3% | 106% | 80% | 52% |
| 81 | D81A | 8% | 9% | 109% | 128% | 292% |
| 119 | C119A | 108% | 108% | 12% | 83% | 85% |
| 124 | L124A | 84% | 92% | 23% | 259% | 169% |
| 201 | C201A | 90% | 58% | 4% | 130% | 109% |
| 216 | F216A | 89% | 74% | 18% | 25% | 140% |
| 230 | L230A | 72% | 111% | 7% | 17% | 64% |
| 254 | C254A | 48% | 81% | 7% | 46% | 67% |
| 262 | L262A | 68% | 97% | 12% | 33% | 83% |
| 272 | Q272A | 145% | 135% | 68% | 191% | 167% |
| 272 | Q272R | 105% | 101% | 71% | 14% | 162% |
| 273 | F273A | 157% | 117% | 89% | 10% | 197% |
| 274 | S274F | 93% | 134% | 101% | 155% | 27% |
| 274 | S274F | 150% | 124% | 80% | 74% | 14% |
| 275 | C275A | 18% | 37% | 0.3% | 14% | 18% |

FIG. 7 shows the location in CD38 of critical residues for binding by CD38-binding protein #4 (SEQ ID NO: 79). In FIG. 7, the critical surface accessible contact residues F216 and L262 are shown in red, the critical structural residues L124 and L230 are shown in purple, and critical structural residues participating in disulfide pairs C119/C201 and C254/C275 are shown in grey.

An epitope mapping assay was performed as described above for CD38-targeting reference molecule #1 (SEQ ID NO:83). The critical residues in CD38 for binding by CD38-targeting reference molecule #1 were F216, L262, Q272, and F273.

6. Cytotoxic Activity in the Presence of Daratumumab

Cell-kill assays were performed as described above but in the presence of the anti-CD38 monoclonal antibody daratumumab to assess whether daratumumab interferes with the activity of the CD38-binding protein being tested. Daratumumab is an approved monoclonal antibody for treating multiple myeloma. Cytotoxicity assays were performed to distinguish which CD38-binding proteins kill CD38-expressing cells in the presence of daratumumab.

CD38-binding proteins of interest were tested for cytotoxic activity in the presence of dartumumab. In this experiment, the cell viability assay was performed similar to as described above. After CD38 positive cells were plated, daratumumab was added to the cells in a dilution series starting at 500 μg/mL (4-fold dilutions to 2 ng/mL). Daratumumab was added to the cells 1.5 hours prior to the addition of CD38-binding proteins, and the daratumumab was left in the wells throughout the experiment. CD38-binding proteins were added to the wells at a constant concentration of 500 ng/mL (1.5 hrs after addition of daratumumab and left in the wells throughout the experiment), so at the top concentration of daratumumab there is a thousand-fold excess of daratumumab to CD38-binding protein. Cell viability readout (CellTiter Glo2.0) was done after 72 hours. Some results of this assay are shown in FIG. 8A-8E. FIG. 8A-8E show that daratumumab can completely block cytotoxic activity of the CD38-targeting reference molecule #1 (SEQ ID NO:83) but has little effect on the cytotoxic activity of CD38-binding protein #1 (SEQ ID NO:76) and CD38-binding protein #2 (SEQ ID NO:77). Regarding H929 and ST486 cell lines, there was no change in cytotoxic activity of CD38-binding protein #4 (SEQ ID NO:79) with the 500 ng/mL treatment of CD38-binding protein (all cells are killed) in the presence of daratumumab. For CD38-binding protein #4 (SEQ ID NO:79), the cytotoxic activity of the CD38-binding protein was reduced in the presence of high concentrations of daratumumab; however, despite the change in potency, CD38-binding protein #4 (SEQ ID NO:79) was still able to affect cell viability to a level that was seen with other CD38-binding proteins, e.g. CD38-binding protein #1 (SEQ ID NO:76) and CD38-binding protein #2 (SEQ ID NO:77), in the presence of daratumumab. Table 13 is focused on the cytotoxic activity of selected CD38-binding proteins in the presence of the monoclonal antibody at a single concentration (0.5 μg/mL) of the CD38-binding proteins and a single concentration of daratumumab (500 μg/mL), 1000 times more monoclonal antibody than CD38-binding protein.

FIG. 8A-8E shows that CD38-binding protein #4 (SEQ ID NO:79) was potently cytotoxic in vitro to CD38-expressing cells in the presence of daratumumab over a range of daratumumab concentrations.

TABLE 13

Cytotoxicity of selected CD38-binding proteins in the presence of excess anti-CD38 monoclonal antibody daratumumab

| Protein | H929 cell viability after treated with 0.5 μg/mL CD38-binding protein | | MOLP-8 cell viability after treated with 0.5 μg/mL CD38-binding protein | | ST486 cell viability after treated with 0.5 μg/mL CD38-binding protein | |
| --- | --- | --- | --- | --- | --- | --- |
| | no daratumumab | 500 μg/mL daratumumab | no daratumumab | 500 μg/mL daratumumab | no daratumumab | 500 μg/mL daratumumab |
| CD38-binding protein #1 | 13.7% | 45.6% | 40.2% | 86.5% | 1.0% | 2.3% |
| CD38-binding protein #2 | 16.7% | 57.5% | 45.4% | 90.6% | 0.8% | 0.9% |
| CD38-binding protein #4 | 0.1% | 3.7% | 3.2% | 59.4% | 0.3% | 0.7% |
| CD38-targeting reference molecule #1 | 1.4% | 118.5% | 13.7% | 121.7% | 3.5% | 114.0% |
| no CD38-binding proteins | 118.6% | 121.8% | 115.5% | 112.9% | 118.0% | 112.9% |

TABLE 14

Cytotoxicity of selected CD38-binding proteins in the presence of excess anti-CD38 monoclonal antibody daratumumab

| Protein | MOLP-8 $CD_{50}$ (ng/mL) | | | ST486 $CD_{50}$ (ng/mL) | | |
| --- | --- | --- | --- | --- | --- | --- |
| | no daratumumab | 10 μg/mL daratumumab | fold change | no daratumumab | 10 μg/mL daratumumab | fold change |
| CD38-binding protein of Family #5 | 34.7 | 293.20 | 8.44 | 2.04 | 9.30 | 4.56 |

TABLE 14-continued

Cytotoxicity of selected CD38-binding proteins in the presence of excess anti-CD38 monoclonal antibody daratumumab

| | MOLP-8 $CD_{50}$ (ng/mL) | | | ST486 $CD_{50}$ (ng/mL) | | |
|---|---|---|---|---|---|---|
| Protein | no daratumumab | 10 µg/mL daratumumab | fold change | no daratumumab | 10 µg/mL daratumumab | fold change |
| CD38-binding protein #7 | 6.4 | >20,000 | >3,000 | 0.64 | ~20,000 | >30,000 |
| CD38-targeting reference molecule #1 | 14.4 | >20,000 | >1,000 | 0.42 | ~20,000 | >30,000 |

CD38-binding proteins of family #5 and 7, as well as the CD38-targeting reference molecule #1, all showed high potency towards CD38 positive MOLP-8 myeloma cells and ST486 lymphoma cells (see Table 14; FIG. 8C).

A CD38-binding protein of Family #5 exhibited cytotoxicity in the presence of daratumumab (see Table 14; FIG. 8D) with $CD_{50}$ values within 10-fold of parallel samples without daratumumab present. In contrast, the cytotoxic activities of CD38-binding protein #7 and the CD38-targeting reference molecule #1 were completely inhibited when target cells were pretreated with 10 µg/mL daratumumab (daratumumab was added 30 minutes prior to addition of CD38-binding proteins in a dilution series (from 0.2 to 20,000 ng/mL) and retained throughout experiment).

CD38-binding protein #4 (SEQ ID NO:79) was cytotoxic in vitro to multiple myeloma subject derived samples, including from a subject with prior exposure to daratumumab (see Table 15). Bone marrow samples were collected from six multiple myeloma subjects and cultured ex vivo using common techniques. The levels of cell surface CD38 on the cells in the six subject samples at baseline were evaluated using common techniques known to the skilled worker and found to be varied from a CD38 density of 137,000 to 6,750,000 antibody binding capacity units (see Table 15: column 2). CD38-binding protein #4 (SEQ ID NO: 79) was administered over a range of concentrations to the cells, which were then cultured for either 48 hours or 72 hours. $CD_{50}$ values were calculated as described above and representative results are reported in Table 15.

TABLE 15

Cytotoxicity of CD38-binding protein #4 to multiple myeloma subject derived bone marrow tumor cells

| Subject # | cell-surface CD38 density | $CD_{50}$ (nM) 48 hours | $CD_{50}$ (nM) 72 hours |
|---|---|---|---|
| 1 | 22.9 × 10⁵ | 3.5 | <2.5 |
| 2 | 1.4 × 10⁵ | 3.9 | 2.2 |
| 3 | 6.2 × 10⁵ | 6.6 | NA |
| 4 | 19.7 × 10⁵ | 8.5 | 3.0 |
| 5 | 44.0 × 10⁵ | 6.5 | 3.3 |
| 6 | 67.5 × 10⁵ | 5.0 | 4.6 |

CD38-binding protein #4 (SEQ ID NO: 79) depleted various multiple myeloma tumor cells that express a broad range of CD38 levels in this ex vivo subject cell culture cohort. CD38-binding protein #4 (SEQ ID NO: 79) depleted tumor cells at $CD_{50}$ concentrations ranging from 0.38-0.85 µg/mL after 48 hours of treatment, and from 0.23-0.51 µg/mL after 72 hours of treatment (with one subject sample being technically unassessable at the 72-hour timepoint).

Competitive binding of illustrative CD38-targeting molecules to CD38 was also tested (see FIG. 23). It was tested whether CTM#1 (SEQ ID NO:228), CTM#2 (SEQ ID NO:229), CTM#3 (SEQ ID NO:230) were able to bind to CD38 in the presence of the anti-CD38 antibody daratumumab (Dara), HB-7, AT13-5, or OKT-10. As shown in FIGS. 23A and 23B, CTM#1 (SEQ ID NO:228) and CTM#2 (SEQ ID NO:229) were able to bind to CD38 in the presence of daratumumab, HB-7, AT13-5, and OKT-10, indicating that these molecules may bind to epitopes on CD38 different from the epitope(s) bound by daratumumab, HB-7, AT13-5, and OKT-10. CTM#3 (SEQ ID NO:230) was able to bind to CD38 in the presence of OKT-10, but not daratumumab, HB-7 and AT13-5, indicating that CTM#3 (SEQ ID NO:230) may bind to an epitope on CD38 different from the epitope bound by OKT-10. These results suggested that CTM#3 (SEQ ID NO:230) shares or partially partially shares an epitope on CD38 with daratumumab, HB-7 and AT13-5 (e.g. a partially overlapping epitope).

Competitive binding illustrative CD38-targeting molecules to CD38-expressing cells was also tested (see FIG. 23C). MOLP-8 cells were incubated with 20 µg/mL of CD38-targeting molecules (~400 nM) or the control molecule (Shiga toxin A subunit effector polypeptide alone) for 70 minutes. Then 0.5 µg/mL of an anti-CD38 was added and incubated with the cells for 48 hours. CD38 binding was detected by a primary antibody recognizing the Shiga toxin A subunit effector polypeptide component, and a FITC conjugated anti-IgG secondary antibody followed by flow cytometry. Mean fluorescence intensity (MFI) of CD38-targeting molecule was calculated after subtracting the signal from the secondary antibody only control, and plotted as a percentage of MFI measured from Shiga toxin A subunit effector polypeptide alone as a control. As shown in FIGS. 23C and 23D, CTM#1 (SEQ ID NO:228) and CTM#2 (SEQ ID NO:229) bind to CD38 in a competitive manner, consistent with the fact that they bind to the same epitope on CD38. CTM#3 (SEQ ID NO:230) binds to CD38 in a semi-competitively manner with CTM#1 (SEQ ID NO:228) and CTM#2 (SEQ ID NO:229).

7. Testing Binding Proteins in Human Bone Marrow Aspirate

To further evaluate cytotoxicity of CTM#4 against human multiple myeloma cells, bone marrow aspirate (BMA) was obtained from various multiple myeloma subjects (labeled 010, 011, 012, 013, 014, and 015), including one subject who was resistant to daratumumab (013). The BMA was treated with increasing concentrations of CTM#4 (ranging from about 0.053 to 33.33 μg/mL). As shown in FIG. 15, CTM#4 was cytotoxic to the BMA tumor cells and exhibited $CD_{50}$ values after 48 hours of about 3.5 to 8.5 nM to these patient-derived multiple myeloma cells and after 72 hours of about 0.23 to 0.51 μg/mL. A strict correlation between CD38 expression level and CTM#4 cytotoxic potency was not observed.

8. Pharmacodynamic Models

To determine the time course of CTM#4 cytotoxicity, cytotoxicity was measured using a Real Time Glo assay in various high-CD38 expressing (MOLP6, RPMI-8226) and medium-CD38 expressing (ANBL6, NCI-H929) cell lines for approximately 72 hours after treatment with CTM#4. As shown in FIG. 16, viability effects were observed within 8 hours in the most sensitive lines (e.g. NCI-H929).

For most multiple myeloma cell types tested, the CTM#4 $CD_{50}$ values reach an asymptote after about 48 hours. In FIG. 16, the table reports $CD_{50}$ values (pM) in the bottom two lines (CTM#4 or CD38TM4). In FIG. 16, the table reports the expression level of cell surface CD38 and characterizes the values as either high or medium in the CD38 expression line. The cytotoxicity of the CD38-targeting moiety of CTM#4, CD38TM4, was tested in isolation (dissociated from the Shiga toxin effector polypeptide) and a precise $CD_{50}$ value could not be determined for the range of CD38TM4 concentrations tested; however, the $CD_{50}$ value was determined to be greater than 180,000 pM for ANBL-6, NCI-H929, MOLP-8, and HCT116 cells in this assay (FIG. 16. Table, last line). A strict correlation between CD38 expression level and CTM#4 cytotoxic potency was not observed.

Two cell lines, NCI-H929 and MOLP 8, demonstrated the shortest induction of cell death, cytotoxicity was observed within the first 8 hours of CTM#4 administration and were characterized by $CD_{50}$ values of <0.038 and 0.081±0.018 ng/mL, respectively. The multiple myeloma cell lines ANBL-6 and RPMI-8226 were less sensitive than NCI-H929 and MOLP 8 to CTM#4 ($CD_{50}$ values of 1.949±0.0467 and 0.136±0.027 ng/mL at 72 hours, respectively and induction of cell death at 28 hours and 24 hours, respectively). CTM#4 demonstrated no effect on CD38-negative HCT 116 colon cancer cells in this study.

To determine whether CTM#4 is active in whole blood, human and cynomolgus monkey whole blood was treated for 72 hours with CTM#4. Natural Killer (NK) cell depletion was determined ex vivo, using flow cytometry. As shown in FIG. 18A-18B, CTM#4 reduced NK cell count in both human and cynomolgus monkey whole blood.

In a separate assay, ANBL-6 multiple myeloma cells were treated either continuously with CTM#4 for 48 or 72 hours, or exposed for 2 hours to CTM#4, washed, and kept in CTM#4-free media until the 48- or 72-hour time point. Cell viability was determined using a RealTime-Glo viability assay. As shown in FIG. 19, the two-hour treatment plus washout results in an a 5-fold increase in cytotoxicity at the 48-hour time point, and a 10-fold increase in cytotoxicity at the 72-hour time point.

9. Murine Models

Murine models for mammalian subjects of other species were used to evaluate selected CD38-binding proteins.

a. Tolerability in a Mouse Model

For evaluating tolerability, toxicity and safety, BALB/C mice were treated with vehicle (20 mM sodium citrate, 200 mM sorbitol, pH 5.5) or CD38-binding proteins, each diluted in PBS, for 6 doses over 12 days (days 1, 3, 5, 8, 10 and 12) at 0.25 to 2 mg/kg. Body weight was monitored and clinical observations done throughout the studies. Some results of these studies are shown in Table 16, Table 17, and FIG. 9. Dosing was to be stopped in any group with a mean body weight loss of >20% or >10% mortality, animals would not be euthanized and recovery would be allowed. Within a group with >20% weight loss, individuals hitting the individual body weight loss endpoint will be euthanized. CD38-binding proteins were tested in different studies as indicated in Tables 16 and 17. Data for multiple CD38-binding proteins at different concentrations is provided in Table 16. Additionally, some clinical chemistry showing changes in liver enzyme function (aspartate aminotransferase (AST), alanine aminotransferase (ALT), alkaline phosphatase (alk phos) and total bilirubin) was done after the 4th dose (12 hours post dose on day 8), and those values are reported in Table 17.

TABLE 16

In vivo comparison of illustrative CD38-binding proteins: Body weight changes and on study deaths

| Binding protein | Study | Dose (mg/kg) | Days dose given (6 doses planned) | Body Weight Nadir Nadir (%) | Day | On study deaths Death/ Total | Mean Day |
|---|---|---|---|---|---|---|---|
| CD38-binding protein #1 | 1 | 2 | 1, 3, 5, 8, 10 | −33.40% | 12 | 2/6 | 12 |
| CD38-binding protein #2 | 1 | 2 | 1, 3, 5, 8, 10, 12 | −16.20% | 12 | 0/6 | N/A |
| CD38-binding protein #3 | 1 | 2 | 1, 3, 5, 8, 10 | −18.70% | 8 | 5/6 | 11 |
| CD38-targeting reference molecule #1 | 1 | 2 | 1, 3, 5, 8, 10, 12 | −0.90% | 2 | 0/6 | N/A |
| Vehicle Control | 2 | N/A | 1, 3, 5, 8, 10, 12 | −2.10% | 14 | 0/6 | N/A |
| CD38-binding protein #1 | 2 | 1 | 1, 3, 5, 8, 10, 12 | −18.50% | 14 | 0/6 | N/A |
| CD38-binding protein #2 | 2 | 1 | 1, 3, 5, 8, 10, 12 | −13.70% | 14 | 0/6 | N/A |
| CD3 8-targeting reference molecule #1 | 2 | 1 | 1, 3, 5, 8, 10, 12 | −0.30% | 7 | 0/6 | N/A |

TABLE 16-continued

In vivo comparison of illustrative CD38-binding proteins: Body weight changes and on study deaths

| Binding protein | Study | Dose (mg/kg) | Days dose given (6 doses planned) | Body Weight Nadir Nadir (%) | Day | On study deaths Death/Total | Mean Day |
|---|---|---|---|---|---|---|---|
| Vehicle Control | 3 | N/A | 1, 3, 5, 8, 10, 12 | −1.50% | 14 | 0/6 | N/A |
| CD38-targeting control molecule #1 | 3 | 0.5 | 1, 3, 5, 8, 10, 12 | −1.80% | 2 | 0/6 | N/A |
| CD38-binding protein #1 | 3 | 0.5 | 1, 3, 5, 8, 10, 12 | −5.20% | 9 | 0/6 | N/A |
| CD38-binding protein #2 | 3 | 0.5 | 1, 3, 5, 8, 10, 12 | −1.60% | 11 | 0/6 | N/A |
| CD38-binding protein #3 | 3 | 0.5 | 1, 3, 5, 8, 10, 12 | −6.40% | 7 | 0/6 | N/A |
| CD38-binding protein #3 | 3 | 1 | 1, 3, 5, 8, 10 | −22.10% | 18 | 3/6 | 11 |
| CD38-binding protein #4 | 3 | 0.5 | 1, 3, 5, 8, 10, 12 | 0 | N/A | 0/6 | N/A |
| CD38-binding protein #4 | 3 | 1 | 1, 3, 5, 8, 10, 12 | −1.90% | 10 | 0/6 | N/A |
| CD38-targeting reference molecule #1 | 3 | 0.5 | 1, 3, 5, 8, 10, 12 | −2.50% | 14 | 0/6 | N/A |

TABLE 17

In vivo comparison of illustrative CD38-binding proteins: Clinical chemistry

| Binding protein | Study | Dose (mg/kg) | AST µg/µL | % of control | ALT µg/uL | % of control | Alk Phos U/L | % of control | Bilirubin mg/dl | % of control |
|---|---|---|---|---|---|---|---|---|---|---|
| Vehicle Control | 2 | N/A | 72 | 100% | 34 | 100% | 118.67 | 100% | 0.25 | 100% |
| CD38-targeting control molecule #1 | 2 | 0.5 | 127.83 | 178% | 61.67 | 181% | 88.33 | 74% | 0.24 | 96% |
| CD38-binding protein #1 | 2 | 0.5 | 188.17 | 261% | 99.17 | 292% | 77.17 | 65% | 0.2 | 80% |
| CD38-binding protein #2 | 2 | 0.5 | 94 | 131% | 51.67 | 152% | 79.33 | 67% | 0.18 | 72% |
| CD38-binding protein #3 | 2 | 0.5 | 244.67 | 340% | 145.17 | 427% | 80.67 | 68% | 0.23 | 92% |
| CD38-binding protein #3 | 2 | 1 | 251.33 | 349% | 103.00 | 303% | 64.83 | 55% | 0.20 | 80% |
| CD38-binding protein #4 | 2 | 0.5 | 92.17 | 128% | 58.67 | 173% | 105 | 88% | 0.2 | 80% |
| CD38-binding protein #4 | 2 | 1 | 156.50 | 217% | 133.67 | 393% | 110.33 | 93% | 0.23 | 93% |
| CD38-targeting reference molecule #1 | 2 | 0.5 | 77.2 | 107% | 36.67 | 108% | 104.5 | 88% | 0.28 | 112% |
| Vehicle Control | 3 | N/A | 81.33 | 100% | 29.67 | 100% | 117.33 | 100% | 0.20 | 100% |
| CD38-binding protein #1 | 3 | 1 | 454.33 | 559% | 524.67 | 1769% | 101.00 | 86% | 0.33 | 167% |
| CD38-binding protein #2 | 3 | 1 | 172.67 | 212% | 276.67 | 933% | 128.00 | 109% | 0.20 | 100% |
| CD38-targeting reference molecule #1 | 3 | 1 | 217.33 | 267% | 49.00 | 165% | 110.00 | 94% | 0.17 | 83% |

CD38-binding protein #3 (SEQ ID NO:78) and the related molecule CD38-binding protein #4 (SEQ ID NO:79) that has the same CDRs in the CD38-binding region were compared within a single study and the body weight changes in treated mice are shown in Table 16 and FIG. 9. Though both were tolerated at 0.5 mg/kg, CD38-binding protein #4 (SEQ ID NO:79) was better tolerated at 1 mg/kg, as seen with a no change in body weight and no deaths, whereas CD38-binding protein #3 (SEQ ID NO:78) at 1 mg/kg was associated with body weight loss and 3/6 deaths (see Table 16). The animals in the CD38-binding protein #3 (SEQ ID NO:78) treatment group that survived did not get the sixth scheduled dose. The differences between the two molecules is an amino acid change in the light chain to facilitate protein L purification, which surprisingly was less toxic and thus can allow higher dosing as well as less frequent dosing, a significant benefit.

b. Relative Immunogenicity

A mammalian model for the human immune system was used to investigate the immunogenic potential of certain CD38-binding proteins. The relative immunogenicities of illustrative binding proteins were determined using an assay for in vivo antibody responses to the binding proteins after repeat, parenteral administrations over periods of many weeks (see e.g. WO 2015/113005). An in-solution ELISA was used to determine the relative amount of serum murine antibodies that were specific to different binding proteins.

This immunogenicity assay involves the use of mice which are indicative of the relative immunogenicities of molecules in mammals generally. Mouse studies were conducted where BALB/c mice were randomly assigned to treatment groups consisting of six mice per group and where the mice in different treatment groups were administered different binding proteins. First, serum samples were collected from each mouse prior to exposure to a binding protein. Next, each mouse in a treatment group was administered 0.25 milligram of the sample molecule per kilogram of body weight (mg/kg) per dose of the sample binding protein by intra-peritoneal injection three times a week for two weeks. After a week without administration of any samples, intra-peritoneal injections of 0.25 mg/kg per dose of the sample binding protein were administered three times a week for an additional two weeks, resulting in a total of 12 doses of binding protein over a five-week interval. During and after the five-week administration interval, sera were collected from all the mice to observe antibodies targeting the administered binding proteins using in-solution ELISAs.

The in-solution ELISAs to detect antibodies recognizing the administered binding proteins were performed as follows. For each CD38-binding protein and its respective mouse-treatment group, a different ELISA assay was performed but using the same general in-solution ELISA assay setup. For in-solution ELISA assays, the ELISA plate wells were coated with CD38 recombinant human protein. The same binding protein used for injections in a mouse-treatment group was incubated overnight at 4° C. in solution with the serum collected from a single mouse from that group, and then any complexes formed (e.g. complexes comprising the binding protein and antibodies present in the serum) were captured using the coated ELISA plate wells. Captured, immune complexes comprising murine, immunoglobulin G molecules (IgGs) were detected using an anti-mouse IgG, secondary antibody conjugated to horseradish peroxidase. HRP activity was detected in the wells by adding a chromogenic HRP substrate and then detecting light emission as a result of chemiluminescence. The HRP activity or "ELISA signal" was measured as at 450 nm using a plate reader. ELISA signal values were calculated as Absorbance values (Abs 450 nm) after subtracting the background signal as measured from "no serum" negative control wells. Serum was diluted to allow for Absorbance value readings below the level of saturation for the assay, and the dilution ratio was the same for all mice in all treatment groups measured on a given day. As a control, CD38-targeting control molecule #1 (SEQ ID NO:84), which comprised the same scFv as CD38-targeting reference molecule #1 (SEQ ID NO:80) but comprised a less de-immunized Shiga toxin effector polypeptide, was administered to the mice and used to show an anti-drug antibody response.

FIG. 10 shows the relative immunogenicity of CD38-binding proteins comprising only deimmunized Shiga toxin A Subunit effector polypeptide components: CD38-binding protein #1 (SEQ ID NO:76), CD38-binding protein #2 (SEQ ID NO:77), and CD38-targeting reference molecule #1 (SEQ ID NO:83) as compared to a CD38-targeting control molecule (SEQ ID NO:84) comprising a less de-immunized Shiga toxin effector polypeptide and the same scFv as CD38-targeting reference molecule #1 (SEQ ID NO:80) over two cycles of low dose (0.25 mg/kg) administration of the molecule of interest, 12 doses total.

The CD38-targeting reference molecule #1 (SEQ ID NO:83) and another control CD38-targeting molecule were administered intravenously at doses of 0.05 mg/kg to non-human primates for two cycles with a two week break between cycles (dosing days 1, 3, 5, 8, 10, 12; 29, 31, 33, 36, 38, and 40). Compared to the less de-immunized CD38-targeting control molecule comprising the same Shiga toxin effector polypeptide as CD38-targeting control molecule #1 (SEQ ID NO:84) the severity of any inflammatory/immune response was reduced (as measured by globulin levels, IgG levels, IgA levels, neutrophil counts, monocyte counts, and albumin reductions) in animals receiving CD38-targeting reference molecule #1 (SEQ ID NO:83). In addition, CD38-targeting reference molecule #1 (SEQ ID NO:83) was detectable after the 6th dose whereas the control CD38-targeting molecule was below the limit of quantitation, presumably due to the formulation of more anti-drug antibodies.

c. Efficacy

Compositions comprising dimers of CD38-binding protein #4 (SEQ ID NO:79) were efficacious in several human myeloma xenograft murine models, both subcutaneous and disseminated. Complete tumor regressions were observed using both a once-weekly and bi-weekly schedule. In addition, a syngeneic murine cell line expressing human CD38 was shown to be responsive to CD38-binding protein #4 (SEQ ID NO:79) treatment in an immunocompetent mouse model.

(i) Murine Xenograft Model: Subcutaneous LP-1

The in vivo activity of CD38-binding protein #4 (SEQ ID NO: 79) was evaluated using a murine xenograft model comprising female CB17 severe combined immunodeficient (SCID) mice bearing LP-1 human multiple myeloma xenografts. The mice were inoculated subcutaneously into the right flank with LP-1 human multiple myeloma cells and were treated once weekly (QW) with intravenous doses of vehicle, once weekly with intravenous doses of CD38-binding protein #4 (SEQ ID NO: 79) for 21 days, or once every other week (Q2W) with intravenous doses of CD38-binding protein #4 (SEQ ID NO: 79) for 14 days. Doses of CD38-binding protein #4 (SEQ ID NO: 79) were 5, 6, or 10 mg/kg body weight.

Tumor volume and body weight were measured twice per week using common techniques known to the skilled worker and the mean tumor volume (MTV) was calculated using the formula (0.5×[length×width2]). When the mean tumor volume reached approximately 94 mm3, the mice were randomized into treatment groups (n=6 mice per group) and dosed intravenously on a QW schedule with vehicle (phosphate buffered saline (PBS)) or CD38-binding protein #4 (SEQ ID NO: 79) at 5.0 or 6.0 mg/kg on a QW schedule, or CD38-binding protein #4 (SEQ ID NO: 79) at 10.0 mg/kg on an Q2W schedule. Mice which received QW administration were treated on Days 0, 7, 14 and 21. Mice which received Q2W administration were treated on Days 0 and 14. All treatments started on Day 0. Tumor size and body weight were measured twice per week and the study was terminated when control tumors reached approximately 1800 mm3 on Day 28.

Growth rate inhibition was determined on Day 28. Inhibition of tumor growth was determined by calculating the percent GRI ([mean growth rate of the control group−mean growth rate of a treated group]/mean growth rate of the vehicle group) using data up to and including Day 28 of the study. Statistical comparisons of tumor growth between treatment groups and vehicle were conducted using a t-test applied to the exponential growth rates of the animals in each group. Some results of these studies are shown in Table 18 (LP-1) and FIG. 11A-11D. FIG. 11A-11D graphically show the mean tumor volume (mm3) over time (days) for each group. The term "BIW" is used in FIG. 11A-11D to mean 'bi-weekly' as referring to the dosing regimen. The term "AUC" stands for the area under a curve.

TABLE 18

CD38-Binding Protein #4 Kills CD38+ Tumor Cells in Xenograft Models

| Cell Line | CD38 expression ($\times 10^3$) | tumor doubling time (days) | Highest % tumor growth inhibition ($AUC_{treated} - AUC_{baseline}$) ÷ ($AUC_{vehicle} - AUC_{baseline}$) × 100% |
|---|---|---|---|
| MM1.S | 18 | 6.1 d | 90% |
| H929 | 88 | 5.6 d | (with tumor regression) 126% |
| LP-1 | 202 | 7.4 d | (with tumor regression) 109% |
| MOLP8 | 707 | 4.7 d | 69% |

Treatments were tolerated in all dose groups. There were no animal deaths or animals removed during treatment and measurements. All animals were included in the analysis on Day 28.

Treatment of female CB17 SCID mice bearing LP-1 human multiple myeloma xenograft with either 5 mg/kg or 6 mg/kg of CD38-binding protein #4 (SEQ ID NO: 79) once a week resulted in significant antitumor activity compared with vehicle treatment.

(ii) Murine Xenograft Model: Subcutaneous H929

The in vivo activity of CD38-binding protein #4 (SEQ ID NO: 79) was evaluated using a murine xenograft model comprising female nonobsese diabetic (NOD) severe combined immunodeficient (SCID) mice bearing NCI-H929 human multiple myeloma xenografts. The mice were inoculated subcutaneously into the right flank with NCI-H929 human multiple myeloma cells and were treated once weekly (QW) for 21 days with intravenous doses of vehicle (PBS) or CD38-binding protein #4 (SEQ ID NO: 79) once every other week (Q2W) for 14 days. Doses of CD38-binding protein #4 (SEQ ID NO: 79) were 5, 6, or 10 mg/kg body weight.

Tumor volume and body weight were measured twice per week using common techniques known to the skilled worker and the mean tumor volume (MTV) was calculated using the formula (0.5×[length×width2]). When the mean tumor volume reached approximately 121 mm3, the mice were randomized into treatment groups (n=8 mice per group) and dosed intravenously on a QW schedule with vehicle (phosphate buffered saline (PBS)) or CD38-binding protein #4 (SEQ ID NO: 79) at 5.0, 6.0, or 10.0 mg/kg on a QW schedule, or CD38-binding protein #4 (SEQ ID NO: 79) at 10.0 mg/kg on an Q2W schedule. Mice which received QW administration were treated on Days 0, 7, 14 and 21. Mice which received Q2W administration were treated on Days 0 and 14. All treatments started on Day 0. Tumor size and body weight were measured twice per week and the study was terminated when control tumors reached approximately 1700 mm3 on Day 29.

Growth rate inhibition was determined (as described above) on Day 29. Some results of these studies are shown in Table 18 (H929) and FIG. 11A-11D.

Treatments were tolerated in all dose groups. There were no animal deaths or animals removed during treatment and measurements. All animals were included in the analysis on Day 29.

Treatment of female nonobsese diabetic (NOD/SCID) mice bearing NCI-H929 human multiple myeloma xenografts with either 5 mg/kg or 6 mg/kg of CD38-binding protein #4 (SEQ ID NO: 79) once a week or 10 mg/kg of CD38-binding protein #4 (SEQ ID NO: 79) once every other week resulted in significant antitumor activity compared with vehicle treatment.

Additional murine subcutaneous xenograft models were used to evaluate in vivo activity of CD38-binding protein #4 (SEQ ID NO: 79) similar to as described above and using techniques known to the skilled worker but using other cell-types, such as, e.g. MOLP8 cells. Some results of these studies are shown in Table 18 (MOLP-8) and FIG. 11D.

(iii) Murine Xenograft Model: Subcutaneous MM1.S

The in vivo activity of CD38-binding protein #4 (CTM#4) was evaluated using a murine xenograft model comprising female CB17 severe combined immunodeficient (SCID) mice bearing MM1.S human multiple myeloma xenografts. The mice were inoculated subcutaneously into the right flank with MM1.S human multiple myeloma cells and were treated once weekly (QW) with intravenous doses of vehicle, once weekly with intravenous doses of CD38-binding protein #4 for 21 days, or once every other week (Q2W) with intravenous doses of CD38-binding protein #4 for 14 days. Doses of CD38-binding protein #4 were 5, 6, or 10 mg/kg body weight.

Tumor volume and body weight were measured twice per week using common techniques known to the skilled worker and the mean tumor volume (MTV) was calculated using the formula (0.5×[length×width2]). When the mean tumor volume reached approximately 94 mm3, the mice were randomized into treatment groups and dosed intravenously on a QW schedule with vehicle (phosphate buffered saline (PBS)), with CD38-binding protein #4 on a QW schedule, with CD38-binding protein #4 on a Q2W schedule, with a CD38-targeting antibody (daratumumab, SOC) on a BIW schedule, with CD38-binding protein #4 on a QW schedule in combination with SOC on a BIW schedule, or with CD38-binding protein #4 on a Q2W schedule in combination with SOC on a BIW schedule. Mice which received QW administration were treated on Days 0, 7, 14 and 21. Mice which received Q2W administration were treated on Days 0 and 14. All treatments started on Day 0. Tumor size and body weight were measured twice per week and the study was terminated when control tumors reached approximately 1800 mm3 on Day 28.

Some results from this study are shown in FIG. 12A-B and FIG. 17. Complete regressions were observed in both combination arms (CTM#4+SOC).

D. Murine Xenograft Model: Disseminated

The in vivo activity of CD38-binding protein #4 (SEQ ID NO: 79) was evaluated using a murine xenograft model comprising female SCID/Beige mice bearing MM1.S-Luc human multiple myeloma disseminated tumors.

SCID Beige mice were inoculated by tail vein injection with MM1.S-Luc tumor cells (MM1.S cells labeled with luciferase expression) using common techniques known to the skilled worker. The tumor burden for each mouse was measured once per week using bioluminescence imaging using common techniques known to the skilled worker. Tumor burden was measured on Days 14, 21, 28, 35, and 42 in photons per second and the mean bioluminescence signal was calculated for each treatment group. On Day 14, when the mean bioluminescence signal reached approximately 1.11×107 photons per second, animals were randomized into treatment groups (n=8/group). Vehicle only or CD38-binding protein #4 (SEQ ID NO: 79) was dosed intraperitoneally at 2 mg/kg once every other day, three times per week (with a two-day hiatus) for two weeks followed by a week hiatus (once every other day×3, 2 off; 2 weeks on 1 week off), before starting the next dosing cycle. Additionally, CD38-binding protein #4 (SEQ ID NO: 79) was dosed at 4, 6, and 10 mg/kg once weekly. All groups were dosed over a 28-day period. Mice which were treated once every other day×3, 2 off; 2 weeks on, 1 week off schedule were administered vehicle (PBS) or CD38-binding protein on Days 14, 16, 18, 21, 23, 25, 35, and 37. Mice which received CD38-binding protein #4 (SEQ ID NO: 79) on a once weekly schedule were treated on Days 14, 21, 27, and 35.

Antitumor activity was determined by calculating the % T/C. Percent T/C is defined as the mean bioluminescence signal (BLI) of the treated group divided by the mean bioluminescence (BLI) signal of the vehicle group×100 and was calculated on Day 42 with some results shown in FIG. 12A. In FIG. 12A, the CD38-binding protein #4 (SEQ ID NO: 79) is referred to as "CTM #4", and this was only protein shown in the experimental data along with a vehicle only control. FIG. 12B also shows images of mice collected using bioluminescence imaging of luciferase activity in the xenograft tumor cells: the mouse administered vehicle only exhibited an intense signal extensively throughout its body, whereas the mouse administered CD38-binding protein #4 (CTM #4) (SEQ ID NO: 79) appears to have no detectable tumor cells by this method.

Treatment of female SCID/Beige mice bearing MM1.S-Luc human multiple myeloma disseminated tumors with 4 mg/kg, 6 mg/kg, or 10 mg/kg of CD38-binding protein #4 once a week resulted in significant antitumor activity compared with vehicle treatment. Significant anti-tumor activity was observed at doses of 4 mg/kg or higher and both at administration schedules of once per week.

The in vivo activity of CD38-targeting reference molecule #1 (SEQ ID NO:83) was evaluated using a murine xenograft model comprising SCID/Beige mice bearing Daudi-Luc human multiple myeloma disseminated tumors. The CD38-targeting reference molecule #1 (SEQ ID NO:83) was administered at doses of 0.5 mg/kg or 0.6 mg/kg to mice for two cycles with a one week break between cycles (dosing days 1, 3, 5, 8, 10, 12; 22, 24, 26, 29, 31, and 33). Compared to the vehicle-only control group, reduced tumor burdens were observed as soon as four days post-injection inoculation of Daudi-Luc cells in mice that received CD38-targeting reference molecule #1 (SEQ ID NO:83) (see FIG. 12-C).

(iv) Toxicity and Pharmacodynamics of CD38-Binding Protein #4 (SEQ ID NO: 79) in Cynomolgus Macaques Intravenous administration once weekly for 1 to 4 weeks of about 0.2 to 0.75 mg/kg of CD38-binding protein #4 (SEQ ID NO: 79) per body weight was tested in non-human primates. Anti-drug antibodies were observed at Days 15 and 22. Administration of 0.75 mg/kg CD38-binding protein #4 (SEQ ID NO: 79) QW for 2 or 4 doses was well tolerated with no associated clinical signs. Testing in non-human primates showed that CD38-binding protein #4 administration can result in decreased numbers of circulating CD38±NK cells, B cells, and T cells.

B. Example 2

CD38-Targeting Fusion Proteins Comprising Shiga Toxin A Subunit Derived Polypeptides CD38-targeting, fusion proteins of this Example comprise a cell-targeting binding region polypeptide comprising a CD38-binding region, a Shiga toxin A Subunit effector polypeptide and a proteinaceous linker (see, e.g., WO 2015/113005, WO 2016/196344, and/or PCT/US2016/043902), prepared using techniques known in the art. Some of the cell-targeting, fusion proteins of this Example are constructed such that each comprised a single, continuous polypeptide comprising a cell-targeting, binding region polypeptide and a Shiga toxin A Subunit effector polypeptide.

1. Testing the CD38-Binding Region for Retention of Binding Functionality after Incorporation into a CD38-Targeting Fusion Protein Comprising a Shiga Toxin A Subunit Effector Polypeptide The CD38-binding characteristics of the CD38-binding proteins of this Example are determined by fluorescence-based, flow-cytometry. The $B_{max}$ for certain CD38-targeting fusion proteins of this Example to CD38 positive cells is measured to be approximately 50,000-200,000 MFI with a KD within the range of 0.01-100 nM.

2. Testing the CD38-Binding Proteins for Retention of Shiga Toxin Functions After the Fusion of Binding Regions Cell-targeting proteins are tested for retention of Shiga toxin A Subunit effector functions after the fusion of heterologous regions. The Shiga toxin A Subunit effector functions analyzed are: catalytic inactivation of eukaryotic ribosomes, cytotoxicity, and by inference self-directing subcellular routing to the cytosol.

3. Testing the Ribosome Inhibition Ability of Binding Proteins

The catalytic activities of Shiga toxin A Subunit derived Shiga toxin effector polypeptide regions of binding proteins are tested using a ribosome inhibition assay.

The ribosome inactivation capabilities of cell-targeting proteins of this Example are determined using a cell-free, in vitro protein translation assay using the TNT® Quick Coupled Transcription/Translation Kit (L1170 Promega Madison, Wis., U.S.). The kit includes Luciferase T7 Control DNA (L4821 Promega Madison, Wis., U.S.) and TNT® Quick Master Mix. The ribosome activity reaction is prepared according to manufacturer's instructions. A series of 10-fold dilutions of the Shiga toxin derived, cell-targeting protein to be tested is prepared in an appropriate buffer and a series of identical TNT reaction mixture components were created for each dilution. Each sample in the dilution series is combined with each of the TNT reaction mixtures along with the Luciferase T7 Control DNA. The test samples are incubated for 1.5 hours at 30 degrees Celsius (° C.). After the incubation, Luciferase Assay Reagent (E1483 Promega, Madison, Wis., U.S.) is added to all test samples and the amount of luciferase protein translation is measured by luminescence according to manufacturer's instructions.

The level of translational inhibition is determined by non-linear regression analysis of log-transformed concentrations of total protein versus relative luminescence units. Using statistical software (GraphPad Prism, San Diego, Calif., U.S.), the half maximal inhibitory concentration ($IC_{50}$) value is calculated for each sample using the Prism software function of log(inhibitor) vs. response (three parameters) [Y=Bottom+((Top−Bottom)/(1+10^(X−Log IC$_{50}$)))] under the heading dose-response-inhibition. The IC$_{50}$ values for each Shiga toxin derived, cell-targeting protein from one or more experiments is calculated.

4. Testing Cytotoxicity of CD38-Binding Proteins to CD38-Expressing Cells

The cytotoxicity characteristics of CD38 cell-targeting fusion proteins of this Example are determined by the general cell-kill assay as described above in the previous Examples. The CD$_{50}$ values of the binding proteins of this Example are approximately 0.01-100 nM for melanoma cells depending on the cell line.

C. Example 3

A Study to Evaluate the Safety, Tolerability, Pharmacokinetics (PK), and Efficacy of an Illustrative CD38-Binding Protein in Participants with Relapsed or Refractory Multiple Myeloma The purpose of this study (a phase 1 trial) is to evaluate the safety and tolerability of an illustrative CD38-binding protein, CD38-binding protein #4 ("CTM #4", SEQ ID NO: 79). This study will establish the maximum tolerated dose (MTD) and/or recommended phase 2 dose (RP2D), and will provide a preliminary evaluation of the CD38-Targeting molecule monotherapy in participants with Relapsed or Refractory Multiple Myeloma (RRMM).

The study will be conducted in 2 phases: Dose Escalation Phase (Part 1) and an Expansion Phase (Part 2). The study will enroll approximately 81 to 102 participants (39 to 60 participants in Part 1 and approximately 54 participants in Part 2).

In the Dose Escalation Phase (Part 1), the starting dose level will be 50 microgram/kilogram (mcg/kg), once weekly. After review of available safety, PK, pharmacodynamic, and efficacy data from Cohort 1, the dose will be escalated in the subsequent cohorts to 100, 200, 335, 500, and 665 mcg/kg, then 1.25 increases beyond 665 mcg/kg if necessary. A separate dose escalation may also occur in which CTM #4 will be administered once every 2 weeks.

In the Expansion Phase (Part 2), the study will evaluate two types of RRMM cohorts: Daratumumab-relapsed or Refractory (RR) Cohorts (once weekly and once every 2 weeks CTM #4 administration) and an Anti-CD38 Therapy Naive Cohort (once weekly CTM #4 administration). The starting dose for each expansion cohort will be the MTD/RP2D (once weekly and once every 2 weeks) determined in Part 1 after review of the available safety, efficacy, PK, and pharmacodynamic data from the dose escalation phase of the study. Subject dosing cohorts are described in Table 19, below.

TABLE 19

| Part | Arm | Intervention | Description |
|---|---|---|---|
| 1 | 50 mcg/kg, once weeekly | CTM #4, by intravenous infusion | Dose of 50 microgram per kilogram (mcg/kg), infusion, intravenously, once weekly on Days 1, 8, 15, and 22 in a 28-day treatment cycle until progressive disease (PD), unacceptable toxicity, or withdraw from the study for other reasons. |
| 1 | 100 mcg/kg, once weekly | CTM #4, by intravenous infusion | Dose of 100 mcg/kg, infusion, intravenously, once weekly on Days 1, 8, 15, and 22 in a 28-day treatment cycle until PD, unacceptable toxicity or withdraw from the study for other reasons. |
| 1 | 200 mcg/kg, once weekly | CTM #4, by intravenous infusion | Dose of 200 mcg/kg, infusion, intravenously, once weekly on Days 1, 8, 15, and 22 in a 28-day treatment cycle until PD, unacceptable toxicity or withdraw from the study for other reasons. |
| 1 | 335 mcg/kg, once weekly | CTM #4, by intravenous infusion | Dose of 335 mcg/kg, infusion, intravenously, once weekly on Days 1, 8, 15, and 22 in a 28-day treatment cycle until PD, unacceptable toxicity or withdraw from the study for other reasons. |
| 1 | 500 mcg/kg, once weekly | CTM #4, by intravenous infusion | Dose of 500 mcg/kg, infusion, intravenously, once weekly on Days 1, 8, 15, and 22 in a 28-day treatment cycle until PD, unacceptable toxicity or withdraw from the study for other reasons. |
| 1 | 665 mcg/kg, once weekly | CTM #4, by intravenous infusion | Dose of 665 mcg/kg, infusion, intravenously, once weekly on Days 1, 8, 15, and 22 in a 28-day treatment cycle until PD, unacceptable toxicity or withdraw from the study for other reasons. |
| 1 | Dose to be determined (TBD), once every two weeks | CTM #4, by intravenous infusion | Dose TBD, infusion, intravenously, once every 2 weeks on Days 1 and 15 in a 28-day treatment cycle until PD, unacceptable toxicity or withdraw from the study for other reasons. Dose escalation of CTM #4 will be based on the investigator and sponsor review of available safety, pharmacokinetic (PK), pharmacodynamic, efficacy data in the previous cohort. |
| 2 | Daratumumab RR, dose TBD, once weekly | CTM #4, by intravenous infusion | Dose TBD, infusion, intravenously, once weekly in participants who are relapsed or refractory (RR) to daratumumab until PD, unacceptable toxicity or withdraw from the study for other reasons. Dose for Part 2 will be determined based on the review of the available safety, efficacy, PK, and pharmacodynamic data from Part 1 of this study. |
| 2 | Daratumumab RR: dose TBD, once every two weeks | CTM #4, by intravenous infusion | Dose TBD, infusion, intravenously, once every 2 weeks in participants who are RR to daratumumab until PD, unacceptable toxicity or withdraw from the study for other reasons. Dose for Part 2 will be determined based on the review of the available safety, efficacy, PK, and pharmacodynamic data from Part 1 of this study. |
| 2 | Anti-CD38 Therapy Naive MM: dose TBD, once weekly | CTM #4, by intravenous infusion | Dose TBD, infusion, intravenously, once weekly in participants with MM who have never received anti-CD38 therapy until PD, unacceptable toxicity or withdraw from the study for other reasons. Dose for Part 2 will be determined based on the review of the available safety, efficacy, PK, and pharmacodynamic data from Part 1 of this study. |

The overall duration of the study is approximately 34 months. Participants will be followed up for 30 days after the last dose of study drug for a follow-up assessment.

Primary Outcome measures of this study will include:
1. Part 1: Number of participants with overall and per dose level treatment-emergent adverse events (TEAEs) [Time Frame: Up to 12 months].
2. Part 1: Number of participants with dose-limiting toxicities (DLTs) at each dose level [Time Frame: Up to 12 months]. DLTs are defined as any of the events that are considered by the investigator to be at least possibly related to therapy with the study medication. The DLT may be a hematologic or a non-hematologic DLT. A hematologic DLT may be any Grade A ≥4 hematologic TEAEs occurring during cycle 1, with the following exceptions: hematologic AEs clearly due to extraneous causes, Grade 4 lymphopenia, Grade 4 neutropenia (ANC <500 cells/mm$^3$) lasting <7 consecutive days, febrile neutropenia of any grade and duration, Grade ≥3 thrombocytopenia with clinically meaningful bleeding, Grade 4 thrombocytopenia of any duration, Grade ≥3 capillary leak syndrome, or Grade ≥3 hemolysis clearly unrelated to the underlying disease (e.g. negative direct Coombs test). A non-hematologic DLT may be any Grade ≥3 nonhematologic TEAEs occurring during cycle 1, with the following exceptions: nonhematologic AEs clearly due to extraneous causes, asymptomatic laboratory changes (other than renal and hepatic laboratory values and Grade 4 lipase/amylase levels) successfully reversible (Grade 4→Grade ≤2; Grade 3→Grade or baseline) within 72 hours, Grade 3 nausea/vomiting manageable with antiemetics, Grade 3 fatigue lasting <72 hours, Grade 3 elevation of ALT or AST that resolves to Grade ≤1 or baseline within 7 days, Grade 3 IRR that responds to symptomatic treatment (e.g. antihistamines, NSAIDs, narcotics, IV fluids), without recurrence of Grade 3 symptoms.
3. Toxicity will be evaluated according to National Cancer Institute Common
Terminology Criteria for Adverse Events version 5.0 (NCI CTCAE 5.0).
4. Part 1: Number of participants with grade greater than or equal to (>=) 3 TEAEs [Time Frame: Up to 12 months]. Grade >=3 TEAEs will be evaluated according to NCI CTCAE 5.0.
5. Part 1: Number of participants with serious adverse events (SAEs) [Time Frame: Up to 12 months].
6. Part 1: Number of participants who discontinued CTM #4 due to TEAEs [Time Frame: Up to 12 months].
7. Part 1: Number of participants with treatment related dose modifications including dose delays, dose interruption and dose reductions [Time Frame: Up to 12 months].
8. Part 1: Number of participants with clinically significant change in laboratory values [Time Frame: Up to 12 months].
9. Part 1: Number of participants with clinically significant change in vital sign measurements [Time Frame: Up to 12 months].
10. Part 2: Overall response rate (ORR) [Time Frame: Up to 12 months]. Percentage of participants who achieved a partial response (PR) or better during study as defined by International Myeloma Working Group (IMWG) Uniform Response Criteria. PR is >=50 percent (%) reduction of serum M protein and reduction in 24-hour urinary M protein by >=90% or less than (<) 200 milligram per (mg/) 24 hour (h). If serum and urine M protein are not measurable, >=50% decrease in difference between involved and uninvolved free light chain (FLC) levels is required in place of M protein criteria. If serum and urine M protein and serum FLC assay are not measurable, >=50% reduction in bone marrow plasma cells is required in place of M protein, provided baseline percentage was >=30%. In addition, if present at baseline, >=50% reduction in size of soft tissue plasmacytomas is required. Two consecutive assessments are needed; no known evidence of progressive or new bone lesions if radiographic studies were performed.

[1] Secondary outcome measures of this study will include:
1. Part 1 and Part 2, Cmax: Maximum observed concentration for CTM #4 [Time Frame: Cycles 1 and 2, Day 1: pre-dose, and at multiple time points (up to 168 hours) post-dose (each cycle is 28 days)].
2. Part 1 and Part 2, Tmax: Time to reach the maximum observed concentration (Cmax) for CTM #4 [Time Frame: Cycles 1 and 2, Day 1: pre-dose, and at multiple time points (up to 168 hours) post-dose (each cycle is 28 days)].
3. Part 1 and Part 2, AUClast: Area Under the Concentration-time Curve From Time 0 to the Time of the Last Quantifiable Concentration for CTM #4 [Time Frame: Cycles 1 and 2, Day 1: pre-dose, and at multiple time points (up to 168 hours) post-dose (each cycle is 28 days)].
4. Part 1: Overall response rate (ORR) [Time Frame: Up to 12 months]. ORR is defined as the percentage of participants who achieved PR or better during study as defined by IMWG Uniform Response Criteria. PR is >=50% reduction of serum M protein and reduction in 24-hour urinary M protein by >=90% or <200 mg/24 h. If serum and urine M protein are not measurable, >=50% decrease in difference between involved and uninvolved FLC levels is required in place of M protein criteria. If serum and urine M protein and serum FLC assay are not measurable, >=50% reduction in bone marrow plasma cells is required in place of M protein, provided baseline percentage was >=30%. In addition, if present at baseline, >=50% reduction in size of soft tissue plasmacytomas is required. Two consecutive assessments are needed; no known evidence of progressive or new bone lesions if radiographic studies were performed.
5. Part 1: Clinical benefit rate (CBR) [Time Frame: Up to 12 months]. CBR is defined as the percentage of participants who achieved a minimal response (MR) or better during study as defined by IMWG Uniform Response Criteria. MR is defined as a >=25% but less than or equal to (<=) 49% reduction of serum M protein and reduction in 24-hour urine M protein by 50% to 89%. In addition, if present at baseline, 25% to 49% reduction in size of soft tissue plasmacytomas is also required. No increase in size or number of lytic bone lesions (development of compression fracture does not exclude response).
6. Part 1 and Part 2: Progression-free survival (PFS) [Time Frame: From date of the dose administration until death due to any cause (up to 12 months)]. PFS is the time from the date of first dose until the date of progressive disease (PD), by IMWG criteria, or the date of death due to any cause. PD: Increase of 25% from lowest response value in: Serum M component with absolute increase >=0.5 gram per deciliter (g/dL); serum M component increases >=1 g/dL, to define relapse if starting M component >=5 g/dL; Urine M component (absolute increase >=200 mg/24 h); Only in participants without measurable serum and urine M protein levels: difference between involved and uninvolved FLC levels (absolute increase >10 milligram per deciliter [mg/dL]); Only in participants without measurable serum and urine M protein levels and without measurable disease by FLC level, bone marrow plasma cell % (absolute%>=10%); Development of new or definite increase in size of existing bone lesions or soft tissue plasmacytomas; Development of hypercalcemia may attributed solely to plasma cell proliferative disorder; Two consecutive assessments before new therapy needed.

7. Part 1 and Part 2: Duration of response (DOR) [Time Frame: From the date of the first documentation of response to the date of the first documented PD (up to 12 months)]. DOR is time from the date of the first documentation of response to the date of the first documented PD. PD is increase of 25% from lowest response value in: Serum M component with absolute increase >=0.5 g/dL; serum M component increases >=1g/dL, to define relapse if starting M component >=5 g/dL; Urine M component (absolute increase >=200 mg/24 h); Only in participants without measurable serum and urine M protein levels: difference between involved and uninvolved FLC levels (absolute increase >10 mg/dL); Only in participants without measurable serum and urine M protein levels and without measurable disease by FLC level, bone marrow plasma cell % (absolute%>=10%); Development of new or definite increase in size of existing bone lesions or soft tissue plasmacytomas; Development of hypercalcemia that can be attributed solely to plasma cell proliferative disorder; Two consecutive assessments before new therapy needed.

8. Part 1 and Part 2: Percentage of participants who achieved MR [Time Frame: Up to 12 months]. Percentage of participants who achieved MR, defined as 25% tumor reduction. MR is defined as a >=25% but <=49% reduction of serum M protein and reduction in 24-hour urine M protein by 50% to 89% as defined by IMWG Uniform Response Criteria.

9. Part 1 and Part 2: Number of participants with anti-drug antibodies following administration of CTM #4 [Time Frame: Up to 12 months].

10. Part 2: Number of participants with DLTs and other TEAEs including dose modifications, treatment discontinuation, and vital signs [Time Frame: Up to 12 months]. DLTs are defined as any of the events that are considered by the investigator to be at least possibly related to therapy with the study medication. Toxicity will be evaluated according to NCI CTCAE 5.0.

11. Part 2: Overall survival (OS) [Time Frame: From date of the dose administration until death due to any cause (up to 12 months)]. OS is defined as time from date of the dose administration until death due to any cause.

12. Part 2: Time to response (TTR) [Time Frame: From the date of the first dose of the study treatment to the date of the first documentation of response (up to 12 months)]. Time from the date of the first dose of the study treatment to the date of the first documentation of response (PR or better). PR is >=50% reduction of serum M protein and reduction in 24-hour urinary M protein by >=90% or to <200 mg/24 hour. If serum and urine M protein are not measurable, >=50% decrease in difference between involved and uninvolved FLC levels is required in place of M protein criteria. If serum and urine M protein and serum FLC assay are not measurable, >=50% reduction in bone marrow plasma cells is required in place of M protein, provided baseline percentage was >=30%. In addition, if present at baseline, >=50% reduction in size of soft tissue plasma cytomas is required. Two consecutive assessments are needed; no known evidence of progressive or new bone lesions if radiographic studies were performed.

13. Part 2: Percentage of participants who achieved complete response (CR) or very good partial response (VGPR) [Time Frame: Up to 12 months]. CR or VGPR is defined by IMWG criteria. CR is defined as negative immunofixation of serum and urine, disappearance of any soft tissue plasmacytomas, and <5% plasma cells in bone marrow; in participants for whom only measurable disease is by serum FLC level, normal FLC ratio of 0.26 to 1.65 in addition to CR criteria is required; Two consecutive assessments are needed. VGPR is defined as serum and urine M component detectable by immunofixation but not on electrophoresis or >=90% reduction in serum M component plus urine M component <100 mg/24 h; in participants for whom only measurable disease is by serum FLC level, >90% decrease in difference between involved and uninvolved FLC levels, in addition to VGPR criteria, is required; Two consecutive assessments are needed.

[2] To participate in the study, subjects must be 18 years or older (adult, older adult), and may be either male or female. Additional inclusion criteria for Part 1 of the study include:

1. Has a confirmed diagnosis of MM.
2. Has RRMM and has failed treatment with, is intolerant to, or is not a candidate for available therapies that are known to confer clinical benefit in this participant population.
3. Should meet all of the following criteria for prior therapy:
   Should be refractory to at least one proteasome inhibitor (PI), at least one immunomodulatory drug (IMiD), and at least 1 steroid.
   Should either have received >=3 prior lines of therapy or should have received at least two prior lines of therapy if one of those lines included a combination of PI and IMiD.
   Prior treatment with an anti-CD38 therapy (including daratumumab) is permitted.
4. Has measurable disease, defined as at least 1 of the following:
   Serum M-protein >=500 mg/dL (>=5 g/L) on serum protein electrophoresis (SPEP).
   Urine M-protein >=200 mg/24 h on urine protein electrophoresis (UPEP).
   Serum FLC assay result with an involved FLC level >=10 mg/dL (>=100 milligram per liter [mg/L]), provided the serum FLC ratio is abnormal.
5. Has an Eastern Cooperative Oncology Group (ECOG) performance status score of 0 or 1.
6. Has a normal QT interval corrected by the Fridericia method (QTcF) on screening electrocardiogram (ECG), defined as QTcF of <=450 millisecond (ms) in males or <=470 ms in females.
7. Meets the following clinical laboratory criteria at study entry:
   Total bilirubin <=1.5*the upper limit of the normal range (ULN), except for participant with Gilbert's syndrome, in whom the direct bilirubin must be <2.0*ULN.

Serum alanine aminotransferase (ALT) and aspartate aminotransferase (AST) must be <=2.5*ULN.

Estimated glomerular filtration rate (eGFR) >=30 milliliters per minute (mL/min/1.73 square meter [m$^2$], using the modification of diet in renal disease (MDRD) equation).

Absolute neutrophil count (ANC) >=1000 per cubic millimeter (/mm$^3$) (>=1.0*10$^9$ per liter [/L]); a count of >=750/mm$^3$ (>=0.75*10$^9$/L) may be acceptable for participants with >50% of plasma cells in bone marrow, after discussion with the sponsor.

Platelet count >=75,000/mm$^3$ (>=75*10$^9$/L); a value of >=50,000/mm$^3$ (>=50*10$^9$/L) may be acceptable for participants with >50% of plasma cells in bone marrow, after discussion with the sponsor.

Hemoglobin >=7.5 g/dL (it is not permissible to transfuse a participant to reach this level).

[3] Additional inclusion criteria for Part 2 of the study include:
1. Has a confirmed diagnosis of MM.
2. Should meet all of the following criteria for prior therapy:
    Should be refractory or intolerant to at least 1 PI and at least 1 IMiD.
    Should either have received >=3 prior lines of therapy or should have received at least 2 prior lines of therapy if 1 of those lines included a combination of PI and IMiD.
    Prior treatment with an anti-CD38 therapy (including daratumumab) is permitted, except for participants enrolled into the anti-CD38-therapy naïve expansion cohort.
    Daratumumab-RR cohorts (once weekly and once every two weeks CTM #4 dosing): Participant must be RR to daratumumab at any time during treatment. Of note, participant's RR to other anti-CD38 therapies are excluded.
    Anti-CD38 therapy naïve cohort (once weekly dosing): Participants must not have received any prior anti-CD38 therapy.
3. Has measurable disease, defined as at least 1 of the following:
    Serum M-protein >=500 mg/dL (>=5 g/L) on SPEP.
    Urine M-protein >=200 mg/24 hours on UPEP.
    Serum FLC assay result with an involved FLC level >=10 mg/d (>=100 mg/L), provided the serum FLC ratio is abnormal.
4. Has an ECOG performance status score of 0 or 1.
5. Has normal QTcF on screening ECG, defined as QTcF of <=450 ms in males or <=470 ms in females.
6. Meets the following clinical laboratory criteria at study entry:
    Total bilirubin <=1.5*the ULN, except for participant with Gilbert's syndrome, in whom the direct bilirubin must be <2.0*ULN.
    Serum ALT and AST must be <=2.5*ULN.
    eGFR >=30 mL/min/1.73 m$^2$, using the MDRD equation.
    ANC >=1000 mm$^3$ (>=1.0*10$^9$/L); a count of >=750/mm$^3$ (>=0.75*10$^9$/L) may be acceptable for participant with >50% of plasma cells in bone marrow, after discussion with the sponsor.
    Platelet count >=75,000/mm$^3$ (>=75*10$^9$/L); a value of >=50,000/mm$^3$ (>=50*10$^9$/L) may be acceptable for participants with >50% of plasma cells in bone marrow, after discussion with the sponsor.
    Hemoglobin >=7.5 g/dL (it is not permissible to transfuse a participant to reach this level).

[4] A subject will be excluded from the study if he or she meets one or more of the following criteria:
1. Has polyneuropathy, organomegaly, endocrinopathy, monoclonal gammopathy and skin changes (POEMS) syndrome, monoclonal gammopathy of unknown significance, smoldering myeloma, solitary plasmacytoma, amyloidosis, Waldenström macroglobulinemia, or Immunoglobulin M (IgM) myeloma.
2. Has sensory or motor neuropathy of NCI CTCAE Grade >=3.
3. Has received a final dose of any of the following treatments/procedures within the following minimum interval before the first dose of CTM #4:
    Myeloma-specific therapy, including PIs and IMiDs-14 days.
    Anti-CD38 (a) therapy (Once the MTD/RP2D has been established, the washout period may be adjusted in the expansion phase (Part 2) of the study for participants who have received anti-CD38 therapy)-90 days.
    Corticosteroid therapy for myeloma-7 days.
    Radiation therapy for localized bone lesions-14 days.
    Major surgery-30 days.
    Autologous stem cell transplant-90 days.
    Investigational therapy-30 days.
4. Has received an allogeneic stem cell transplant or organ transplantation.
5. Has not recovered, to NCI CTCAE V5 Grade <=1 or baseline, from adverse reactions to prior myeloma treatment or procedures (chemotherapy, immunotherapy, radiation therapy) excluding alopecia.
6. Has clinical signs of central nervous system (CNS) involvement of MM.
7. Has known or suspected light chain amyloidosis of any organ (the presence of amyloid on the bone marrow biopsy without other evidence of amyloidosis is acceptable).
8. Has congestive heart failure (New York Heart Association) class >=II or left ventricular ejection fraction (LVEF <40%, cardiac myopathy, active ischemia, or any other uncontrolled cardiac condition such as angina pectoris or myocardial infarction within the past 6 months, clinically significant arrhythmia requiring therapy including anticoagulants, or clinically significant uncontrolled hypertension.
9. Has chronic or active infection requiring systemic therapy, as well as a history of symptomatic viral infection that has not been fully cured (example, human immunodeficiency viruses (HIV) or viral hepatitis B or C).
10. Has a history of systemic inflammatory response syndrome (SIRS)/cytokine release syndrome (CRS) reactions following infusion with any monoclonal antibodies or Chimeric Antigen Receptor (CAR) T-cell therapy
11. With a chronic condition requiring the use of systemic corticosteroids at a dose of >10 milligram per day (mg/day) of prednisone or equivalent.

While some embodiments of the invention have been described by way of illustration, it will be apparent that the invention may be put into practice with many modifications, variations and adaptations, and with the use of numerous equivalents or alternative solutions that are within the scope of persons skilled in the art, without departing from the spirit of the invention or exceeding the scope of the claims.

All publications, patents, and patent applications are herein incorporated by reference in their entirety to the same extent as if each individual publication, patent or patent application was specifically and individually indicated to be incorporated by reference in its entirety. The international patent application publications WO 2014/164680, WO 2014/164693, WO 2015/138435, WO 2015/138452, WO 2015/113005, WO 2015/113007, WO 2015/191764, WO 2016/196344, WO 2017/019623, WO 2018/106895, and WO 2018/140427, are each incorporated herein by reference their entireties. The inventions of U.S. patent applications US2015/259428, US2016/17784, and US2017/143814 are each incorporated herein by reference in their entireties. The complete inventions of all electronically available biological sequence information from GenBank (National Center for Biotechnology Information, U.S.) for amino acid and nucleotide sequences cited herein are each incorporated herein by reference in their entirety.

TABLE 20

Sequences

| SEQ ID No. | Text Description | Biological Sequence |
|---|---|---|
| SEQ ID NO: 1 | Shiga-like toxin 1 Subunit A (SLT-1A) | KEFTLDFSTAKTYVDSLNVIRSAIGTPLQTISSGGTSLLMIDSGS<br>GDNLFAVDVRGIDPEEGRFNNLRLIVERNNLYVTGFVNRTNN<br>VFYRFADFSHVTFPGTTAVTLSGDSSYTTLQRVAGISRTGMQI<br>NRHSLTTSYLDLMSHSGTSLTQSVARAMLRFVTVTAEALRFR<br>QIQRGFRTTLDDLSGRSYVMTAEDVDLTLNWGRLSSVLPDYH<br>GQDSVRVGRISFGSINAILGSVALILNCHHHASRVARMASDEF<br>PSMCPADGRVRGITHNKILWDSSTLGAILMRRTISS |
| SEQ ID NO: 2 | Shiga toxin Subunit A (StxA) | KEFTLDFSTAKTYVDSLNVIRSAIGTPLQTISSGGTSLLMIDSGT<br>GDNLFAVDVRGIDPEEGRFNNLRLIVERNNLYVTGFVNRTNN<br>VFYRFADFSHVTFPGTTAVTLSGDSSYTTLQRVAGISRTGMQI<br>NRHSLTTSYLDLMSHSGTSLTQSVARAMLRFVTVTAEALRFR<br>QIQRGFRTTLDDLSGRSYVMTAEDVDLTLNWGRLSSVLPDYH<br>GQDSVRVGRISFGSINAILGSVALILNCHHHASRVARMASDEF<br>PSMCPADGRVRGITHNKILWDSSTLGAILMRRTISS |
| SEQ ID NO: 3 | Shiga-like toxin 2 Subunit A (SLT-2A) | DEFTVDFSSQKSYVDSLNSIRSAISTPLGNISQGGVSVSVINHV<br>LGGNYISLNVRGLDPYSERFNHLRLIMERNNLYVAGFINTETN<br>IFYRFSDFSHISVPDVITVSMTTDSSYSSLQRIADLERTGMQIGR<br>HSLVGSYLDLMEFRGRSMTRASSRAMLRFVTVIAEALRFRQI<br>QRGFRPALSEASPLYTMTAQDVDLTLNWGRISNVLPEYRGEE<br>GVRIGRISFNSLSAILGSVAVILNCHSTGSYSVRSVSQKQKTEC<br>QIVGDRAAIKVNNVLWEANTIAALLNRKPQDLTEPNQ |
| SEQ ID NO: 4 | Shiga toxin subtype 2c Subunit A (Stx2cA) variant 1 | REFTIDFSTQQSYVSSLNSIRTEISTPLEHISQGTTSVSVINHTPP<br>GSYFAVDIRGLDVYQARFDHLRLIIEQNNLYVAGFVNTATNT<br>FYRFSDFTHISVPGVTTVSMTTDSSYTTLQRVAALERSGMQIS<br>RHSLVSSYLALMEFSGNTMTRDASRAVLRFVTVTAEALRFRQ<br>IQREFRQALSETAPVYTMTPGDVDLTLNWGRISNVLPEYRGE<br>DGVRVGRISFNNISAILGTVAVILNCHHQGARSVR |
| SEQ ID NO: 5 | Shiga toxin subtype 2c Subunit A (Stx2cA) variant 2 | REFTIDFSTQQSYVSSLNSIRTEISTPLEHISQGTTSVSVINHTPP<br>GSYFAVDIRGLDVYQARFDHLRLIIEQNNLYVAGFVNTATNT<br>FYRFSDFAHISVPGVTTVSMTTDSSYTTLQRVAALERSGMQIS<br>RHSLVSSYLALMEFSGNTMTRDASRAVLRFVTVTAEALRFRQ<br>IQREFRQALSETAPVYTMTPGDVDLTLNWGRISNVLPEYRGE<br>DGVRVGRISFNNISAILGTVAVILNCHHQGARSVR |
| SEQ ID NO: 6 | Shiga toxin subtype 2c Subunit A (Stx2cA) variant 3 | REFTIDFSTQQSYVSSLNSIRTEISTPLEHISQGTTSVSVINHTPP<br>GSYFAVDIRGLDIYQARFDHLRLIIEQNNLYVAGFVNTATNTF<br>YRFSDFTHISVPGVTTVSMTTDSSYTTLQRVAALERSGMQISR<br>HSLVSSYLALMEFSGNTMTRDASRAVLRFVTVTAEALRFRQI<br>QREFRQALSETAPVYTMTPGDVDLTLNWGRISNVLPEYRGED<br>GVRVGRISFNNISAILGTVAVILNCHHQGARSVR |
| SEQ ID NO: 7 | Shiga toxin subtype 2c Subunit A (Stx2cA) variant 4 | REFTIDFSTQQSYVSSLNSIRTEISTPLEHISQGTTSVSVINHTPP<br>GSYFAVDIRGLDVYQARFDHLRLIIEQNNLYVAGFVNTATNT<br>FYRFSDFTHISVPSVTTVSMTTDSSYTTLQRVAALERSGMQIS<br>RHSLVSSYLALMEFSGNTMTRDASRAVLRFVTVTAEALRFRQ<br>IQREFRQALSETAPVYTMTPGDVDLTLNWGRISNVLPEYRGE<br>DGVRVGRISFNNISAILGTVAVILNCHHQGARSVR |
| SEQ ID NO: 8 | Shiga toxin subtype 2c Subunit A (Stx2cA) variant 5 | REFTIDFSTQQSYVSSLNSIRTEISTPLEHISQGTTSVSVINHTPP<br>GSYFAVDIRGLDVYQARFDHLRLIIEQNNLYMAGFVNTATNT<br>FYRFSDFTHISVPSVTTVSMTTDSSYTTLQRVAALERSGMQIS<br>RHSLVSSYLALMEFSGNTMTRDASRAVLRFVTVTAEALRFRQ<br>IQREFRQALSETAPVYTMTPGDVDLTLNWGRISNVLPEYRGE<br>DGVRVGRISFNNISAILGTVAVILNCHHQGARSVR |

TABLE 20-continued Sequences

| SEQ ID No. | Text Description | Biological Sequence |
|---|---|---|
| SEQ ID NO: 9 | Shiga toxin subtype 2c Subunit A (Stx2cA) variant 6 | REFTIDFSTQQSYVSSLNSIRTEISTPLEHISQGTTSVSVINHTPP GSYFAVDIRGLDVYQARFDHLRLIIEQNNLYVAGFVNTATNT FYRFSDFTHISVPGVTTVSMTTDSSYTTLQRVAALERSGMQIS RHSLVSSYLALMEFSGNTMTRDASRAVLRFVTVTAEALRFRQ IQREFRQVLSETAPVYTMTPGDVDLTLNWGRISNVLPEYRGE DGVRVGRISFNNISAILSTVAVILNCHHQGARSVR |
| SEQ ID NO: 10 | Shiga toxin subtype 2d Subunit A (Stx2dA) variant 1 | REFTIDFSTQQSYVSSLNSIRTEISTPLEHISQGTTSVSVINHTPP GSYFAVDIRGLDVYQARFDHLRLIIEQNNLYVAGFVNTATNT FYRFSDFAHISVPGVTTVSMTTDSSYTTLQRVAALERSGMQIS RHSLVSSYLALMEFSGNTMTRDASRAVLRFVTVTAEALRFRQ IQREFRQALSETAPVYTMTPGDVDLTLNWGRISNVIPEYRGED GVRVGRISFNNISAILGTVAVILNCHHQGARSVR |
| SEQ ID NO: 11 | Shiga toxin subtype 2d Subunit A (Stx2dA) variant 2 | REFMIDFSTQQSYVSSLNSIRTEISTPLEHISQGTTSVSVINHTPP GSYFAVDIRGLDVYQARFDHLRLIIEQNNLYVAGFVNTATNT FYRFSDFTHISVPGVTTVSMTTDSSYTTLQRVAALERSGMQIS RHSLVSSYLALMEFSGNTMTRDASRAVLRFVTVTAEALRFRQ IQREFRQALSETAPVYTMTPEEVDLTLNWGRISNVLPEFRGEG GVRVGRISFNNISAILGTVAVILNCHHQGARSVR |
| SEQ ID NO: 12 | Shiga toxin subtype 2d Subunit A (Stx2dA) variant 3 | REFTIDFSTQQSYVSSLNSIRTEISTPLEHISQGTTSVSVINHTPP GSYFAVDIRGLDVYQARFDHLRLIIEQNNLYVAGFVNTATNT FYRFSDFTHISVPGVTTVSMTTDSSYTTLQRVAALERSGMQIS RHSLVSSYLALMEFSGNTMTRDASRAVLRFVTVTAEALRFRQ IQREFRQALSETAPVYTMTPGDVDLTLNWGRISNVIPEYRGED GVRVGRISFNNISAILSTVAVILNCHHQGARSVR |
| SEQ ID NO: 13 | Shiga toxin subtype 2e Subunit A (Stx2eA) variant 1 | QEFTIDFSTQQSYVSSLNSIRTAISTPLEHISQGATSVSVINHTPP GSYISVGIRGLDVYQERFDHLRLIIERNNLYVAGFVNTTTNTF YRFSDFAHISLPGVTTISMTTDSSYTTLQRVAALERSGMQISRH SLVSSYLALMEFSGNTMTRDASRAVLRFVTVTAEALRFRQIQ REFRLALSETAPVYTMTPEDVDLTLNWGRISNVLPEYRGEAG VRVGRISFNNISAILGTVAVILNCHHQGARSVR |
| SEQ ID NO: 14 | Shiga toxin subtype 2e Subunit A (Stx2eA) variant 2 | QEFTIDFSTQQSYVSSLNSIRTAISTPLEHISQGATSVSVINHTPP GSYISVGIRGLDVYQAHFDHLRLIIEQNNLYVAGFVNTATNTF YRFSDFAHISLPGVTTISMTTDSSYTTLQRVAALERSGMQISRH SLVSSYLALMEFSGNTMTREASRAVLRFVTVTAEALRFRQIQ REFRQALSETAPVYTMTPEDVDLTLNWGRISNVLPEYRGEDG VRVGRISFNNISAILGTVAVILNCHHQGARSVR |
| SEQ ID NO: 15 | Shiga toxin subtype 2f Subunit A (Stx2fA) | DEFTVDFSSQKSYVDSLNSIRSAISTPLGNISQGGVSVSVINHV PGGNYISLNVRGLDPYSERFNHLRLIMERNNLYVAGFINTETN TFYRFSDFSHISVPDVITVSMTTDSSYSSLQRIADLERTGMQIG RHSLVGSYLDLMEFRGRSMTRASSRAMLRFVTVIAEALRFRQ IQRGFRPALSEASPLYTMAQDVDLTLNWGRISNVLPEYRGEE GVRIGRISFNSLSAILGSVAVILNCHSTGSYSVR |
| SEQ ID NO: 16 | Shiga toxin subtype c Subunit A (Stx1cA) | KEFTLDFSTAKTYVDSLNVIRSAIGTPLQTISSGGTSLLMIDSGT GDNLFAVDVRGIDPEEGRFNNLRLIVERNNLYVTGFVNRTNN VFYRFADFSHVTFPGTTAVTLSGDSSYTTLQRVAGISRTGMQI NRHSLTTSYLDLMSHSGTSLTQSVARAMLRFVTVTAEALRFR QIQRGFRTTLDDLSGRSYVMTAEDVDLTLNWGRLSSVLPDYH GQDSVRVGRISFGSVNAILGSVALILNCHHHASRVAR |
| SEQ ID NO: 17 | Shiga toxin subtype d Subunit A (Stx1dA) | KEFTLDFSTAKKYVDSLNVIRSAIGTPLQTISSGGTSLLMIDSG TGDNLFAVDIMGLEPEEERFNNLRLIVERNNLYVTGFVNRTN NVFYRFADFSHVTFPGTRAVTLSGDSSYTTLQRVAGISRTGM QINRHSLTTSYLDLMSYSGTSLTQSVARAMLRFVTVTAEALR FRQIQRGFRTTLDDLSGRSYVMTAEDVDLTLNWGRLSSILPD YHGQDSVRVGRISFGSINAILGSVALILNCHHHASRVAR |
| SEQ ID NO: 18 | Shiga toxin subtype e Subunit A (Stx1eA) | QDFTVDFSTAKKYVDSLNAIRSAIGTPLHSISSGGTSLLMIDNG TGDNLFAVDIRGLDPEEERFDNLRLIIERNNLYVTGFVNRTSNI FYRFADFSHVTFPGTRAVTLSGDSSYTTLQRVAGIGRTGMQIN RHSLTTSYLDLMSYSGSSLTQPVARAMLRFVTVTAEALRFQI QRGFRTTLDDLVSGHSYTMTVEDVDLTLNWGRLSSVLPDYHG QDSVRVGRISFGGVNAILGSVALILNCHHHTSRVSR |
| SEQ ID NO: 19 | Family 1 light chain CDR1 | SSNIGSNY |

TABLE 20-continued

Sequences

| SEQ ID No. | Text Description | Biological Sequence |
|---|---|---|
| SEQ ID NO: 20 | Family 1 light chain CDR2 | GNS |
| SEQ ID NO: 21 | Family 1 light chain CDR3 | QSYDSSLSGSG |
| SEQ ID NO: 22 | Family 1 heavy chain CDR1 | GFTFSDYY |
| SEQ ID NO: 23 | Family 1 heavy chain CDR2 | ISGSGGST |
| SEQ ID NO: 24 | Family 1 heavy chain CDR3 | AREHSNYFYGMDV |
| SEQ ID NO: 25 | Family 2 light chain CDR1 | SSNIGGNY |
| SEQ ID NO: 26 | Family 2 light chain CDR2 | RNN |
| SEQ ID NO: 27 | Family 2 light chain CDR3 | QSYDSSLSVS |
| SEQ ID NO: 28 | Family 2 heavy chain CDR1 | GFTFSSYW |
| SEQ ID NO: 29 | Family 2 heavy chain CDR2 | ISGSGGGT |
| SEQ ID NO: 30 | Family 2 heavy chain CDR3 | AREGETSFGLDV |
| SEQ ID NO: 31 | Family 3 light chain CDR1 | TGAVTSGFY |
| SEQ ID NO: 32 | Family 3 light chain CDR2 | ATN |
| SEQ ID NO: 33 | Family 3 light chain CDR3 | LVYYDGAW |
| SEQ ID NO: 34 | Family 3 heavy chain CDR1 | GYSFTSYW |
| SEQ ID NO: 35 | Family 3 heavy chain CDR2 | IYPGDSDT |
| SEQ ID NO: 36 | Family 3 heavy chain CDR3 | ARGPSTGFWSGNYFDY |
| SEQ ID NO: 37 | light chain | QSVLTQPPSASGTPGQRVTISCSGSSSNIGSNYVYWYQQLPGT APKLLIYGNSNRPSGVPDRFSGSKSGTSASLAISGLRSEDEADY YCQSYDSSLSGSGVFGGGTKLTVLG |
| SEQ ID NO: 38 | heavy chain | EVQLLESGGGLVQPGGSLRLSCAASGFTFSDYYMSWVRQAP GKGLEWVSAISGSGGSTYYADSVKGRFTISRDNSKNTLYLQM NSLRAEDTAVYYCAREHSNYFYGMDVWGQGTLVTVSS |

TABLE 20-continued

Sequences

| SEQ ID No. | Text Description | Biological Sequence |
|---|---|---|
| SEQ ID NO: 39 | light chain | QSVLTQPPSASGTPGQRVTISCSGSSSNIGGNYVYWYQQLPGT APKLLIYRNNQRPSGVPDRFSGSKSGTSASLAISGLRSEDEAD YYCQSYDSSLSVSVFGGGTKLTVLG |
| SEQ ID NO: 40 | heavy chain | EVQLLESGGGLVQPGGSLRLSCAASGFTFSSYVVMHWVRQAP GKGLEWVSAISGSGGGTFYADSVKGRFTISRDNSKNTLYLQM NSLRAEDTAVYYCAREGETSFGLDVWGQGTLVTVSS |
| SEQ ID NO: 41 | light chain | QTVVTQEPSLTVSPGETVTLTCASSTGAVTSGFYPNWFQQKP GQAPRALIYATNNKYSWTPARFSGSLLGDKAALTLSRVQPED EADYYCLVYYDGAWVFGGGTKLTVLG |
| SEQ ID NO: 42 | heavy chain | QVQLVQSGAEVKKPGESLKISCKGSGYSFTSYWIGWVRQMP GKGLEWMGIIYPGDSDTRYSPSFQGQVTISADKSISTAYLQWS SLKASDTAMYYCARGPSTGFWSGNYFDYWGQGTLVTVSS |
| SEQ ID NO: 43 | light chain | DIQMTQSPSSLSASVGDRVTITCASSTGAVTSGFYPNVVFQQKP GQAPRALIYATNNKYSWTPARFSGSLLGDKAALTLSRVQPED EADYYCLVYYDGAWVFGGGTKLTVLG |
| SEQ ID NO: 44 | heavy chain | QVQLVQSGAEVKKPGESLKISCKGSGYSFTSYWIGWVRQMP GKGLEWMGIIYPGDSDTRYSPSFQGQVTISADKSISTAYLQWS SLKASDTAMYYCARGPSTGFWSGNYFDYWGQGTLVTVSS |
| SEQ ID NO: 45 | Shiga toxin effector polypeptide SLT-1A-DI | AEFTLDFSTAKTYVDSLNVIRSAIGTPLQTISSGGTSLLMIDSGI GDNLFAVDILGFDFTLGRFNNLRLIVERNNLYVTGFVNRTNN VFYRFADFSHVTFPGTTAVTLSADSSYTTLQRVAGISRTGMQI NRHSLTTSYLDLMSHSATSLTQSVARAMLRFVTVTAEALRFR QIQRGFRTTLDDLSGRSYVMTAEDVDLTLNWGRLSSVLPDYH GQDSVRVGRISFGSINAILGSVALILNSHHHASAVAA |
| SEQ ID NO: 46 | Shiga toxin effector polypeptide SLT-1A-DI-1 | KEFTLDFSTAKTYVDSLNVIRSAIGTPLQTISSGGTSLLMIDSGI GDNLFAVDILGFDFTLGRFNNLRLIVERNNLYVTGFVNRTNN VFYRFADFSHVTFPGTTAVTLSADSSYTTLQRVAGISRTGMQI NRHSLTTSYLDLMSHSGTSLTQSVARAMLRFVTVTAEALRFR QIQRGFRTTLDDLSGASYVMTAEDVDLTLNWGRLSSVLPDYH GQDSVRVGRISFGSINAILGSVALILNSHHHASAVAA |
| SEQ ID NO: 47 | Shiga toxin effector polypeptide SLT-1A-DI-2 | KEFTLDFSTAKTYVDSLNVIRSAIGTPLQTISSGGTSLLMIDSGI GDNLFAVDILGFDFTLGRFNNLRLIVERNNLYVTGFVNRTNN VFYRFADFSHVTFPGTTAVTLSADSSYTTLQRVAGISRTGMQI NRHSLTTSYLALMSHSGTSLTQSVARAMLRFVTVTAEALRFR QIQRGFRTTLDDLSGASYVMTAEDVDLTLNWGRLSSVLPDYH GQDSVRVGRISFGSINAILGSVALILNSHHHASAVAA |
| SEQ ID NO: 48 | Shiga toxin effector polypeptide SLT-1A-DI-3 | KEFTLDFSTAKTYVDSLNVIRSAIGTPLQTISSGGTSLLMIDSGI GDNLFAVDILGFDFTLGRFNNLRLIVERNNLYVTGFVNRTNN AFYRFADFSHVTFPGTTAVTLSADSSYTTLQRVAGISRTGMQI NRHSLTTSYLALMSHSGTSLTQSAARAMLRFVTVTAEALRFR QIQRGFRTTLDDLSGASYVMTAEDVDLTLNWGRLSSVLPDYH GQDSVRVGRISFGSINAILGSVALILNSHHHASAVAA |
| SEQ ID NO: 49 | Shiga toxin effector polypeptide SLT-1A-DI-4 | KEFTLDFSTAKTYVDSLNVIRSAIGTPLQTISSGGTSLLMIDSGS GDNLFAVDVRGIDPEEGRFNNLRLIVERNNLYVTGFVNRTNN VFYRFADFSHVTFPGTTAVTLSGDSSYTTLQRVAGISRTGMQI NRHSLTTSYLDLMSHSGTSLTQSVARAMLRFVTVTAEALRFR QIQRGFRTTLDDLSGRSYVMTAEDVDLTLNWGRLSSVLPDYH GQDSVRVGRISFGSINAILGSVALILNCHHHASAVAA |
| SEQ ID NO: 50 | Shiga toxin effector polypeptide SLT-1A-DI inactive | AEFTLDFSTAKTYVDSLNVIRSAIGTPLQTISSGGTSLLMIDSGI GDNLFAVDILGFDFTLGRFNNLRLIVERNNLYVTGFVNRTNN VFYRFADFSHVTFPGTTAVTLSADSSYTTLQRVAGISRTGMQI NRHSLTTSYLDLMSHSATSLTQSVARAMLRFVTVTADALRFR QIQRGFRTTLDDLSGRSYVMTAEDVDLTLNWGRLSSVLPDYH GQDSVRVGRISFGSINAILGSVALILNSHHHASAVAA |
| SEQ ID NO: 51 | Shiga toxin effector polypeptide SLT-1A-DI-1 inactive | KEFTLDFSTAKTYVDSLNVIRSAIGTPLQTISSGGTSLLMIDSGI GDNLFAVDILGFDFTLGRFNNLRLIVERNNLYVTGFVNRTNN VFYRFADFSHVTFPGTTAVTLSADSSYTTLQRVAGISRTGMQI NRHSLTTSYLDLMSHSGTSLTQSVARAMLRFVTVTADALRFR QIQRGFRTTLDDLSGASYVMTAEDVDLTLNWGRLSSVLPDYH GQDSVRVGRISFGSINAILGSVALILNSHHHASAVAA |

TABLE 20-continued

Sequences

| SEQ ID No. | Text Description | Biological Sequence |
|---|---|---|
| SEQ ID NO: 52 | Shiga toxin effector polypeptide SLT-1A-DI-2 inactive | KEFTLDFSTAKTYVDSLNVIRSAIGTPLQTISSGGTSLLMIDSGI GDNLFAVDILGFDFTLGRFNNLRLIVERNNLYVTGFVNRTNN VFYRFADFSHVTFPGTTAVTLSADSSYTTLQRVAGISRTGMQI NRHSLTTSYLALMSHSGTSLTQSVARAMLRFVTVTADALRFR QIQRGFRTTLDDLSGASYVMTAEDVDLTLNWGRLSSVLPDYH GQDSVRVGRISFGSINAILGSVALILNSHHHASAVAA |
| SEQ ID NO: 53 | Shiga toxin effector polypeptide SLT-1A-DI-3 inactive | KEFTLDFSTAKTYVDSLNVIRSAIGTPLQTISSGGTSLLMIDSGI GDNLFAVDILGFDFTLGRFNNLRLIVERNNLYVTGFVNRTNN AFYRFADFSHVTFPGTTAVTLSADSSYTTLQRVAGISRTGMQI NRHSLTTSYLALMSHSGTSLTQSAARAMLRFVTVTADALRFR QIQRGFRTTLDDLSGASYVMTAEDVDLTLNWGRLSSVLPDYH GQDSVRVGRISFGSINAILGSVALILNSHHHASAVAA |
| SEQ ID NO: 54 | Shiga toxin effector polypeptide SLT-1A-DI-4 | KEFTLDFSTAKTYVDSLNVIRSAIGTPLQTISSGGTSLLMIDSGS GDNLFAVDVRGIDPEEGRFNNLRLIVERNNLYVTGFVNRTNN VFYRFADFSHVTFPGTTAVTLSGDSSYTTLQRVAGISRTGMQI NRHSLTTSYLDLMSHSGTSLTQSVARAMLRFVTVTADALRFR QIQRGFRTTLDDLSGRSYVMTAEDVDLTLNWGRLSSVLPDYH GQDSVRVGRISFGSINAILGSVALILNCHHHASAVAA |
| SEQ ID NO: 55 | SLT-1A-combo variant 1 | KEFILRFSVAHKYVDSLNVIRSAIGTPLQTISSGGTSLLMIDSGS GDNLFAVDVRGIDPEEGRFNNLRLIVERNNLYVTGFVNRTNN VFYRFADFSHVTFPGTTAVTLSGDSSYTTLQRVAGISRTGMQI NRHSLTTSYLDLMSHSGTSLTQSVARAMLRFVTVTAEALRFR QIQRGFRTTLDDLSGRSYVMTAEDVDLTLNWGRLSSVLPDYH GQDSVRVGRISFGSINAILGSVALILNCHHHASAVAA |
| SEQ ID NO: 56 | SLT-1A-combo variant 2 | KEFTLDFSTAKTYVDSLNVIRSAIGTPLQTISSGGTSLLMIDNL VPMVATVVDVRGIDPEEGRFNNLRLIVERNNLYVTGFVNRTN NVFYRFADFSHVTFPGTTAVTLSGDSSYTTLQRVAGISRTGM QINRHSLTTSYLDLMSHSGTSLTQSVARAMLRFVTVTAEALR FRQIQRGFRTTLDDLSGRSYVMTAEDVDLTLNWGRLSSVLPD YHGQDSVRVGRISFGSINAILGSVALILNCHHHASAVAA |
| SEQ ID NO: 57 | SLT-1A-combo variant 3 | KEFTLDFSTAKTYVDSLNVIRSAIGTPLQTISSGGTSLLMIDSNL VPMVATVDVRGIDPEEGRFNNLRLIVERNNLYVTGFVNRTNN VFYRFADFSHVTFPGTTAVTLSGDSSYTTLQRVAGISRTGMQI NRHSLTTSYLDLMSHSGTSLTQSVARAMLRFVTVTAEALRFR QIQRGFRTTLDDLSGRSYVMTAEDVDLTLNWGRLSSVLPDYH GQDSVRVGRISFGSINAILGSVALILNCHHHASAVAA |
| SEQ ID NO: 58 | SLT-1A-combo variant 4 | KEFTLDFSTAKTYVDSLNVIRSAIGTPLQTISSGGTSLLMIDSGI LGFVFTLDVRGIDPEEGRFNNLRLIVERNNLYVTGFVNRTNNV FYRFADFSHVTFPGTTAVTLSGDSSYTTLQRVAGISRTGMQIN RHSLTTSYLDLMSHSGTSLTQSVARAMLRFVTVTAEALRFRQI QRGFRTTLDDLSGRSYVMTAEDVDLTLNWGRLSSVLPDYHG QDSVRVGRISFGSINAILGSVALILNCHHHASAVAA |
| SEQ ID NO: 59 | SLT-1A-combo variant 5 | KEFTLDFSTAKTYVDSLNVIRSAIGTPLQTISSGGTSLLMIDSGS GDNLFAVGILGFDFTLGRFNNLRLIVERNNLYVTGFVNRTNN VFYRFADFSHVTFPGTTAVTLSGDSSYTTLQRVAGISRTGMQI NRHSLTTSYLDLMSHSGTSLTQSVARAMLRFVTVTAEALRFR QIQRGFRTTLDDLSGRSYVMTAEDVDLTLNWGRLSSVLPDYH GQDSVRVGRISFGSINAILGSVALILNCHHHASAVAA |
| SEQ ID NO: 60 | SLT-1A-combo variant 6 | KEFTLDFSTAKTYVDSLNVIRSAIGTPLQTISSGGTSLLMIDSGS GDNLFAVDILGFVFTLGRFNNLRLIVERNNLYVTGFVNRTNN VFYRFADFSHVTFPGTTAVTLSGDSSYTTLQRVAGISRTGMQI NRHSLTTSYLDLMSHSGTSLTQSVARAMLRFVTVTAEALRFR QIQRGFRTTLDDLSGRSYVMTAEDVDLTLNWGRLSSVLPDYH GQDSVRVGRISFGSINAILGSVALILNCHHHASAVAA |
| SEQ ID NO: 61 | SLT-1A-combo variant 7 | KEFTLDFSTAKTYVDSLNVIRSAIGTPLQTISSGGTSLLMIDSGS GDNLFAVDILGFDFTLGRFNNLRLIVERNNLYVTGFVNRTNN VFYRFADFSHVTFPGTTAVTLSGDSSYTTLQRVAGISRTGMQI NRHSLTTSYLDLMSHSGTSLTQSVARAMLRFVTVTAEALRFR QIQRGFRTTLDDLSGRSYVMTAEDVDLTLNWGRLSSVLPDYH GQDSVRVGRISFGSINAILGSVALILNCHHHASAVAA |
| SEQ ID NO: 62 | SLT-1A-combo variant 8 | KEFTLDFSTAKTYVDSLNVIRSAIGTPLQTISSGGTSLLMIDSGS GDNLFAVGILGFVFTLGRFNNLRLIVERNNLYVTGFVNRTNN VFYRFADFSHVTFPGTTAVTLSGDSSYTTLQRVAGISRTGMQI NRHSLTTSYLDLMSHSGTSLTQSVARAMLRFVTVTAEALRFR |

TABLE 20-continued

| Sequences | | |
|---|---|---|
| SEQ ID No. | Text Description | Biological Sequence |
| | | QIQRGFRTTLDDLSGRSYVMTAEDVDLTLNWGRLSSVLPDYH GQDSVRVGRISFGSINAILGSVALILNCHHHASAVAA |
| SEQ ID NO: 63 | SLT-1A-combo variant 9 | KEFILDFSTAKTYVDSLNVIRSAIGTPLQTISSGGTSLLMIDSGI GDNLFAVDVRGIAPIEARFNNLRLIVERNNLYVTGFVNRTNN VFYRFADFSHVTFPGTTAVTLSADSSYTTLQRVAGISRTGMQI NRHSLTTSYLDLMSHSATSLTQSVARAMLRFVTVTAEALRFR QIQRGFRTTLAALSGASYVMTAEDVDLTLNWGRLSSVLPDYH GQDSVRVGRISFGSINAILGSVALILNSHHHASAVAA |
| SEQ ID NO: 64 | SLT-1A-combo variant 10 | KEFTLDFSTAKTYVDSLNVIRSAIGTPLQTISSGGTSLLMIDSGS GDNLFAVGILGFVFTLEGRFNNLRLIVERNNLYVTGFVNRTN NVFYRFADFSHVTFPGTTAVTLSGDSSYTTLQRVAGISRTGM QINRHSLTTSYLDLMSHSGTSLTQSVARAMLRFVTVTAEALR FRQIQRGFRTTLDDLSGRSYVMTAEDVDLTLNWGRLSSVLPD YHGQDSVRVGRISFGSINAILGSVALILNCHHHASAVAA |
| SEQ ID NO: 65 | SLT-1A-combo variant 11 | KEFTLDFSTAKTYVDSLNVIRSAIGTPLQTISSGGTSLLMIDSGS GDNLFAVNLVPMVATVGRFNNLRLIVERNNLYVTGFVNRTN NVFYRFADFSHVTFPGTTAVTLSGDSSYTTLQRVAGISRTGM QINRHSLTTSYLDLMSHSGTSLTQSVARAMLRFVTVTAEALR FRQIQRGFRTTLDDLSGRSYVMTAEDVDLTLNWGRLSSVLPD YHGQDSVRVGRISFGSINAILGSVALILNCHHHASAVAA |
| SEQ ID NO: 66 | SLT-1A-combo variant 12 | KEFTLDFSTAKTYVDSLNVIRSAIGTPLQTISSGGTSLLMIDSGS GDNLFAVDVRGIDPEEGRFNNLRLIVERNNLYVTGFVNRTNN VFYRFADFSHVTFPGTNLVPMVATVSYTTLQRVAGISRTGMQ INRHSLTTSYLDLMSHSGTSLTQSVARAMLRFVTVTAEALRFR QIQRGFRTTLDDLSGRSYVMTAEDVDLTLNWGRLSSVLPDYH GQDSVRVGRISFGSINAILGSVALILNCHHHASAVAA |
| SEQ ID NO: 67 | SLT-1A-combo variant 13 | KEFTLDFSTAKTYVDSLNVIRSAIGTPLQTISSGGTSLLMIDSGS GDNLFAVDVRGIDPEEGRFNNLRLIVERNNLYVTGFVNRTNN VFYRFADFSHVTFPGTTAVTLSGDSSYTTLQRVAGISRTGMQI NRHSLTTSYLDLMSHSGTSLTQSVARAMLRFVTVTAEALRFR QIQRGFRGILGDVFTLSYVMTAEDVDLTLNWGRLSSVLPDYH GQDSVRVGRISFGSINAILGSVALILNSHHHASAVAA |
| SEQ ID NO: 68 | SLT-1A-combo variant 14 | KEFTLDFSTAKTYVDSLNVIRSAIGTPLQTISSGGTSLLMIDSGS GDNLFAVDVRGIDPEEGRFNNLRLIVERNNLYVTGFVNRTNN VFYRFADFSHVTFPGTTAVTLSGDSSYTTLQRVAGISRTGMQI NRHSLTTSYLDLMSHSGTSLTQSVARAMLRFVTVTAEALRFR QIQRGFRTTLDDLSGRSYVMTAEDVDLTLNWGRLSSVLPDYH GQDSVRVGRISFGSINAILGSVALILNCHHHILRFSVAHKASAV AA |
| SEQ ID NO: 69 | SLT-1A-combo variant 15 | KEFTLDFSTAKTYVDSLNVIRSAIGTPLQTISSGGTSLLMIDSGS GDNLFAVDILGFDFTLGRFNNLRLIVERNNLYVTGFVNRTNN VFYRFADFSHVTFPGTTAVTLSGDSSYTTLQRVAGISRTGMQI NRHSLTTSYLDLMSHSGTSLTQSVARAMLRFVTVTAEALRFR QIQRGFRTTLDDLSGRSYVMTAEDVDLTLNWGRLSSVLPDYH GQDSVRVGRISFGSINAILGSVALILNCHHHARNLVPMVATVA SAVAA |
| SEQ ID NO: 70 | linker 1 | EFPKPSTPPGSSGGAP |
| SEQ ID NO: 71 | linker 2 | EFPKPSTPPGSSGGAPGILGFVFTL |
| SEQ ID NO: 72 | linker 3 | GGGGSGG |
| SEQ ID NO: 73 | linker 4 | GGGGSGGGGSGGGGSGGGGSGGGGS |
| SEQ ID NO: 74 | linker 5 | GSTSGSGKPGSGEGS |
| SEQ ID NO: 75 | linker 6 | GGGGS |

TABLE 20-continued

Sequences

| SEQ ID No. | Text Description | Biological Sequence |
|---|---|---|
| SEQ ID NO: 76 | CD38-binding protein #1 | MKEFTLDFSTAKTYVDSLNVIRSAIGTPLQTISSGGTSLLMIDS GIGDNLFAVDILGFDFTLGRFNNLRLIVERNNLYVTGFVNRTN NVFYRFADFSHVTFPGTTAVTLSADSSYTTLQRVAGISRTGM QINRHSLTTSYLDLMSHSGTSLTQSVARAMLRFVTVTAEALR FRQIQRGFRTTLDDLSGASYVMTAEDVDLTLNWGRLSSVLPD YHGQDSVRVGRISFGSINAILGSVALILNSHHHASAVAAEFPK PSTPPGSSGGAPQSVLTQPPSASGTPGQRVTISCSGSSSNIGSNY VYWYQQLPGTAPKLLIYGNSNRPSGVPDRFSGSKSGTSASLAI SGLRSEDEADYYCQSYDSSLSGSGVFGGGTKLTVLGGGGGSE VQLLESGGGLVQPGGSLRLSCAASGFTFSDYYMSWVRQAPG KGLEWVSAISGSGGSTYYADSVKGRFTISRDNSKNTLYLQMN SLRAEDTAVYYCAREHSNYFYGMDVWGQGTLVTVSS |
| SEQ ID NO: 77 | CD38-binding protein #2 | MKEFTLDFSTAKTYVDSLNVIRSAIGTPLQTISSGGTSLLMIDS GIGDNLFAVDILGFDFTLGRFNNLRLIVERNNLYVTGFVNRTN NVFYRFADFSHVTFPGTTAVTLSADSSYTTLQRVAGISRTGM QINRHSLTTSYLDLMSHSGTSLTQSVARAMLRFVTVTAEALR FRQIQRGFRTTLDDLSGASYVMTAEDVDLTLNWGRLSSVLPD YHGQDSVRVGRISFGSINAILGSVALILNSHHHASAVAAEFPK PSTPPGSSGGAPQSVLTQPPSASGTPGQRVTISCSGSSSNIGGN YVYWYQQLPGTAPKLLIYRNNQRPSGVPDRFSGSKSGTSASL AISGLRSEDEADYYCQSYDSSLSVSVFGGGTKLTVLGGGGGS EVQLLESGGGLVQPGGSLRLSCAASGFTFSSYWMHWVRQAP GKGLEWVSAISGSGGGTFYADSVKGRFTISRDNSKNTLYLQM NSLRAEDTAVYYCAREGETSFGLDVWGQGTLVTVSS |
| SEQ ID NO: 78 | CD38-binding protein #3 | MKEFTLDFSTAKTYVDSLNVIRSAIGTPLQTISSGGTSLLMIDS GIGDNLFAVDILGFDFTLGRFNNLRLIVERNNLYVTGFVNRTN NVFYRFADFSHVTFPGTTAVTLSADSSYTTLQRVAGISRTGM QINRHSLTTSYLDLMSHSGTSLTQSVARAMLRFVTVTAEALR FRQIQRGFRTTLDDLSGASYVMTAEDVDLTLNWGRLSSVLPD YHGQDSVRVGRISFGSINAILGSVALILNSHHHHHASAVAAE FPKPSTPPGSSGGAPQVQLVQSGAEVKKPGESLKISCKGSGYS FTSYWIGWVRQMPGKGLEWMGIIYPGDSDTRYSPSFQGQVTI SADKSISTAYLQWSSLKASDTAMYYCARGPSTGFWSGNYFD YWGQGTLVTVSSGGGGSQTVVTQEPSLTVSPGETVTLTCASS TGAVTSGFYPNWFQQKPGQAPRALIYATNNKYSWTPARFSGS LLGDKAALTLSRVQPEDEADYYCLVYYDGAWVFGGGTKLT VLG |
| SEQ ID NO: 79 | CD38-binding protein #4 | MKEFTLDFSTAKTYVDSLNVIRSAIGTPLQTISSGGTSLLMIDS GIGDNLFAVDILGFDFTLGRFNNLRLIVERNNLYVTGFVNRTN NVFYRFADFSHVTFPGTTAVTLSADSSYTTLQRVAGISRTGM QINRHSLTTSYLDLMSHSGTSLTQSVARAMLRFVTVTAEALR FRQIQRGFRTTLDDLSGASYVMTAEDVDLTLNWGRLSSVLPD YHGQDSVRVGRISFGSINAILGSVALILNSHHHASAVAAEFPK PSTPPGSSGGAPQVQLVQSGAEVKKPGESLKISCKGSGYSFTS YWIGWVRQMPGKGLEWMGITYPGDSDTRYSPSFQGQVTISAD KSISTAYLQWSSLKASDTAMYYCARGPSTGFWSGNYFDYWG QGTLVTVSSGGGGSDIQMTQSPSSLSASVGDRVTITCASSTGA VTSGFYPNWFQQKPGQAPRALIYATNNKYSWTPARFSGSLLG DKAALTLSRVQPEDEADYYCLVYYDGAWVFGGGTKLTVLG |
| SEQ ID NO: 80 | CD38-binding protein #5 | MKEFTLDFSTAKTYVDSLNVIRSAIGTPLQTISSGGTSLLMIDS GIGDNLFAVDILGFDFTLGRFNNLRLIVERNNLYVTGFVNRTN NVFYRFADFSHVTFPGTTAVTLSADSSYTTLQRVAGISRTGM QINRHSLTTSYLDLMSHSGTSLTQSVARAMLRFVTVTAEALR FRQIQRGFRTTLDDLSGASYVMTAEDVDLTLNWGRLSSVLPD YHGQDSVRVGRISFGSINAILGSVALILNSHHHASAVAAEFPK PSTPPGSSGGAPQSVLTQPPSASGTPGQRVTISCSGSNSIGSNT VNWYQQLPGTAPKLLIYSDSNRPSGVPDRFSGSKSGTSASLAI SGLRSEDEADYYCQSYDSSLSGSRVFGGGTKLTVLGGGGSG GGGSGGGGSGGGGSGGGGSEVQLLESGGGLVQPGGSLRLSC AASGFTFNNYDMTWVRQAPGKGLEWVAVISYDGSDKDYAD SVKGRFTISRDNSKNTLYLQMNSLRAEDTAVYYCARVYYYG FSGPSMDVWGQGTLVTVSS |
| SEQ ID NO: 81 | CD38-binding protein #6 | MKEFTLDFSTAKTYVDSLNVIRSAIGTPLQTISSGGTSLLMIDS GIGDNLFAVDILGFDFTLGRFNNLRLIVERNNLYVTGFVNRTN NVFYRFADFSHVTFPGTTAVTLSADSSYTTLQRVAGISRTGM QINRHSLTTSYLDLMSHSGTSLTQSVARAMLRFVTVTAEALR FRQIQRGFRTTLDDLSGASYVMTAEDVDLTLNWGRLSSVLPD YHGQDSVRVGRISFGSINAILGSVALILNSHHHHHASAVAAE FPKPSTPPGSSGGAPQSVLTQPPSASGTPGQRVTISCSGSSSNIG |

TABLE 20-continued

Sequences

| SEQ ID No. | Text Description | Biological Sequence |
|---|---|---|
| | | SNYVYWYQQLPGTAPKLLIYGNSNRPSGVPDRFSGSKSGTSA SLAISGLRSEDEADYYCQSYDNTLSGVIFGGGTKLTVLGGGG GSEVQLLESGGGLVQPGGSLRLSCAASGFTFSDYYMNWIRQA PGKGLEWVSSISSSSSYIYYADSVKGRFTISRDNSKNTLYLQM NSLRAEDTAVYYCATEGPYYLYGFDIWGQGTLVTVSS |
| SEQ ID NO: 82 | CD38- binding protein #7 | MKEFTLDFSTAKTYVDSLNVIRSAIGTPLQTISSGGTSLLMIDS GIGDNLFAVDILGFDFTLGRFNNLRLIVERNNLYVTGFVNRTN NVFYRFADFSHVTFPGTTAVTLSADSSYTTLQRVAGISRTGM QINRHSLTTSYLDLMSHSGTSLTQSVARAMLRFVTVTAEALR FRQIQRGFRTTLDDLSGASYVMTAEDVDLTLNWGRLSSVLPD YHGQDSVRVGRISFGSINAILGSVALILNSHHASAVAAEFPK PSTPPGSSGGAPQSVLTQPPSASGTPGQRVTISCSGSSSNIGNSY VSWYQQLPGTAPKLLIYRNNQRPSGVPDRFSGSKSGTSASLAI SGLRSEDEADYYCSAWDDNLSVLFGGGTKLTVLGGGGGSEV QLLESGGGLVQPGGSLRLSCAASGFTFDDYGMTWVRQAPGK GLEWVSGINWNGGSTGYADSVKGRFTISRDNSKNTLYLQMN SLRAEDTAVYYCARGGLFHDSSGYYFGHWGQGTLVTVSSA |
| SEQ ID NO: 83 | CD38- targeting reference molecule 1 | MKEFTLDFSTAKTYVDSLNVIRSAIGTPLQTISSGGTSLLMIDS GIGDNLFAVDILGFDFTLGRFNNLRLIVERNNLYVTGFVNRTN NVFYRFADFSHVTFPGTTAVTLSADSSYTTLQRVAGISRTGM QINRHSLTTSYLDLMSHSGTSLTQSVARAMLRFVTVTAEALR FRQIQRGFRTTLDDLSGASYVMTAEDVDLTLNWGRLSSVLPD YHGQDSVRVGRISFGSINAILGSVALILNSHHASAVAAEFPK PSTPPGSSGGAPDIQMTQSPSSLSASVGDRVTITCKASEDIYNR LTWYQQKPGKAPKLLISGATSLETGVPSRFSGSGSGTDFTFTIS SLQPEDIATYYCQQYWSNPYTFGQGTKVEIKGGGGSQVQLQE SGPGLVRPSQTLSLTCTVSGFSLTSYGVHWVRQPPGRGLEWIG VMWRGGSTDYNAAFMSRLNITKDNSKNQVSLRLSSVTAADT AVYYCAKSMITTGFVMDSWGQGSLVTVSS |
| SEQ ID NO: 84 | CD38- targeting control molecule #1 | MKEFTLDFSTAKTYVDSLNVIRSAIGTPLQTISSGGTSLLMIDS GSGDNLFAVDVRGIDPEEGRFNNLRLIVERNNLYVTGFVNRT NNVFYRFADFSHVTFPGTTAVTLSGDSSYTTLQRVAGISRTG MQINRHSLTTSYLDLMSHSGTSLTQSVARAMLRFVTVTAEAL RFRQIQRGFRTTLDDLSGRSYVMTAEDVDLTLNWGRLSSVLP DYHGQDSVRVGRISFGSINAILGSVALILNCHHHASAVAAEFP KPSTPPGSSGGAPDIQMTQSPSSLSASVGDRVTITCKASEDIYN RLTWYQQKPGKAPKLLISGATSLETGVPSRFSGSGSGTDFTFTI SSLQPEDIATYYCQQYWSNPYTFGQGTKVEIKGGGGSQVQLQ ESGPGLVRPSQTLSLTCTVSGFSLTSYGVHWVRQPPGRGLEWI GVMWRGGSTDYNAAFMSRLNITKDNSKNQVSLRLSSVTAAD TAVYYCAKSMITTGFVMDSWGQGSLVTVSS |
| SEQ ID NO: 85 | CD38 from Homo sapiens | MANCEFSPVSGDKPCCRLSRRAQLCLGVSILVLILVVVLAVV VPRWRQQWSGPGTTKRFPETVLARCVKYTEIHPEMRHVDCQ SVWDAFKGAFISKHPCNITEEDYQPLMKLGTQTVPCNKILLW SRIKDLAHQFTQVQRDMFTLEDTLLGYLADDLTWCGEFNTSK INYQSCPDWRKDCSNNPVSVFWKTVSRRFAEAACDVVHVML NGSRSKIFDKNSTFGSVEVHNLQPEKVQTLEAWVIHGGREDS RDLCQDPTIKELESIISKRNIQFSCKNIYRPDKFLQCVKNPEDSS CTSEI |
| SEQ ID NO: 86 | CD38 extracellular domain (ECD) from Homo sapiens | VPRWRQQWSGPGTTKRFPETVLARCVKYTEIHPEMRHVDCQ SVWDAFKGAFISKHPCNITEEDYQPLMKLGTQTVPCNKILLW SRIKDLAHQFTQVQRDMFTLEDTLLGYLADDLTWCGEFNTSK INYQSCPDWRKDCSNNPVSVFWKTVSRRFAEAACDVVHVML NGSRSKIFDKNSTFGSVEVHNLQPEKVQTLEAWVIHGGREDS RDLCQDPTIKELESIISKRNIQFSCKNIYRPDKFLQCVKNPEDSS CTSEI |
| SEQ ID NO: 87 | CD38 from Macaca fascicularis | MANCEFSPVSGDKPCCRLSRRAQVCLGVCLLVLLILVVVAV VLPRWRQQWSGSGTTSRFPETVLARCVKYTEVHPEMRHVDC QSVWDAFKGAFISKYPCNITEEDYQPLVKLGTQTVPCNKTLL WSRIKDLAHQFTQVQRDMFTLEDMLLGYLADDLTWCGEFNT FEINYQSCPDWRKDCSNNPVSVFWKTVSRRFAETACGVVHV MLNGSRSKIFDKNSTFGSVEVHNLQPEKVQALEAWVIHGGRE DSRDLCQDPTIKELESIISKRNIRFFCKNIYRPDKFLQCVKNPED SSCLSGI |

TABLE 20-continued

Sequences

| SEQ ID No. | Text Description | Biological Sequence |
|---|---|---|
| SEQ ID NO: 88 | CD38 extracellular domain (ECD) from *Macaca fascicularis* | LPRWRQQWSGSGTTSRFPETVLARCVKYTEVHPEMRHVDCQ SVWDAFKGAFISKYPCNITEEDYQPLVKLGTQTVPCNKTLLW SRIKDLAHQFTQVQRDMFTLEDMLLGYLADDLTWCGEFNTF EINYQSCPDWRKDCSNNPVSVFWKTVSRRFAETACGVVHVM LNGSRSKIFDKNSTFGSVEVHNLQPEKVQALEAWVIHGGRED SRDLCQDPTIKELESIISKRNIRFFCKNIYRPDKFLQCVKNPEDS SCLSGI |
| SEQ ID NO: 101 | VH domain | QVQLVQSGAEVKKPGESLKISCKGSGYSFTSYWIGWVRQMP GKGLEWMGIIYPGDSDTRYSPSFQGQVTISADKSISTAYLQWS SLKASDTAMYYCARGPSTGFWSGNYFDYWGQGTLVTVSS |
| SEQ ID NO: 102 | vhCDR1 | GYSFTSYW |
| SEQ ID NO: 103 | vhCDR2 | IYPGDSDT |
| SEQ ID NO: 104 | vhCDR3 | ARGPSTGFWSGNYFDY |
| SEQ ID NO: 105 | VL domain | QTVVTQEPSLTVSPGETVTLTCASSTGAVTSGFYPNWFQQKP GQAPRALIYATNNKYSWTPARFSGSLLGDKAALTLSRVQPED EADYYCLVYYDGAWVFGGGTKLTVLG |
| SEQ ID NO: 106 | vlCDR1 | TGAVTSGFY |
| SEQ ID NO: 107 | vlCDR2 | ATN |
| SEQ ID NO: 108 | vlCDR3 | LVYYDGAW |
| SEQ ID NO: 109 | VH domain | EVQLLESGGGLVQPGGSLRLSCAASGFTFSDYYMSWVRQAP GKGLEWVSAISGSGGSTYYADSVKGRFTISRDNSKNTLYLQM NSLRAEDTAVYYCAREHSNYFYGMDVWGQGTLVTVSS |
| SEQ ID NO: 110 | vhCDR1 | GFTFSDYY |
| SEQ ID NO: 111 | vhCDR2 | ISGSGGST |
| SEQ ID NO: 112 | vhCDR3 | AREHSNYFYGMDV |
| SEQ ID NO: 113 | VL domain | QSVLTQPPSASGTPGQRVTISCSGSSSNIGSNYVYWYQQLPGT APKLLIYGNSNRPSGVPDRFSGSKSGTSASLAISGLRSEDEADY YCQSYDSSLSGSGVFGGGTKLTVLG |
| SEQ ID NO: 114 | vlCDR1 | SSNIGSNY |
| SEQ ID NO: 115 | vlCDR2 | GNS |
| SEQ ID NO: 116 | vlCDR3 | QSYDSSLSGSG |
| SEQ ID NO: 117 | VH domain | EVQLLESGGGLVQPGGSLRLSCAASGFTFSSYWMHWVRQAP GKGLEWVSAISGSGGGTFYADSVKGRFTISRDNSKNTLYLQM NSLRAEDTAVYYCAREGETSFGLDVWGQGTLVTVSS |
| SEQ ID NO: 118 | vhCDR1 | GFTFSSYW |
| SEQ ID NO: 119 | vhCDR2 | ISGSGGGT |
| SEQ ID NO: 120 | vhCDR3 | AREGETSFGLDV |

TABLE 20-continued

Sequences

| SEQ ID No. | Text Description | Biological Sequence |
|---|---|---|
| SEQ ID NO: 121 | VL domain | QSVLTQPPSASGTPGQRVTISCSGSSSNIGGNYVYWYQQLPGT APKLLIYRNNQRPSGVPDRFSGSKSGTSASLAISGLRSEDEAD YYCQSYDSSLSVSVFGGGTKLTVLG |
| SEQ ID NO: 122 | vlCDR1 | SSNIGGNY |
| SEQ ID NO: 123 | vlCDR2 | RNN |
| SEQ ID NO: 124 | vlCDR3 | QSYDSSLSVS |
| SEQ ID NO: 125 | VL domain | QTVVTQEPSLTVSPGETVTLTCASSTGAVTSGFYPNWFQQKP GQAPRALIYATNNKYSWTPARFSGSLLGDKAALTLSRVQPED EADYYCLVYYDGAWVFGGGTKLTVLG |
| SEQ ID NO: 126 | VH domain | QVQLQESGPGLVRPSQTLSLTCTVSGFSLTSYGVHWVRQPPG RGLEWIGVMWRGGSTDYNAAFMSRLNITKDNSKNQVSLRLS SVTAADTAVYYCAKSMITTGFVMDSWGQGSLVTVSS |
| SEQ ID NO: 127 | VL domain | DIQMTQSPSSLSASVGDRVTITCKASEDIYNRLTWYQQKPGK APKLLISGATSLETGVPSRFSGSGSGTDFTFTISSLQPEDIATYY CQQYVVSNPYTFGQGTKVEIK |
| SEQ ID NO: 128 | CD38 Homo sapiens | MANCEFSPVSGDKPCCRLSRRAQLCLGVSILVLILVVVLAVV VPRWRQQWSGPGTTKRFPETVLARCVKYTEIHPEMRHVDCQ SVWDAFKGAFISKHPCNITEEDYQPLMKLGTQTVPCNKILLW SRIKDLAHQFTQVQRDMFTLEDTLLGYLADDLTWCGEFNTSK INYQSCPDWRKDCSNNPVSVFWKTVSRRFAEAACDVVHVML NGSRSKIFDKNSTFGSVEVHNLQPEKVQTLEAWVIHGGREDS RDLCQDPTIKELESIISKRNIQFSCKNIYRPDKFLQCVKNPEDSS CTSEI |
| SEQ ID NO: 129 | CD38 Homo sapiens extracellular domain (ECD) | VPRWRQQWSGPGTTKRFPETVLARCVKYTEIHPEMRHVDCQ SVWDAFKGAFISKHPCNITEEDYQPLMKLGTQTVPCNKILLW SRIKDLAHQFTQVQRDMFTLEDTLLGYLADDLTWCGEFNTSK INYQSCPDWRKDCSNNPVSVFWKTVSRRFAEAACDVVHVML NGSRSKIFDKNSTFGSVEVHNLQPEKVQTLEAWVIHGGREDS RDLCQDPTIKELESIISKRNIQFSCKNIYRPDKFLQCVKNPEDSS CTSEI |
| SEQ ID NO: 130 | CD38 Macaca fascicularis | MANCEFSPVSGDKPCCRLSRRAQVCLGVCLLVLLILVVVVAV VLPRWRQQWSGSGTTSRFPETVLARCVKYTEVHPEMRHVDC QSVWDAFKGAFISKYPCNITEEDYQPLVKLGTQTVPCNKTLL WSRIKDLAHQFTQVQRDMFTLEDMLLGYLADDDLTWCGEFNT FEINYQSCPDWRKDCSNNPVSVFWKTVSRRFAETACGVVHV MLNGSRSKIFDKNSTFGSVEVHNLQPEKVQALEAWVIHGGRE DSRDLCQDPTIKELESIISKRNIRFFCKNIYRPDKFLQCVKNPED SSCLSGI |
| SEQ ID NO: 131 | CD38 Macaca fascicularis extracellular domain (ECD) | LPRWRQQWSGSGTTSRFPETVLARCVKYTEVHPEMRHVDCQ SVWDAFKGAFISKYPCNITEEDYQPLVKLGTQTVPCNKTLLW SRIKDLAHQFTQVQRDMFTLEDMLLGYLADDDLTWCGEFNTF EINYQSCPDWRKDCSNNPVSVFWKTVSRRFAETACGVVHVM LNGSRSKIFDKNSTFGSVEVHNLQPEKVQALEAWVIHGGRED SRDLCQDPTIKELESIISKRNIRFFCKNIYRPDKFLQCVKNPEDS SCLSGI |

What is claimed is:

1. A CD38-binding fusion protein comprising:
   1) a Shiga toxin A subunit effector polypeptide; and
   2) a CD38-binding domain, comprising:
      a) a heavy chain variable domain (VH) comprising:
         i) a vHCDR1 comprising the sequence of SEQ ID NO: 34;
         ii) a vHCDR2 comprising the sequence of SEQ ID NO: 35; and
         iii) a vHCDR3 comprising the sequence of SEQ ID NO: 36; and
      b) a light chain variable domain (VL) comprising:
         i) a vLCDR1 comprising the sequence of SEQ ID NO: 31;
         ii) a vLCDR2 comprising the sequence of SEQ ID NO: 32; and
         iii) a vLCDR3 comprising the sequence of SEQ ID NO: 33.

2. The CD38-binding fusion protein of claim 1, wherein the CD38-binding fusion protein comprises the sequence of SEQ ID NO: 79.

3. The CD38-binding fusion protein of claim 1, wherein the VL comprises the sequence of SEQ ID NO: 43, and the VH comprises the sequence of SEQ ID NO: 44.

4. The CD38-binding fusion protein of claim 1, wherein the CD38-binding fusion protein comprises a first linker between the Shiga toxin A subunit effector polypeptide and the CD38-binding domain.

5. The CD38-binding fusion protein of claim 4, wherein the first linker is a proteinaceous linker.

6. The CD38-binding fusion protein of claim 5, wherein the first linker comprises the sequence of SEQ ID NO: 70.

7. The CD38-binding fusion protein of claim 4, wherein the CD38-binding fusion protein comprises a second linker between the VH and the VL.

8. The CD38-binding fusion protein of claim 7, wherein the CD38-binding fusion protein comprises, from its N- to C-terminus, the Shiga toxin A subunit effector polypeptide-first linker-VH-second linker-VL.

9. The CD38-binding fusion protein of claim 8, wherein the Shiga toxin A subunit effector polypeptide comprises the sequence of SEQ ID NO: 46.

10. The CD38-binding fusion protein of claim 1, wherein the Shiga toxin A subunit effector polypeptide comprises the sequence of SEQ ID NO: 46, the VL comprises the sequence of SEQ ID NO: 43, and the VH comprises the sequence of SEQ ID NO: 44.

11. The CD38-binding fusion protein of claim 1, wherein the CD38-binding fusion protein is a homodimer.

12. The CD38-binding fusion protein of claim 1, wherein the CD38-binding fusion protein comprises two identical polypeptides, each polypeptide comprising the sequence of SEQ ID NO: 79.

13. A nucleic acid encoding the CD38-binding protein fusion of claim 2.

14. An expression vector comprising the nucleic acid of claim 13.

15. A host cell comprising the expression vector of claim 14.

16. A composition comprising (i) the CD38-binding fusion protein of claim 2 and (ii) a pharmaceutically acceptable carrier or excipient.

17. The composition of claim 16, wherein at least about 90% of the CD38-binding fusion protein is in the form of a homodimer.

18. The composition of claim 17, wherein at least about 95% of the CD38-binding fusion protein is in the form of a homodimer.

* * * * *